(12) United States Patent
Krieg et al.

(10) Patent No.: US 7,271,156 B2
(45) Date of Patent: Sep. 18, 2007

(54) IMMUNOSTIMULATORY NUCLEIC ACIDS

(75) Inventors: Arthur M. Krieg, Wellesley, MA (US); Jörg Vollmer, Düsseldorf (DE); Christian Schetter, Hilden (DE)

(73) Assignees: University of Iowa Research Foundation, Iowa City, IA (US); Coley Pharmaceutical GmbH, Dusseldorf (DE)

( * ) Notice: Subject to any disclaimer, the term of this patent is extended or adjusted under 35 U.S.C. 154(b) by 0 days.

(21) Appl. No.: 10/314,578

(22) Filed: Dec. 9, 2002

(65) Prior Publication Data

US 2003/0212026 A1    Nov. 13, 2003

Related U.S. Application Data

(63) Continuation of application No. 09/669,187, filed on Sep. 25, 2000.

(60) Provisional application No. 60/227,436, filed on Aug. 23, 2000, provisional application No. 60/156,135, filed on Sep. 27, 1999, provisional application No. 60/156,113, filed on Sep. 25, 1999.

(51) Int. Cl.
  *C07H 21/00* (2006.01)
  *C07H 21/04* (2006.01)
  *A61K 31/70* (2006.01)
  *A61K 9/22* (2006.01)
  *A61K 9/52* (2006.01)
  *A01N 25/08* (2006.01)
  *A01N 43/04* (2006.01)

(52) U.S. Cl. ............ 514/44; 536/23.1; 536/25.3; 536/25.6; 424/408; 424/409; 424/422; 424/430; 424/434; 424/450; 424/457; 424/468; 424/490

(58) Field of Classification Search ............ 514/44; 536/23.1, 23.6, 23.4, 23.5, 23.51, 23.52, 536/24.3, 25.3, 25.6; 424/408, 409, 422, 424/430, 434, 450, 457, 468, 490
See application file for complete search history.

(56) References Cited

U.S. PATENT DOCUMENTS

| | | | |
|---|---|---|---|
| 5,663,153 A | 9/1997 | Hutcherson et al. | |
| 5,723,335 A | 3/1998 | Hutcherson et al. | |
| 6,194,388 B1 | 2/2001 | Krieg et al. | |
| 6,207,646 B1 | 3/2001 | Krieg et al. | |
| 6,214,806 B1 * | 4/2001 | Krieg et al. | 514/44 |
| 6,218,371 B1 * | 4/2001 | Krieg et al. | 514/44 |
| 6,221,882 B1 | 4/2001 | Macfarlane | |
| 6,239,116 B1 * | 5/2001 | Krieg et al. | 514/44 |
| 6,339,068 B1 * | 1/2002 | Krieg et al. | 514/44 |
| 6,399,630 B1 | 6/2002 | Macfarlane | |
| 6,406,705 B1 * | 6/2002 | Davis et al. | 424/278.1 |
| 6,429,199 B1 * | 8/2002 | Krieg et al. | 514/44 |
| 6,479,504 B1 | 11/2002 | Macfarlane et al. | |
| 6,521,637 B2 | 2/2003 | Macfarlane | |
| 6,544,518 B1 * | 4/2003 | Friede et al. | 424/184.1 |
| 6,653,292 B1 * | 11/2003 | Krieg et al. | 514/44 |
| 6,727,230 B1 | 4/2004 | Hutcherson et al. | |
| 6,821,957 B2 | 11/2004 | Krieg et al. | |
| 6,943,240 B2 | 9/2005 | Bauer et al. | |
| 6,949,520 B1 | 9/2005 | Hartmann et al. | |
| 2001/0044416 A1 | 11/2001 | McCluskie et al. | |
| 2002/0091097 A1 | 7/2002 | Bratzler et al. | |
| 2002/0156033 A1 | 10/2002 | Bratzler et al. | |
| 2002/0164341 A1 | 11/2002 | Davis et al. | |
| 2002/0165178 A1 | 11/2002 | Schetter et al. | |
| 2002/0198165 A1 | 12/2002 | Bratzler et al. | |
| 2003/0026782 A1 | 2/2003 | Krieg et al. | |
| 2003/0026801 A1 | 2/2003 | Weiner et al. | |
| 2003/0050261 A1 | 3/2003 | Krieg et al. | |
| 2003/0050268 A1 * | 3/2003 | Krieg et al. | 514/44 |
| 2003/0055014 A1 | 3/2003 | Bratzler | |
| 2003/0091599 A1 | 5/2003 | Davis et al. | |
| 2003/0100527 A1 | 5/2003 | Krieg et al. | |
| 2003/0139364 A1 | 7/2003 | Krieg et al. | |
| 2003/0148316 A1 | 8/2003 | Lipford et al. | |
| 2003/0148976 A1 * | 8/2003 | Krieg et al. | 514/44 |
| 2003/0166001 A1 | 9/2003 | Lipford | |
| 2003/0181406 A1 * | 9/2003 | Schetter et al. | 514/44 |
| 2003/0191079 A1 | 10/2003 | Krieg et al. | |
| 2003/0212026 A1 * | 11/2003 | Krieg et al. | 514/44 |
| 2003/0224010 A1 | 12/2003 | Davis et al. | |

(Continued)

FOREIGN PATENT DOCUMENTS

| | | |
|---|---|---|
| WO | WO96/02555 A1 | 2/1996 |
| WO | WO98/37919 A1 * | 9/1998 |
| WO | WO98/40100 | 9/1998 |
| WO | WO99/56755 A1 | 11/1999 |
| WO | WO99/58118 | 11/1999 |

(Continued)

OTHER PUBLICATIONS

Krieg et al, Immunopharmacology, 2000, 48:303-305.*
Tighe et al, J. Allergy Clin. Immunol. 2000, 106:124-134.*
McCluskie et al, Vaccine, 2001, 19:2657-2660.*
Jones et al, Vaccine, 1999, 17:3065-3071.*

(Continued)

*Primary Examiner*—Nita Minnifield
(74) *Attorney, Agent, or Firm*—Wolf Greenfield & Sacks, P.C.

(57) ABSTRACT

The invention relates to immunostimulatory nucleic acid compositions and methods of using the compositions. The T-rich nucleic acids contain poly T sequences and/or have greater than 25% T nucleotide residues. The TG nucleic acids have TG dinucleotides. The C-rich nucleic acids have at least one poly-C region and/ore greater than 50% c nucleotides. These immunostimulatory nucleic acids function in a similar manner to nucleic acids containing CpG motifs. The invention also encompasses preferred CpG nucleic acids.

33 Claims, 12 Drawing Sheets

U.S. PATENT DOCUMENTS

| | | |
|---|---|---|
| 2003/0232074 A1 | 12/2003 | Lipford et al. |
| 2003/0232856 A1 | 12/2003 | Macfarlane |
| 2004/0009949 A1 | 1/2004 | Krieg |
| 2004/0030118 A1 | 2/2004 | Wagner et al. |
| 2004/0053880 A1* | 3/2004 | Krieg .................. 514/44 |
| 2004/0067902 A9* | 4/2004 | Bratzler et al. ............ 514/44 |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1* | 5/2004 | Krieg .................. 514/44 |
| 2004/0106568 A1* | 6/2004 | Krieg et al. ............ 514/44 |
| 2004/0131628 A1* | 7/2004 | Bratzler et al. ......... 424/184.1 |
| 2004/0132685 A1* | 7/2004 | Krieg et al. ............ 514/44 |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1* | 8/2004 | Krieg .................. 514/44 |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1* | 9/2004 | Krieg et al. ............ 514/44 |
| 2004/0181045 A1 | 9/2004 | Krieg et al. |
| 2004/0198680 A1* | 10/2004 | Krieg .................. 514/44 |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1* | 11/2004 | Davis et al. ............ 514/44 |
| 2004/0235774 A1* | 11/2004 | Bratzler et al. ............ 514/44 |
| 2004/0235777 A1 | 11/2004 | Wagner et al. |
| 2004/0235778 A1 | 11/2004 | Wagner et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0032734 A1 | 2/2005 | Davis et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0080034 A1* | 4/2005 | Standring et al. ............ 514/46 |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartman et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215500 A1 | 9/2005 | Krieg et al. |
| 2005/0215501 A1 | 9/2005 | Lipford et al. |
| 2005/0244410 A1* | 11/2005 | Bassiri et al. ............ 424/144.1 |
| 2005/0250716 A1* | 11/2005 | Schmidt et al. ............ 514/44 |
| 2005/0260216 A1* | 11/2005 | Ashman et al. ......... 424/184.1 |
| 2005/0267057 A1* | 12/2005 | Krieg .................. 514/44 |
| 2006/0229271 A1* | 10/2006 | Krieg et al. ............ 514/44 |
| 2006/0241076 A1* | 10/2006 | Uhlmann et al. ............ 514/44 |
| 2007/0037767 A1* | 2/2007 | Bratzler et al. ............ 514/44 |

FOREIGN PATENT DOCUMENTS

| | | |
|---|---|---|
| WO | WO99/61056 | 12/1999 |
| WO | WO 00/06588 A1 | 2/2000 |
| WO | WO 00/75304 A1 | 12/2000 |
| WO | WO 01/22972 A2 * | 4/2001 |
| WO | WO 01/62909 A1 | 8/2001 |
| WO | WO 02/069369 A2 * | 9/2002 |
| WO | WO 03/015711 A2 * | 2/2003 |
| WO | WO 2004/007743 A2 | 1/2004 |
| WO | WO 2004/026888 A2 | 4/2004 |
| WO | WO 2004/094671 A2 | 11/2004 |

OTHER PUBLICATIONS

Askenase, J. Allergy Clin. Immunol., 2000, 106:37-40.*

Vollmer et al, Antisense and Nucleic Acid Drug Development, 2002, 12:165-175.*

Weiner, J. Leukocyte Biology, 200, 68:455-463.*

Agrawal et al, TRENDS in Molecular Medicine, 2002. 8/3:114-121.*

Gelfand, J. Allergy Clin. Immunol., 2004, 114:S135-S138.*

Saito et al, Immunology, 2001, 104:226-234.*

Taube et al, Int. Arch. Allergy Immunol., 2004, 135:173-186.*

Asakura et al, International Archives of Alllergy and Immunology, 1998, 116:49-52.*

Takeda et al, J. Exp. Med., Aug. 4, 1997, 186/3:449-454.*

Kataoka, et al., "Antitumor activity of synthetic oligonucleotides with sequences from cDNA encoding proteins of *Mycobacterium bovis* BCG", *Jpn. J. Cancer Res.*, 83:244-247 (1992).

Krieg, et al., "Editorial:Phosphorothioate oligodeoxynucleotides: antisense or anti-protein?", *Anitsense Res. Devlp.*, 5:241 (1995).

Krieg, A.M., "Leukocyte stimulation by oligodeoxynucleotides", *Applied Antisense Oligonucleotide Technology*, 24:431-448 (1998).

Sun, et al., "Mitogenicity of DNA from different organisms for murine B cells", *J. Immunol.*, 159:3119-3125 (1997(.

Krieg, et al., "Brief Communication: Oligodeoxynucleotide modifications determine the magnitude of B cell stimulation by CpG motifs", *Antisense Nucleic Acid. Drug Developmen*, 6:133-139 (1996).

Messina, et al., "Stimulation of in vitro murine lymphocyte proliferation by bacterial DNA", *J. of Immunol.*, 147(6):1759-1764 (1991).

McIntyre, et al., "A sense phosphorothioate oligonucleotide directed to the intiation codon of transcription factor NF-kB p65 causes sequence-specific immune stimulation", *Antisense Res. and Devlop.*, 3:309-322 (1993).

Hartmann, et al., "Mechanism and function of a newly identified CpG DNA motif in human primary b cells", *J. of Immunol.*, 164:944-952 (2000).

Yi, et al., "CpG DNA rescues B cells from apoptosis by activating NFκB and preventing mitochondrial membrane potential disruption via a chloroquine-sensitive pathway", *International Immunol.*, 11(2):2015-2024 (1999).

Hartmann, et al., "Delineation of CpG phosphorothioate oligodeoxynucleotide for activating primate immune responses in vitro and in vivo", *J. of Immunol.*, 164:1617-1624 (2000).

Pisetsky, et al., "The influence of base sequence on the immunological properties of defined oligonucleotides", *Immunopharmacology*, 40:199-208 (1998).

Tokunaga, et al., "A synthetic single-stranded DNA, poly(dG,dC), induces interferon-α/β activity, and suppresses tumor growth", *Jpn. J. Cancer Res.*, 79:982-686 (1988).

Tokunaga, et al., "Synthetic oligonucleotides with particular base sequences from the cDNA encoding proteins of *Mycobacterium bovis* BCG induce interferons and activate natural killer cells", *Jpn J. Cancer Res.*, 36(1):55-66 (1992).

Lipford, GB et al., CpG-containing synthetic oligonucleotides promote B and cytotoxic T cell responses to protein antigen: a new class of vaccine adjuvants, *Eur J Immunol.* 27(9):2340 (1997).

Goukassian et al., "Topical DNA Oligonucleotide Therapy Reduces UV-induced Mutations and Photocarcinogenesis in Hairless Mice", *PNAS*, 101(11):3933-3938, 2004.

Bohle et al. Oligodeoxynucleotides containing CpG motifs induce IL-12, IL-18 and IFN-gamma production in cells from allergic individuals and inhibit IgE synthesis in vitro. Eur J Immunol. Jul. 1999;29(7):2344-53.

Vollmer et al., Highly immunostimulatory CpG-free oligodeoxynucleotides for activation of human leukocytes. Antisense Nucleic Acid Drug Dev. Jun. 2002;12(3):165-75.

Liang et al., Activation of human B cells by phosphorothioate oligodeoxynucleotides. J Clin Invest. Sep. 1, 1996;98(5):1119-29.

Agrawal et al., Novel immunomodulatory oligonucleotide prevent development of allergic airway inflammation and airway hyper-responsiveness in asthma. Int Immunopharmacol. Jan. 2004;4(1):127-38.

Broide et al., Immunostimulatory DNA sequences inhibit IL-5, eosinophilic inflammation, and airway hyperresponsiveness in mice. J Immunol. Dec. 15, 1998;161(12):7054-62.

Jain et al., CpG DNA and immunotherapy of allergic airway diseases. Clin Exp Allergy. Oct. 2003;33(10):1330-5.

Kline et al., DNA therapy for asthma. Curr Opin Allergy Clin Immunol. Feb. 2002;2(1):69-73.

Kline et al., Modulation of airway inflammation by CpG oligodeoxynucleotides in a murine model of asthma. J Immunol. Mar. 15, 1998;160(6):2555-9.

Metzger et al., Oligonucleotide therapy of allergic asthma. J Allergy Clin Immunol. Aug. 1999;104(2 Pt 1):260-6.

Satoh et al., The study of mechanisms in CpG oligodeoxynucleotides-induced aggravation in murine allergic contact dermititis to 2,4-dinitrofluorobenzene. Fukushima Igaku Zasshi. 2002;52(3):237-50. Abstract.

Silverman et al., Immunostimulatory DNA for asthma: better than eating dirt. Am J Respir Cell Mol Biol. Jun. 2003;28(6):645-7.

Wohlleben et al., Atopic disorders: a vaccine around the corner? Trends Immunol. Nov. 2001;22(11):618-26.

\* cited by examiner

STATISTICAL ANALYSIS

| | MEAN | STD.DEV. | STD.ERROR | NUMBER | MINIMUM | MAXIMUM | # MISSING |
|---|---|---|---|---|---|---|---|
| o1758 | 46.70 | - | - | 1 | 46.70 | 46.70 | 3 |
| o1812 | 20.70 | .14 | .10 | 2 | 20.60 | 20.80 | 2 |
| o2006 | 23.60 | .14 | .10 | 2 | 23.50 | 23.70 | 2 |
| o2117 | 22.10 | 0.00 | 0.00 | 2 | 22.10 | 22.10 | 2 |
| o2137 | 29.75 | 1.48 | 1.05 | 2 | 28.70 | 30.80 | 2 |
| o2178 | 20.00 | .71 | .50 | 2 | 19.50 | 20.50 | 2 |
| o2182 | 27.15 | .35 | .25 | 2 | 26.30 | 27.40 | 2 |
| o2183 | 26.35 | 2.90 | 2.05 | 2 | 24.30 | 29.40 | 2 |
| o2177 | 21.55 | 1.77 | 1.25 | 2 | 20.30 | 22.80 | 2 |
| o2143 | 22.55 | 1.48 | 1.05 | 2 | 21.50 | 23.60 | 2 |
| o2116 | 20.55 | 1.48 | 1.05 | 2 | 19.50 | 21.60 | 2 |
| o2181 | 26.90 | .57 | .40 | 2 | 26.50 | 27.30 | 2 |
| o2180 | 26.75 | 1.77 | 1.25 | 2 | 25.50 | 23.00 | 2 |
| o2179 | 29.10 | 1.98 | 1.40 | 2 | 27.70 | 30.50 | 2 |
| o2133 | 28.80 | .99 | .70 | 2 | 28.10 | 23.50 | 2 |
| o1965 | 31.05 | .92 | .65 | 2 | 30.40 | 31.70 | 2 |
| o1968 | 22.95 | 1.20 | .85 | 2 | 22.10 | 23.80 | 2 |
| o2159 | 26.55 | 4.88 | 3.45 | 2 | 23.10 | 30.00 | 2 |
| o2140 | 40.85 | 2.47 | 1.75 | 2 | 39.10 | 42.60 | 2 |
| o2141 | 31.30 | 3.11 | 2.20 | 2 | 29.10 | 33.50 | 2 |
| o2142 | 22.10 | 1.13 | .80 | 2 | 21.30 | 22.90 | 2 |
| o1840 | 24.45 | .07 | .05 | 2 | 24.40 | 24.50 | 2 |
| o1979 | 57.65 | .49 | .35 | 2 | 57.30 | 55.00 | 2 |
| o2186 | 20.85 | .35 | .25 | 2 | 20.80 | 21.10 | 2 |
| o2187 | 21.15 | .07 | .05 | 2 | 21.10 | 21.20 | 2 |
| o2188 | 20.70 | .14 | .10 | 2 | 20.60 | 20.80 | 2 |
| o2189 | 19.45 | .07 | .05 | 2 | 19.40 | 19.50 | 2 |
| o2190 | 21.85 | 2.47 | 1.75 | 2 | 20.10 | 23.60 | 2 |
| o2191 | 21.40 | 3.25 | 2.30 | 2 | 19.10 | 23.70 | 2 |
| o2192 | 19.50 | .14 | .10 | 2 | 19.40 | 19.60 | 2 |
| o2193 | 20.65 | .21 | .15 | 2 | 20.50 | 20.80 | 2 |
| o2194 | 23.50 | 1.70 | 1.20 | 2 | 22.30 | 24.70 | 2 |
| o2195 | 23.00 | .85 | .60 | 2 | 22.40 | 23.60 | 2 |
| o2196 | 21.05 | 1.77 | 1.25 | 2 | 19.80 | 22.30 | 2 |
| NO ADDITION | 20.90 | 2.77 | 1.38 | 4 | 18.60 | 24.90 | 0 |

Fig. 1B

STATISTICAL ANALYSIS

| | MEAN | STD.DEV. | STD.ERROR | NUMBER | MINIMUM | MAXIMUM | # MISSING |
|---|---|---|---|---|---|---|---|
| o1758 | 57.60 | .71 | .50 | 2 | 57.10 | 58.10 | 2 |
| o1812 | 20.70 | .57 | .40 | 2 | 20.30 | 21.10 | 2 |
| o2006 | 56.35 | .35 | .25 | 2 | 56.10 | 56.60 | 2 |
| o2117 | 40.00 | 1.13 | .80 | 2 | 39.20 | 40.80 | 2 |
| o2137 | 47.60 | 3.39 | 2.40 | 2 | 45.20 | 50.00 | 2 |
| o2178 | 21.00 | .99 | .70 | 2 | 20.30 | 21.70 | 2 |
| o2182 | 37.75 | .35 | .25 | 2 | 37.50 | 38.00 | 2 |
| o2183 | 35.30 | 1.84 | 1.30 | 2 | 34.00 | 36.60 | 2 |
| o2177 | 25.00 | .71 | .50 | 2 | 24.50 | 25.50 | 2 |
| o2143 | 34.70 | .71 | .50 | 2 | 34.20 | 35.20 | 2 |
| o2116 | 24.35 | .64 | .45 | 2 | 23.90 | 24.80 | 2 |
| o2181 | 44.25 | 3.18 | 2.25 | 2 | 42.00 | 46.50 | 2 |
| o2180 | 45.90 | 5.94 | 4.20 | 2 | 41.70 | 50.10 | 2 |
| o2179 | 50.70 | 6.93 | 4.90 | 2 | 45.80 | 55.60 | 2 |
| o2133 | 53.75 | 4.31 | 3.05 | 2 | 50.70 | 56.80 | 2 |
| o1965 | 56.20 | 3.82 | 2.70 | 2 | 53.50 | 58.90 | 2 |
| o1968 | 49.35 | 1.91 | 1.35 | 2 | 48.00 | 50.70 | 2 |
| o2159 | 46.80 | 7.92 | 5.60 | 2 | 41.20 | 52.40 | 2 |
| o2140 | 53.25 | 4.74 | 3.35 | 2 | 49.90 | 56.60 | 2 |
| o2141 | 47.40 | 4.10 | 2.90 | 2 | 44.50 | 50.30 | 2 |
| o2142 | 23.20 | .42 | .30 | 2 | 22.90 | 23.50 | 2 |
| o1840 | 33.50 | 1.13 | .80 | 2 | 32.70 | 34.30 | 2 |
| o1979 | 59.50 | 1.70 | 1.20 | 2 | 58.30 | 60.70 | 2 |
| o2186 | 36.90 | .14 | .10 | 2 | 36.80 | 37.00 | 2 |
| o2187 | 27.15 | .78 | .55 | 2 | 26.60 | 27.70 | 2 |
| o2188 | 22.25 | .21 | .15 | 2 | 22.10 | 22.40 | 2 |
| o2189 | 21.45 | 1.20 | .85 | 2 | 20.60 | 22.30 | 2 |
| o2190 | 22.95 | 1.20 | .85 | 2 | 22.10 | 23.80 | 2 |
| o2191 | 28.35 | .49 | .35 | 2 | 28.00 | 28.70 | 2 |
| o2192 | 20.40 | 1.70 | 1.20 | 2 | 19.20 | 21.60 | 2 |
| o2193 | 19.70 | .57 | .40 | 2 | 19.30 | 20.10 | 2 |
| o2194 | 34.00 | 1.70 | 1.20 | 2 | 32.80 | 35.20 | 2 |
| o2195 | 27.30 | 1.27 | .90 | 2 | 26.40 | 28.20 | 2 |
| o2196 | 22.45 | 2.76 | 1.95 | 2 | 20.50 | 24.40 | 2 |
| NO ADDITION | 20.90 | 2.77 | 1.38 | 4 | 18.60 | 24.90 | 0 |

Fig. 1D

SEQUENCE LISTING

<160> NUMBER OF SEQ ID NOS: 1145

<210> SEQ ID NO 1
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1
tctcccagcg tgcgccat                                                     18

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 2
ataatccagc ttgaaccaag                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 3
ataatcgacg ttcaagcaag                                                   20

<210> SEQ ID NO 4
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 4
taccgcgtgc gaccctct                                                     18

<210> SEQ ID NO 5
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 5 ggggagggt                                                                9

<210> SEQ ID NO 6
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 6 ggggagggg                                                                9

<210> SEQ ID NO 7
<211> LENGTH: 9

```
<212> TYPE: DNA
<213> ORGANISM: Artificial Sequence
<220> FEATURE:
<223> OTHER INFORMATION: Synthetic Sequence

<400> SEQUENCE: 7 ggtgaggtg                                                            9

<210> SEQ ID NO 8
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 8
tccatgtngt tcctgatgct                                                20

<210> SEQ ID NO 9
<211> LENGTH: 15
<212> TYPE: DNA
<213> ORGANISM: Artificial Sequence
<220> FEATURE:
<221> NAME/KEY: modified_base
<222> LOCATION: (11)...(11)
<223> OTHER INFORMATION: m5c
<220> FEATURE:
<223> OTHER INFORMATION: Synthetic Sequence

<400> SEQUENCE: 9
gctaccttag ngtga                                                     15

<210> SEQ ID NO 10
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 10
tccatgangt tcctgatgct                                                20

<210> SEQ ID NO 11
<211> LENGTH: 20
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
<220> FEATURE:
<223> OTHER INFORMATION: Synthetic Sequence

<400> SEQUENCE: 11
tccatgacgt tcntgatgct                                                20

<210> SEQ ID NO 12
<211> LENGTH: 15
<212> TYPE: DNA
<213> ORGANISM: Artificial Sequence
<220> FEATURE:
```

```
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 12
gctagangtt agtgt                                            15

<210> SEQ ID NO 13
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 13
agctccatgg tgctcactg                                        19

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 14
ccacgtcgac cctcaggcga                                       20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 15
gcacatcgtc ccgcagccga                                       20

<210> SEQ ID NO 16
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 16
gtcactcgtg gtacctcga                                        19

<210> SEQ ID NO 17
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 17
gttggataca ggccagactt tgttg                                 25

<210> SEQ ID NO 18
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 18
```
gattcaactt gcgctcatct taggc						25

<210> SEQ ID NO 19
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 19
accatggacg aactgtttcc cctc						24

<210> SEQ ID NO 20
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 20
accatggacg agctgtttcc cctc						24

<210> SEQ ID NO 21
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 21
accatggacg acctgtttcc cctc						24

<210> SEQ ID NO 22
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 22
accatggacg tactgtttcc cctc						24

<210> SEQ ID NO 23
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 23
accatggacg gtctgtttcc cctc						24

<210> SEQ ID NO 24
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 24
accatggacg ttctgtttcc cctc						24

<210> SEQ ID NO 25
<211> LENGTH: 25
<212> TYPE: DNA

```
<213> ORGANISM: Artificial Sequence
<220> FEATURE:
<223> OTHER INFORMATION: Synthetic Sequence

<400> SEQUENCE: 25
ccactcacat ctgctgctcc acaag                                           25

<210> SEQ ID NO 26
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 26
acttctcata gtccctttgg tccag                                           25

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
tccatgagct tcctgagtct                                                 20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (9)...(9)
<223> OTHER INFORMATION: I
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (15)...(15)
<223> OTHER INFORMATION: I

<400> SEQUENCE: 28
gaggaaggng nggangacgt                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (7)...(7)
<223> OTHER INFORMATION: I
<220> FEATURE:
<221> NAME/KEY: modified_base
<222> LOCATION: (13)...(13)
<223> OTHER INFORMATION: I
<220> FEATURE:
<221> NAME/KEY: modified_base
<222> LOCATION: (18)...(18)
<223> OTHER INFORMATION: I

<400> SEQUENCE: 29
gtgaatncgt tcncgggnct                                                 20
```

```
<210> SEQ ID NO 30
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 30 aaaaaa                                                                      6

<210> SEQ ID NO 31
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 31 cccccc                                                                      6

<210> SEQ ID NO 32
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 32 ctgtca                                                                      6

<210> SEQ ID NO 33
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 33 tcgtag                                                                      6

<210> SEQ ID NO 34
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 34 tcgtgg                                                                      6

<210> SEQ ID NO 35
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 35 cgtcgt                                                                      6

<210> SEQ ID NO 36
<211> LENGTH: 20
<212> TYPE: DNA
<213> ORGANISM: Artificial Sequence
<220> FEATURE:
```

-continued

<223> OTHER INFORMATION: Synthetic Sequence

<400> SEQUENCE: 36
tccatgtcgg tcctgagtct					20

<210> SEQ ID NO 37
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 37
tccatgccgg tcctgagtct					20

<210> SEQ ID NO 38
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 38
tccatgacgg tcctgagtct					20

<210> SEQ ID NO 39
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 39
tccatgacgg tcctgagtct					20

<210> SEQ ID NO 40
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 40
tccatgtcga tcctgagtct					20

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
tccatgtcgc tcctgagtct					20

<210> SEQ ID NO 42
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 42
tccatgtcgt tcctgagtct					20

```
<210> SEQ ID NO 43
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 43
tccatgacgt tcctgagtct                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 44
tccataacgt tcctgagtct                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
tccatgacgt ccctgagtct                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 46
tccatcacgt gcctgagtct                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 47
tccatgctgg tcctgagtct                                               20

<210> SEQ ID NO 48
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 48
tccatgtngg tcctgagtct                                               20

<210> SEQ ID NO 49
<211> LENGTH: 39
<212> TYPE: DNA
```

<213> ORGANISM: Artificial Sequence
<220> FEATURE:
<223> OTHER INFORMATION: Synthetic Sequence

<400> SEQUENCE: 49
ccgcttcctc cagatgagct catgggtttc tccaccaag                    39

<210> SEQ ID NO 50
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 50
cttggtggag aaacccatga gctcatctgg aggaagcgg                    39

<210> SEQ ID NO 51
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 51
ccccaaaggg atgagaagtt                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 52
agatagcaaa tcggctgacg                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 53
ggttcacgtg ctcatggctg                                          20

<210> SEQ ID NO 54
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 54
tctcccagcg tgcgccat                                            18

<210> SEQ ID NO 55
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 55
tctcccagcg tgcgccat                                            18

```
<210> SEQ ID NO 56
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 56
taccgcgtgc gaccctct                                                 18

<210> SEQ ID NO 57
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 57
ataatccagc ttgaaccaag                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 58
ataatcgacg ttcaagcaag                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 59
tccatgattt tcctgatttt                                               20

<210> SEQ ID NO 60
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 60
ttgttttttt gttttttttgt tttt                                         24

<210> SEQ ID NO 61
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 61 tttttttttgt tttttttgttt tt                                          22

<210> SEQ ID NO 62
<211> LENGTH: 24
<212> TYPE: DNA
<213> ORGANISM: Artificial Sequence
<220> FEATURE:
```

```
<223> OTHER INFORMATION: Synthetic Sequence

<400> SEQUENCE: 62
tgctgctttt gtgcttttgt gctt                                          24

<210> SEQ ID NO 63
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 63
tgctgcttgt gcttttgtgc tt                                            22

<210> SEQ ID NO 64
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 64
gcattcatca ggcgggcaag aat                                           23

<210> SEQ ID NO 65
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 65
taccgagctt cgacgagatt tca                                           23

<210> SEQ ID NO 66
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 66
gcatgacgtt gagct                                                    15

<210> SEQ ID NO 67
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 67
cacgttgagg ggcat                                                    15

<210> SEQ ID NO 68
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 68
ctgctgagac tggag                                                    15
```

<210> SEQ ID NO 69
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 69
tccatgacgt tcctgacgtt                                        20

<210> SEQ ID NO 70
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 70
gcatgagctt gagctga                                           17

<210> SEQ ID NO 71
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 71
tcagcgtgcg cc                                                12

<210> SEQ ID NO 72
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 72
atgacgttcc tgacgtt                                           17

<210> SEQ ID NO 73
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 73
ttttggggtt ttggggtttt                                        20

<210> SEQ ID NO 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
tctaggcttt ttaggcttcc                                        20

<210> SEQ ID NO 75
<211> LENGTH: 20
<212> TYPE: DNA
<213> ORGANISM: Artificial Sequence
<220> FEATURE:
<223> OTHER INFORMATION: Synthetic Sequence -continued

```
<400> SEQUENCE: 75
tgcatttttt aggccaccat                                           20

<210> SEQ ID NO 76
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 76
tctcccagcg tgcgtgcgcc at                                        22

<210> SEQ ID NO 77
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 77
tctcccagcg ggcgcat                                              17

<210> SEQ ID NO 78
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 78
tctcccagcg agcgccat                                             18

<210> SEQ ID NO 79
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 79
tctcccagcg cgcgccat                                             18

<210> SEQ ID NO 80
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 80
ggggtgacgt tcagggggg                                            19

<210> SEQ ID NO 81
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 81
ggggtccagc gtgcgccatg gggg                                      24

<210> SEQ ID NO 82
<211> LENGTH: 19
```

```
<212> TYPE: DNA
<213> ORGANISM: Artificial Sequence
<220> FEATURE:
<223> OTHER INFORMATION: Synthetic Sequence

<400> SEQUENCE: 82 gggtgtcgt tcagggggg                                           19

<210> SEQ ID NO 83
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 83
tccatgtcgt tcctgtcgtt                                         20

<210> SEQ ID NO 84
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 84
tccatagcgt tcctagcgtt                                         20

<210> SEQ ID NO 85
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 85
tcgtcgctgt ctccgcttct t                                       21

<210> SEQ ID NO 86
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 86
gcatgacgtt gagct                                              15

<210> SEQ ID NO 87
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 87
tctcccagcg tgcgccatat                                         20

<210> SEQ ID NO 88
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<221> NAME/KEY: modified_base
```

```
<222> LOCATION: (17)...(17)
<223> OTHER INFORMATION: m5c
<220> FEATURE:
<223> OTHER INFORMATION: Synthetic Sequence

<400> SEQUENCE: 88
tccatgangt tcctgangtt                                                    20

<210> SEQ ID NO 89
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 89
gcatgangtt gagct                                                         15

<210> SEQ ID NO 90
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 90
tccagcgtgc gccata                                                        16

<210> SEQ ID NO 91
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 91
tctcccagcg tgcgccat                                                      18

<210> SEQ ID NO 92
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 92
tccatgagct tcctgagtct                                                    20

<210> SEQ ID NO 93
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 93
gcatgtcgtt gagct                                                         15

<210> SEQ ID NO 94
<211> LENGTH: 19
<212> TYPE: DNA
<213> ORGANISM: Artificial Sequence
<220> FEATURE:
```

<223> OTHER INFORMATION: Synthetic Sequence

<400> SEQUENCE: 94
tcctgacgtt cctgacgtt                                              19

<210> SEQ ID NO 95
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 95
gcatgatgtt gagct                                                  15

<210> SEQ ID NO 96
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 96
gcatttcgag gagct                                                  15

<210> SEQ ID NO 97
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 97
gcatgtagct gagct                                                  15

<210> SEQ ID NO 98
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 98
tccaggacgt tcctagttct                                             20

<210> SEQ ID NO 99
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 99
tccaggagct tcctagttct                                             20

<210> SEQ ID NO 100
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 100
tccaggatgt tcctagttct                                             20

```
<210> SEQ ID NO 101
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 101
tccagtctag gcctagttct                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 102
tccagttcga gcctagttct                                               20

<210> SEQ ID NO 103
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 103
gcatggcgtt gagct                                                    15

<210> SEQ ID NO 104
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 104
gcatagcgtt gagct                                                    15

<210> SEQ ID NO 105
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 105
gcattgcgtt gagct                                                    15

<210> SEQ ID NO 106
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 106
gcttgcgttg cgttt                                                    15

<210> SEQ ID NO 107
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 107
tctcccagcg ttgcgccata t                                              21

<210> SEQ ID NO 108
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 108
tctcccagcg tgcgttatat                                                20

<210> SEQ ID NO 109
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 109
tctccctgcg tgcgccatat                                                20

<210> SEQ ID NO 110
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 110
tctgcgtgcg tgcgccatat                                                20

<210> SEQ ID NO 111
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 111
tctcctagcg tgcgccatat                                                20

<210> SEQ ID NO 112
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 112
tctcccagcg tgcgcctttt                                                20

<210> SEQ ID NO 113
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_difference
<222> LOCATION: (5)...(5)
<223> OTHER INFORMATION: n is a or g or c or t/u
<220> FEATURE:
<221> NAME/KEY: misc_difference
<222> LOCATION: (6)...(6)
<223> OTHER INFORMATION: d is a or g or t/u; not c
```

```
<220> FEATURE:
<221> NAME/KEY: misc_difference
<222> LOCATION: (9)...(10)
<223> OTHER INFORMATION: h is a or c or t/u; not g

<400> SEQUENCE: 113
gctandcghh agc                                                          13

<210> SEQ ID NO 114
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 114
tcctgacgtt ccc                                                          13

<210> SEQ ID NO 115
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 115
ggaagacgtt aga                                                          13

<210> SEQ ID NO 116
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 116
tcctgacgtt aga                                                          13

<210> SEQ ID NO 117
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 117
tcagaccagc tggtcgggtg ttcctga                                           27

<210> SEQ ID NO 118
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 118
tcaggaacac ccgaccagct ggtctga                                           27

<210> SEQ ID NO 119
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 119
```

```
gctagtcgat agc                                                          13

<210> SEQ ID NO 120
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 120
gctagtcgct agc                                                          13

<210> SEQ ID NO 121
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 121
gcttgacgtc tagc                                                         14

<210> SEQ ID NO 122
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 122
gcttgacgtt tagc                                                         14

<210> SEQ ID NO 123
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 123
gcttgacgtc aagc                                                         14

<210> SEQ ID NO 124
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 124
gctagacgtt tagc                                                         14

<210> SEQ ID NO 125
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 125
tccatgacat tcctgatgct                                                   20

<210> SEQ ID NO 126
<211> LENGTH: 14
<212> TYPE: DNA
<213> ORGANISM: Artificial Sequence
```

```
<220> FEATURE:
<223> OTHER INFORMATION: Synthetic Sequence

<400> SEQUENCE: 126
gctagacgtc tagc                                                          14

<210> SEQ ID NO 127
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 127
ggctatgtcg ttcctagcc                                                     19

<210> SEQ ID NO 128
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 128
ggctatgtcg atcctagcc                                                     19

<210> SEQ ID NO 129
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 129
ctcatgggtt tctccaccaa g                                                  21

<210> SEQ ID NO 130
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 130
cttggtggag aaacccatga g                                                  21

<210> SEQ ID NO 131
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 131
tccatgacgt tcctagttct                                                    20

<210> SEQ ID NO 132
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 132
ccgcttcctc cagatgagct catg                                               24
```

<210> SEQ ID NO 133
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 133
catgagctca tctggaggaa gcgg                                              24

<210> SEQ ID NO 134
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 134
ccagatgagc tcatgggttt ctcc                                              24

<210> SEQ ID NO 135
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 135
ggagaaaccc atgagctcat ctgg                                              24

<210> SEQ ID NO 136
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 136
agcatcagga acgacatgga                                                   20

<210> SEQ ID NO 137
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 137
tccatgacgt tcctgacgtt                                                   20

<210> SEQ ID NO 138
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 138
gcgcgcgcgc gcgcgcgcg                                                    19

<210> SEQ ID NO 139
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 139
ccggccggcc ggccggccgg                                           20

<210> SEQ ID NO 140
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 140
ttccaatcag ccccacccgc tctggcccca ccctcaccct cca                 43

<210> SEQ ID NO 141
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 141
tggagggtga gggtggggcc agagcgggtg gggctgattg gaa                 43

<210> SEQ ID NO 142
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 142
tcaaatgtgg gattttccca tgagtct                                   27

<210> SEQ ID NO 143
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 143
agactcatgg gaaaatccca catttga                                   27

<210> SEQ ID NO 144
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 144
tgccaagtgc tgagtcacta ataaaga                                   27

<210> SEQ ID NO 145
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 145
tctttattag tgactcagca cttggca                                   27

<210> SEQ ID NO 146

```
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 146
tgcaggaagt ccgggttttc cccaaccccc c                              31

<210> SEQ ID NO 147
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 147 gggggggttgg ggaaaacccg gacttcctgc a                             31

<210> SEQ ID NO 148
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 148
ggggactttc cgctggggac tttccagggg gactttcc                       38

<210> SEQ ID NO 149
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 149
tccatgacgt tcctctccat gacgttcctc tccatgacgt tcctc               45

<210> SEQ ID NO 150
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 150
gaggaacgtc atggagagga acgtcatgga gaggaacgtc atgga               45

<210> SEQ ID NO 151
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 151
ataatagagc ttcaagcaag                                           20

<210> SEQ ID NO 152
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 152
```

```
tccatgacgt tcctgacgtt                                          20

<210> SEQ ID NO 153
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 153
tccatgacgt tcctgacgtt                                          20

<210> SEQ ID NO 154
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 154
tccaggactt tcctcaggtt                                          20

<210> SEQ ID NO 155
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 155
tcttgcgatg ctaaaggacg tcacattgca caatcttaat aaggt             45

<210> SEQ ID NO 156
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 156
accttattaa gattgtgcaa tgtgacgtcc tttagcatcg caaga             45

<210> SEQ ID NO 157
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 157
tcctgacgtt cctggcggtc ctgtcgct                                 28

<210> SEQ ID NO 158
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 158
tcctgtcgct cctgtcgct                                           19

<210> SEQ ID NO 159
<211> LENGTH: 15
<212> TYPE: DNA
```

```
<213> ORGANISM: Artificial Sequence
<220> FEATURE:
<223> OTHER INFORMATION: Synthetic Sequence

<400> SEQUENCE: 159
tcctgacgtt gaagt                                                    15

<210> SEQ ID NO 160
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 160
tcctgtcgtt gaagt                                                    15

<210> SEQ ID NO 161
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 161
tcctggcgtt gaagt                                                    15

<210> SEQ ID NO 162
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 162
tcctgccgtt gaagt                                                    15

<210> SEQ ID NO 163
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 163
tccttacgtt gaagt                                                    15

<210> SEQ ID NO 164
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 164
tcctaacgtt gaagt                                                    15

<210> SEQ ID NO 165
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 165
tcctcacgtt gaagt                                                    15
```

<210> SEQ ID NO 166
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 166
tcctgacgat gaagt                                                  15

<210> SEQ ID NO 167
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 167
tcctgacgct gaagt                                                  15

<210> SEQ ID NO 168
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 168
tcctgacggt gaagt                                                  15

<210> SEQ ID NO 169
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 169
tcctgacgta gaagt                                                  15

<210> SEQ ID NO 170
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 170
tcctgacgtc gaagt                                                  15

<210> SEQ ID NO 171
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 171
tcctgacgtg gaagt                                                  15

<210> SEQ ID NO 172
<211> LENGTH: 15
<212> TYPE: DNA
<213> ORGANISM: Artificial Sequence
<220> FEATURE:

-continued

<223> OTHER INFORMATION: Synthetic Sequence

<400> SEQUENCE: 172
tcctgagctt gaagt                                                15

<210> SEQ ID NO 173
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 173
gggggacgtt ggggg                                                15

<210> SEQ ID NO 174
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 174
tcctgacgtt ccttc                                                15

<210> SEQ ID NO 175
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 175
tctcccagcg agcgagcgcc at                                        22

<210> SEQ ID NO 176
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 176
tcctgacgtt cccctggcgg tccctgtcg ct                              32

<210> SEQ ID NO 177
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 177
tcctgtcgct cctgtcgctc ctgtcgct                                  28

<210> SEQ ID NO 178
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 178
tcctggcggg gaagt                                                15

<210> SEQ ID NO 179
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 179
tcctgangtt gaagt          15

<210> SEQ ID NO 180
<211> LENGTH: 15
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<220> FEATURE:
<223> OTHER INFORMATION: Synthetic Sequence

<400> SEQUENCE: 180
tcntgacgtt gaagt          15

<210> SEQ ID NO 181
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 181
tcctagcgtt gaagt          15

<210> SEQ ID NO 182
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 182
tccagacgtt gaagt          15

<210> SEQ ID NO 183
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 183
tcctgacggg gaagt          15

<210> SEQ ID NO 184
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 184
tcctggcggt gaagt          15

```
<210> SEQ ID NO 185
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 185
ggctccgggg agggaattttt tgtctat                                27

<210> SEQ ID NO 186
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 186
atagacaaaa attccctccc cggagcc                                 27

<210> SEQ ID NO 187
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 187
tccatgagct tccttgagtc t                                       21

<210> SEQ ID NO 188
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 188
tcgtcgctgt ctccgcttct t                                       21

<210> SEQ ID NO 189
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 189
tcgtcgctgt ctccgcttct t                                       21

<210> SEQ ID NO 190
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 190
tcgagacatt gcacaatcat ctg                                     23

<210> SEQ ID NO 191
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 191
cagattgtgc aatgtctcga                                               20

<210> SEQ ID NO 192
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 192
tccatgtcgt tcctgatgcg                                               20

<210> SEQ ID NO 193
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 193
gcgatgtcgt tcctgatgct                                               20

<210> SEQ ID NO 194
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 194
gcgatgtcgt tcctgatgcg                                               20

<210> SEQ ID NO 195
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 195
tccatgtcgt tccgcgcgcg                                               20

<210> SEQ ID NO 196
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 196
tccatgtcgt tcctgccgct                                               20

<210> SEQ ID NO 197
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 197
tccatgtcgt tcctgtagct                                               20

<210> SEQ ID NO 198
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 198
gcggcgggcg gcgcgcgccc                                                   20

<210> SEQ ID NO 199
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 199
atcaggaacg tcatgggaag c                                                 21

<210> SEQ ID NO 200
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 200
tccatgagct tcctgagtct                                                   20

<210> SEQ ID NO 201
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 201 tcaacgtt                                                                 8

<210> SEQ ID NO 202
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 202 tcaagctt                                                                 8

<210> SEQ ID NO 203
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 203
tcctgtcgtt cctgtcgtt                                                    19

<210> SEQ ID NO 204
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 204
```

```
tccatgtcgt ttttgtcgtt                                              20

<210> SEQ ID NO 205
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 205
tcctgtcgtt ccttgtcgtt                                              20

<210> SEQ ID NO 206
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 206
tccttgtcgt tcctgtcgtt                                              20

<210> SEQ ID NO 207
<211> LENGTH: 29
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 207
tccattccat gacgttcctg atgcttcca                                    29

<210> SEQ ID NO 208
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 208
tcctgtcgtt ttttgtcgtt                                              20

<210> SEQ ID NO 209
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 209
tcgtcgctgt ctccgcttct t                                            21

<210> SEQ ID NO 210
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 210
tcgtcgctgt ctgcccttct t                                            21
```

<210> SEQ ID NO 211
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 211
tcgtcgctgt tgtcgtttct t     21

<210> SEQ ID NO 212
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 212
tcctgtcgtt cctgtcgttg gaacgacagg     30

<210> SEQ ID NO 213
<211> LENGTH: 40
<212> TYPE: DNA
<213> ORGANISM: Artificial Sequence
<220> FEATURE:
<223> OTHER INFORMATION: Synthetic Sequence

<400> SEQUENCE: 213
tcctgtcgtt cctgtcgttt caacgtcagg aacgacagga     40

<210> SEQ ID NO 214
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 214
ggggtctgtc gttttggggg g     21

<210> SEQ ID NO 215
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 215
ggggtctgtg cttttggggg g     21

<210> SEQ ID NO 216
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 216
tccggccgtt gaagt     15

<210> SEQ ID NO 217
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 217
tccggacggt gaagt                                                15

<210> SEQ ID NO 218
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 218
tcccgccgtt gaagt                                                15

<210> SEQ ID NO 219
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 219
tccagacggt gaagt                                                15

<210> SEQ ID NO 220
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 220
tcccgacggt gaagt                                                15

<210> SEQ ID NO 221
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 221
tccagagctt gaagt                                                15

<210> SEQ ID NO 222
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<221> NAME/KEY: modified_base
<222> LOCATION: (17)...(17)
<223> OTHER INFORMATION: m5c
<220> FEATURE:
<223> OTHER INFORMATION: Synthetic Sequence

<400> SEQUENCE: 222
tccatgtngt tcctgtngtt                                           20

<210> SEQ ID NO 223
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 223
tccatgacgt tcctgacgtt                                           20

<210> SEQ ID NO 224
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 224
ggggttgacg ttttgggggg                                           20

<210> SEQ ID NO 225
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 225
tccaggactt ctctcaggtt                                           20

<210> SEQ ID NO 226
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 226
tttttttttt tttttttttt                                           20

<210> SEQ ID NO 227
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 227
tccatgccgt tcctgccgtt                                           20

<210> SEQ ID NO 228
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 228
tccatggcgg gcctggcggg                                           20

<210> SEQ ID NO 229
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 229
tccatgacgt tcctgccgtt                                           20

<210> SEQ ID NO 230
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 230
tccatgacgt tcctggcggg                                                    20

<210> SEQ ID NO 231
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 231
tccatgacgt tcctgcgttt                                                    20

<210> SEQ ID NO 232
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 232
tccatgacgg tcctgacggt                                                    20

<210> SEQ ID NO 233
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 233
tccatgcgtg cgtgcgtttt                                                    20

<210> SEQ ID NO 234
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 234
tccatgcgtt gcgttgcgtt                                                    20

<210> SEQ ID NO 235
<211> LENGTH: 30
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 235
tccattccat tctaggcctg agtcttccat                                         30

<210> SEQ ID NO 236
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 236
tccatagcgt tcctagcgtt                                           20

<210> SEQ ID NO 237
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 237
tccatgtcgt tcctgtcgtt                                           20

<210> SEQ ID NO 238
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 238
tccatagcga tcctagcgat                                           20

<210> SEQ ID NO 239
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 239
tccattgcgt tccttgcgtt                                           20

<210> SEQ ID NO 240
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 240
tccatagcgg tcctagcggt                                           20

<210> SEQ ID NO 241
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 241
tccatgattt tcctgcagtt cctgattt                                  29

<210> SEQ ID NO 242
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 242
tccatgacgt tcctgcagtt cctgacgtt                                 29
```

<210> SEQ ID NO 243
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 243
ggcggcggcg gcggcggcgg                                                    20

<210> SEQ ID NO 244
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 244
tccacgacgt tttcgacgtt                                                    20

<210> SEQ ID NO 245
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 245
tcgtcgttgt cgttgtcgtt                                                    20

<210> SEQ ID NO 246
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 246
tcgtcgtttt gtcgttttgt cgtt                                               24

<210> SEQ ID NO 247
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 247
tcgtcgttgt cgttttgtcg tt                                                 22

<210> SEQ ID NO 248
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 248
gcgtgcgttg tcgttgtcgt t                                                  21

<210> SEQ ID NO 249
<211> LENGTH: 19
<212> TYPE: DNA
<213> ORGANISM: Artificial Sequence
<220> FEATURE:
<223> OTHER INFORMATION: Synthetic Sequence

```
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (6)...(6)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (15)...(15)
<223> OTHER INFORMATION: m5c

<400> SEQUENCE: 249
cnggcnggcn gggcnccgg                                           19

<210> SEQ ID NO 250
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 250
gcggcgggcg gcgcgcgccc                                          20

<210> SEQ ID NO 251
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (8)...(8)
<223> OTHER INFORMATION: I
<220> FEATURE:
<221> NAME/KEY: modified_base
<222> LOCATION: (14)...(14)
<223> OTHER INFORMATION: I

<400> SEQUENCE: 251
agncccgnga acgnattcac                                          20

<210> SEQ ID NO 252
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 252
tgtcgtttgt cgtttgtcgt t                                        21

<210> SEQ ID NO 253
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 253
```

-continued

```
tgtcgttgtc gttgtcgttg tcgtt                                    25

<210> SEQ ID NO 254
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 254
tgtcgttgtc gttgtcgttg tcgtt                                    25

<210> SEQ ID NO 255
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 255
tcgtcgtcgt cgtt                                                14

<210> SEQ ID NO 256
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 256
tgtcgttgtc gtt                                                 13

<210> SEQ ID NO 257
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 257
cccccccccc cccccccccc                                          20

<210> SEQ ID NO 258
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 258
tctagcgttt ttagcgttcc                                          20

<210> SEQ ID NO 259
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 259
tgcatccccc aggccaccat                                          20

<210> SEQ ID NO 260
<211> LENGTH: 23
<212> TYPE: DNA
<213> ORGANISM: Artificial Sequence
```

```
<220> FEATURE:
<223> OTHER INFORMATION: Synthetic Sequence

<400> SEQUENCE: 260
tcgtcgtcgt cgtcgtcgtc gtt                                            23

<210> SEQ ID NO 261
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 261
tcgtcgttgt cgttgtcgtt                                                20

<210> SEQ ID NO 262
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 262
tcgtcgtttt gtcgttttgt cgtt                                           24

<210> SEQ ID NO 263
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 263
tcgtcgttgt cgttttgtcg tt                                             22

<210> SEQ ID NO 264
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 264
ggggagggag gaacttctta aaattccccc agaatgttt                           39

<210> SEQ ID NO 265
<211> LENGTH: 39
<212> TYPE: DNA
<213> ORGANISM: Artificial Sequence
<220> FEATURE:
<223> OTHER INFORMATION: Synthetic Sequence

<400> SEQUENCE: 265
aaacattctg ggggaatttt aagaagttcc tccctcccc                           39

<210> SEQ ID NO 266
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 266
atgtttactt cttaaaattc ccccagaatg ttt                                 33
```

<210> SEQ ID NO 267
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 267
aaacattctg ggggaatttt aagaagtaaa cat                33

<210> SEQ ID NO 268
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 268
atgtttacta gacaaaattc ccccagaatg ttt                33

<210> SEQ ID NO 269
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 269
aaacattctg ggggaatttt gtctagtaaa cat                33

<210> SEQ ID NO 270
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 270
aaaattgacg ttttaaaaaa                               20

<210> SEQ ID NO 271
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 271 cccettgacg ttttccccce                               20

<210> SEQ ID NO 272
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 272
ttttcgttgt ttttgtcgtt                               20

<210> SEQ ID NO 273
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 273
tcgtcgtttt gtcgttttgt cgtt                                    24

<210> SEQ ID NO 274
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 274
ctgcagcctg ggac                                               14

<210> SEQ ID NO 275
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 275
acccgtcgta attatagtaa aaccc                                   25

<210> SEQ ID NO 276
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 276
ggtacctgtg gggacattgt g                                       21

<210> SEQ ID NO 277
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 277
agcaccgaac gtgagagg                                           18

<210> SEQ ID NO 278
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 278
tccatgccgt tcctgccgtt                                         20

<210> SEQ ID NO 279
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 279
tccatgacgg tcctgacggt                                         20

<210> SEQ ID NO 280

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 280
tccatgccgg tcctgccggt                                               20

<210> SEQ ID NO 281
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 281
tccatgcgcg tcctgcgcgt                                               20

<210> SEQ ID NO 282
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 282
ctggtctttc tggtttttttt ctgg                                         24

<210> SEQ ID NO 283
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 283 tcagggtgg ggggaacctt                                                20

<210> SEQ ID NO 284
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 284
tccatgangt tcctagttct                                               20

<210> SEQ ID NO 285
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 285
tccatgatgt tcctagttct                                               20

<210> SEQ ID NO 286
<211> LENGTH: 26
<212> TYPE: DNA
<213> ORGANISM: Artificial Sequence
```

```
<220> FEATURE:
<223> OTHER INFORMATION: Synthetic Sequence

<400> SEQUENCE: 286
cccgaagtca tttcctctta acctgg                                              26

<210> SEQ ID NO 287
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 287
ccaggttaag aggaaatgac ttcggg                                              26

<210> SEQ ID NO 288
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence

<400> SEQUENCE: 288
tcctggnggg gaagt                                                          15

<210> SEQ ID NO 289
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (9)...(9)
<223> OTHER INFORMATION: m5c
<220> FEATURE:
<221> NAME/KEY: modified_base
<222> LOCATION: (12)...(12)
<223> OTHER INFORMATION: m5c
<220> FEATURE:
<221> NAME/KEY: modified_base
<222> LOCATION: (14)...(14)
<223> OTHER INFORMATION: m5c
<221> NAME/KEY: modified_base
<222> LOCATION: (16)...(16)
<223> OTHER INFORMATION: m5c
<220> FEATURE:
<223> OTHER INFORMATION: Synthetic Sequence

<400> SEQUENCE: 289
gnggngggng gngngngccc                                                     20

<210> SEQ ID NO 290
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 290
```
tccatgtgct tcctgatgct                                           20

<210> SEQ ID NO 291
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 291
tccatgtcct tcctgatgct                                           20

<210> SEQ ID NO 292
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 292
tccatgtcgt tcctagttct                                           20

<210> SEQ ID NO 293
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 293
tccaagtagt tcctagttct                                           20

<210> SEQ ID NO 294
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 294
tccatgtagt tcctagttct                                           20

<210> SEQ ID NO 295
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 295
tcccgcgcgt tccgcgcgtt                                           20

<210> SEQ ID NO 296
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 296
tcctggcggt cctggcggtt                                           20

<210> SEQ ID NO 297
<211> LENGTH: 15
<212> TYPE: DNA

```
<213> ORGANISM: Artificial Sequence
<220> FEATURE:
<223> OTHER INFORMATION: Synthetic Sequence

<400> SEQUENCE: 297
tcctggaggg gaagt                                                    15

<210> SEQ ID NO 298
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 298
tcctgggggg gaagt                                                    15

<210> SEQ ID NO 299
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 299
tcctggtggg gaagt                                                    15

<210> SEQ ID NO 300
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 300
tcgtcgtttt gtcgttttgt cgtt                                          24

<210> SEQ ID NO 301
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 301
ctggtctttc tggttttttt ctgg                                          24

<210> SEQ ID NO 302
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 302
tccatgacgt tcctgacgtt                                               20

<210> SEQ ID NO 303
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 303
tccaggactt ctctcaggtt                                               20
```

```
<210> SEQ ID NO 304
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 304
tngtngtttt gtngttttgt ngtt                                    24

<210> SEQ ID NO 305
<211> LENGTH: 29
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 305
tcgtcgtttt gtcgttttgt cgttttttt                               29

<210> SEQ ID NO 306
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 306
gctatgacgt tccaaggg                                           18

<210> SEQ ID NO 307
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 307 tcaacgtt                                                       8

<210> SEQ ID NO 308
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 308
```
tccaggactt tcctcaggtt                                                       20

<210> SEQ ID NO 309
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 309
ctctctgtag gcccgcttgg                                                       20

<210> SEQ ID NO 310
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 310
ctttccgttg gacccctggg                                                       20

<210> SEQ ID NO 311
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 311
gtccgggcca ggccaaagtc                                                       20

<210> SEQ ID NO 312
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 312
gtgcgcgcga gcccgaaatc                                                       20

<210> SEQ ID NO 313
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: I
<221> NAME/KEY: modified_base
<222> LOCATION: (17)...(17)
<223> OTHER INFORMATION: I
<220> FEATURE:
<223> OTHER INFORMATION: Synthetic Sequence

<400> SEQUENCE: 313
tccatgangt tcctgangtt                                                       20

<210> SEQ ID NO 314
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 314
aatagtcgcc ataacaaaac                                              20

<210> SEQ ID NO 315
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 315
aatagtcgcc atggcggggc                                              20

<210> SEQ ID NO 316
<211> LENGTH: 28
<212> TYPE: DNA
<213> ORGANISM: Artificial Sequence
<220> FEATURE:
<221> NAME/KEY: misc_difference
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 316
tttttccatg tcgttcctga tgcttttt                                     28

<210> SEQ ID NO 317
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 317
tcctgtcgtt gaagttttt                                               20

<210> SEQ ID NO 318
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 318
gctagcttta gagctttaga gctt                                         24

<210> SEQ ID NO 319
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 319
tgctgcttcc cccccccccc                                              20

<210> SEQ ID NO 320
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 320
tcgacgttcc cccccccccc                                              20

```
<210> SEQ ID NO 321
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 321
tcgtcgttcc cccccccccc                                              20

<210> SEQ ID NO 322
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 322
tcgtcgttcc cccccccccc                                              20

<210> SEQ ID NO 323
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 323
tcgccgttcc cccccccccc                                              20

<210> SEQ ID NO 324
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 324
tcgtcgatcc cccccccccc                                              20

<210> SEQ ID NO 325
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 325
tcctgacgtt gaagt                                                   15

<210> SEQ ID NO 326
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 326
tcctgccgtt gaagt                                                   15

<210> SEQ ID NO 327
<211> LENGTH: 15
<212> TYPE: DNA
<213> ORGANISM: Artificial Sequence
<220> FEATURE:
<223> OTHER INFORMATION: Synthetic Sequence
```

```
<400> SEQUENCE: 327
tcctgacggt gaagt                                                15

<210> SEQ ID NO 328
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 328
tcctgagctt gaagt                                                15

<210> SEQ ID NO 329
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 329
tcctggcggg gaagt                                                15

<210> SEQ ID NO 330
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 330
aaaatctgtg cttttaaaaa a                                         21

<210> SEQ ID NO 331
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 331
gatccagtca cagtgacctg gcagaatctg gat                            33

<210> SEQ ID NO 332
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 332
gatccagatt ctgccaggtc actgtgactg gat                            33

<210> SEQ ID NO 333
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 333
gatccagtca cagtgactca gcagaatctg gat                            33

<210> SEQ ID NO 334
<211> LENGTH: 33
```

```
<212> TYPE: DNA
<213> ORGANISM: Artificial Sequence
<220> FEATURE:
<223> OTHER INFORMATION: Synthetic Sequence

<400> SEQUENCE: 334
gatccagatt ctgctgagtc actgtgactg gat                              33

<210> SEQ ID NO 335
<211> LENGTH: 20
<212> TYPE: DNA
<213> ORGANISM: Artificial Sequence
<220> FEATURE:
<221> NAME/KEY: modified_base
<222> LOCATION: (16)...(16)
<223> OTHER INFORMATION: m5c
<220> FEATURE:
<223> OTHER INFORMATION: Synthetic Sequence

<400> SEQUENCE: 335
tcgtcgttcc ccccncccc                                              20

<210> SEQ ID NO 336
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 336
tngtngttcc ccccccccc                                              20

<210> SEQ ID NO 337
<211> LENGTH: 20
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 337
tngtcgttcc ccccccccc                                              20

<210> SEQ ID NO 338
<211> LENGTH: 20
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 338
tcgtngttcc ccccccccc                                              20

<210> SEQ ID NO 339
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 339
tcgtcgctcc cccccccccc                                             20

<210> SEQ ID NO 340
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 340
tcgtcggtcc cccccccccc                                             20

<210> SEQ ID NO 341
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 341
tcggcgttcc cccccccccc                                             20

<210> SEQ ID NO 342
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 342
ggccttttcc cccccccccc                                             20

<210> SEQ ID NO 343
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 343
tcgtcgtttt gacgttttgt cgtt                                        24

<210> SEQ ID NO 344
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 344
tcgtcgtttt gacgttttga cgtt                                        24

<210> SEQ ID NO 345
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 345
```
ccgtcgttcc cccccccccc                                                20

<210> SEQ ID NO 346
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 346
gcgtcgttcc cccccccccc                                                20

<210> SEQ ID NO 347
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 347
tcgtcattcc cccccccccc                                                20

<210> SEQ ID NO 348
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 348
acgtcgttcc cccccccccc                                                20

<210> SEQ ID NO 349
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 349
ctgtcgttcc cccccccccc                                                20

<210> SEQ ID NO 350
<211> LENGTH: 24
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 350
tttttcgtcg ttcccccccc cccc                                           24

<210> SEQ ID NO 351
<211> LENGTH: 20
<212> TYPE: DNA
<213> ORGANISM: Artificial Sequence
<220> FEATURE:
<221> NAME/KEY: misc_feature
<222> LOCATION: (18)...(20)
<223> OTHER INFORMATION: Biotin moiety attached at 3' end of sequence.
<220> FEATURE:
<223> OTHER INFORMATION: Synthetic Sequence

<400> SEQUENCE: 351
tcgtcgttcc cccccccccc                                               20

<210> SEQ ID NO 352
<211> LENGTH: 24
<212> TYPE: DNA
<213> ORGANISM: Artificial Sequence
<220> FEATURE:
<221> NAME/KEY: misc_feature
<222> LOCATION: (22)...(24)
<223> OTHER INFORMATION: Biotin moiety attached at 3' end of sequence.
<220> FEATURE:
<223> OTHER INFORMATION: Synthetic Sequence

<400> SEQUENCE: 352
tcgtcgtttt gtcgttttgt cgtt                                          24

<210> SEQ ID NO 353
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 353
tccagttcct tcctcagtct                                               20

<210> SEQ ID NO 354
<211> LENGTH: 24
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 354
tngtcgtttt gtcgttttgt cgtt                                          24

<210> SEQ ID NO 355
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 355
tcctggaggg gaagt                                                    15

<210> SEQ ID NO 356
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 356
tcctgaaaag gaagt                                                    15

<210> SEQ ID NO 357
<211> LENGTH: 17
<212> TYPE: DNA
<213> ORGANISM: Artificial Sequence
<220> FEATURE:
<223> OTHER INFORMATION: Synthetic Sequence

```
<400> SEQUENCE: 357
tcgtcgttcc ccccccc                                                        17

<210> SEQ ID NO 358
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (2)...(2)
<223> OTHER INFORMATION: m5c
<220> FEATURE:
<221> NAME/KEY: modified_base
<222> LOCATION: (5)...(5)
<223> OTHER INFORMATION: m5c
<220> FEATURE:
<221> NAME/KEY: modified_base
<222> LOCATION: (13)...(13)
<223> OTHER INFORMATION: m5c
<220> FEATURE:
<221> NAME/KEY: modified_base
<222> LOCATION: (21)...(21)
<223> OTHER INFORMATION: m5c

<400> SEQUENCE: 358
tngtngtttt gtngttttgt ngtt                                                24

<210> SEQ ID NO 359
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 359
ggggtcaagc ttgaggggggg                                                    20

<210> SEQ ID NO 360
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 360
tgctgcttcc cccccccccc                                                     20

<210> SEQ ID NO 361
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 361
tcgtcgtcgt cgtt                                                           14

<210> SEQ ID NO 362
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 362
tcgtcgtcgt cgtt                                                           14
```

<210> SEQ ID NO 363
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 363
tcgtcgtcgt cgtt                                                         14

<210> SEQ ID NO 364
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 364
tcaacgttga                                                              10

<210> SEQ ID NO 365
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 365 tcaacgtt                                                                 8

<210> SEQ ID NO 366
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 366
atagttttcc attttttac                                                    20

<210> SEQ ID NO 367
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 367
aatagtcgcc atcgcgcgac                                                   20

<210> SEQ ID NO 368
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 368
aatagtcgcc atcccgggac                                                   20

<210> SEQ ID NO 369
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 369
aatagtcgcc atcccccccc                                              20

<210> SEQ ID NO 370
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 370
tgctgctttt gtgcttttgt gctt                                         24

<210> SEQ ID NO 371
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 371
ctgtgctttc tgtgttttc tgtg                                          24

<210> SEQ ID NO 372
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 372
ctaatctttc taatttttt ctaa                                          24

<210> SEQ ID NO 373
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 373
tcgtcgttgg tgtcgttggt gtcgtt                                       26

<210> SEQ ID NO 374
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 374
tcgtcgttgg ttgtcgtttt ggtt                                         24

<210> SEQ ID NO 375
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 375
accatggacg agctgtttcc cctc                                         24

```
<210> SEQ ID NO 376
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 376
tcgtcgtttt gcgtgcgttt                                                   20

<210> SEQ ID NO 377
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 377
ctgtaagtga gcttggagag                                                   20

<210> SEQ ID NO 378
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 378
gagaacgctg gaccttcc                                                     18

<210> SEQ ID NO 379
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 379
cgggcgactc agtctatcgg                                                   20

<210> SEQ ID NO 380
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 380
gttctcagat aaagcggaac cagcaacaga cacagaa                                37

<210> SEQ ID NO 381
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 381
ttctgtgtct gttgctggtt ccgctttatc tgagaac                                37

<210> SEQ ID NO 382
<211> LENGTH: 23
<212> TYPE: DNA
<213> ORGANISM: Artificial Sequence
<220> FEATURE:
<223> OTHER INFORMATION: Synthetic Sequence
```

```
<400> SEQUENCE: 382
cagacacaga agcccgatag acg                                    23

<210> SEQ ID NO 383
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 383
agacagacac gaaacgaccg                                        20

<210> SEQ ID NO 384
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 384
gtctgtccca tgatctcgaa                                        20

<210> SEQ ID NO 385
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 385
gctggccagc ttacctcccg                                        20

<210> SEQ ID NO 386
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 386
ggggcctcta tacaacctgg g                                      21

<210> SEQ ID NO 387
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 387
ggggtccctg agactgcc                                          18

<210> SEQ ID NO 388
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 388
gagaacgctg gaccttccat                                        20

<210> SEQ ID NO 389
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 389
tccatgtcgg tcctgatgct                                              20

<210> SEQ ID NO 390
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 390
ctcttgcgac ctggaaggta                                              20

<210> SEQ ID NO 391
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 391
aggtacagcc aggactacga                                              20

<210> SEQ ID NO 392
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 392
accatggacg acctgtttcc cctc                                         24

<210> SEQ ID NO 393
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 393
accatggatt acctttttcc cctt                                         24

<210> SEQ ID NO 394
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 394
atggaaggtc cagcgttctc                                              20

<210> SEQ ID NO 395
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 395
```
agcatcagga ccgacatgga                                              20

<210> SEQ ID NO 396
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 396
ctctccaagc tcacttacag                                              20

<210> SEQ ID NO 397
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 397
tccctgagac tgccccacct t                                            21

<210> SEQ ID NO 398
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 398
gccaccaaaa cttgtccatg                                              20

<210> SEQ ID NO 399
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 399
gtccatggcg tgcgggatga                                              20

<210> SEQ ID NO 400
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 400
cctctataca acctgggac                                               19

<210> SEQ ID NO 401
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 401
cgggcgactc agtctatcgg                                              20

<210> SEQ ID NO 402
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 402
gcgctaccgg tagcctgagt                                                 20

<210> SEQ ID NO 403
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 403
cgactgccga acaggatatc ggtgatcagc actgg                                35

<210> SEQ ID NO 404
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 404
ccagtgctga tcaccgatat cctgttcggc agtcg                                35

<210> SEQ ID NO 405
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 405
ccaggttgta tagaggc                                                    17

<210> SEQ ID NO 406
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 406
tctcccagcg tacgccat                                                   18

<210> SEQ ID NO 407
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 407
tctcccagcg tgcgtttt                                                   18

<210> SEQ ID NO 408
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 408
tctcccgacg tgcgccat                                                   18
```

<210> SEQ ID NO 409
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 409
tctcccgtcg tgcgccat                                                      18

<210> SEQ ID NO 410
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 410
ataatcgtcg ttcaagcaag                                                    20

<210> SEQ ID NO 411
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 411
tcgtcgtttt gtcgttttgt cgt                                                23

<210> SEQ ID NO 412
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 412
tcgtcgtttt gtcgttttgt cgtt                                               24

<210> SEQ ID NO 413
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 413
tcgtcgtttt gtcgttttgt cgtt                                               24

<210> SEQ ID NO 414
<211> LENGTH: 24
<212> TYPE: DNA
<213> ORGANISM: Artificial Sequence
<220> FEATURE:
<221> NAME/KEY: misc_difference
<222> LOCATION: (3)...(3)
<223> OTHER INFORMATION: n is a or c or g or t/u
<220> FEATURE:
<221> NAME/KEY: misc_difference
<222> LOCATION: (8)...(8)
<223> OTHER INFORMATION: n is a or c or g or t/u
<220> FEATURE:
<221> NAME/KEY: misc_difference
<222> LOCATION: (11)...(11)
<223> OTHER INFORMATION: n is a or c or g or t/u
<220> FEATURE:
<221> NAME/KEY: misc_difference
<222> LOCATION: (16)...(16)
<223> OTHER INFORMATION: n is a or c or g or t/u
<220> FEATURE:
<221> NAME/KEY: misc_difference
<222> LOCATION: (19)...(19)
<223> OTHER INFORMATION: n is a or c or g or t/u
<221> NAME/KEY: misc_difference
<222> LOCATION: (24)...(24)
<223> OTHER INFORMATION: n is a or c or g or t/u
<220> FEATURE:
<223> OTHER INFORMATION: Synthetic Sequence

<400> SEQUENCE: 414
tcntcgtntt ntcgtnttnt cgtn                                          24

<210> SEQ ID NO 415
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 415
tctcccagcg tcgccat                                                  17

<210> SEQ ID NO 416
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 416
tctcccatcg tcgccat                                                  17

<210> SEQ ID NO 417
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 417
ataatcgtgc gttcaagaaa g                                             21

<210> SEQ ID NO 418
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 418
ataatcgacg ttcccccccc                                               20

<210> SEQ ID NO 419
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 419
tctatcgacg ttcaagcaag                                               20

<210> SEQ ID NO 420
<211> LENGTH: 14

```
<212> TYPE: DNA
<213> ORGANISM: Artificial Sequence
<220> FEATURE:
<223> OTHER INFORMATION: Synthetic Sequence

<400> SEQUENCE: 420
tcctgacggg gagt                                                     14

<210> SEQ ID NO 421
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 421
tccatgacgt tcctgatcc                                                19

<210> SEQ ID NO 422
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 422
tccatgacgt tcctgatcc                                                19

<210> SEQ ID NO 423
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 423
tccatgacgt tcctgatcc                                                19

<210> SEQ ID NO 424
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 424
tcctggcgtg gaagt                                                    15

<210> SEQ ID NO 425
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 425
tccatgacgt tcctgatcc                                                19

<210> SEQ ID NO 426
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 426
```

```
tcgtcgctgt tgtcgtttct t                                        21
```

<210> SEQ ID NO 427
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 427

```
agcagcttta gagctttaga gctt                                     24
```

<210> SEQ ID NO 428
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 428

```
cccccccccc cccccccccc cccc                                     24
```

<210> SEQ ID NO 429
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 429

```
tcgtcgtttt gtcgttttgt cgttttgtcg tt                            32
```

<210> SEQ ID NO 430
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 430

```
tcgtcgtttt ttgtcgtttt ttgtcgtt                                 28
```

<210> SEQ ID NO 431
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 431

```
tcgtcgtttt tttttttttt                                          20
```

<210> SEQ ID NO 432
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 432

```
tttttcaacg ttgatttttt                                          20
```

<210> SEQ ID NO 433
<211> LENGTH: 24
<212> TYPE: DNA
<213> ORGANISM: Artificial Sequence

```
<220> FEATURE:
<223> OTHER INFORMATION: Synthetic Sequence

<400> SEQUENCE: 433
tttttttttt tttttttttt tttt                                              24

<210> SEQ ID NO 434
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 434
ggggtcgtcg ttttggggggg                                                  20

<210> SEQ ID NO 435
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 435
tcgtcgtttt gtcgttttgg gggg                                              24

<210> SEQ ID NO 436
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 436
tcgtcgctgt ctccgcttct tcttgcc                                           27

<210> SEQ ID NO 437
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 437
tcgtcgctgt ctccg                                                        15

<210> SEQ ID NO 438
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 438
ctgtaagtga gcttggagag                                                   20

<210> SEQ ID NO 439
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 439
gagaacgctg gaccttccat                                                   20
```

<210> SEQ ID NO 440
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 440
ccaggttgta tagaggc                                           17

<210> SEQ ID NO 441
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 441
gctagacgtt agcgtga                                           17

<210> SEQ ID NO 442
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 442
ggagctcttc gaacgccata                                        20

<210> SEQ ID NO 443
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 443
tctccatgat ggttttatcg                                        20

<210> SEQ ID NO 444
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 444
aaggtggggc agtctcaggg a                                      21

<210> SEQ ID NO 445
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 445
atcggaggac tggcgcgccg                                        20

<210> SEQ ID NO 446
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 446
ttaggacaag gtctagggtg					20

<210> SEQ ID NO 447
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 447
accacaacga gaggaacgca					20

<210> SEQ ID NO 448
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 448
ggcagtgcag gctcaccggg					20

<210> SEQ ID NO 449
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 449
gaaccttcca tgctgtt					17

<210> SEQ ID NO 450
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 450
gctagacgtt agcgtga					17

<210> SEQ ID NO 451
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 451
gcttggaggg cctgtaagtg					20

<210> SEQ ID NO 452
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 452
gtagccttcc ta					12

<210> SEQ ID NO 453

```
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 453
cggtagcctt ccta                                              14

<210> SEQ ID NO 454
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 454
cacggtagcc ttccta                                            16

<210> SEQ ID NO 455
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 455
agcacggtag ccttccta                                          18

<210> SEQ ID NO 456
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 456
gaacgctgga ccttccat                                          18

<210> SEQ ID NO 457
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 457
gaccttccat                                                   10

<210> SEQ ID NO 458
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 458
tggaccttcc at                                                12

<210> SEQ ID NO 459
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 459
```

```
gctggacctt ccat                                                    14

<210> SEQ ID NO 460
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 460
acgctggacc ttccat                                                  16

<210> SEQ ID NO 461
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 461
taagctctgt caacgccagg                                              20

<210> SEQ ID NO 462
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 462
gagaacgctg gaccttccat gt                                           22

<210> SEQ ID NO 463
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 463
tccatgtcgg tcctgatgct                                              20

<210> SEQ ID NO 464
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 464
ttcatgcctt gcaaaatggc g                                            21

<210> SEQ ID NO 465
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 465
tgctagctgt gcctgtacct                                              20

<210> SEQ ID NO 466
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 466
agcatcagga ccgacatgga                                                      20

<210> SEQ ID NO 467
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 467
gaccttccat gtcggtcctg at                                                   22

<210> SEQ ID NO 468
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 468
acaaccacga gaacgggaac                                                      20

<210> SEQ ID NO 469
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 469
gaaccttcca tgctgttccg                                                      20

<210> SEQ ID NO 470
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 470
caatcaatct gaggagaccc                                                      20

<210> SEQ ID NO 471
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 471
tcagctctgg tactttttca                                                      20

<210> SEQ ID NO 472
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 472
tggttacggt ctgtcccatg                                                      20
```

<210> SEQ ID NO 473
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 473
gtctatcgga ggactggcgc                                          20

<210> SEQ ID NO 474
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 474
cattttacgg gcgggcgggc                                          20

<210> SEQ ID NO 475
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 475 gagggacca ttttacgggc                                           20

<210> SEQ ID NO 476
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 476
tgtccagccg aggggaccat                                          20

<210> SEQ ID NO 477
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 477
cgggcttacg gcggatgctg                                          20

<210> SEQ ID NO 478
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 478
tggaccttct atgtcggtcc                                          20

<210> SEQ ID NO 479
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 479
tgtcccatgt ttttagaagc        20

<210> SEQ ID NO 480
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 480
gtggttacgg tcgtgcccat        20

<210> SEQ ID NO 481
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 481
cctccaaatg aaagaccccc        20

<210> SEQ ID NO 482
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 482
ttgtactctc catgatggtt        20

<210> SEQ ID NO 483
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 483
ttccatgctg ttccggctgg        20

<210> SEQ ID NO 484
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 484
gaccttctat gtcggtcctg        20

<210> SEQ ID NO 485
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 485
gagaccgctc gaccttcgat        20

```
<210> SEQ ID NO 486
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 486
ttgccccata ttttagaaac                                              20

<210> SEQ ID NO 487
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 487
ttgaaactga ggtgggac                                                18

<210> SEQ ID NO 488
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 488
ctatcggagg actggcgcgc c                                            21

<210> SEQ ID NO 489
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 489
cttggagggc ctcccggcgg                                              20

<210> SEQ ID NO 490
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 490
gctgaacctt ccatgctgtt                                              20

<210> SEQ ID NO 491
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 491
tagaaacagc attcttcttt tagggcagca ca                                32

<210> SEQ ID NO 492
<211> LENGTH: 24
<212> TYPE: DNA
<213> ORGANISM: Artificial Sequence
<220> FEATURE:
<223> OTHER INFORMATION: Synthetic Sequence
```

```
<400> SEQUENCE: 492
agatggttct cagataaagc ggaa                                          24

<210> SEQ ID NO 493
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 493
ttccgcttta tctgagaacc atct                                          24

<210> SEQ ID NO 494
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 494
gtcccaggtt gtatagaggc tgc                                           23

<210> SEQ ID NO 495
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 495
gcgccagtcc tccgatagac                                               20

<210> SEQ ID NO 496
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 496
atcggaggac tggcgcgccg                                               20

<210> SEQ ID NO 497
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 497
ggtctgtccc atattttag                                                20

<210> SEQ ID NO 498
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 498
tttttcaacg ttgagggggg                                               20

<210> SEQ ID NO 499
<211> LENGTH: 21
```

<212> TYPE: DNA
<213> ORGANISM: Artificial Sequence
<220> FEATURE:
<223> OTHER INFORMATION: Synthetic Sequence

<400> SEQUENCE: 499
tttttcaagc gttgatttttt t                                                21

<210> SEQ ID NO 500
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 500
ggggtcaacg ttgattttttt                                                  20

<210> SEQ ID NO 501
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 501
ggggttttca acgttttgag ggggg                                             25

<210> SEQ ID NO 502
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 502
ggttacggtc tgtcccatat                                                   20

<210> SEQ ID NO 503
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 503
ctgtcccata tttttagaca                                                   20

<210> SEQ ID NO 504
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 504
accatcctga ggccattcgg                                                   20

<210> SEQ ID NO 505
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 505

-continued cgtctatcgg gcttctgtgt ctg	23

<210> SEQ ID NO 506
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 506
ggccatccca cattgaaagt t	21

<210> SEQ ID NO 507
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 507
ccaaatatcg gtggtcaagc ac	22

<210> SEQ ID NO 508
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 508
gtgcttgacc accgatattt gg	22

<210> SEQ ID NO 509
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 509
gtgctgatca ccgatatcct gttcgg	26

<210> SEQ ID NO 510
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 510
ggccaacttt caatgtggga tggcctc	27

<210> SEQ ID NO 511
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 511
ttccgccgaa tggcctcagg atggtac	27

<210> SEQ ID NO 512
<211> LENGTH: 36
<212> TYPE: DNA
<213> ORGANISM: Artificial Sequence

```
<220> FEATURE:
<223> OTHER INFORMATION: Synthetic Sequence

<400> SEQUENCE: 512
tatagtccct gagactgccc caccttctca acaacc                              36

<210> SEQ ID NO 513
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 513
gcagcctcta tacaacctgg gacggga                                        27

<210> SEQ ID NO 514
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 514
ctatcggagg actggcgcgc cg                                             22

<210> SEQ ID NO 515
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 515
tatcggagga ctggcgcgcc g                                              21

<210> SEQ ID NO 516
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 516
gatcggagga ctggcgcgcc g                                              21

<210> SEQ ID NO 517
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 517
ccgaacagga tatcggtgat cagcac                                         26

<210> SEQ ID NO 518
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 518
ttttggggtc aacgttgagg gggg                                           24
```

<210> SEQ ID NO 519
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 519
ggggtcaacg ttgaggggggg  20

<210> SEQ ID NO 520
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 520
cgcgcgcgcg cgcgcgcgcg  20

<210> SEQ ID NO 521
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 521
ggggcatgac gttcggggggg  20

<210> SEQ ID NO 522
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 522
ggggcatgac gttcaaaaaa  20

<210> SEQ ID NO 523
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 523
ggggcatgag cttcggggggg  20

<210> SEQ ID NO 524
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 524
ggggcatgac gttcggggggg  20

<210> SEQ ID NO 525
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 525
aaaacatgac gttcaaaaaa                                               20

<210> SEQ ID NO 526
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 526
aaaacatgac gttcggggggg                                              20

<210> SEQ ID NO 527
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 527
ggggcatgac gttcaaaaaa                                               20

<210> SEQ ID NO 528
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 528
accatggacg atctgtttcc cctc                                          24

<210> SEQ ID NO 529
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 529
gccatggacg aactgttccc cctc                                          24

<210> SEQ ID NO 530
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 530
cccccccccc cccccccccc                                               20

<210> SEQ ID NO 531
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 531
gggggggggg gggggggggg                                               20

<210> SEQ ID NO 532

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 532
gctgtaaaat gaatcggccg                                               20

<210> SEQ ID NO 533
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 533
ttcgggcgga ctcctccatt                                               20

<210> SEQ ID NO 534
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 534
tatgccgcgc ccggacttat                                               20

<210> SEQ ID NO 535
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 535
ggggtaatcg atcaggggggg                                              20

<210> SEQ ID NO 536
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 536
tttgagaacg ctggaccttc                                               20

<210> SEQ ID NO 537
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 537
gatcgctgat ctaatgctcg                                               20

<210> SEQ ID NO 538
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 538
```
gtcggtcctg atgctgttcc                                            20

<210> SEQ ID NO 539
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 539
tcgtcgtcag ttcgctgtcg                                            20

<210> SEQ ID NO 540
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 540
ctggaccttc catgtcgg                                              18

<210> SEQ ID NO 541
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 541
gctcgttcag cgcgtct                                               17

<210> SEQ ID NO 542
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 542
ctggaccttc catgtc                                                16

<210> SEQ ID NO 543
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 543
cactgtcctt cgtcga                                                16

<210> SEQ ID NO 544
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 544
cgctggacct tccatgtcgg                                            20

<210> SEQ ID NO 545
<211> LENGTH: 20
<212> TYPE: DNA

```
<213> ORGANISM: Artificial Sequence
<220> FEATURE:
<223> OTHER INFORMATION: Synthetic Sequence

<400> SEQUENCE: 545
gctgagctca tgccgtctgc                                               20

<210> SEQ ID NO 546
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 546
aacgctggac cttccatgtc                                               20

<210> SEQ ID NO 547
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 547
tgcatgccgt acacagctct                                               20

<210> SEQ ID NO 548
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 548
ccttccatgt cggtcctgat                                               20

<210> SEQ ID NO 549
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 549
tactcttcgg atcccttgcg                                               20

<210> SEQ ID NO 550
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 550
ttccatgtcg gtcctgat                                                 18

<210> SEQ ID NO 551
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 551
ctgattgctc tctcgtga                                                 18
```

<210> SEQ ID NO 552
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 552
ggcgttattc ctgactcgcc                                                  20

<210> SEQ ID NO 553
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 553
cctacgttgt atgcgcccag ct                                               22

<210> SEQ ID NO 554
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 554
ggggtaatcg atgagggggg                                                  20

<210> SEQ ID NO 555
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 555
ttcgggcgga ctcctccatt                                                  20

<210> SEQ ID NO 556
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 556
tttttttttt tttttttttt                                                  20

<210> SEQ ID NO 557
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 557
gggggttttt tttttggggg                                                  20

<210> SEQ ID NO 558
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 558
tttttggggg ggggttttt         20

<210> SEQ ID NO 559
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 559
gggggggggg ggggggggt         19

<210> SEQ ID NO 560
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 560
aaaaaaaaaa aaaaaaaaaa         20

<210> SEQ ID NO 561
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 561
cccccaaaaa aaaaaccccc         20

<210> SEQ ID NO 562
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 562
aaaaaccccc cccccaaaaa         20

<210> SEQ ID NO 563
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 563
tttgaattca ggactggtga ggttgag         27

<210> SEQ ID NO 564
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 564
tttgaatcct cagcggtctc cagtggc         27

```
<210> SEQ ID NO 565
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 565
aattctctat cggggcttct gtgtctgttg ctggttccgc tttat            45

<210> SEQ ID NO 566
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 566
ctagataaag cggaaccagc aacagacaca gaagccccga tagag            45

<210> SEQ ID NO 567
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 567
ttttctagag aggtgcacaa tgctctgg                               28

<210> SEQ ID NO 568
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 568
tttgaattcc gtgtacagaa gcgagaagc                              29

<210> SEQ ID NO 569
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 569
tttgcggccg ctagacttaa cctgagagat a                           31

<210> SEQ ID NO 570
<211> LENGTH: 29
<212> TYPE: DNA
<213> ORGANISM: Artificial Sequence
<220> FEATURE:
<223> OTHER INFORMATION: Synthetic Sequence

<400> SEQUENCE: 570
tttgggccca cgagagacag agacacttc                              29

<210> SEQ ID NO 571
<211> LENGTH: 29
<212> TYPE: DNA
<213> ORGANISM: Artificial Sequence
<220> FEATURE:
<223> OTHER INFORMATION: Synthetic Sequence
```

```
<400> SEQUENCE: 571
tttgggcccg cttctcgctt ctgtacacg                                29

<210> SEQ ID NO 572
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 572
gagaacgctg gaccttccat                                          20

<210> SEQ ID NO 573
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 573
tccatgtcgg tcctgatgct                                          20

<210> SEQ ID NO 574
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 574 ctgtcg                                                         6

<210> SEQ ID NO 575
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 575 tcgtga                                                         6

<210> SEQ ID NO 576
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 576 cgtcga                                                         6

<210> SEQ ID NO 577
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 577 agtgct                                                         6

<210> SEQ ID NO 578
<211> LENGTH: 6
```

```
<212> TYPE: DNA
<213> ORGANISM: Artificial Sequence
<220> FEATURE:
<223> OTHER INFORMATION: Synthetic Sequence

<400> SEQUENCE: 578 ctgtcg                                                                          6

<210> SEQ ID NO 579
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 579 agtgct                                                                          6

<210> SEQ ID NO 580
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 580 cgtcga                                                                          6

<210> SEQ ID NO 581
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 581 tcgtga                                                                          6

<210> SEQ ID NO 582
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 582
gagaacgctc cagcttcgat                                                          20

<210> SEQ ID NO 583
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 583
gctagacgta agcgtga                                                             17

<210> SEQ ID NO 584
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 584
```

```
gagaacgctc gaccttccat                                               20
```

<210> SEQ ID NO 585
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 585

```
gagaacgctg gacctatcca t                                             21
```

<210> SEQ ID NO 586
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 586

```
gctagaggtt agcgtga                                                  17
```

<210> SEQ ID NO 587
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 587

```
gagaacgctg gacttccat                                                19
```

<210> SEQ ID NO 588
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 588

```
tcacgctaac gtctagc                                                  17
```

<210> SEQ ID NO 589
<211> LENGTH: 17
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 589

```
gctagacgtt agcgtga                                                  17
```

<210> SEQ ID NO 590
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 590

```
atggaaggtc gagcgttctc                                               20
```

```
<210> SEQ ID NO 591
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 591
gagaacgctg gaccttcgat                                               20

<210> SEQ ID NO 592
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 592
gagaacgatg gaccttccat                                               20

<210> SEQ ID NO 593
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 593
gagaacgctg gatccat                                                  17

<210> SEQ ID NO 594
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 594
gagaacgctc cagcactgat                                               20

<210> SEQ ID NO 595
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 595
tccatgtcgg tcctgctgat                                               20

<210> SEQ ID NO 596
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 596
atgtcctcgg tcctgatgct                                               20

<210> SEQ ID NO 597
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 597
gagaacgctc caccttccat                                              20

<210> SEQ ID NO 598
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 598
gagaacgctg gaccttcgta                                              20

<210> SEQ ID NO 599
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 599
atggaaggtc cagcgttctc                                              20

<210> SEQ ID NO 600
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 600 tcctga                                                              6

<210> SEQ ID NO 601
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 601 tcaacgtt                                                            8

<210> SEQ ID NO 602
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 602 aacgtt                                                              6

<210> SEQ ID NO 603
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 603 aacgttga                                                            8
```

<210> SEQ ID NO 604
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 604
tcacgctaac ctctagc                                                    17

<210> SEQ ID NO 605
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 605
gagaacgctg gaccttgcat                                                 20

<210> SEQ ID NO 606
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 606
gctggacctt ccat                                                       14

<210> SEQ ID NO 607
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 607
gagaacgctg gacctcatcc at                                              22

<210> SEQ ID NO 608
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 608
gagaacgctg gacgctcatc cat                                             23

<210> SEQ ID NO 609
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 609
aacgttgagg ggcat                                                      15

<210> SEQ ID NO 610
<211> LENGTH: 15
<212> TYPE: DNA
<213> ORGANISM: Artificial Sequence
<220> FEATURE:

<223> OTHER INFORMATION: Synthetic Sequence

<400> SEQUENCE: 610
atgcccctca acgtt                                              15

<210> SEQ ID NO 611
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 611
tcaacgttga                                                    10

<210> SEQ ID NO 612
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 612
gctggacctt ccat                                               14

<210> SEQ ID NO 613
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 613 caacgtt                                                       7

<210> SEQ ID NO 614
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 614
acaacgttga                                                    10

<210> SEQ ID NO 615
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 615 tcacgt                                                        6

<210> SEQ ID NO 616
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 616 tcaagctt                                                      8

```
<210> SEQ ID NO 617
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 617 tcgtca                                                                    6

<210> SEQ ID NO 618
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 618 aggatatc                                                                  8

<210> SEQ ID NO 619
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 619 tagacgtc                                                                  8

<210> SEQ ID NO 620
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 620 gacgtcat                                                                  8

<210> SEQ ID NO 621
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 621 ccatcgat                                                                  8

<210> SEQ ID NO 622
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 622 atcgatgt                                                                  8

<210> SEQ ID NO 623
<211> LENGTH: 8
<212> TYPE: DNA
<213> ORGANISM: Artificial Sequence
<220> FEATURE:
<223> OTHER INFORMATION: Synthetic Sequence
```

-continued

```
<400> SEQUENCE: 623 atgcatgt                                                          8

<210> SEQ ID NO 624
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 624 ccatgcat                                                          8

<210> SEQ ID NO 625
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 625 agcgctga                                                          8

<210> SEQ ID NO 626
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 626 tcagcgct                                                          8

<210> SEQ ID NO 627
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 627 ccttcgat                                                          8

<210> SEQ ID NO 628
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 628
gtgccggggt ctccgggc                                              18

<210> SEQ ID NO 629
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 629
gctgtggggc ggctcctg                                              18

<210> SEQ ID NO 630
<211> LENGTH: 8
```

```
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 630 tcaacgtt                                                                  8

<210> SEQ ID NO 631
<211> LENGTH: 8
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to FITC moiety.
<220> FEATURE:
<223> OTHER INFORMATION: Synthetic Sequence

<400> SEQUENCE: 631 tcaacgtt                                                                  8

<210> SEQ ID NO 632
<211> LENGTH: 8
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to FITC moiety.
<220> FEATURE:
<223> OTHER INFORMATION: Synthetic Sequence

<400> SEQUENCE: 632 aacgttga                                                                  8

<210> SEQ ID NO 633
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 633 tcaacgt                                                                   7

<210> SEQ ID NO 634
<211> LENGTH: 7
<212> TYPE: DNA
<213> ORGANISM: Artificial Sequence
<220> FEATURE:
<223> OTHER INFORMATION: Synthetic Sequence

<400> SEQUENCE: 634 aacgttg                                                                   7

<210> SEQ ID NO 635
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 635
```

```
cgacga                                                              6
```

<210> SEQ ID NO 636
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 636

```
tcaacgtt                                                            8
```

<210> SEQ ID NO 637
<211> LENGTH: 5
<212> TYPE: DNA
<213> ORGANISM: Artificial Sequence
<220> FEATURE:
<223> OTHER INFORMATION: Synthetic Sequence

<400> SEQUENCE: 637

```
tcgga                                                               5
```

<210> SEQ ID NO 638
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 638

```
agaacgtt                                                            8
```

<210> SEQ ID NO 639
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 639

```
tcatcgat                                                            8
```

<210> SEQ ID NO 640
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 640

```
taaacgtt                                                            8
```

<210> SEQ ID NO 641
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 641

```
ccaacgtt                                                            8
```

<210> SEQ ID NO 642
<211> LENGTH: 6
<212> TYPE: DNA
<213> ORGANISM: Artificial Sequence

```
<220> FEATURE:
<223> OTHER INFORMATION: Synthetic Sequence

<400> SEQUENCE: 642 gctcga                                                                        6

<210> SEQ ID NO 643
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 643 cgacgt                                                                        6

<210> SEQ ID NO 644
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 644 cgtcgt                                                                        6

<210> SEQ ID NO 645
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 645 acgtgt                                                                        6

<210> SEQ ID NO 646
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 646 cgttcg                                                                        6

<210> SEQ ID NO 647
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 647
gagcaagctg gaccttccat                                                        20

<210> SEQ ID NO 648
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 648 cgcgta                                                                        6
```

```
<210> SEQ ID NO 649
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 649 cgtacg                                                                      6

<210> SEQ ID NO 650
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 650 tcaccggt                                                                    8

<210> SEQ ID NO 651
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 651
caagagatgc taacaatgca                                                      20

<210> SEQ ID NO 652
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 652
acccatcaat agctctgtgc                                                      20

<210> SEQ ID NO 653
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 653 ccatcgat                                                                    8

<210> SEQ ID NO 654
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 654 tcgacgtc                                                                    8

<210> SEQ ID NO 655
<211> LENGTH: 8
<212> TYPE: DNA
<213> ORGANISM: Artificial Sequence
<220> FEATURE:
<223> OTHER INFORMATION: Synthetic Sequence
```

```
<400> SEQUENCE: 655 ctagcgct                                                              8

<210> SEQ ID NO 656
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 656 taagcgct                                                              8

<210> SEQ ID NO 657
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 657
tcgcgaattc gcg                                                       13

<210> SEQ ID NO 658
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 658
atggaaggtc cagcgttct                                                 19

<210> SEQ ID NO 659
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 659
actggacgtt agcgtga                                                   17

<210> SEQ ID NO 660
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 660
cgcctggggc tggtctgg                                                  18

<210> SEQ ID NO 661
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 661
gtgtcggggt ctccgggc                                                  18

<210> SEQ ID NO 662
```

```
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 662
gtgccggggt ctccgggc                                                 18

<210> SEQ ID NO 663
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 663
cgccgtcgcg gcggttgg                                                 18

<210> SEQ ID NO 664
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 664
gaagttcacg ttgagggca t                                              21

<210> SEQ ID NO 665
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 665
atctggtgag ggcaagctat g                                             21

<210> SEQ ID NO 666
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 666
gttgaaaccc gagaacatca t                                             21

<210> SEQ ID NO 667
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 667 gcaacgtt                                                             8

<210> SEQ ID NO 668
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 668
``` gtaacgtt 8

<210> SEQ ID NO 669
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 669 cgaacgtt 8

<210> SEQ ID NO 670
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 670 gaaacgtt 8

<210> SEQ ID NO 671
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 671 caaacgtt 8

<210> SEQ ID NO 672
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 672 ctaacgtt 8

<210> SEQ ID NO 673
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 673 ggaacgtt 8

<210> SEQ ID NO 674
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 674 tgaacgtt 8

<210> SEQ ID NO 675
<211> LENGTH: 8
<212> TYPE: DNA

```
<213> ORGANISM: Artificial Sequence
<220> FEATURE:
<223> OTHER INFORMATION: Synthetic Sequence

<400> SEQUENCE: 675 acaacgtt                                                                    8

<210> SEQ ID NO 676
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 676 ttaacgtt                                                                    8

<210> SEQ ID NO 677
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 677 aaaacgtt                                                                    8

<210> SEQ ID NO 678
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 678 ataacgtt                                                                    8

<210> SEQ ID NO 679
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 679 aacgttct                                                                    8

<210> SEQ ID NO 680
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 680 tccgatcg                                                                    8

<210> SEQ ID NO 681
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 681 tccgtacg                                                                    8
```

<210> SEQ ID NO 682
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 682
gctagacgct agcgtga                                                17

<210> SEQ ID NO 683
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 683
gagaacgctg gacctcatca tccat                                       25

<210> SEQ ID NO 684
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 684
gagaacgcta gaccttctat                                             20

<210> SEQ ID NO 685
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 685
actagacgtt agtgtga                                                17

<210> SEQ ID NO 686
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 686
cacaccttgg tcaatgtcac gt                                          22

<210> SEQ ID NO 687
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 687
tctccatcct atggttttat cg                                          22

<210> SEQ ID NO 688
<211> LENGTH: 15
<212> TYPE: DNA
<213> ORGANISM: Artificial Sequence
<220> FEATURE:

<223> OTHER INFORMATION: Synthetic Sequence

<400> SEQUENCE: 688
cgctggacct tccat                                                        15

<210> SEQ ID NO 689
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 689
caccaccttg gtcaatgtca cgt                                               23

<210> SEQ ID NO 690
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 690
gctagacgtt agctgga                                                      17

<210> SEQ ID NO 691
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 691
agtgcgattg cagatcg                                                      17

<210> SEQ ID NO 692
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 692
ttttcgtttt gtggttttgt ggtt                                              24

<210> SEQ ID NO 693
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 693
ttttcgtttg tcgttttgtc gtt                                               23

<210> SEQ ID NO 694
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 694
tttttgtttt gtggttttgt ggtt                                              24

```
<210> SEQ ID NO 695
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 695
accgcatgga ttctaggcca                                               20

<210> SEQ ID NO 696
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 696
gctagacgtt agcgt                                                    15

<210> SEQ ID NO 697
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 697
aacgctggac cttccat                                                  17

<210> SEQ ID NO 698
<211> LENGTH: 8
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence

<400> SEQUENCE: 698 tcaangtt                                                             8

<210> SEQ ID NO 699
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 699 ccttcgat                                                             8

<210> SEQ ID NO 700
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 700
actagacgtt agtgtga                                                  17

<210> SEQ ID NO 701
<211> LENGTH: 17
<212> TYPE: DNA
```

<213> ORGANISM: Artificial Sequence
<220> FEATURE:
<223> OTHER INFORMATION: Synthetic Sequence

<400> SEQUENCE: 701
gctagaggtt agcgtga                                              17

<210> SEQ ID NO 702
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 702
atggactctc cagcgttctc                                           20

<210> SEQ ID NO 703
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 703
atcgactctc gagcgttctc                                           20

<210> SEQ ID NO 704
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 704
gctagacgtt agc                                                  13

<210> SEQ ID NO 705
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 705 gctagacgt                                                        9

<210> SEQ ID NO 706
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 706
agtgcgattc gagatcg                                              17

<210> SEQ ID NO 707
<211> LENGTH: 8
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<220> FEATURE:
<223> OTHER INFORMATION: Synthetic Sequence

```
<400> SEQUENCE: 707 tcagngct                                                              8

<210> SEQ ID NO 708
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 708
ctgattgctc tctcgtga                                                  18

<210> SEQ ID NO 709
<211> LENGTH: 8
<212> TYPE: DNA
<213> ORGANISM: Artificial Sequence
<220> FEATURE:
<221> NAME/KEY: modified_base
<222> LOCATION: (2)...(2)
<223> OTHER INFORMATION: m5c
<220> FEATURE:
<223> OTHER INFORMATION: Synthetic Sequence

<400> SEQUENCE: 709 tnaacgtt                                                              8

<210> SEQ ID NO 710
<211> LENGTH: 20
<212> TYPE: DNA
<213> ORGANISM: Artificial Sequence
<220> FEATURE:
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 710
gagaangctg gaccttccat                                                20

<210> SEQ ID NO 711
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 711
gctagacgtt aggctga                                                   17

<210> SEQ ID NO 712
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 712
gctacttagc gtga                                                      14

<210> SEQ ID NO 713
<211> LENGTH: 15
<212> TYPE: DNA
<213> ORGANISM: Artificial Sequence
<220> FEATURE:
```

-continued

<223> OTHER INFORMATION: Synthetic Sequence

<400> SEQUENCE: 713
gctaccttag cgtga                                                    15

<210> SEQ ID NO 714
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 714
atcgacttcg agcgttctc                                                19

<210> SEQ ID NO 715
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 715
atgcactctg cagcgttctc                                               20

<210> SEQ ID NO 716
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 716
agtgactctc cagcgttctc                                               20

<210> SEQ ID NO 717
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 717
gccagatgtt agctgga                                                  17

<210> SEQ ID NO 718
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 718
atcgactcga gcgttctc                                                 18

<210> SEQ ID NO 719
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 719
atcgatcgag cgttctc                                                  17

```
<210> SEQ ID NO 720
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 720
gagaacgctc gaccttcgat                                              20

<210> SEQ ID NO 721
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 721
gctagacgtt agctgga                                                 17

<210> SEQ ID NO 722
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 722
atcgactctc gagcgttctc                                              20

<210> SEQ ID NO 723
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 723
tagacgttag cgtga                                                   15

<210> SEQ ID NO 724
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 724
cgactctcga gcgttctc                                                18

<210> SEQ ID NO 725
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 725
ggggtcgacc ttggaggggg g                                            21

<210> SEQ ID NO 726
<211> LENGTH: 16
<212> TYPE: DNA
```

```
<213> ORGANISM: Artificial Sequence
<220> FEATURE:
<223> OTHER INFORMATION: Synthetic Sequence

<400> SEQUENCE: 726
gctaacgtta gcgtga                                                        16

<210> SEQ ID NO 727
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 727 cgtcgtcgt                                                                 9

<210> SEQ ID NO 728
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<220> FEATURE:
<223> OTHER INFORMATION: Synthetic Sequence

<400> SEQUENCE: 728
gagaacgctg gacnttccat                                                    20

<210> SEQ ID NO 729
<211> LENGTH: 20
<212> TYPE: DNA
<213> ORGANISM: Artificial Sequence
<220> FEATURE:
<221> NAME/KEY: modified_base
<222> LOCATION: (18)...(18)
<223> OTHER INFORMATION: m5c
<220> FEATURE:
<223> OTHER INFORMATION: Synthetic Sequence

<400> SEQUENCE: 729
atcgacctac gtgcgttntc                                                    20

<210> SEQ ID NO 730
<211> LENGTH: 20
<212> TYPE: DNA
<213> ORGANISM: Artificial Sequence
<220> FEATURE:
<221> NAME/KEY: modified_base
<222> LOCATION: (3)...(3)
<223> OTHER INFORMATION: m5c
<220> FEATURE:
<223> OTHER INFORMATION: Synthetic Sequence

<400> SEQUENCE: 730
atngacctac gtgcgttctc                                                    20

<210> SEQ ID NO 731
<211> LENGTH: 15
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<220> FEATURE:
<223> OTHER INFORMATION: Synthetic Sequence
```

```
<400> SEQUENCE: 731
gctagangtt agcgt                                                    15

<210> SEQ ID NO 732
<211> LENGTH: 20
<212> TYPE: DNA
<213> ORGANISM: Artificial Sequence
<220> FEATURE:
<221> NAME/KEY: modified_base
<222> LOCATION: (14)...(14)
<223> OTHER INFORMATION: m5c
<220> FEATURE:
<223> OTHER INFORMATION: Synthetic Sequence

<400> SEQUENCE: 732
atcgactctc gagngttctc                                               20

<210> SEQ ID NO 733
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 733
ggggtaatgc atcagggggg                                               20

<210> SEQ ID NO 734
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 734
ggctgtattc ctgactgccc                                               20

<210> SEQ ID NO 735
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 735
ccatgctaac ctctagc                                                  17

<210> SEQ ID NO 736
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 736
gctagatgtt agcgtga                                                  17

<210> SEQ ID NO 737
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 737
```

```
cgtaccttac ggtga                                                    15
```

<210> SEQ ID NO 738
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 738

```
tccatgctgg tcctgatgct                                               20
```

<210> SEQ ID NO 739
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 739

```
atcgactctc tcgagcgttc tc                                            22
```

<210> SEQ ID NO 740
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 740

```
gctagagctt agcgtga                                                  17
```

<210> SEQ ID NO 741
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 741

```
atcgactctc gagtgttctc                                               20
```

<210> SEQ ID NO 742
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 742

```
aacgctcgac cttcgat                                                  17
```

<210> SEQ ID NO 743
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 743

```
ctcaacgctg gaccttccat                                               20
```

<210> SEQ ID NO 744
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 744
atcgacctac gtgcgttctc                                               20

<210> SEQ ID NO 745
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 745
gagaatgctg gaccttccat                                               20

<210> SEQ ID NO 746
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 746
tcacgctaac ctctgac                                                  17

<210> SEQ ID NO 747
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 747
gagaacgctc cagcactgat                                               20

<210> SEQ ID NO 748
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Biotin moiety attached at 5' end of sequence.
<220> FEATURE:
<223> OTHER INFORMATION: Synthetic Sequence

<400> SEQUENCE: 748
gagcaagctg gaccttccat                                               20

<210> SEQ ID NO 749
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 749
cgctagaggt tagcgtga                                                 18

<210> SEQ ID NO 750
<211> LENGTH: 15
<212> TYPE: DNA
```

```
<213> ORGANISM: Artificial Sequence
<220> FEATURE:
<223> OTHER INFORMATION: Synthetic Sequence

<400> SEQUENCE: 750
gctagatgtt aacgt                                                    15

<210> SEQ ID NO 751
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 751
atggaaggtc cacgttctc                                                19

<210> SEQ ID NO 752
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 752
gctagatgtt agcgt                                                    15

<210> SEQ ID NO 753
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 753
gctagacgtt agtgt                                                    15

<210> SEQ ID NO 754
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 754
tccatgacgg tcctgatgct                                               20

<210> SEQ ID NO 755
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 755
tccatggcgg tcctgatgct                                               20

<210> SEQ ID NO 756
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 756
gctagacgat agcgt                                                    15
```

<210> SEQ ID NO 757
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 757
gctagtcgat agcgt                                                        15

<210> SEQ ID NO 758
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 758
tccatgacgt tcctgatgct                                                   20

<210> SEQ ID NO 759
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 759
tccatgtcgt tcctgatgct                                                   20

<210> SEQ ID NO 760
<211> LENGTH: 15
<212> TYPE: DNA
<213> ORGANISM: Artificial Sequence
<220> FEATURE:
<221> NAME/KEY: modified_base
<222> LOCATION: (13)...(13)
<223> OTHER INFORMATION: m5c
<220> FEATURE:
<223> OTHER INFORMATION: Synthetic Sequence

<400> SEQUENCE: 760
gctagacgtt agngt                                                        15

<210> SEQ ID NO 761
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 761
gctaggcgtt agcgt                                                        15

<210> SEQ ID NO 762
<211> LENGTH: 20
<212> TYPE: DNA
<213> ORGANISM: Artificial Sequence
<220> FEATURE:
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 762
tccatgtngg tcctgatgct                                              20

<210> SEQ ID NO 763
<211> LENGTH: 20
<212> TYPE: DNA
<213> ORGANISM: Artificial Sequence
<220> FEATURE:
<221> NAME/KEY: modified_base
<222> LOCATION: (12)...(12)
<223> OTHER INFORMATION: m5c
<220> FEATURE:
<223> OTHER INFORMATION: Synthetic Sequence

<400> SEQUENCE: 763
tccatgtcgg tnctgatgct                                              20

<210> SEQ ID NO 764
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (3)...(3)
<223> OTHER INFORMATION: m5c
<220> FEATURE:
<221> NAME/KEY: modified_base
<222> LOCATION: (10)...(10)
<223> OTHER INFORMATION: m5c
<220> FEATURE:
<221> NAME/KEY: modified_base
<222> LOCATION: (14)...(14)
<223> OTHER INFORMATION: m5c

<400> SEQUENCE: 764
atngactctn gagngttctc                                              20

<210> SEQ ID NO 765
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 765
atggaaggtc cagtgttctc                                              20

<210> SEQ ID NO 766
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 766
gcatgacgtt gagct                                                   15

<210> SEQ ID NO 767
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 767
ggggtcaacg ttgaggggggg                                             20

```
<210> SEQ ID NO 768
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 768
ggggtcaagt ctgaggggggg                                              20

<210> SEQ ID NO 769
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 769
cgcgcgcgcg cgcgcgcgcg                                               20

<210> SEQ ID NO 770
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 770
cccccccccc cccccccccc ccccccc                                       28

<210> SEQ ID NO 771
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 771
cccccccccc cccccccccc cccccccccc ccccc                              35

<210> SEQ ID NO 772
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 772
tccatgtcgc tcctgatcct                                               20

<210> SEQ ID NO 773
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 773
gctaaacgtt agcgt                                                    15

<210> SEQ ID NO 774
<211> LENGTH: 20
<212> TYPE: DNA
<213> ORGANISM: Artificial Sequence
<220> FEATURE:
<223> OTHER INFORMATION: Synthetic Sequence
```

```
-continued

<400> SEQUENCE: 774
tccatgtcga tcctgatgct                                           20

<210> SEQ ID NO 775
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 775
tccatgccgg tcctgatgct                                           20

<210> SEQ ID NO 776
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 776
aaaatcaacg ttgaaaaaaa                                           20

<210> SEQ ID NO 777
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 777
tccataacgt tcctgatgct                                           20

<210> SEQ ID NO 778
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 778
tggaggtccc accgagatcg gag                                       23

<210> SEQ ID NO 779
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 779
cgtcgtcgtc gtcgtcgtcg t                                         21

<210> SEQ ID NO 780
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 780
ctgctgctgc tgctgctgct g                                         21

<210> SEQ ID NO 781
<211> LENGTH: 21
```

```
<212> TYPE: DNA
<213> ORGANISM: Artificial Sequence
<220> FEATURE:
<223> OTHER INFORMATION: Synthetic Sequence

<400> SEQUENCE: 781
gagaacgctc cgaccttcga t                                              21

<210> SEQ ID NO 782
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 782
gctagatgtt agcgt                                                     15

<210> SEQ ID NO 783
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 783
gcatgacgtt gagct                                                     15

<210> SEQ ID NO 784
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 784
tcaatgctga                                                           10

<210> SEQ ID NO 785
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 785
tcaacgttga                                                           10

<210> SEQ ID NO 786
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 786
```
tcaacgttga 10

<210> SEQ ID NO 787
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 787
gcaatattgc 10

<210> SEQ ID NO 788
<211> LENGTH: 10
<212> TYPE: DNA
<213> ORGANISM: Artificial Sequence
<220> FEATURE:
<221> NAME/KEY: misc_feature
<222> LOCATION: (8)...(10)
<223> OTHER INFORMATION: Conjugated to FITC moiety.
<220> FEATURE:
<223> OTHER INFORMATION: Synthetic Sequence

<400> SEQUENCE: 788
gcaatattgc 10

<210> SEQ ID NO 789
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 789
agttgcaact 10

<210> SEQ ID NO 790
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 790 tcttcgaa 8

<210> SEQ ID NO 791
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 791 tcaacgtc 8

<210> SEQ ID NO 792
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 792

-continued ccatgtcggt cctgatgct                                                19

<210> SEQ ID NO 793
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 793
gtttttatat aatttggg                                                 18

<210> SEQ ID NO 794
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 794
tttttgtttg tcgttttgtc gtt                                           23

<210> SEQ ID NO 795
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 795
ttgggggggg tt                                                       12

<210> SEQ ID NO 796
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 796
ggggttgggg gtt                                                      13

<210> SEQ ID NO 797
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 797
ggtggtgtag gttttgg                                                  17

<210> SEQ ID NO 798
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 798

```
gagaangctc gaccttcgat                                              20

<210> SEQ ID NO 799
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 799
tcaacgttaa cgttaacgtt                                              20

<210> SEQ ID NO 800
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (8)...(8)
<223> OTHER INFORMATION: m5c
<220> FEATURE:
<223> OTHER INFORMATION: Synthetic Sequence

<400> SEQUENCE: 800
gagcaagntg gaccttccat                                              20

<210> SEQ ID NO 801
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 801
gagaangctc cagcactgat                                              20

<210> SEQ ID NO 802
<211> LENGTH: 10
<212> TYPE: DNA
<213> ORGANISM: Artificial Sequence
<220> FEATURE:
<221> NAME/KEY: modified_base
<222> LOCATION: (5)...(5)
<223> OTHER INFORMATION: m5c
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 802 tcaangttga                                                         10

<210> SEQ ID NO 803
<211> LENGTH: 10
<212> TYPE: DNA
<213> ORGANISM: Artificial Sequence
<220> FEATURE:
<221> NAME/KEY: modified_base
```

```
<222> LOCATION: (2)...(2)
<223> OTHER INFORMATION: m5c
<221> NAME/KEY: misc_feature
<222> LOCATION: (8)...(10)
<223> OTHER INFORMATION: Conjugated to biotin moiety.
<220> FEATURE:
<223> OTHER INFORMATION: Synthetic Sequence

<400> SEQUENCE: 803 gnaatattgc                                                          10

<210> SEQ ID NO 804
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 804
tgctgctttt gtcgttttgt gctt                                          24

<210> SEQ ID NO 805
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 805
ctgcgttagc aatttaactg tg                                            22

<210> SEQ ID NO 806
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 806
tccatgacgt tcctgatgct                                               20

<210> SEQ ID NO 807
<211> LENGTH: 28
<212> TYPE: DNA
<213> ORGANISM: Artificial Sequence
<220> FEATURE:
<223> OTHER INFORMATION: Synthetic Sequence

<400> SEQUENCE: 807
tgcatgccgt gcatccgtac acagctct                                      28

<210> SEQ ID NO 808
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 808
tgcatgccgt acacagctct                                               20

<210> SEQ ID NO 809
<211> LENGTH: 12
<212> TYPE: DNA
<213> ORGANISM: Artificial Sequence
<220> FEATURE:
<223> OTHER INFORMATION: Synthetic Sequence
```

```
<400> SEQUENCE: 809
tgcatcagct ct                                                    12

<210> SEQ ID NO 810
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 810 tgcgctct                                                          8

<210> SEQ ID NO 811
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 811
cccccccccc cccccccccc                                            20

<210> SEQ ID NO 812
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 812
cccccccccc cc                                                    12

<210> SEQ ID NO 813
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 813 cccccccc                                                          8

<210> SEQ ID NO 814
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 814
tgcatcagct ct                                                    12

<210> SEQ ID NO 815
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 815
tgcatgccgt acacagctct                                            20

<210> SEQ ID NO 816
```

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 816
gagcaagctg gaccttccat                                                    20

<210> SEQ ID NO 817
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 817
tcaacgttaa cgttaacgtt aacgttaacg tt                                      32

<210> SEQ ID NO 818
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 818
gagaacgctc gaccttcgat                                                    20

<210> SEQ ID NO 819
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 819
gtccccattt cccagaggag gaaat                                              25

<210> SEQ ID NO 820
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 820
ctagcggctg acgtcatcaa gctag                                              25

<210> SEQ ID NO 821
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 821
ctagcttgat gacgtcagcc gctag                                              25

<210> SEQ ID NO 822
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 822
```
cggctgacgt catcaa                                          16

<210> SEQ ID NO 823
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 823 ctgacgtg                                                    8

<210> SEQ ID NO 824
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 824
ctgacgtcat                                                 10

<210> SEQ ID NO 825
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 825
attcgatcgg ggcggggcga g                                    21

<210> SEQ ID NO 826
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 826
ctcgccccgc ccgatcgaa t                                     21

<210> SEQ ID NO 827
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 827
gactgacgtc agcgt                                           15

<210> SEQ ID NO 828
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 828
ctagcggctg acgtcataaa gctagc                               26

<210> SEQ ID NO 829
<211> LENGTH: 26
<212> TYPE: DNA

```
<213> ORGANISM: Artificial Sequence
<220> FEATURE:
<223> OTHER INFORMATION: Synthetic Sequence

<400> SEQUENCE: 829
ctagctttat gacgtcagcc gctagc                                       26

<210> SEQ ID NO 830
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 830
ctagcggctg agctcataaa gctagc                                       26

<210> SEQ ID NO 831
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 831
ctagtggctg acgtcatcaa gctag                                        25

<210> SEQ ID NO 832
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 832
tccaccacgt ggtctatgct                                              20

<210> SEQ ID NO 833
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 833
gggaatgaaa gattttatta taag                                         24

<210> SEQ ID NO 834
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 834
tctaaaaacc atctattctt aaccct                                       26

<210> SEQ ID NO 835
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 835
agctcaacgt catgc                                                   15
```

-continued

```
<210> SEQ ID NO 836
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 836
ttaacggtgg tagcggtatt ggtc                                              24

<210> SEQ ID NO 837
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 837
ttaagaccaa taccgctacc accg                                              24

<210> SEQ ID NO 838
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 838
gatctagtga tgagtcagcc ggatc                                             25

<210> SEQ ID NO 839
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 839
gatccggctg actcatcact agatc                                             25

<210> SEQ ID NO 840
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 840
tccaagacgt tcctgatgct                                                   20

<210> SEQ ID NO 841
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 841
tccatgacgt ccctgatgct                                                   20

<210> SEQ ID NO 842
<211> LENGTH: 20
<212> TYPE: DNA
<213> ORGANISM: Artificial Sequence
<220> FEATURE:
```

```
<223> OTHER INFORMATION: Synthetic Sequence

<400> SEQUENCE: 842
tccaccacgt ggctgatgct                                              20

<210> SEQ ID NO 843
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 843
ccacgtggac ctctagc                                                 17

<210> SEQ ID NO 844
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 844
tcagaccacg tggtcgggtg ttcctga                                      27

<210> SEQ ID NO 845
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 845
tcaggaacac ccgaccacgt ggtctga                                      27

<210> SEQ ID NO 846
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 846
catttccacg atttccca                                                18

<210> SEQ ID NO 847
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 847
ttcctctctg caagagact                                               19

<210> SEQ ID NO 848
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 848
tgtatctctc tgaaggact                                               19
```

<210> SEQ ID NO 849
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 849
ataaagcgaa actagcagca gtttc                                   25

<210> SEQ ID NO 850
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 850
gaaactgctg ctagtttcgc tttat                                   25

<210> SEQ ID NO 851
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 851
tgcccaaaga ggaaaatttg tttcatacag                              30

<210> SEQ ID NO 852
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 852
ctgtatgaaa caaattttcc tctttgggca                              30

<210> SEQ ID NO 853
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 853
ttagggttag ggttagggtt                                         20

<210> SEQ ID NO 854
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 854
tccatgagct tcctgatgct                                         20

<210> SEQ ID NO 855
<211> LENGTH: 20
<212> TYPE: DNA
<213> ORGANISM: Artificial Sequence
<220> FEATURE:
<223> OTHER INFORMATION: Synthetic Sequence

```
<400> SEQUENCE: 855
aaaacatgac gttcaaaaaa                                              20

<210> SEQ ID NO 856
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 856
aaaacatgac gttcggggggg                                             20

<210> SEQ ID NO 857
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 857
ggggcatgag cttcggggg                                               20

<210> SEQ ID NO 858
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 858
ctaggctgac gtcatcaagc tagt                                         24

<210> SEQ ID NO 859
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 859
tctgacgtca tctgacgttg gctgacgtct                                   30

<210> SEQ ID NO 860
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 860
ggaattagta atagatatag aagtt                                        25

<210> SEQ ID NO 861
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 861
tttacctttt ataaacataa ctaaaacaaa                                   30

<210> SEQ ID NO 862
<211> LENGTH: 15
```

```
<212> TYPE: DNA
<213> ORGANISM: Artificial Sequence
<220> FEATURE:
<223> OTHER INFORMATION: Synthetic Sequence

<400> SEQUENCE: 862
gcgttttttt ttgcg                                                         15

<210> SEQ ID NO 863
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 863
atatctaatc aaaacattaa caaa                                               24

<210> SEQ ID NO 864
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 864
tctatcccag gtggttcctg ttag                                               24

<210> SEQ ID NO 865
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 865
tccatgacgt tcctgatgct                                                    20

<210> SEQ ID NO 866
<211> LENGTH: 20
<212> TYPE: DNA
<213> ORGANISM: Artificial Sequence
<220> FEATURE:
<221> NAME/KEY: misc_feature
<222> LOCATION: (1)...(3)
<223> OTHER INFORMATION: Conjugated to biotin moiety.
<220> FEATURE:
<223> OTHER INFORMATION: Synthetic Sequence

<400> SEQUENCE: 866
tccatgagct tcctgatgct                                                    20

<210> SEQ ID NO 867
<211> LENGTH: 13
<212> TYPE: DNA
<213> ORGANISM: Artificial Sequence
<220> FEATURE:
<221> NAME/KEY: misc_feature
<222> LOCATION: (11)...(13)
<223> OTHER INFORMATION: Conjugated to FITC moiety.
<221> NAME/KEY: misc_feature
<222> LOCATION: (0)...(0)
<223> OTHER INFORMATION: Has  phosphodiester backbone.
<220> FEATURE:
<223> OTHER INFORMATION: Synthetic Sequence
```

<400> SEQUENCE: 867
tttttttttt ttt                                                13

<210> SEQ ID NO 868
<211> LENGTH: 13
<212> TYPE: DNA
<213> ORGANISM: Artificial Sequence
<220> FEATURE:
<221> NAME/KEY: misc_feature
<222> LOCATION: (11)...(13)
<223> OTHER INFORMATION: Conjugated to biotin moiety.
<221> NAME/KEY: misc_feature
<222> LOCATION: (0)...(0)
<223> OTHER INFORMATION: Has phosphorothioate and phosphodiester
      chimeric backbone with phosphodiester on 3' end.
<220> FEATURE:
<223> OTHER INFORMATION: Synthetic Sequence

<400> SEQUENCE: 868
tttttttttt ttt                                                13

<210> SEQ ID NO 869
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 869
ctagcttgat gagctcagcc gctag                                   25

<210> SEQ ID NO 870
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 870
ttcagttgtc ttgctgctta gctaa                                   25

<210> SEQ ID NO 871
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 871
tccatgagct tcctgagtct                                         20

<210> SEQ ID NO 872
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 872
ctagcggctg acgtcatcaa tctag                                   25

<210> SEQ ID NO 873
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 873
tgctagctgt gcctgtacct                                         20

<210> SEQ ID NO 874
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 874
atgctaaagg acgtcacatt gca                                     23

<210> SEQ ID NO 875
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 875
tgcaatgtga cgtcctttag cat                                     23

<210> SEQ ID NO 876
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 876
gtaggggact tccgagctc gagatcctat g                             31

<210> SEQ ID NO 877
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 877
cataggatct cgagctcgga aagtcccta c                             31

<210> SEQ ID NO 878
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 878
ctgtcaggaa ctgcaggtaa gg                                      22

<210> SEQ ID NO 879
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 879
cataacatag gaatatttac tcctcgc                                 27

<210> SEQ ID NO 880
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 880
ctccagctcc aagaaaggac g                                              21

<210> SEQ ID NO 881
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 881
gaagtttctg gtaagtcttc g                                              21

<210> SEQ ID NO 882
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 882
tgctgctttt gtgcttttgt gctt                                           24

<210> SEQ ID NO 883
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 883
tcgtcgtttt gtggttttgt ggtt                                           24

<210> SEQ ID NO 884
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 884
tcgtcgtttg tcgttttgtc gtt                                            23

<210> SEQ ID NO 885
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 885
tcctgacgtt cggcgcgcgc cc                                             22

<210> SEQ ID NO 886
<211> LENGTH: 24
<212> TYPE: DNA
<213> ORGANISM: Artificial Sequence
<220> FEATURE:
<223> OTHER INFORMATION: Synthetic Sequence -continued

```
<400> SEQUENCE: 886
tgctgctttt gtgcttttgt gctt                                          24

<210> SEQ ID NO 887
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 887
tccatgagct tcctgagctt                                               20

<210> SEQ ID NO 888
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 888
tcgtcgtttc gtcgttttga cgtt                                          24

<210> SEQ ID NO 889
<211> LENGTH: 26
<212> TYPE: DNA
<213> ORGANISM: Artificial Sequence
<220> FEATURE:
<223> OTHER INFORMATION: Synthetic Sequence

<400> SEQUENCE: 889
tcgtcgtttg cgtgcgtttc gtcgtt                                        26

<210> SEQ ID NO 890
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 890
tcgcgtgcgt tttgtcgttt tgacgtt                                       27

<210> SEQ ID NO 891
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 891
ttcgtcgttt tgtcgttttg tcgtt                                         25

<210> SEQ ID NO 892
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 892
tcctgacggg gaagt                                                    15

<210> SEQ ID NO 893
<211> LENGTH: 15
```

```
<212> TYPE: DNA
<213> ORGANISM: Artificial Sequence
<220> FEATURE:
<223> OTHER INFORMATION: Synthetic Sequence

<400> SEQUENCE: 893
tcctggcgtg gaagt                                                   15

<210> SEQ ID NO 894
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 894
tcctggcggt gaagt                                                   15

<210> SEQ ID NO 895
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 895
tcctggcgtt gaagt                                                   15

<210> SEQ ID NO 896
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 896
tcctgacgtg gaagt                                                   15

<210> SEQ ID NO 897
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 897
gcgacgttcg gcgcgcgccc                                              20

<210> SEQ ID NO 898
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 898
gcgacgggcg gcgcgcgccc                                              20

<210> SEQ ID NO 899
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 899
```

-continued gcggcgtgcg gcgcgcgccc    20

<210> SEQ ID NO 900
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 900
gcggcggtcg gcgcgcgccc    20

<210> SEQ ID NO 901
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 901
gcgacggtcg gcgcgcgccc    20

<210> SEQ ID NO 902
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 902
gcggcgttcg gcgcgcgccc    20

<210> SEQ ID NO 903
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 903
gcgacgtgcg gcgcgcgccc    20

<210> SEQ ID NO 904
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 904
tcgtcgctgt ctccg    15

<210> SEQ ID NO 905
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 905
tgtgggggtt ttggttttgg    20

<210> SEQ ID NO 906
<211> LENGTH: 20
<212> TYPE: DNA
<213> ORGANISM: Artificial Sequence

```
<220> FEATURE:
<223> OTHER INFORMATION: Synthetic Sequence

<400> SEQUENCE: 906 aggggaggggg aggggaggggg                                          20

<210> SEQ ID NO 907
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 907
tgtgtgtgtg tgtgtgtgtg t                                          21

<210> SEQ ID NO 908
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 908
ctctctctct ctctctctct ct                                         22

<210> SEQ ID NO 909
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 909
ggggtcgacg tcgagggggg                                            20

<210> SEQ ID NO 910
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 910
atatatatat atatatatat at                                         22

<210> SEQ ID NO 911
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 911
tttttttttt tttttttttt ttttttt                                    27

<210> SEQ ID NO 912
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 912
tttttttttt tttttttttt t                                          21
```

<210> SEQ ID NO 913
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 913
tttttttttt tttttttt                                                 18

<210> SEQ ID NO 914
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 914
gctagagggg agggt                                                    15

<210> SEQ ID NO 915
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 915
gctagatgtt agggg                                                    15

<210> SEQ ID NO 916
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 916
gcatgagggg gagct                                                    15

<210> SEQ ID NO 917
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 917
atggaaggtc cagggggctc                                               20

<210> SEQ ID NO 918
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 918
atggactctg gagggggctc                                               20

<210> SEQ ID NO 919
<211> LENGTH: 20
<212> TYPE: DNA
<213> ORGANISM: Artificial Sequence
<220> FEATURE:
<223> OTHER INFORMATION: Synthetic Sequence -continued

<400> SEQUENCE: 919
atggaaggtc caagggggctc                                                    20

<210> SEQ ID NO 920
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 920
gagaaggggg gaccttggat                                                     20

<210> SEQ ID NO 921
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 921
gagaaggggg gaccttccat                                                     20

<210> SEQ ID NO 922
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 922 gagaagggggc cagcactgat                                                    20

<210> SEQ ID NO 923
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 923
tccatgtggg gcctgatgct                                                     20

<210> SEQ ID NO 924
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 924
tccatgaggg gcctgatgct                                                     20

<210> SEQ ID NO 925
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 925
tccatgtggg gcctgctgat                                                     20

<210> SEQ ID NO 926

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 926
atggactctc cggggttctc                                                  20

<210> SEQ ID NO 927
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 927
atggaaggtc cggggttctc                                                  20

<210> SEQ ID NO 928
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 928
atggactctg gagggtctc                                                   20

<210> SEQ ID NO 929
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 929
atggaggctc catggggctc                                                  20

<210> SEQ ID NO 930
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 930
atggactctg ggggttctc                                                   20

<210> SEQ ID NO 931
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 931
tccatgtggg tggggatgct                                                  20

<210> SEQ ID NO 932
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 932
```
tccatgcggg tgggatgct                                              20

<210> SEQ ID NO 933
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 933
tccatggggg tcctgatgct                                              20

<210> SEQ ID NO 934
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 934
tccatggggt ccctgatgct                                              20

<210> SEQ ID NO 935
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 935
tccatggggt gcctgatgct                                              20

<210> SEQ ID NO 936
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 936
tccatggggt tcctgatgct                                              20

<210> SEQ ID NO 937
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 937
tccatcgggg gcctgatgct                                              20

<210> SEQ ID NO 938
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 938
gctagaggga gtgt                                                    14

<210> SEQ ID NO 939
<211> LENGTH: 18
<212> TYPE: DNA

<213> ORGANISM: Artificial Sequence
<220> FEATURE:
<223> OTHER INFORMATION: Synthetic Sequence

<400> SEQUENCE: 939
tttttttttt tttttttt                                              18

<210> SEQ ID NO 940
<211> LENGTH: 21
<212> TYPE: DNA
<213> ORGANISM: Artificial Sequence
<220> FEATURE:
<221> NAME/KEY: misc_difference
<222> LOCATION: (2)...(2)
<223> OTHER INFORMATION: m is a or c
<221> NAME/KEY: misc_difference
<222> LOCATION: (18)...(18)
<223> OTHER INFORMATION: m is a or c
<220> FEATURE:
<223> OTHER INFORMATION: Synthetic Sequence

<400> SEQUENCE: 940
gmggtcaacg ttgagggmgg g                                          21

<210> SEQ ID NO 941
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 941
ggggagttcg ttgagggggg g                                          21

<210> SEQ ID NO 942
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 942
tcgtcgtttc cccccccccc                                            20

<210> SEQ ID NO 943
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 943 ttgggggtt ttttttttt ttttt                                        25

<210> SEQ ID NO 944
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 944
tttaaatttt aaaatttaaa ata                                        23

<210> SEQ ID NO 945
<211> LENGTH: 24
<212> TYPE: DNA

```
<213> ORGANISM: Artificial Sequence
<220> FEATURE:
<223> OTHER INFORMATION: Synthetic Sequence

<400> SEQUENCE: 945 ttggttttt tggtttttt ttgg                                          24

<210> SEQ ID NO 946
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 946
tttccctttt cccctttcc cctc                                         24

<210> SEQ ID NO 947
<211> LENGTH: 21
<212> TYPE: DNA
<213> ORGANISM: Artificial Sequence
<220> FEATURE:
<221> NAME/KEY: misc_difference
<222> LOCATION: (21)...(21)
<223> OTHER INFORMATION: s is g or c
<220> FEATURE:
<223> OTHER INFORMATION: Synthetic Sequence

<400> SEQUENCE: 947
ggggtcatcg atgagggggg s                                           21

<210> SEQ ID NO 948
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 948
tccatgacgt tcctgacgtt                                             20

<210> SEQ ID NO 949
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 949
tccatgacgt tcctgacgtt                                             20

<210> SEQ ID NO 950
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 950
tccatgacgt tcctgacgtt                                             20

<210> SEQ ID NO 951
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 951
tccatgacgt tcctgacgtt					20

<210> SEQ ID NO 952
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 952
tccatgacgt tcctgacgtt					20

<210> SEQ ID NO 953
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 953
tccatgacgt tcctgacgtt					20

<210> SEQ ID NO 954
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 954
tccatgacgt tcctgacgtt					20

<210> SEQ ID NO 955
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 955
tccatgacgt tcctgacgtt					20

<210> SEQ ID NO 956
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 956
tccatgacgt tcctgacgtt					20

<210> SEQ ID NO 957
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 957
tccatgacgt tcctgacgtt					20

<210> SEQ ID NO 958

```
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 958
tccatgacgt tcctgacgtt                                              20

<210> SEQ ID NO 959
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 959
gggggacgat cgtcggggg                                               19

<210> SEQ ID NO 960
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 960
gggggtcgta cgacggggg                                               20

<210> SEQ ID NO 961
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 961
tttttttttt tttttttttt tttt                                         24

<210> SEQ ID NO 962
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 962
aaaaaaaaaa aaaaaaaaaa aaaa                                         24

<210> SEQ ID NO 963
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 963
cccccccccc cccccccccc cccc                                         24

<210> SEQ ID NO 964
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 964
```

```
tcgtcgtttt gtcgttttgt cgtt                                          24

<210> SEQ ID NO 965
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 965
tcgtcgtttt gtcgttttgt cgtt                                          24

<210> SEQ ID NO 966
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 966
tcgtcgtttt gtcgttttgt cgtt                                          24

<210> SEQ ID NO 967
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 967
tcgtcgtttt gtcgttttgt cgtt                                          24

<210> SEQ ID NO 968
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 968
ggggtcaacg ttgagggggg                                               20

<210> SEQ ID NO 969
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 969
ggggtcaacg ttgagggggg                                               20

<210> SEQ ID NO 970
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 970
ggggtcaagc ttgagggggg                                               20

<210> SEQ ID NO 971
<211> LENGTH: 20
<212> TYPE: DNA
```

```
<213> ORGANISM: Artificial Sequence
<220> FEATURE:
<223> OTHER INFORMATION: Synthetic Sequence

<400> SEQUENCE: 971
tgctgcttcc cccccccccc                                              20

<210> SEQ ID NO 972
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 972
ggggacgtcg acgtgggggg                                              20

<210> SEQ ID NO 973
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 973
ggggtcgtcg acgaggggggg                                             20

<210> SEQ ID NO 974
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 974
ggggtcgacg tacgtcgagg gggg                                         24

<210> SEQ ID NO 975
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 975
ggggaccggt accggtgggg gg                                           22

<210> SEQ ID NO 976
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 976
gggtcgacgt cgaggggggg                                              19

<210> SEQ ID NO 977
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 977
ggggtcgacg tcgaggggg                                               19
```

<210> SEQ ID NO 978
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 978
ggggaacgtt aacgttgggg gg                                    22

<210> SEQ ID NO 979
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 979
ggggtcaccg gtgagggggg                                       20

<210> SEQ ID NO 980
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 980
ggggtcgttc gaacgagggg gg                                    22

<210> SEQ ID NO 981
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 981
ggggacgttc gaacgtgggg gg                                    22

<210> SEQ ID NO 982
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 982
tcaactttga                                                  10

<210> SEQ ID NO 983
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 983
tcaagcttga                                                  10

<210> SEQ ID NO 984
<211> LENGTH: 12
<212> TYPE: DNA
<213> ORGANISM: Artificial Sequence
<220> FEATURE:

```
<223> OTHER INFORMATION: Synthetic Sequence

<400> SEQUENCE: 984
tcacgatcgt ga                                                           12

<210> SEQ ID NO 985
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 985
tcagcatgct ga                                                           12

<210> SEQ ID NO 986
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 986
gggggagcat gctggggggg                                                   20

<210> SEQ ID NO 987
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 987
gggggggggg gggggggggg                                                   20

<210> SEQ ID NO 988
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 988
gggggacgat atcgtcgggg gg                                                22

<210> SEQ ID NO 989
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 989
gggggacgac gtcgtcgggg gg                                                22

<210> SEQ ID NO 990
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 990
gggggacgag ctcgtcgggg gg                                                22
```

```
<210> SEQ ID NO 991
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 991
gggggacgta cgtcggggggg                                          20

<210> SEQ ID NO 992
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 992 tcaacgtt                                                         8

<210> SEQ ID NO 993
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 993
tccataccgg tcctgatgct                                           20

<210> SEQ ID NO 994
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 994
tccataccgg tcctaccggt                                           20

<210> SEQ ID NO 995
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 995
gggggacgat cgttgggggg                                           20

<210> SEQ ID NO 996
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 996
ggggaacgat cgtcgggggg                                           20

<210> SEQ ID NO 997
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 997 gggggacga tcgtcggggg g                                    21

<210> SEQ ID NO 998
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 998 ggggacgat cgtcggggg g                                     21

<210> SEQ ID NO 999
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 999
aaagacgtta aa                                             12

<210> SEQ ID NO 1000
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1000
aaagagctta aa                                             12

<210> SEQ ID NO 1001
<211> LENGTH: 12
<212> TYPE: DNA
<213> ORGANISM: Artificial Sequence
<220> FEATURE:
<221> NAME/KEY: modified_base
<222> LOCATION: (6)...(6)
<223> OTHER INFORMATION: m5c
<220> FEATURE:
<223> OTHER INFORMATION: Synthetic Sequence

<400> SEQUENCE: 1001
aaagangtta aa                                             12

<210> SEQ ID NO 1002
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1002
aaattcggaa aa                                             12

<210> SEQ ID NO 1003
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1003 ggggtcatc gatgagggg g                                     21
```

<210> SEQ ID NO 1004
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1004
gggggtcaac gttgaggggg g                                       21

<210> SEQ ID NO 1005
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1005
atgtagctta ataacaaagc                                         20

<210> SEQ ID NO 1006
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1006
ggatcccttg agttacttct                                         20

<210> SEQ ID NO 1007
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1007
ccattccact tctgattacc                                         20

<210> SEQ ID NO 1008
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1008
tatgtattat catgtagata                                         20

<210> SEQ ID NO 1009
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1009
agcctacgta ttcaccctcc                                         20

<210> SEQ ID NO 1010
<211> LENGTH: 20
<212> TYPE: DNA
<213> ORGANISM: Artificial Sequence
<220> FEATURE:

```
<223> OTHER INFORMATION: Synthetic Sequence

<400> SEQUENCE: 1010
ttcctgcaac tactattgta                                        20

<210> SEQ ID NO 1011
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1011
atagaaggcc ctacaccagt                                        20

<210> SEQ ID NO 1012
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1012
ttacaccggt ctatggaggt                                        20

<210> SEQ ID NO 1013
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1013
ctaaccagat caagtctagg                                        20

<210> SEQ ID NO 1014
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1014
cctagacttg atctggttag                                        20

<210> SEQ ID NO 1015
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1015
tataagcctc gtccgacatg                                        20

<210> SEQ ID NO 1016
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1016
catgtcggac gaggcttata                                        20
```

```
<210> SEQ ID NO 1017
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1017
tggtggtggg gagtaagctc                                              20

<210> SEQ ID NO 1018
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1018
gagctactcc cccaccacca                                              20

<210> SEQ ID NO 1019
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1019
gccttcgatc ttcgttggga                                              20

<210> SEQ ID NO 1020
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1020
tggacttctc tttgccgtct                                              20

<210> SEQ ID NO 1021
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1021
atgctgtagc ccagcgataa                                              20

<210> SEQ ID NO 1022
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1022
accgaatcag cggaaagtga                                              20

<210> SEQ ID NO 1023
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 1023
tccatgacgt tcctgacgtt                                            20

<210> SEQ ID NO 1024
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1024
ggagaaaccc atgagctcat ctgg                                       24

<210> SEQ ID NO 1025
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1025
accacagacc agcaggcaga                                            20

<210> SEQ ID NO 1026
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1026
gagcgtgaac tgcgcgaaga                                            20

<210> SEQ ID NO 1027
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1027
tcggtaccct tgcagcggtt                                            20

<210> SEQ ID NO 1028
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1028
ctggagccct agccaaggat                                            20

<210> SEQ ID NO 1029
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1029
gcgactccat caccagcgat                                            20

<210> SEQ ID NO 1030
<211> LENGTH: 21

```
<212> TYPE: DNA
<213> ORGANISM: Artificial Sequence
<220> FEATURE:
<223> OTHER INFORMATION: Synthetic Sequence

<400> SEQUENCE: 1030
cctgaagtaa gaaccagatg t                                              21

<210> SEQ ID NO 1031
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1031
ctgtgttatc tgacatacac c                                              21

<210> SEQ ID NO 1032
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1032
aattagcctt aggtgattgg g                                              21

<210> SEQ ID NO 1033
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1033
acatctggtt cttacttcag g                                              21

<210> SEQ ID NO 1034
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 1034
ataagtcata ttttgggaac tac                                            23

<210> SEQ ID NO 1035
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1035
cccaatcacc taaggctaat t                                              21

<210> SEQ ID NO 1036
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1036
```

| | |
|---|---|
| ggggtcgtcg acgaggggggg | 20 |

<210> SEQ ID NO 1037
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1037

| | |
|---|---|
| ggggtcgttc gaacgagggg gg | 22 |

<210> SEQ ID NO 1038
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1038

| | |
|---|---|
| ggggacgttc gaacgtgggg gg | 22 |

<210> SEQ ID NO 1039
<211> LENGTH: 15
<212> TYPE: DNA
<213> ORGANISM: Artificial Sequence
<220> FEATURE:
<221> NAME/KEY: modified_base
<222> LOCATION: (9)...(9)
<223> OTHER INFORMATION: n is 5-methylcytosine.
<220> FEATURE:
<223> OTHER INFORMATION: Synthetic Sequence

<400> SEQUENCE: 1039

| | |
|---|---|
| tcctggcgng gaagt | 15 |

<210> SEQ ID NO 1040
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1040

| | |
|---|---|
| ggggaacgac gtcgttgggg gg | 22 |

<210> SEQ ID NO 1041
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1041

| | |
|---|---|
| ggggaacgta cgtcggggggg | 20 |

<210> SEQ ID NO 1042
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1042

| | |
|---|---|
| ggggaacgta cgtacgttgg gggg | 24 |

```
<210> SEQ ID NO 1043
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1043
ggggtcaccg gtgaggggg                                                    20

<210> SEQ ID NO 1044
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1044
ggggtcgacg tacgtcgagg gggg                                              24

<210> SEQ ID NO 1045
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1045
ggggaccggt accggtgggg gg                                                22

<210> SEQ ID NO 1046
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1046
gggtcgacgt cgaggggg                                                     19

<210> SEQ ID NO 1047
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1047
ggggtcgacg tcgagggg                                                     18

<210> SEQ ID NO 1048
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 1048
ggggaacgtt aacgttgggg gg                                                22

<210> SEQ ID NO 1049
<211> LENGTH: 19
<212> TYPE: DNA
<213> ORGANISM: Artificial Sequence
<220> FEATURE:
<223> OTHER INFORMATION: Synthetic Sequence
```

```
<400> SEQUENCE: 1049
ggggacgtcg acgtggggg                                           19

<210> SEQ ID NO 1050
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 1050
gcactcttcg aagctacagc cggcagcctc tgat                          34

<210> SEQ ID NO 1051
<211> LENGTH: 32
<212> TYPE: DNA
<213> ORGANISM: Artificial Sequence
<220> FEATURE:
<223> OTHER INFORMATION: Synthetic Sequence

<400> SEQUENCE: 1051
cggctcttcc atgaggtctt tgctaatctt gg                            32

<210> SEQ ID NO 1052
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 1052
cggctcttcc atgaaagtct ttggacgatg tgagc                         35

<210> SEQ ID NO 1053
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1053
tcctgcaggt taagt                                               15

<210> SEQ ID NO 1054
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1054
gggggtcgtt cgttgggggg                                          20

<210> SEQ ID NO 1055
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1055
gggggatgat tgttgggggg                                          20

<210> SEQ ID NO 1056
<211> LENGTH: 20
```

```
<212> TYPE: DNA
<213> ORGANISM: Artificial Sequence
<220> FEATURE:
<221> NAME/KEY: modified_base
<222> LOCATION: (7)...(7)
<223> OTHER INFORMATION: m5c
<221> NAME/KEY: modified_base
<222> LOCATION: (11)...(11)
<223> OTHER INFORMATION: m5c
<220> FEATURE:
<223> OTHER INFORMATION: Synthetic Sequence

<400> SEQUENCE: 1056
gggggangat ngttgggggg                                            20

<210> SEQ ID NO 1057
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1057
gggggagcta gcttgggggg                                            20

<210> SEQ ID NO 1058
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1058
ggttcttttg gtccttgtct                                            20

<210> SEQ ID NO 1059
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1059
ggttcttttg gtcctcgtct                                            20

<210> SEQ ID NO 1060
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1060
ggttcttttg gtccttatct                                            20

<210> SEQ ID NO 1061
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1061
ggttcttggt ttccttgtct                                            20

<210> SEQ ID NO 1062
<211> LENGTH: 20
```

```
<212> TYPE: DNA
<213> ORGANISM: Artificial Sequence
<220> FEATURE:
<223> OTHER INFORMATION: Synthetic Sequence

<400> SEQUENCE: 1062
tggtcttttg gtccttgtct                                               20

<210> SEQ ID NO 1063
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1063
ggttcaaatg gtccttgtct                                               20

<210> SEQ ID NO 1064
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1064
gggtcttttg ggccttgtct                                               20

<210> SEQ ID NO 1065
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1065
tccaggactt ctctcaggtt tttt                                          24

<210> SEQ ID NO 1066
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1066
tccaaaactt ctctcaaatt                                               20

<210> SEQ ID NO 1067
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1067
tactactttt atacttttat actt                                          24

<210> SEQ ID NO 1068
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1068
```

-continued

```
tgtgtgtgtg tgtgtgtgtg tgtg                                          24

<210> SEQ ID NO 1069
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 1069
ttgttgttgt tgtttgttgt tgttg                                         25

<210> SEQ ID NO 1070
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 1070
ggctccgggg agggaatttt tgtctat                                       27

<210> SEQ ID NO 1071
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1071
gggacgatcg tcggggggg                                                19

<210> SEQ ID NO 1072
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1072
gggtcgtcga cgagggggggg                                              20

<210> SEQ ID NO 1073
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 1073
ggtcgtcgac gagggggggg                                               19

<210> SEQ ID NO 1074
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1074
gggtcgtcgt cgtggggggg                                               20

<210> SEQ ID NO 1075
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 1075
ggggacgatc gtcggggggg                                         20

<210> SEQ ID NO 1076
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1076
ggggacgtcg tcgtggggggg                                        20

<210> SEQ ID NO 1077
<211> LENGTH: 27
<212> TYPE: DNA
<213> ORGANISM: Artificial Sequence
<220> FEATURE:
<223> OTHER INFORMATION: Synthetic Sequence

<400> SEQUENCE: 1077
ggggtcgacg tcgacgtcga gggggggg                                27

<210> SEQ ID NO 1078
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1078
ggggaaccgc ggttggggggg g                                      21

<210> SEQ ID NO 1079
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1079
ggggacgacg tcgtggggggg g                                      21

<210> SEQ ID NO 1080
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 1080
tcgtcgtcgt cgtcgtgggg ggg                                     23

<210> SEQ ID NO 1081
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1081
tcctgccggg gaagt                                              15
```

```
<210> SEQ ID NO 1082
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1082
tcctgcaggg gaagt                                                    15

<210> SEQ ID NO 1083
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1083
tcctgaaggg gaagt                                                    15

<210> SEQ ID NO 1084
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1084
tcctggcggg caagt                                                    15

<210> SEQ ID NO 1085
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1085
tcctggcggg taagt                                                    15

<210> SEQ ID NO 1086
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1086
tcctggcggg aaagt                                                    15

<210> SEQ ID NO 1087
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1087
tccgggcggg gaagt                                                    15

<210> SEQ ID NO 1088
<211> LENGTH: 15
<212> TYPE: DNA
<213> ORGANISM: Artificial Sequence
<220> FEATURE:
<223> OTHER INFORMATION: Synthetic Sequence
```

```
<400> SEQUENCE: 1088
tcggggcggg gaagt                                                    15

<210> SEQ ID NO 1089
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1089
tcccggcggg gaagt                                                    15

<210> SEQ ID NO 1090
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 1090
gggggacgtt ggggg                                                    15

<210> SEQ ID NO 1091
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1091
ggggtttttt ttttggggggg                                              20

<210> SEQ ID NO 1092
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1092
ggggcccccc ccccggggggg                                              20

<210> SEQ ID NO 1093
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 1093
ggggttgttg ttgttggggg g                                             21

<210> SEQ ID NO 1094
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1094
tttttttttt tttttttttt tttttttttt                                    30

<210> SEQ ID NO 1095
```

```
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1095
aaaaaaaaaa aaaaaaaaaa aaaaaaaaaa                                    30

<210> SEQ ID NO 1096
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1096
cccccccccc cccccccccc cccccccccc                                    30

<210> SEQ ID NO 1097
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 1097
cgcgcgcgcg cgcgcgcgcg cgcgcgcgcg                                    30

<210> SEQ ID NO 1098
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1098
gattttatcg tc                                                       12

<210> SEQ ID NO 1099
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1099 tcgattttc ga                                                        12

<210> SEQ ID NO 1100
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1100
tcatttttat ga                                                       12

<210> SEQ ID NO 1101
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1101
``` gtttttttacg ac                                              12

<210> SEQ ID NO 1102
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1102
tcaatttttt ga                                               12

<210> SEQ ID NO 1103
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1103 acgttttttac gt                                              12

<210> SEQ ID NO 1104
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1104 tcgttttttac ga                                              12

<210> SEQ ID NO 1105
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 1105
tcgattttta cgtcga                                           16

<210> SEQ ID NO 1106
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1106
aattttttaa cgtt                                             14

<210> SEQ ID NO 1107
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1107
tcgtttttta acga                                             14

<210> SEQ ID NO 1108
<211> LENGTH: 14
<212> TYPE: DNA

```
<213> ORGANISM: Artificial Sequence
<220> FEATURE:
<223> OTHER INFORMATION: Synthetic Sequence

<400> SEQUENCE: 1108 acgttttta acgt                                                      14

<210> SEQ ID NO 1109
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 1109
gatttttatc gtc                                                      13

<210> SEQ ID NO 1110
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1110
gacgattttt cgtc                                                     14

<210> SEQ ID NO 1111
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1111
gattttagct cgtc                                                     14

<210> SEQ ID NO 1112
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1112
gatttttacg tc                                                       12

<210> SEQ ID NO 1113
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1113
attttatcgt                                                          10

<210> SEQ ID NO 1114
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1114
aacgattttt cgtt                                                     14
```

<210> SEQ ID NO 1115
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1115
tcacttttgt ga                                                          12

<210> SEQ ID NO 1116
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1116
tcgtatttta                                                             10

<210> SEQ ID NO 1117
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1117
acttttgtac cggt                                                        14

<210> SEQ ID NO 1118
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 1118 tcgattttttc gacgtcga                                                   18

<210> SEQ ID NO 1119
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1119 acgattttttc gt                                                         12

<210> SEQ ID NO 1120
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1120
gatgatcgtc                                                             10

<210> SEQ ID NO 1121
<211> LENGTH: 10
<212> TYPE: DNA
<213> ORGANISM: Artificial Sequence
<220> FEATURE:

```
<223> OTHER INFORMATION: Synthetic Sequence

<400> SEQUENCE: 1121
tcgatgtcga                                                          10

<210> SEQ ID NO 1122
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1122
tcatgtatga                                                          10

<210> SEQ ID NO 1123
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1123
gtgttacgac                                                          10

<210> SEQ ID NO 1124
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1124
tcaatgttga                                                          10

<210> SEQ ID NO 1125
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1125
acgtgtacgt                                                          10

<210> SEQ ID NO 1126
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1126
tcgtgtacga                                                          10

<210> SEQ ID NO 1127
<211> LENGTH: 14
<212> TYPE: DNA
<213> ORGANISM: Artificial Sequence
<220> FEATURE:
<223> OTHER INFORMATION: Synthetic Sequence

<400> SEQUENCE: 1127
tcgatgtacg tcga                                                     14
```

<210> SEQ ID NO 1128
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1128
aatgttaacg tt                                                             12

<210> SEQ ID NO 1129
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1129
tcgtgttaac ga                                                             12

<210> SEQ ID NO 1130
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1130
acgtgttaac gt                                                             12

<210> SEQ ID NO 1131
<211> LENGTH: 11
<212> TYPE: DNA
<213> ORGANISM: Artificial Sequence
<220> FEATURE:
<223> OTHER INFORMATION: Synthetic Sequence

<400> SEQUENCE: 1131
gatgtatcgt c                                                              11

<210> SEQ ID NO 1132
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1132
gacgatgtcg tc                                                             12

<210> SEQ ID NO 1133
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1133
gatgagctcg tc                                                             12

<210> SEQ ID NO 1134
<211> LENGTH: 10
<212> TYPE: DNA
<213> ORGANISM: Artificial Sequence
<220> FEATURE:
<223> OTHER INFORMATION: Synthetic Sequence -continued

```
<400> SEQUENCE: 1134
gatgtacgtc                                                            10

<210> SEQ ID NO 1135
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 1135 atgatcgt                                                              8

<210> SEQ ID NO 1136
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1136
aacgatgtcg tt                                                         12

<210> SEQ ID NO 1137
<211> LENGTH: 10
<212> TYPE: DNA
<213> ORGANISM: Artificial Sequence
<220> FEATURE:
<223> OTHER INFORMATION: Synthetic Sequence

<400> SEQUENCE: 1137
tcactggtga                                                            10

<210> SEQ ID NO 1138
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 1138 tcgtatga                                                              8

<210> SEQ ID NO 1139
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 1139
actggtaccg gt                                                         12

<210> SEQ ID NO 1140
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 1140
tcgatgtcga cgtcga                                                     16

<210> SEQ ID NO 1141
<211> LENGTH: 10
```

```
<212> TYPE: DNA
<213> ORGANISM: Artificial Sequence
<220> FEATURE:
<223> OTHER INFORMATION: Synthetic Sequence

<400> SEQUENCE: 1141
acgatgtcgt                                                              10

<210> SEQ ID NO 1142
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 1142
tgcaggaagt ccgggttttc cccaacccccc c                                     31

<210> SEQ ID NO 1143
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 1143 gacgtt                                                                  6

<210> SEQ ID NO 1144
<211> LENGTH: 6
<212> TYPE: DNA
<213> ORGANISM: Artificial Sequence
<220> FEATURE:
<223> OTHER INFORMATION: Synthetic Sequence

<400> SEQUENCE: 1144 gtcgtt                                                                  6

<210> SEQ ID NO 1145
<211> LENGTH: 8
<212> TYPE: DNA
<213> ORGANISM: Artificial Sequence
<220> FEATURE:
<223> OTHER INFORMATION: Synthetic Sequence

<400> SEQUENCE: 1145 tcgtcgtt                                                                8
```

IMMUNOSTIMULATORY NUCLEIC ACIDS

RELATED APPLICATIONS

This application claims priority to U.S. Non-Provisional Patent Application No. 09/669,187, filed Sep. 25, 2000, which claims priority under 35 U.S.C. §119 to U.S. Provisional Patent Application Nos. 60/156,113, filed Sep. 25, 1999, 60/156,135, filed Sep. 27, 1999, and No. 60/227,436, filed Aug. 23, 2000, the entire contents of which are hereby incorporated by reference.

FIELD OF THE INVENTION

The present invention relates generally to immunostimulatory nucleic acids, compositions thereof and methods of using the immunostimulatory nucleic acids.

BACKGROUND OF THE INVENTION

Bacterial DNA has immune stimulatory effects to activate B cells and natural killer cells, but vertebrate DNA does not (Tokunaga, T., et al., 1988. Jpn. J. Cancer Res. 79:682-686; Tokunaga, T., et al., 1984, JNCI 72:955-962; Messina, J. P., et al., 1991, J. Immunol. 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are essentially abolished if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10). Phosphodiester CpG ODN can be formulated in lipids, alum, or other types of vehicles with depot properties or improved cell uptake in order to enhance the immune stimulatory effects (Yamamoto et al, 1994 Microbiol. Immunol. 38:831-836; Gramzinski et al, 1998 Mol. Med. 4:109-118).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129).

Several past investigators have looked at whether the nucleotide content of ODN may have effects independently of the sequence of the ODN. Interestingly, antisense ODN have been found to be generally enriched in the content of GG, CCC, CC, CAC, and CG sequences, while having reduced frequency of TT or TCC nucleotide sequences compared to what would be expected if base usage were random (Smetsers et al., 1996 Antisense Nucleic Acid Drug Develop. 6:63-67). This raised the possibility that the over-represented sequences may comprise preferred targeting elements for antisense oligonucleotides or visa versa. One reason to avoid the use of thymidine-rich ODN for antisense experiments is that degradation of the ODN by nucleases present in cells releases free thymidine which competes with $^3$H-thymidine which is frequently used in experiments to assess cell proliferation (Matson et al., 1992 Antisense Research and Development 2:325-330).

SUMMARY OF THE INVENTION

The present invention relates in part to pyrimidine rich (Py-rich) and in some embodiments thymidine (T) rich immunostimulatory nucleic acids which do not require the presence of a CpG motif. The present invention also relates in part to the discovery that nucleic acids which contain a TG dinucleotide motif are also immunostimulatory. The invention is based in part on the unexpected finding that nucleic acid sequences which do not contain CpG motifs are immunostimulatory. It was discovered upon analysis of the immune stimulation properties of many nucleic acid sequences that these sequences may be Py-rich e.g., T-rich or that they may contain TG motifs. It was also discovered that these sequences preferentially activate non-rodent immune cells. The Py-rich and TG sequences are only minimally immunostimulatory with respect to rodent immune cells, compared to non-rodent immune cells. Thus, it is possible according to the methods of the invention to induce an immune response in a non-rodent subject by administering Py-rich or TG immunostimulatory nucleic acids. The Py-rich and TG immunostimulatory nucleic acids of the invention may optionally include CpG motifs. These findings have important implications for the clinical development of immunostimulatory CpG containing and non-CpG containing nucleic acids.

In one aspect the invention is a pharmaceutical composition comprising an effective amount for stimulating an immune response of isolated Py-rich or TG immunostimulatory nucleic acids, and a pharmaceutically acceptable carrier. In other aspects the invention is a composition of matter, comprising an isolated Py-rich or TG immunostimulatory nucleic acid. In other embodiments, the immunostimulatory nucleic acid may be T-rich. In still other embodiments, the immunostimulatory nucleic acid may be T-rich and also have at least one TG motif.

Preferably the Py-rich nucleic acid is a T-rich nucleic acid. In some embodiments the T-rich immunostimulatory nucleic acid is a poly T nucleic acid comprising 5' TTTT 3'. In yet other embodiments the poly T nucleic acid comprises 5' $X_1X_2$TTTT$X_3X_4$ 3' wherein $X_1$, $X_2$, $X_3$ and $X_4$ are nucleotides. In some embodiments $X_1X_2$ is TT and/or $X_3X_4$ is TT. In other embodiments $X_1X_2$ is selected from the group consisting of TA, TG, TC, AT, AA, AG, AC, CT, CC, CA, CG, GT, GG, GA, and GC; and/or $X_3X_4$ is selected from the group consisting of TA, TG, TC, AT, AA, AG, AC, CT, CC, CA, CG, GT, GG, GA, and GC.

The T-rich immunostimulatory nucleic acid may have only a single poly T motif or it may have a plurality of poly T nucleic acid motifs. In some embodiments the T-rich immunostimulatory nucleic acid comprises at least 2, at least 3, at least 4, at least 5, at least 6, at least 7, or at least 8 T motifs. In other embodiments it comprises at least 2, at least 3, at least 4, at least 5, at least 6, at least 7, or at least 8 CpG motifs. In preferred embodiments the plurality of CpG motifs and poly T motifs are interspersed.

In yet other embodiments at least one of the plurality of poly T motifs comprises at least 3, at least 4, at least 5, at least 6, at least 7, at least 8, or at least 9 contiguous T nucleotide residues. In other embodiments the plurality of poly T motifs is at least 3 motifs and wherein at least 3 motifs each comprises at least 3 contiguous T nucleotide residues or the plurality of poly T motifs is at least 4 motifs and wherein the at least 4 motifs each comprises at least 3 contiguous T nucleotide residues.

In some cases the T-rich immunostimulatory nucleic acid may be free of poly T motifs but may rather comprise a nucleotide composition of greater than 25% T. In other embodiments the T-rich immunostimulatory nucleic acids have poly T motifs and also comprise a nucleotide composition of greater than 25% T. In preferred embodiments the T-rich immunostimulatory nucleic acid comprises a nucleotide composition of greater than 35% T, greater than 40% T, greater than 50% T, greater than 60% T, greater than 80% T, or greater than 90% T nucleotide residues. In important embodiments, the nucleic acid is at least 50% T.

The T-rich and TG immunostimulatory nucleic acids can have any length greater than 7 nucleotides, but in some embodiments can be between 8 and 100 nucleotide residues in length. In preferred embodiments the T-rich immunostimulatory nucleic acid comprises at least 20 nucleotides, at least 24 nucleotides, at least 27, nucleotides, or at least 30 nucleotides. In preferred embodiments, the TG immunostimulatory nucleic acid is between 15 and 25 nucleotides in length. The T-rich and TG immunostimulatory nucleic acids may be single stranded or double stranded.

In one preferred embodiment, the immunostimulatory nucleic acid has a T-rich region located in the middle of its length (i.e., an approximately equal number of nucleotides flank the T-rich region on the 5' and 3' ends).

The T rich nucleic acid in some embodiments is selected from the group consisting of SEQ ID NO: 59-63, 73-75, 142, 215, 226, 241, 267-269, 282, 301, 304, 330, 342, 358, 370-372, 393, 433, 471, 479, 486, 491, 497, 503, 556-558, 567, 694, 793-794, 797, 833, 852, 861, 867, 868, 882, 886, 905, 907, 908, and 910-913. In other embodiments the T rich nucleic acids are sequence selected from the group consisting of SEQ ID NO: 64, 98, 112, 146, 185, 204, 208, 214, 224, 233, 244, 246, 247, 258, 262, 263, 265, 270-273, 300, 305, 316, 317, 343, 344, 350, 352, 354, 374, 376, 392, 407, 411-413, 429-432, 434, 435, 443, 474, 475, 498-501, 518, 687, 692, 693, 804, 862, 883, 884, 888, 890, and 891.

In other embodiments the Py-rich immunostimulatory nucleic acid is a C-rich nucleic acid. An immunostimulatory C-rich nucleic acid is a nucleic acid including at least one and preferably at least 2 poly-C regions or which includes 50% or greater C nucleotides.

The Py-rich and TG immunostimulatory nucleic acids may include one or more CpG motifs. The motifs may be methylated or unmethylated. In other embodiments the Py-rich and TG immunostimulatory nucleic acids are free of one or more CpG dinucleotides.

In other embodiments the Py-rich and TG immunostimulatory nucleic acids also include poly-A, poly G, and/or poly C motifs. In yet other embodiments the Py-rich or TG immunostimulatory nucleic acid is free of two poly C sequences of at least 3 contiguous C nucleotide residues or is free of two poly A sequences of at least 3 contiguous A nucleotide residues. In other embodiments the Py-rich or TG immunostimulatory nucleic acid comprises a nucleotide composition of greater than 25% C or greater than 25% A. In yet other embodiments the Py-rich or TG immunostimulatory nucleic acid is free of poly-C sequences, poly-G sequences or poly-A sequences.

A poly G nucleic acid in some embodiments is selected from the group consisting of SEQ ID NO: 5, 6, 73, 215, 267-269, 276, 282, 288, 297-299, 355, 359, 386, 387, 444, 476, 531, 557-559, 733, 768, 795, 796, 914-925, 928-931, 933-936, and 938. In other embodiments the poly G nucleic acid includes a sequence selected from the group consisting of SEQ ID NO: 67, 80-82, 141, 147, 148, 173, 178, 183, 185, 214, 224, 264, 265, 315, 329, 434, 435, 475, 519, 521-524, 526, 527, 535, 554, 565, 609, 628, 660, 661, 662, 725, 767, 825, 856, 857, 876, 892, 909, 926, 927, 932, and 937.

According to another aspect of the invention, the immunostimulatory nucleic acids may be defined as those which possess a TG motif, herein referred to as TG immunostimulatory nucleic acids. The TG nucleic acid in one embodiment contains at least one TG dinucleotide having a sequence including at least the following formula: 5'$N_1X_1TGX_2N_2$3'. In related embodiments, $N_1$ is a nucleic acid sequence composed of a number of nucleotides ranging from $(11-N_2)$ to $(21-N_2)$ and $N_2$ is a nucleic acid sequence composed of a number of nucleotides ranging from $(11-N_1)$ to $(21-N_1)$. In a preferred embodiment, $X_2$ is thymidine.

In other embodiments, the TG nucleic acid has at least the following formula: 5' $X_1$ $X_2TGX_3$ $X_4$ 3'. In yet another embodiment, the TG nucleic acid comprises the following sequence: 5'$N_1X_1X_2TGX_3X_4N_2$3'. In a related embodiment, $N_1$ is a nucleic acid sequence composed of a number of nucleotides ranging from $(9-N_2)$ to $(19-N_2)$ and $N_2$ is a nucleic acid sequence composed of a number of nucleotides ranging from $(9-N_1)$ to $(19-N_1)$. In one preferred embodiment, $X_3$ is thymidine. $X_1X_2$ are nucleotides which may be selected from the group consisting of GT, GG, GA, AA, AT, AG, CT, CA, CG, TA and TT, and $X_3X_4$ are nucleotides which may be selected from the group consisting of TT, CT, AT, AG, CG, TC, AC, CC, TA, AA, and CA. In some preferred embodiments, $X_3$ is a thymidine. In important embodiments, $X_3X_4$ are nucleotides selected from the group consisting of TT, TC, TA and TG. In other embodiments $X_1X_2$ are GA or GT and $X_3X_4$ are TT. In yet other embodiments $X_1$ or $X_2$ or both are purines and $X_3$ or $X_4$ or both are pyrimidines or $X_1X_2$ are GpA and $X_3$ or $X_4$ or both are pyrimidines. In one embodiment $X_2$ is a T and $X_3$ is a pyrimidine.

In one embodiment the 5' $X_1$ $X_2TGX_3X_4$ 3' sequence of the TG nucleic acid or the entire length or some fragment thereof of the TG nucleic acid is a non-palindromic sequence, and in other embodiments it is a palindromic sequence.

In some preferred embodiments, the TG nucleic acid is also T-rich.

The Py-rich and TG immunostimulatory nucleic acids in some embodiments have a nucleotide backbone which includes at least one backbone modification, such as a phosphorothioate modification. The nucleotide backbone may be chimeric, or preferably the nucleotide backbone is entirely modified. In one preferred embodiment, the immunostimulatory nucleic acid has a poly T motif and a phosphorothioate backbone.

In another aspect the invention is a composition of an immunostimulatory nucleic acid, in the form of a Py-rich or a TG nucleic acid, and an antigen, wherein the nucleic acid is free of unmethylated CpG motifs.

Another composition of the invention is a Py-rich or TG immunostimulatory nucleic acid and an anti-microbial agent, wherein the Py-rich or TG nucleic acid is free of unmethylated CpG motifs. Preferably the anti-microbial agent is selected from the group consisting of an anti-viral agent, an anti-parasitic agent, an anti-bacterial agent and an anti-fungal agent.

A composition of a sustained release device including a Py-rich and/or TG immunostimulatory nucleic acid, wherein the Py-rich and/or TG nucleic acid is free of unmethylated CpG motifs, is provided according to another aspect of the invention.

The invention also includes nutritional supplements of a Py-rich or TG immunostimulatory nucleic acid in a delivery device selected from the group consisting of a capsule, a pill, and a sublingual tablet, wherein the Py-rich or TG nucleic acid is free of unmethylated CpG motifs.

It should be understood that when it is useful to administer a Py-rich e.g., poly T, T-rich, C-rich, or TG oligonucleotide and a CpG oligonucleotide, it may also be desirable to co-administer a Py-rich or a TG oligonucleotide together with a physically separate CpG, Py-rich or TG oligonucleotide. Alternatively, the CpG, Py-rich or TG motif may be present on the same contiguous nucleic acid as the Py-rich or TG oligonucleotide. In yet a further embodiment, all or some combination of Py-rich, TG and CpG nucleic acids may be co-administered either on separate nucleic acids or in the same nucleic acid molecule. By co-administer it is intended that the nucleic acids be administered close enough in time to one another to achieve a combined benefit of both oligonucleotides, preferably more than the benefit achieved by administering each of the oligonucleotides alone at the same dose.

CpG oligonucleotides have, in general, the formula 5'$X_1X_2CGX_3X_4$3', wherein $X_1$, $X_2$, $X_3$ and $X_4$ are nucleotides and wherein at least the C of CpG is unmethylated. Preferred CpG oligonucleotides are 8-100 nucleotides in length and have modified back bones. Particular structures are detailed in the published PCT applications, U.S. applications and references cited herein, the disclosures of which are incorporated herein in their entirety. In one embodiment, the CpG oligonucleotide is free of poly T and TG motifs and is not T-rich.

In other embodiments, the CpG oligonucleotide has a sequence selected from the group consisting of SEQ ID NO: 1, 3, 4, 14-16, 18-24, 28, 29, 33-46, 49, 50, 52-56, 58, 64-67, 69, 71, 72, 76-87, 90, 91, 93, 94, 96, 98, 102-124, 126-128, 131-133, 136-141, 146-150, 152-153, 155-171, 173-178, 180-186, 188-198, 201, 203-214, 216-220, 223, 224, 227-240, 242-256, 258, 260-265, 270-273, 275, 277-281, 286-287, 292, 295-296, 300, 302, 305-307, 309-312, 314-317, 320-327, 329, 335, 337-341, 343-352, 354, 357, 361-365, 367-369, 373-376, 378-385, 388-392, 394, 395, 399, 401-404, 406-426, 429-433, 434-437, 439, 441-443, 445, 447, 448, 450, 453-456, 460-464, 466-469, 472-475, 477, 478, 480, 483-485, 488, 489, 492, 493, 495-502, 504-505, 507-509, 511, 513-529, 532-541, 543-555, 564-566, 568-576, 578, 580, 599, 601-605, 607-611, 613-615, 617, 619-622, 625-646, 648-650, 653-664, 666-697, 699-706, 708, 709, 711-716, 718-732, 736, 737, 739-744, 746, 747, 749-761, 763, 766-767, 769, 772-779, 781-783, 785-786, 7900792, 798-799, 804-808, 810, 815, 817, 818, 820-832, 835-846, 849-850, 855-859, 862, 865, 872, 874-877, 879-881, 883-885, 888-904, and 909-913.

In another embodiment, the Py-rich or TG oligonucleotide is free of a CpG motifs. This embodiment of the invention also involves pharmaceutical compositions and kits which contain both a CpG oligonucleotide (which can be free of poly T and TG motifs and not be T-rich) and a Py-rich and/or TG oligonucleotide physically separate from the CpG oligonucleotide. The pharmaceutical preparations are in effective amounts and typically include pharmaceutically acceptable carriers, all as set forth in detail herein with respect to Py-rich and TG oligonucleotides. The kits include at least one container containing an oligonucleotide which is a Py-rich or TG oligonucleotide (or some combination thereof). The same container, or in other embodiments, a second container, may contain an oligonucleotide with a CpG motif, which may be free of Py-rich and/or TG motifs. The kit also contains instructions for administering the oligonucleotides to a subject. The kits also may include a container containing a solvent or a diluent.

In summary, as if fully recited herein, a CpG oligonucleotide physically separate from the Py-rich or TG oligonucleotide can be used together with the Py-rich or TG oligonucleotides in the methods, compositions and products described above.

The invention relates in other aspects to immunostimulatory oligonucleotides which have chimeric backbones and which do not require the presence of a CpG motif. The invention is based in part on the discovery that nucleic acid sequences which did not contain CpG motifs were immunostimulatory, and that those which have chimeric backbones have unexpectedly enhanced immune stimulating properties. Thus the invention in one aspect relates to a composition of an oligonucleotide having a formula: 5' $Y_1N_1ZN_2Y_2$ 3', wherein $Y_1$ and $Y_2$ are, independent of one another, nucleic acid molecules having between 1 and 10 nucleotides, wherein $Y_1$ includes at least one modified internucleotide linkage and $Y_2$ includes at least one modified internucleotide linkage and wherein $N_1$ and $N_2$ are nucleic acid molecules, each independent of one another, having between 0 and 5 nucleotides, but wherein $N_1ZN_2$ has at least 6 nucleotides in total and wherein the nucleotides of $N_1ZN_2$ have a phosphodiester backbone, and wherein Z is an immunostimulatory nucleic acid motif but does not include a CG. In one embodiment Z is a nucleic acid sequence selected from the group consisting of TTTT, TG, and a sequence wherein at least 50% of the bases of the sequence are Ts.

In some embodiments $Y_1$ and/or $Y_2$ have between 3 and 8 nucleotides. In other embodiments $Y_1$ and/or $Y_2$ are comprised of at least three Gs, at least four Gs, least seven Gs, or all Gs. In other embodiments $Y_1$ and/or $Y_2$ are selected from the group consisting of TCGTCG, TCGTCGT, and TCGTCGTT (SEQ ID NO:1145). In yet other embodiments $Y_1$ and/or $Y_2$ include at least one, two, three, four, or five poly-A, poly-T, or poly-C sequences.

The center nucleotides ($N_1ZN_2$) of the formula $Y_1N_1ZN_2Y_2$ have phosphodiester internucleotide linkages and $Y_1$ and $Y_2$ have at least one modified internucleotide linkage. In some embodiments $Y_1$ and/or $Y_2$ have at least two modified internucleotide linkages. In other embodiments $Y_1$ and/or $Y_2$ have between two and five modified internucleotide linkages. In yet other embodiments $Y_1$ has two modified internucleotide linkages and $Y_2$ has five modified internucleotide linkages or $Y_1$ has five modified internucleotide linkages and $Y_2$ has two modified internucleotide linkages. The modified internucleotide linkage, in some embodiments is a phosphorothioate modified linkage, a phosphorodithioate modified linkage or a p-ethoxy modified linkage.

Portions of the formula $Y_1N_1ZN_2Y_2$ may optionally form a palindrome. Thus, in some embodiments the nucleotides of $N_1ZN_2$ form a palindrome. In some embodiments the palindrome is not a direct repeat. In yet other embodiments the nucleotides of $N_1ZN_2$ do not form a palindrome.

According to other embodiments $N_1ZN_2$ has a sequence of nucleotides selected from the group consisting of GATTTTATCGTC (SEQ ID NO: 1098); TCGATTTTTCGA (SEQ ID NO: 1099); TCATTTTTATGA (SEQ ID NO: 1100); GTTTTTTACGAC (SEQ ID NO: 1101); TCAATTTTTTGA (SEQ ID NO: 1102); ACGTTTTTACGT (SEQ ID NO: 1103); TCGTTTTTACGA (SEQ ID NO: 1104); TCGATTTTTACGTCGA (SEQ ID NO: 1105); AATTTTTAACGTT (SEQ ID NO: 1106); TCGTTTTTTAACGA (SEQ ID NO: 1107); ACGTTTTTTAACGT (SEQ ID NO: 1108); GATTTTTATCGTC (SEQ ID NO: 1109); GACGATTTTTCGTC (SEQ ID NO: 1110); GATTTTAGCTCGTC (SEQ ID NO: 1111); GATTTTTACGTC (SEQ ID NO: 1112); ATTTTATCGT (SEQ ID NO: 1113); AACGATTTTTCGTT (SEQ ID NO: 1114); TCACTTTTGTGA (SEQ ID NO: 1115); TCGTATTTTA (SEQ ID NO: 1116); ACTTTTGTACCGGT (SEQ ID NO: 1117); TCGATTTTTCGACGTCGA (SEQ ID NO: 1118); ACGATTTTTCGT (SEQ ID NO: 1119); GATGATCGTC (SEQ ID NO: 1120); TCGATGTCGA (SEQ ID NO: 1121); TCATGTATGA (SEQ ID NO: 1122); GTGTTACGAC (SEQ ID NO: 1123); TCAATGTTGA (SEQ ID NO: 1124); ACGTGTACGT (SEQ ID NO: 1125); TCGTGTACGA (SEQ ID NO: 1126); TCGATGTACGTCGA (SEQ ID NO: 1127); AATGTTAACGTT (SEQ ID NO: 1128); TCGTGTTAACGA (SEQ ID NO: 1129); ACGTGTTAACGT (SEQ ID NO: 1130); GATGTATCGTC (SEQ ID NO: 1131); GACGATGTCGTC (SEQ ID NO: 1132); GATGAGCTCGTC (SEQ ID NO: 1133); GATGTACGTC (SEQ ID NO: 1134); ATGATCGT (SEQ ID NO: 1135); AACGATGTCGTT (SEQ ID NO: 1136); TCACTGGTGA (SEQ ID NO: 1137); TCGTATGA (SEQ ID NO: 1138); ACTGGTACCGGT (SEQ ID NO: 1139); TCGATGTCGACGTCGA (SEQ ID NO: 1140); and ACGATGTCGT (SEQ ID NO: 1141).

The composition may optionally include a pharmaceutical carrier and/or be formulated in a delivery device. In some embodiments the delivery device is selected from the group consisting of cationic lipids, cell permeating proteins, and sustained release devices. In one preferred embodiment the sustained release device is a biodegradable polymer. In another embodiment the sustained release device is a microparticle.

In another aspect the invention is a composition of an immunostimulatory oligonucleotide having the formula $Y_1N_1ZN_2Y_2$, and an antigen.

Another composition of the invention is an immunostimulatory oligonucleotide having the formula $Y_1N_1ZN_2Y_2$, and an anti-microbial therapeutic agent. Preferably the anti-microbial therapeutic agent is selected from the group consisting of an anti-viral agent, an anti-parasitic agent, an anti-bacterial agent, or an anti-fungal agent.

A composition of a sustained release device including an immunostimulatory oligonucleotide having the formula $Y_1N_1ZN_2Y_2$, is provided according to another aspect of the invention.

The invention also includes nutritional supplements of an immunostimulatory oligonucleotide having the formula $Y_1N_1ZN_2Y_2$, in a delivery device selected from the group consisting of a capsule, a sublingual tablet, and a pill.

In another aspect the compositions described above also include an immunostimulatory nucleic acid having an unmethylated CG dinucleotide, a TG dinucleotide or a Py-rich sequence wherein the immunostimulatory nucleic acid having an unmethylated CG dinucleotide, a TG dinucleotide or a Py-rich sequence has a different sequence than the oligonucleotide comprising 5' $Y_1N_1ZN_2Y_2$ 3'.

In some embodiments the immunostimulatory nucleic acid having an unmethylated CG dinucleotide, a TG dinucleotide or a Py-rich sequence has a completely phosphodiester backbone and in other embodiments the immunostimulatory nucleic acid having an unmethylated CG dinucleotide, a TG dinucleotide or a Py-rich sequence has a modified backbone, which optionally may have internucleotide linkages selected from the group consisting of phosphorothioate, phosphorodithioate, and p-ethoxy.

In one embodiment immunostimulatory nucleic acid having an unmethylated CG dinucleotide has a formula comprising: 5' $X_1X_2CGX_3X_4$ 3' wherein $X_1$, $X_2$, $X_3$ and $X_4$ are nucleotides. In other embodiments the immunostimulatory nucleic acid sequence includes at least the following formula: 5' $TCNTX_1X_2CGX_3X_4$ 3' wherein N is a nucleic acid sequence composed of from about 0-25 nucleotides, wherein at least one nucleotide has a modified internucleotide linkage, and wherein the nucleic acid has less than or equal to 100 nucleotides. According to some embodiments $X_1X_2$ are nucleotides selected from the group consisting of: GT, GG, GA and AA and $X_3X_4$ are nucleotides selected from the group consisting of: TT, CT or GT. In a preferred embodiment $X_1X_2$ are GA and $X_3X_4$ are TT.

In another embodiment the immunostimulatory nucleic acid sequence having an unmethylated CG dinucleotide includes at least one of the following sequences: ATCGACTCTCGAGCGTTCT (SEQ ID No. 15); TCCATGTCGGTCCTGCTGAT (SEQ ID No. 32); TCCATGTCGGTZCTGATGCT (SEQ ID No. 31); ATCGACTCTCGAGCGTTZTC (SEQ ID No. 18); TCCATGTCGGTCCTGATGCT (SEQ ID No. 28); GGGGGG (SEQ ID No. 12); TCCATGACGGTCCTGATGCT (SEQ ID No. 35); TCCATGGCGGTCCTGATGCT (SEQ ID No. 34); TCCATGACGTTCCTGATGCT (SEQ ID No. 7); TCCATGTCGTTCCTGATGCT (SEQ ID No. 38); GGGGTCAGTCTTGACGGGG (SEQ ID No. 41); TCCATGTCGCTCCTGATGCT (SEQ ID No. 37); TCCATGTCGATCCTGATGCT (SEQ ID No. 36); TCCATGCCGGTCCTGATGCT (SEQ ID No. 33); TCCATAACGTTCCTGATGCT (SEQ ID No. 3); TCCATGACGTTCCTGATGCT (SEQ ID No. 7); TCCATGACGTCCCTGATGCT (SEQ ID No 39); TCCATCACGTGCCTGATGCT (SEQ ID No. 48); TCCATGACGTTCCTGACGTT (SEQ ID No. 10); ATGACGTTCCTGACGTT (SEQ ID No. 70); TCTCCCAGCGCGCGCCAT (SEQ ID No. 72); TCCATGTCGTTCCTGTCGTT (SEQ ID No. 73); TCCATAGCGTTCCTAGCGTT (SEQ ID No. 74); TCCTGACGTTCCTGACGTT (SEQ ID No. 76); TCCTGTCGTTCCTGTCGTT (SEQ ID No. 77); TCCTGTCGTTCCTTGTCGTT (SEQ ID No. 52); TCCTTGTCGTTCCTGTCGTT (SEQ ID No 121); TCCTGTCGTTTTTTGTCGTT (SEQ ID No. 208); TCGTCGCTGTTGTCGTTTCTT (SEQ ID No. 120); TCCATGCGTTGCGTTGCGTT (SEQ ID No. 81); TCCACGACGTTTTCGACGTT (SEQ ID No. 82); TCGTCGTTGTCGTTGTCGTT (SEQ ID No. 47); TCGTCGTTTTGTCGTTTTGTCGTT (SEQ ID No. 46);

TCGTCGTTGTCGTTTTGTCGTT (SEQ ID No. 49); GCGTGCGTTGTCGTTGTCGTT (SEQ ID No. 56); TGTCGTTTGTCGTTTGTCGTT (SEQ ID No. 48); TGTCGTTGTCGTTGTCGTTGTCGTT (SEQ ID No. 84); TGTCGTTGTCGTTGTCGTT (SEQ ID No. 50); TCGTCGTCGTCGTT (SEQ ID No. 51); and TGTCGT-TGTCGTT (SEQ ID No. 85). In another embodiment the immunostimulatory nucleic acid having a Py-rich or TG sequence is a nucleic acid as described above.

In another aspect the invention relates to pharmaceutical compositions and kits which contain both an oligonucleotide having the formula $Y_1N_1ZN_2Y_2$ and a CpG oligonucleotide (which optionally may be free of poly T and TG motifs and not be Py-rich), a Py-rich and/or TG oligonucleotide physically separate from the oligonucleotide having the formula $Y_1N_1ZN_2Y_2$. The pharmaceutical preparations are in effective amounts and typically include pharmaceutically acceptable carriers, all as set forth in detail herein. The kits include at least one container containing an oligonucleotide having the formula $Y_1N_1ZN_2Y_2$. The same container, or in other embodiments, a second container, may contain an oligonucleotide with a CpG motif, which optionally may be free of Py-rich and/or TG motifs and/or a Py-rich or TG oligonucleotide (or some combination thereof). The kit also contains instructions for administering the oligonucleotides to a subject. The kits also may include a container containing a solvent or a diluent.

In summary, as if fully recited herein, an oligonucleotide having the formula $Y_1N_1ZN_2Y_2$ which is physically separate from the CpG, Py-rich or TG oligonucleotide can be used together with the CpG, Py-rich, TG oligonucleotides, in the methods, compositions and products described herein.

In another aspect the invention relates to a pharmaceutical composition including at least two oligonucleotides of the invention, wherein the at least two oligonucleotides have different sequences from one another and a pharmaceutically acceptable carrier.

A vaccine formulation is provided according to another aspect of the invention. The vaccine includes any of the compositions of the invention in combination with an antigen.

According to another aspect of the invention a method of stimulating an immune response is provided. The method involves administering a Py-rich or a TG immunostimulatory nucleic acid to a non-rodent subject in an amount effective to induce an immune response in the non-rodent subject. Preferably the Py-rich or TG immunostimulatory nucleic acid is administered orally, locally, in a sustained release device, mucosally to a mucosal surface, systemically, parenterally, or intramuscularly. When the Py-rich or TG immunostimulatory nucleic acid is administered to the mucosal surface it may be delivered in an amount effective for inducing a mucosal immune response or a systemic immune response. In preferred embodiments the mucosal surface is selected from the group consisting of an oral, nasal, rectal, vaginal, and ocular surface.

In some embodiments the method includes exposing the subject to an antigen wherein the immune response is an antigen-specific immune response. The antigen may be encoded by a nucleic acid vector which can be delivered to the subject. In some embodiments the antigen is selected from the group consisting of a tumor antigen, a viral antigen, a bacterial antigen, a parasitic antigen and a peptide antigen.

Py-rich and TG immunostimulatory nucleic acids are capable of provoking a broad spectrum of immune response. For instance these immunostimulatory nucleic acids can be used to redirect a Th2 to a Th1 immune response. Py-rich and TG nucleic acids may also be used to activate an immune cell, such as a leukocyte, a dendritic cell, and an NK cell. The activation can be performed in vivo, in vitro, or ex vivo, i.e., by isolating an immune cell from the subject, contacting the immune cell with an effective amount to activate the immune cell of the Py-rich or TG immunostimulatory nucleic acid and re-administering the activated immune cell to the subject. In some embodiments the dendritic cell expresses a cancer antigen. The dendritic cell can be exposed to the cancer antigen ex vivo.

The immune response produced by Py-rich or TG nucleic acids may also result in induction of cytokine production, e.g., production of IL-6, IL-12, IL-18 TNF, IFN-α and IFN-γ.

In still another embodiment, the Py-rich and TG nucleic acids are useful for treating cancer. The Py-rich and TG nucleic acids are also useful according to other aspects of the invention in preventing cancer (e.g., reducing a risk of developing cancer) in a subject at risk of developing a cancer. The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreas cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

Py-rich and TG nucleic acids may also be used for increasing the responsiveness of a cancer cell to a cancer therapy (e.g., an anti-cancer therapy), optionally when the Py-rich or TG immunostimulatory nucleic acid is administered in conjunction with an anti-cancer therapy. The anti-cancer therapy may be a chemotherapy, a vaccine (e.g., an in vitro primed dendritic cell vaccine or a cancer antigen vaccine) or an antibody based therapy. This latter therapy may also involve administering an antibody specific for a cell surface antigen of, for example, a cancer cell, wherein the immune response results in antigen dependent cellular cytotoxicity (ADCC). In one embodiment, the antibody may be selected from the group consisting Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART ID10 Ab, SMART ABL 364 Ab and ImmuRAIT-CEA.

Thus, according to some aspects of the invention, a subject having cancer or at risk of having a cancer is administered an immunostimulatory nucleic acid and an anti-cancer therapy. In some embodiments, the anti-cancer therapy is selected from the group consisting of a chemotherapeutic agent, an immunotherapeutic agent and a cancer vaccine. The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, pro drug of guanine arabino side, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-1, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

In still another embodiment of the methods directed to preventing or treating cancer, the subject may be further administered interferon-α.

The invention in other aspects relates to methods for preventing disease in a subject. The method involves administering to the subject a Py-rich or a TG immunostimulatory nucleic acid on a regular basis to promote immune system responsiveness to prevent disease in the subject. Examples of diseases or conditions sought to be prevented using the prophylactic methods of the invention include microbial infections (e.g., sexually transmitted diseases) and anaphylactic shock from food allergies.

In other aspects, the invention is a method for inducing an innate immune response by administering to the subject a Py-rich or a TG immunostimulatory nucleic acid in an amount effective for activating an innate immune response.

According to another aspect of the invention a method for treating or preventing a viral or retroviral infection is provided. The method involves administering to a subject having or at risk of having a viral or retroviral infection, an effective amount for treating or preventing the viral or retroviral infection of any of the compositions of the invention. In some embodiments the virus is caused by a hepatitis virus, HIV, hepatitis B, hepatitis C, herpes virus, or papilomavirus.

A method for treating or preventing a bacterial infection is provided according to another aspect of the invention. The method involves administering to a subject having or at risk of having a bacterial infection, an effective amount for treating or preventing the bacterial infection of any of the compositions of the invention. In one embodiment the bacterial infection is due to an intracellular bacteria.

In another aspect the invention is a method for treating or preventing a parasite infection by administering to a subject having or at risk of having a parasite infection, an effective amount for treating or preventing the parasite infection of any of the compositions of the invention. In one embodiment the parasite infection is due to an intracellular parasite. In another embodiment the parasite infection is due to a non-helminthic parasite.

In some embodiments the subject is a human and in other embodiments the subject is a non-human vertebrate selected from the group consisting of a dog, cat, horse, cow, pig, goat, fish, monkey, chicken, and sheep.

In yet another aspect, the invention is a method for treating or preventing asthma, by administering to a subject having or at risk of having asthma, an effective amount for treating or preventing the asthma of any of the compositions of the invention. In one embodiment the asthma is allergic asthma.

In another aspect the invention relates to a method for treating or preventing allergy. The method involves administering to a subject having or at risk of having allergy, an effective amount for treating or preventing the allergy of any of the compositions of the invention.

A method for treating or preventing an immune deficiency is provided according to another aspect of the invention. The method involves administering to a subject having or at risk of an immune deficiency, an effective amount for treating or preventing the immune deficiency of any of the compositions of the invention.

In another aspect the invention relates to a method for inducing a TH1 immune response by administering to a subject any of the compositions of the invention in an effective amount to produce a TH1 immune response.

In one embodiment the methods of the invention involve administering an oligonucleotide of formula 5' $Y_1N_1ZN_2Y_2$ 3' and an immunostimulatory nucleic acid having an unmethylated CG dinucleotide a TG dinucleotide or a T-rich sequence. In an embodiment the oligonucleotide comprising 5' $Y_1N_1ZN_2Y_2$ 3' is administered separately from the immunostimulatory nucleic acid. In some embodiments the oligonucleotide comprising 5' $Y_1N_1ZN_2Y_2$ 3' and the immunostimulatory nucleic acid are administered on an alternating weekly schedule and in other embodiments the oligonucleotide comprising 5' $Y_1N_1ZN_2Y_2$ 3' and the immunostimulatory nucleic acid are administered on an alternating biweekly schedule.

The invention provides in another aspect a composition, comprising an immunostimulatory nucleic acid and an anti-cancer therapy, formulated in a pharmaceutically-acceptable carrier and in an effective amount to treat a cancer or to reduce the risk of developing a cancer. In important embodiments, the immunostimulatory nucleic acid is selected from the group consisting of a T-rich nucleic acid, a TG nucleic acid and a C-rich nucleic acid.

The invention further provides a kit comprising a first container housing an immunostimulatory nucleic acid and at least one other container (e.g., a second container) housing a an anti-cancer therapy, and instructions for use. In one embodiment, the kit further comprises interferon-α, which may be separately housed in yet another container (e.g., a third container). In an important embodiment, the kit comprises a sustained-release vehicle containing an immunostimulatory nucleic acid, and at least one container housing an anti-cancer therapy, and instructions for timing of administration of the anti-cancer therapy. The immunostimulatory nucleic acid may be selected from the group consisting of a Py-rich nucleic acid, a TG nucleic acid and a CpG nucleic acid, wherein the CpG nucleic acid has a nucleotide sequence comprising SEQ ID NO: 246.

The invention further provides a method for preventing or treating asthma or allergy, comprising administering an immunostimulatory nucleic acid and an asthma/allergy medicament in an effective amount to treat or prevent the asthma or allergy. In important embodiments, the immunostimulatory nucleic acid is selected from the group consisting of a T-rich nucleic acid, a TG nucleic acid and a C-rich nucleic acid.

In one embodiment the immunostimulatory nucleic acid is a T-rich nucleic acid. In a related embodiment, the T-rich nucleic acid has a nucleotide sequence selected from the group consisting of SEQ ID NO: 59-63, 73-75, 142, 215, 226, 241, 267-269, 282, 301, 304, 330, 342, 358, 370-372, 393, 433, 471, 479, 486, 491, 497, 503, 556-558, 567, 694, 793-794, 797, 833, 852, 861, 867, 868, 882, 886, 905, 907, 908, and 910-913. In other embodiments the T-rich nucleic acids are sequence selected from the group consisting of SEQ ID NO: 64, 98, 112, 146, 185, 204, 208, 214, 224, 233, 244, 246, 247, 258, 262, 263, 265, 270-273, 300, 305, 316, 317, 343, 344, 350, 352, 354, 374, 376, 392, 407, 411-413, 429-432, 434, 435, 443, 474, 475, 498-501, 518, 687, 692, 693, 804, 862, 883, 884, 888, 890, and 891.

In yet a further related embodiment, the T-rich nucleic acid is not a TG nucleic acid. In yet still another embodiment, the T-rich nucleic acid is not a CpG nucleic acid.

In one embodiment, the immunostimulatory nucleic acid is a TG nucleic acid. In a further related embodiment, the TG nucleic acid is not a T-rich nucleic acid. In another related embodiment, the TG nucleic acid is not a CpG nucleic acid.

In one embodiment, the immunostimulatory nucleic acid is a CpG nucleic acid, wherein the CpG nucleic acid has a nucleotide sequence comprising SEQ ID NO: 246.

In another embodiment, the asthma/allergy medicament is a medicament selected from the group consisting of PDE-4 inhibitor, Bronchodilator/beta-2 agonist, K+ channel opener, VLA-4 antagonist, Neurokin antagonist, TXA2 synthesis inhibitor, Xanthanine, Arachidonic acid antagonist, 5 lipoxygenase inhibitor, Thromboxin A2 receptor antagonist, Thromboxane A2 antagonist, Inhibitor of 5-lipox activation protein, and Protease inhibitor, but is not so limited. In some important embodiments, the asthma/allergy medicament is a Bronchodilator/beta-2 agonist selected from the group consisting of salmeterol, salbutamol, terbutaline, D2522/formoterol, fenoterol, and orciprenaline.

In another embodiment, the asthma/allergy medicament is a medicament selected from the group consisting of Anti-histamines and Prostaglandin inducers. In one embodiment, the anti-histamine is selected from the group consisting of loratidine, cetirizine, buclizine, ceterizine analogues, fexofenadine, terfenadine, desloratadine, norastemizole, epinastine, ebastine, ebastine, astemizole, levocabastine, azelastine, tranilast, terfenadine, mizolastine, betatastine, CS 560, and HSR 609. In another embodiment, the Prostaglandin inducer is S-5751.

In yet another embodiment, the asthma/allergy medicament is selected from the group consisting of Steroids and Immunomodulators. The immunomodulators may be selected from the group consisting of anti-inflammatory agents, leukotriene antagonists, IL4 muteins, Soluble IL-4 receptors, Immunosuppressants, anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, and Downregulators of IgE, but are not so limited. In one embodiment, the downregulator of IgE is an anti-IgE.

In another embodiment, the Steroid is selected from the group consisting of beclomethasone, fluticasone, tramcinolone, budesonide, and budesonide. In still a further embodiment, the Immunosuppressant is a Tolerizing peptide vaccine.

In one embodiment, the immunostimulatory nucleic acid is administered concurrently with the asthma/allergy medicament. In another embodiment, the subject is an immunocompromised subject The immunostimulatory nucleic acids to be administered to a subject in the methods disclosed herein relating to the prevention and treatment of asthma/allergy are as described for other method aspects of the invention.

In another aspect, the invention provides a kit comprising a first container housing an immunostimulatory nucleic acid, and at least another container (e.g., a second container) housing an asthma/allergy medicament, and instructions for use. The immunostimulatory nucleic acid useful in the kit is as described herein. In important embodiments, the immunostimulatory nucleic acid is selected from the group consisting of a T-rich nucleic acid, a TG nucleic acid and a C-rich nucleic acid. In another important embodiment, the kit comprises a sustained-release vehicle containing an immunostimulatory nucleic acid, and at least one container housing an asthma/allergy medicament, and instructions for timing of administration of the asthma/allergy medicament. The asthma/allergy medicament may be selected from the group of asthma/allergy medicaments described in the foregoing methods directed towards the prevention or treatment of asthma/allergy.

In yet another aspect, the invention provides a composition, comprising an immunostimulatory nucleic acid and an asthma/allergy medicament, formulated in a pharmaceutically-acceptable carrier and in an effective amount for preventing or treating an immune response associated with exposure to a mediator of asthma or allergy. The immunostimulatory nucleic acid may be selected from the group of immunostimulatory nucleic acids described for the foregoing methods and compositions. In important embodiments, the immunostimulatory nucleic acid is selected from the group consisting of a T-rich nucleic acid, a TG nucleic acid and a C-rich nucleic acid. The asthma/allergy medicament may be selected from the group consisting of asthma medicaments and allergy medicaments as described in the foregoing methods and compositions.

In still a further aspect, the invention provides a composition comprising an immunostimulatory nucleic acid selected from the group consisting of SEQ ID NO: 95-136, SEQ ID NO: 138-152, SEQ ID NO: 154-222, SEQ ID NO: 224-245, SEQ ID NO: 247-261, SEQ ID NO: 263-299, SEQ ID NO: 301, SEQ ID NO: 303-4109, SEQ ID NO: 414-420, SEQ ID NO: 424, SEQ ID NO: 426-947, SEQ ID NO: 959-1022, SEQ ID NO: 1024-1093, and a pharmaceutically acceptable carrier. Preferably the immunostimulatory nucleic acid is present in the composition in an effective amount. In one embodiment, the immunostimulatory nucleic acid is present in an effective amount to induce an immune response. In another embodiment, the immunostimulatory nucleic acid is present in an effective amount to prevent or treat cancer. In yet a further embodiment, the immunostimulatory nucleic acid is present in an effective amount to prevent or treat asthma/allergy. The invention also provides kits comprising any of the foregoing immunostimulatory nucleic acid compositions, and instructions for use.

In another aspect the invention includes a composition of an immunostimulatory nucleic acid consisting essentially of: 5' $M_1$TCGTCGTT$M_2$ 3' wherein at least one of the Cs is unmethylated, wherein M1 is a nucleic acid having at least one nucleotide, wherein $M_2$ is a nucleic acid having between 0 and 50 nucleotides, and wherein the immunostimulatory nucleic acid has less than 100 nucleotides.

In yet other aspects the invention relates to a pharmaceutical composition of an immunostimulatory nucleic acid comprising: 5' TCGTCGTT 3' wherein at least one of the Cs is unmethylated, wherein the immunostimulatory nucleic acid has less than 100 nucleotides and a phosphodiester backbone, and a sustained release device. In some embodiments the sustained release device is a microparticle. In other embodiments the composition includes an antigen.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 1B is a table with the data from FIG. 1A.

FIG. 1D is a table with the data from FIG. 1C.

DETAILED DESCRIPTION

Figure 1A:
FIG. 1A is a histogram of the expression of CD86 (Y-axis) by CD19+ cells following exposure of these cells to the oligonucleotides shown on the X-axis at a concentration of 0.15 µg/ml.

The invention in one aspect involves the finding that pyrimidine (Py) rich and preferably thymidine (T) rich nucleic acids as well as nucleic acids that contain TG dinucleotide motifs are effective in mediating immune stimulatory effects. It was known in the prior art that CpG containing nucleic acids are therapeutic and prophylactic compositions that stimulate the immune system to treat cancer, infectious diseases, allergy, asthma and other disorders and to help protect against opportunistic infections following cancer chemotherapies. The strong yet balanced, cellular and humoral immune responses that result from CpG stimulation reflect the body's own natural defense system against invading pathogens and cancerous cells. CpG sequences, while relatively rare in human DNA are commonly found in the DNA of infectious organisms such as bacteria. The human immune system has apparently evolved to recognize CpG sequences as an early warning sign of infection, and to initiate an immediate and powerful immune response against invading pathogens without causing adverse reactions frequently seen with other immune stimulatory agents. Thus CpG containing nucleic acids, relying on this innate immune defense mechanism, can utilize a unique and natural pathway for immune therapy. The effects of CpG nucleic acids on immune modulation were discovered by the inventor of the instant patent application and have been described extensively in co-pending patent applications, such as U.S. patent application Ser. No. 08/386,063, now U.S. Pat. No. 6,194,388, filed on Feb. 7, 1995 (and related PCT US95/01570); Ser. No. 08/738,652, now U.S. Pat. No. 6,207,646, filed on Oct. 30, 1996; Ser. No. 08/960,774, now U.S. Pat. No. 6,429,199, filed on Oct. 30, 1997 (and related PCT/US97/19791, WO 98/18810); Ser. No. 09/191,170 filed on Nov. 13, 1998; Ser. No. 09/030,701, now U.S. Pat. No. 6,214,806, filed on Feb. 25, 1998 (and related PCT/US98/03678; Ser. No. 09/082,649, now U.S. Pat. No. 6,339,068, filed on May 20, 1998 (and related PCT/US98/10408); Ser. No. 09/325,193, now U.S. Pat. No. 6,405,705, filed on Jun. 3, 1999 (and related PCT/US98/04703); Ser. No. 09/286,098, now U.S. Pat. No. 6,218,371, filed on Apr. 2, 1999 (and related PCT/US99/07335); Ser. No. 09/306,281 filed on May 6, 1999 (and related PCT/US99/09863). The entire contents of each of these patents and patent applications is hereby incorporated by reference.

The findings of the instant invention are applicable to all of the above described uses of CpG containing nucleic acids as well as any other known use for CpG nucleic acids. The invention involves, in one aspect, the discovery that Py-rich and preferably T-rich and TG nucleic acids have similar immune stimulatory properties to CpG oligonucleotides regardless of whether a CpG motif is present. Thus the invention is useful for any method for stimulating the immune system using Py-rich or TG nucleic acids. It was also discovered surprisingly according to the invention that chimeric oligonucleotides which lack a CpG motif are immune stimulatory and have many of the same prophylactic and therapeutic activities as a CpG oligonucleotide.

A Py-rich nucleic acid is a T-rich or C-rich immunostimulatory nucleic acid. In some embodiments T-rich nucleic acids are preferred. A T-rich nucleic acid is a nucleic acid which includes at least one poly T sequence and/or which has a nucleotide composition of greater than 25% T nucleotide residues. A nucleic acid having a poly-T sequence includes at least four Ts in a row, such as 5'TTTT3'. Preferably the T-rich nucleic acid includes more than one poly T sequence. In preferred embodiments the T-rich nucleic acid may have 2, 3, 4, etc poly T sequences, such as oligonucleotide #2006 (SEQ ID NO:246). One of the most highly immunostimulatory T-rich oligonucleotides discovered according to the invention is a nucleic acid composed entirely of T nucleotide residues, e.g., oligonucleotide #2183 (SEQ ID NO:433). Other T-rich nucleic acids according to the invention have a nucleotide composition of greater than 25% T nucleotide residues, but do not necessarily include a poly T sequence. In these T-rich nucleic acids the T nucleotide resides may be separated from one another by other types of nucleotide residues, i.e., G, C, and A. In some embodiments the T-rich nucleic acids have a nucleotide composition of greater than 35%, 40%, 50%, 60%, 70%, 80%, 90%, and 99%, T nucleotide residues and every integer % in between. Preferably the T-rich nucleic acids have at least one poly T sequence and a nucleotide composition of greater than 25% T nucleotide residues.

It was discovered according to the invention that the T content of an ODN has a dramatic effect on the immune stimulatory effect of the ODN and that T-rich ODN can activate multiple human immune cell types in the absence of any CpG motifs. An oligonucleotide having a 3' poly-T region and 25'CGs e.g., ODN 2181 (SEQ ID NO:431) is highly immune stimulatory. An oligonucleotide of similar length, ODN 2116 (SEQ ID NO:357) which contains two CG dinucleotides at the 5' end and a poly-C region at the 3' end was also immune stimulatory but to a lesser extent than the T-rich oligonucleotide using standard experimental conditions. Thus, although C and T have almost identical structures, their effects on the immune properties of an ODN are varied. They both are capable of inducing an immune response but to different extents. Thus both T-rich and C-rich oligonucleotides are useful according to the invention, but T-rich oligonucleotides are preferred. Furthermore, if the T content of the ODN is reduced by incorporating other bases such as G, A, or C, then the immune stimulatory effects are reduced (ODN #2188 (SEQ ID NO:905), 2190 (SEQ ID NO:907), 2191 (SEQ ID NO:908), and 2193 (SEQ ID NO:910)).

A C-rich nucleic acid is a nucleic acid molecule having at least one or preferably at least two poly-C regions or which is composed of at least 50% C nucleotides. A poly-C region is at least four C residues in a row. Thus a poly-C region is encompassed by the formula 5'CCCC 3'. In some embodiments it is preferred that the poly-C region have the formula 5'CCCCCC 3'. Other C-rich nucleic acids according to the invention have a nucleotide composition of greater than 50% C nucleotide residues, but do not necessarily include a poly C sequence. In these C-rich nucleic acids the C nucleotide residues may be separated from one another by other types of nucleotide residues, i.e., G, T, and A. In some embodiments the C-rich nucleic acids have a nucleotide composition of greater than 60%, 70%, 80%, 90%, and 99%, C nucleotide residues and every integer % in between. Preferably the C-rich nucleic acids have at least one poly C sequence and a nucleotide composition of greater than 50% C nucleotide residues, and in some embodiments are also T-rich.

As shown in the Examples, several ODN previously believed to be non-immunostimulatory, including two ODNs SEQ ID NO.: 225 and SEQ ID NO.: 282 previously described to be non-stimulatory and mainly used as control ODNs (Takahashi, T., M. Nieda, Y. Koezuka, A. Nicol, S. A.

Figure 6:
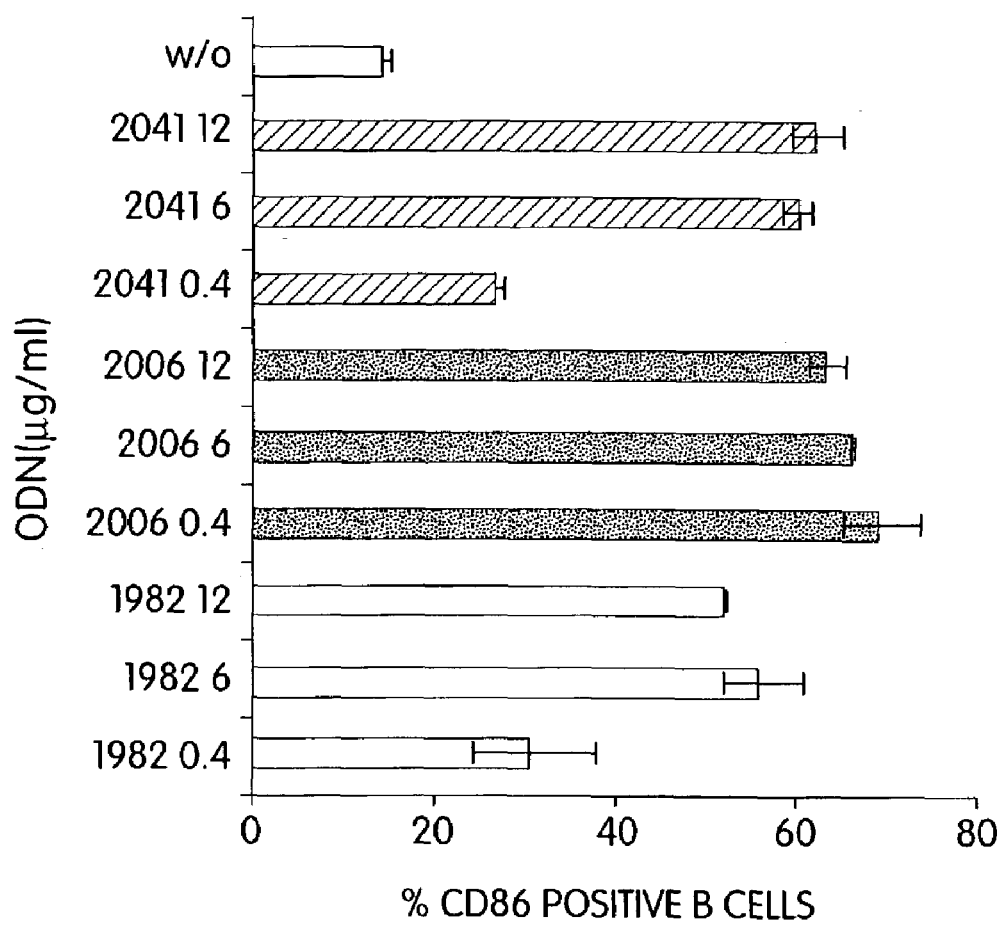
FIG. 6 is a bar graph depicting B cell activation by non-CpG ODNs 1982 and 2041. PBMC were incubated with the indicated concentrations of ODN 2006 (SEQ ID NO.: 246), 1982 (SEQ ID NO.: 225) and 2041 (SEQ ID NO.: 282) and B cell activation (expression of the activation marker CD86) was measured by flow cytometry.

Porcelli, Y. Ishikawa, K. Tadokoro, H. Hirai, and T. Juji. 2000. Analysis of human VA24+CD4+NKT cells activated by a-glycosylceramide-pulsed monocyte-derived dendritic cells. *J. Immunol.* 164:4458) were found to be immunostimulatory. Our experiments, demonstrated that these ODNs can stimulate B cells, although at higher concentrations compared to CpG ODNs (FIG. 6). A long Poly T ODN (30mer) induced, at least in some experiments, comparable strong activation of B cells to one of the strongest CpG ODN activators of B cells. These experiments also revealed the surprising finding that even Poly C ODNs can lead to stimulation of B cells.

Immunostimulation by these ODNs, however, was not limited to human B cells. Different experimental assays clearly demonstrated in addition that monocytes, NK cells and even NKT cells can be activated by such non-CpG ODNs (FIGS. 7-10). In contrast to Poly T and Poly C sequences, immunostimulation by Poly A sequences (at least for monocytes, B and NK cells) was not achieved. Interestingly it was found that the introduction of a CpG motif into SEQ ID NO.: 225 enhanced the immunostimulatory activity whereas the elongation with a Poly T stretch did not enhance immunostimulation. This suggests that CpG and T-rich ODN may operate through different mechanisms or pathways. It is also possible that insertion of a poly-T motif into a different position of SEQ ID NO.: 225 may result in a change in immunostimulatory properties.

A "TG nucleic acid" or a "TG immunostimulatory nucleic acid" as used herein is a nucleic acid containing at least one TpG dinucleotide (thymidine-guanine dinucleotide sequence, i.e. "TG DNA" or DNA containing a 5' thymidine followed by 3' guanosine and linked by a phosphate bond) and activates a component of the immune system.

In one embodiment the invention provides a TG nucleic acid represented by at least the formula:

$5'N_1X_1TGX_2N_23'$ wherein $X_1$ and $X_2$ are nucleotides and N is any nucleotide and $N_1$ and $N_2$ are nucleic acid sequences composed of any number of N provided that the sum total of $N_1$ and $N_2$ is in the range of 11 to 21. As an example, if $N_1$ is 5, then $N_2$ may be 6 (leading to a total length for the oligonucleotide of 15 nucleotides). The TG may be located anywhere within the oligonucleotide stretch, including the 5' end, the center and the 3' end. Thus, $N_1$ may be zero through to 21, inclusive, provided that $N_2$ is appropriately chosen to give a sum of $N_2$ and $N_1$ equal to 11 through to 21, inclusive. Similarly, $N_2$ may be zero through to 21, inclusive, provided that the sum total of $N_1$ and $N_2$ equals 11 to 21, inclusive. In some embodiments $X_1$ is adenine, guanine, or thymidine and $X_2$ is cytosine, adenine, or thymidine. In one preferred embodiment, $X_2$ is thymidine. In other embodiments $X_1$ is cytosine and/or $X_2$ is guanine. In other embodiments, as discussed herein, the nucleic acid may encompass other motifs, provided it is long enough to do so.

In other embodiments the TG nucleic acid is represented by at least the formula:

$5'N_1X_1X_2TGX_3X_4N_23'$ wherein $X_1$, $X_2$, $X_3$, and $X_4$ are nucleotides. In some embodiments, $X_1X_2$ are nucleotides selected from the group consisting of: GpT, GpG, GpA, ApA, ApT, ApG, CpT, CpA, TpA and TpT; and $X_3X_4$ are nucleotides selected from the group consisting of: TpT, CpT, ApT, ApG, TpC, ApC, CpC, TpA, ApA, and CpA; N is any nucleotide and $N_1$ and $N_2$ are nucleic acid sequences composed of any number of nucleotides provide that the sum total of $N_1$ and $N_2$ is in the range of 9 to 19. In some embodiments, $X_1X_2$ are GpA or GpT and $X_3X_4$ are TpT. In other embodiments $X_1$ or $X_2$ or both are purines and $X_3$ or $X_4$ or both are pyrimidines or $X_1X_2$ are GpA and $X_3$ or $X_4$ or both are pyrimidines. In one preferred embodiment, $X_3X_4$ are nucleotides selected from the group consisting of: TpT, TpC and TpA.

The immunostimulatory nucleic acid may be any size (i.e., length) provided it is at least 4 nucleotides. In important embodiments, the immunostimulatory nucleic acids have a length in the range of between 6 and 100. In still other embodiments, the length is in the range of between 8 and 35 nucleotides. Preferably, the TG oligonucleotides range in size from 15 to 25 nucleotides.

The size (i.e., the number of nucleotide residues along the length of the nucleic acid) of the immunostimulatory nucleic acid may also contribute to the stimulatory activity of the nucleic acid. It has been discovered, surprisingly that even for highly immune stimulating immunostimulatory nucleic acids, the length of the nucleic acid influences the extent of immunostimulation that can be achieved. It has been demonstrated that increasing the length of a T-rich nucleic acid up to 24 nucleotides causes increased immune stimulation. The experiments presented in the examples demonstrate that when the length of the T-rich nucleic acid is increased from 18 to 27 nucleotides the ability of the nucleic acid to stimulate an immune response is increased significantly (compare ODN #2194, 2183, 2195, and 2196 decreasing in size from 27-18 nucleotides). Increasing the length of the nucleic acid up to 30 nucleotides had a dramatic impact on the biological properties of the nucleic acid but increasing the length beyond 30 nucleotides did not appear to further influence the immune stimulatory effect (e.g., compare ODN 2179 to 2006).

It has been shown that TG nucleic acids ranging in length from 15 to 25 nucleotides in length may exhibit an increased immune stimulation. Thus, in one aspect, the invention provides an oligonucleotide that is 15-27 nucleotides in length (i.e., an oligonucleotide that is 15, 16, 17, 18, 19, 20, 21, 22, 23, 24, 25, 26 or 27 nucleotides in length) that may be a T-rich nucleic acid or may be a TG nucleic acid, or may be both a T-rich and a TG nucleic acid. In one embodiment, the oligonucleotide is not a T-rich nucleic acid nor is it a TG nucleic acid. In other embodiments, the oligonucleotide does not have a CG motif. The invention similarly provides oligonucleotides that are 15-27 nucleotides in length, oligonucleotides that are 18-25 nucleotides in length, oligonucleotides that are 20-23 nucleotides in length, and oligonucleotides that are 23-25 nucleotides in length. Any of the foregoing embodiments relating to oligonucleotides 15-27 in length also relate to the oligonucleotides of these differing lengths. The invention further embraces the use of any of these foregoing oligonucleotides in the methods recited herein.

Although a maximal level of immune stimulation is achieved with some T-rich nucleic acids when the nucleic acid is 24-30 nucleotide residues in length, as well as with some TG nucleic acids that range from 15 to 25 nucleotides in length, shorter or longer immunostimulatory nucleic acids can also be used according to the methods of the invention. For facilitating uptake into cells immunostimulatory nucleic acids preferably have a minimum length of 6 nucleotide residues. Nucleic acids of any size greater than 6 nucleotides (even many kb long) are capable of inducing an immune response according to the invention if sufficient immunostimulatory motifs are present, since larger nucleic acids are degraded inside of cells. Preferably the immunostimulatory nucleic acids are in the range of between 8 and 100 and in some embodiments T-rich containing immunostimulatory nucleic acids are between 24 and 40 nucleotides in length and TG containing immunostimulatory nucleic acids are between 15 and 25 nucleotides in length.

In one embodiment the T-rich nucleic acid is represented by at least the formula:

5'$X_1X_2$TTTT$X_3X_4$3' wherein $X_1$, $X_2$, $X_3$, and $X_4$ are nucleotides. In one embodiment $X_1X_2$ is TT and/or $X_3X_4$ is TT. In another embodiment $X_1X_2$ are any one of the following nucleotides TA, TG, TC, AT, AA, AG, AC, CT, CC, CA, GT, GG, GA, and GC; and $X_3X_4$ are any one of the following nucleotides TA, TG, TC, AT, AA, AG, AC, CT, CC, CA, GT, GG, GA, and GC.

In some embodiments it is preferred that the immunostimulatory nucleic acids do not contain poly-C (CCCC), or poly-A (AAAA). In other embodiments it is preferred that the immunostimulatory nucleic acid include poly-C, poly-A, poly-G (GGGG) or multiple GGs. In particular poly-G or multiple GG motifs have dramatic effects on some immunostimulatory nucleic acids. The effect of these non-T sequences depends in part on the status of the nucleic acid backbone. For instance, if the nucleic acid has a phosphodiester backbone or a chimeric backbone the inclusion of these sequences in the nucleic acid will only have minimal if any effect on the biological activity of the nucleic acid. If the backbone is completely phosphorothioate (or other phosphate modification) or significantly phosphorothioate then the inclusion of these sequences may have more influence on the biological activity or the kinetics of the biological activity, causing a decrease in potency of the T-rich and TG immunostimulatory nucleic acids.

Although C-rich nucleic acids have been demonstrated to have immune stimulating properties, insertion of Poly-C sequences into a T-rich nucleic acid in a manner that would reduce the relative proportion of T nucleotides in the nucleic acid can have a negative impact on the nucleic acid. Although applicants are not bound by a proposed mechanism, it is believed that the immune system has developed a mechanism for distinguishing nucleic acids having different nucleotide properties, possibly resulting from different sets of binding proteins which recognize different sequences or specific binding proteins which recognize all the immunostimulatory sequences but with different affinities. In general nucleic acids including unmethylated CpG motifs are the most immunostimulatory, followed by T-rich nucleic acids, TG nucleic acids and C-rich nucleic acids. This generalization, however, has many exceptions. For instance a strong T-rich nucleic acid like SEQ ID NO.: 886 is more immune stimulatory in some assays than some CpG containing nucleic acids (e.g., a phosphorothioate CpG nucleic acid containing a single CpG motif).

It has also been discovered that the addition of a poly-A tail to an immunostimulatory nucleic acid can enhance the activity of the nucleic acid. It was discovered that when a highly immune stimulatory CpG nucleic acid (SEQ ID NO.: 246) was modified with the addition of a poly-A tail (AAAAAA) or a poly-T tail (TTTTTT), the resultant oligonucleotides increased in immune stimulatory activity. The ability of the poly-A tail and the poly-T tail to increase the immunostimulating properties of the oligonucleotide was very similar. SEQ ID NO.: 246 is a T-rich oligonucleotide. It is likely that if poly-A and poly-T tails are added to a nucleic acid which is not T-rich, it would have a bigger impact on the immune stimulating capability of the nucleic acid. Since the poly-T tail was added to a nucleic acid that was already highly T-rich the immune stimulating properties of the poly-T addition was diluted somewhat, although not completely. This finding has important implications for the use of poly-A regions. Thus in some embodiments the immunostimulatory nucleic acids include a poly-A region and in other embodiments they do not.

Some of the immunostimulatory nucleic acids of the invention include one or more CG motifs. The presence of CG motifs in the immunostimulatory nucleic acids also has an influence on the biological activity of the nucleic acids. If the total length of an immunostimulatory nucleic acid is 20 nucleotide residues or less, then CpG motifs are important in determining the immune effect of the nucleic acid, and methylation of these motifs reduces the potency of the immune stimulatory effects of the nucleic acid. If the length of the immunostimulatory nucleic acid is increased to 24, then the immune stimulatory effects of the nucleic acid become less dependent on the CpG motifs, and are no longer abolished by methylation of the CpG motifs or by their inversion to GC dinucleotides, provided the other immunestimulatory properties described herein are present.

For example, ODN 2006 (SEQ ID NO:246) is a highly immune stimulatory T-rich nucleic acid of 24 nucleotide residues in length with four CpG dinucleotides. However, ODN 2117 (SEQ ID NO:358), in which the CpG motifs are methylated is also highly immune stimulatory. ODN 2137 (SEQ ID NO:886), in which the CpG motifs of ODN 2006 are inverted to GpC, and which as a result possesses six TG dinucleotides is also immune stimulatory. The immune stimulatory effects of nucleic acids such as ODN 2117 and 2137 are regulated by their T and TG content. Each of these three nucleic acids is T-rich and ODN 2137 is additionally TG rich. If their T content is reduced by inserting other bases such as A (ODN 2117 (SEQ ID NO:358)) or if their TG content is reduced by substituting TG with AG, then the immune stimulatory effects are somewhat reduced. In another example, a nucleic acid 24 nucleotides in length in which all of the positions are randomized has only a modest immune stimulatory effect (ODN 2182 (SEQ ID NO:432)). Likewise, a nucleic acid 24 nucleotides in length with other nucleotide compositions have variable immune stimulatory effects, depending on their T content (ODN 2188 (SEQ ID NO:905), 2189 (SEQ ID NO:906), 2190 (SEQ ID NO:907), 2191 (SEQ ID NO:908), 2193 (SEQ ID NO:910), 2183 (SEQ ID NO:433), and 2178 (SEQ ID NO:428)). ODN 2190 which contains TGT motifs is more immune stimulatory than ODN 2202 which possesses TGG motifs. Thus, in some embodiments, TGT motifs are preferred. In still other embodiments, the number of TG motifs is important in that an increase in the number of TG motifs leads to an increase in immune stimulation. Some preferred TG nucleic acids contain at least three TG motifs.

Examples of CpG nucleic acids include but are not limited to those listed in Table A, such as SEQ ID NO: 1, 3, 4, 14-16, 18-24, 28, 29, 33-46, 49, 50, 52-56, 58, 64-67, 69, 71, 72, 76-87, 90, 91, 93, 94, 96, 98, 102-124, 126-128, 131-133, 136-141, 146-150, 152-153, 155-171, 173-178, 180-186, 188-198, 201, 203-214, 216-220, 223, 224, 227-240, 242-256, 258, 260-265, 270-273, 275, 277-281, 286-287, 292, 295-296, 300, 302, 305-307, 309-312, 314-317, 320-327, 329, 335, 337-341, 343-352, 354, 357, 361-365, 367-369, 373-376, 378-385, 388-392, 394, 395, 399, 401-404, 406-426, 429-433, 434-437, 439, 441-443, 445, 447, 448, 450, 453-456, 460-464, 466-469, 472-475, 477, 478, 480, 483-485, 488, 489, 492, 493, 495-502, 504-505, 507-509, 511, 513-529, 532-541, 543-555, 564-566, 568-576, 578, 580, 599, 601-605, 607-611, 613-615, 617, 619-622, 625-646, 648-650, 653-664, 666-697, 699-706, 708, 709, 711-716, 718-732, 736, 737, 739-744, 746, 747, 749-761, 763, 766-767, 769, 772-779, 781-783, 785-786, 7900792, 798-799, 804-808, 810, 815, 817, 818, 820-832, 835-846, 849-850, 855-859, 862, 865, 872, 874-877, 879-881, 883-885, 888-904, and 909-913.

In some embodiments of the invention the immunostimulatory nucleic acids include CpG dinucleotides and in other embodiments the immunostimulatory nucleic acids are free of CpG dinucleotides. The CpG dinucleotides may be methylated or unmethylated. A nucleic acid containing at least one unmethylated CpG dinucleotide is a nucleic acid molecule which contains an unmethylated cytosine-guanine dinucleotide sequence (i.e. "CpG DNA" or DNA containing an unmethylated 5' cytosine followed by 3' guanosine and linked by a phosphate bond) and activates the immune system. A nucleic acid containing at least one methylated CpG dinucleotide is a nucleic acid which contains a methylated cytosine-guanine dinucleotide sequence (i.e., a methylated 5' cytosine followed by a 3' guanosine and linked by a phosphate bond).

Examples of T rich nucleic acids that are free of CpG nucleic acids include but are not limited to those listed in Table A, such as SEQ ID NO: 59-63, 73-75, 142, 215, 226, 241, 267-269, 282, 301, 304, 330, 342, 358, 370-372, 393, 433, 471, 479, 486, 491, 497, 503, 556-558, 567, 694, 793-794, 797, 833, 852, 861, 867, 868, 882, 886, 905, 907, 908, and 910-913. Examples of T rich nucleic acids that include CpG nucleic acids include but are not limited to those listed in Table A, such as SEQ ID NO: 64, 98, 112, 146, 185, 204, 208, 214, 224, 233, 244, 246, 247, 258, 262, 263, 265, 270-273, 300, 305, 316, 317, 343, 344, 350, 352, 354, 374, 376, 392, 407, 411-413, 429-432, 434, 435, 443, 474, 475, 498-501, 518, 687, 692, 693, 804, 862, 883, 884, 888, 890, and 891.

The immunostimulatory nucleic acids can be double-stranded or single-stranded. Generally, double-stranded molecules are more stable in vivo, while single-stranded molecules have increased immune activity. Thus in some aspects of the invention it is preferred that the nucleic acid be single stranded and in other aspects it is preferred that the nucleic acid be double stranded.

The term T-rich nucleic acid and TG nucleic acid, as used herein, refers to an immunostimulatory T-rich nucleic acid and an immunostimulatory TG nucleic acid, respectively, unless otherwise indicated. The T-rich nucleic acid sequences of the invention are those broadly described above as well as the nucleic acids shown in Table A that have at least one poly T motif and/or have a composition of greater than 25% T or preferably 35% nucleotide residues. The C-rich nucleic acids are those having at least one and preferably at least two poly-C regions. The TG nucleic acids of the invention are those broadly described above as well as the specific nucleic acids shown in Table A that have at least one TG motif.

The nucleic acids of the invention may, but need not, also include a poly G motif. Poly G containing nucleic acids are also immunostimulatory. A variety of references, including Pisetsky and Reich, 1993 *Mol. Biol. Reports*, 18:217-221; Krieger and Herz, 1994, *Ann. Rev. Biochem.*, 63:601-637; Macaya et al., 1993, *PNAS*, 90:3745-3749; Wyatt et al., 1994, *PNAS*, 91:1356-1360; Rando and Hogan, 1998, In Applied Antisense Oligonucleotide Technology, ed. Krieg and Stein, p. 335-352; and Kimura et al., 1994, *J. Biochem.* 116, 991-994 also describe the immunostimulatory properties of poly G nucleic acids.

Poly G nucleic acids preferably are nucleic acids having the following formulas:

wherein $X_1$, $X_2$, $X_3$, and $X_4$ are nucleotides. In preferred embodiments at least one of $X_3$ and $X_4$ are a G. In other embodiments both of $X_3$ and $X_4$ are a G. In yet other embodiments the preferred formula is 5' GGGNGGG 3', or 5' GGGNGGGNGGG 3' wherein N represents between 0 and 20 nucleotides. In other embodiments the poly G nucleic acid is free of unmethylated CG dinucleotides, such as, for example, the nucleic acids listed below as SEQ ID NO: 5, 6, 73, 215, 267-269, 276, 282, 288, 297-299, 355, 359, 386, 387, 444, 476, 531, 557-559, 733, 768, 795, 796, 914-925, 928-931, 933-936, and 938. In other embodiments the poly G nucleic acid includes at least one unmethylated CG dinucleotide, such as, for example, the nucleic acids listed above as SEQ ID NO: 67, 80-82, 141, 147, 148, 173, 178, 183, 185, 214, 224, 264, 265, 315, 329, 434, 435, 475, 519, 521-524, 526, 527, 535, 554, 565, 609, 628, 660, 661, 662, 725, 767, 825, 856, 857, 876, 892, 909, 926, 927, 932, and 937.

The terms "nucleic acid" and "oligonucleotide" are used interchangeably to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). As used herein, the terms refer to oligoribonucleotides as well as oligodeoxyribonucleotides. The terms shall also include polynucleosides (i.e. a polynucleotide minus the phosphate) and any other organic base containing polymer. Nucleic acid molecules can be obtained from existing nucleic acid sources (e.g., genomic or cDNA), but are preferably synthetic (e.g. produced by nucleic acid synthesis).

The terms nucleic acid and oligonucleotide also encompass nucleic acids or oligonucleotides with substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus modified nucleic acids may include a 2'-O-alkylated ribose group. In addition, modified nucleic acids may include sugars such as arabinose instead of ribose. Thus the nucleic acids may be heterogeneous in backbone composition thereby containing any possible combination of polymer units linked together such as peptide-nucleic acids (which have amino acid backbone with nucleic acid bases). In some embodiments, the nucleic acids are homogeneous in backbone composition. Nucleic acids also include substituted purines and pyrimidines such as C-5 propyne modified bases (Wagner et al., *Nature Biotechnology* 14:840-844, 1996). Purines and pyrimidines include but are not limited to adenine, cytosine, guanine, thymidine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties. Other such modifications are well known to those of skill in the art.

For use in the instant invention, the nucleic acids of the invention can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid. Res.* 14:5399-5407, 1986, ; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These nucleic acids are referred to as synthetic nucleic acids. Alternatively, T-rich and/or TG dinucleotides can be produced on a large scale in plasmids, (see Sambrook, T., et al., "Molecular Cloning: A Laboratory Manual", Cold Spring Harbor laboratory Press, New York, 1989) and separated into smaller pieces or administered whole. Nucleic acids can be prepared from existing nucleic acid sequences (e.g., genomic or cDNA) using known techniques, such as those employing restriction enzymes, exonucleases or endonucleases. Nucleic acids prepared in this manner are referred to as isolated nucleic acid. An isolated nucleic acid generally refers to a nucleic acid which is separated from components which it is normally associated with in nature. As an example, an isolated nucleic acid may be one which is separated from a cell, from a nucleus, from mitochondria or from chromatin. The terms Py-rich nucleic acids and TG nucleic acids encompasses both synthetic and isolated Py-rich nucleic acids and TG nucleic acids.

For use in vivo, the Py-rich and TG nucleic acids may optionally be relatively resistant to degradation (e.g., are stabilized). A "stabilized nucleic acid molecule" shall mean a nucleic acid molecule that is relatively resistant to in vivo degradation (e.g. via an exo- or endo-nuclease). Stabilization can be a function of length or secondary structure. Nucleic acids that are tens to hundreds of kbs long are relatively resistant to in vivo degradation. For shorter nucleic acids, secondary structure can stabilize and increase their effect. For example, if the 3' end of an nucleic acid has self-complementarity to an upstream region, so that it can fold back and form a sort of stem loop structure, then the nucleic acid becomes stabilized and therefore exhibits more activity.

Alternatively, nucleic acid stabilization can be accomplished via phosphate backbone modifications. Preferred stabilized nucleic acids of the instant invention have a modified backbone. It has been demonstrated that modification of the nucleic acid backbone provides enhanced. activity of the Py-rich and TG nucleic acids when administered in vivo. These stabilized structures are preferred because the Py-rich and TG molecules of the invention have at least a partial modified backbone. Py-rich and TG constructs having phosphorothioate linkages provide maximal activity and protect the nucleic acid from degradation by intracellular exo- and endo-nucleases. Other modified nucleic acids include phosphodiester modified nucleic acids, combinations of phosphodiester and phosphorothioate nucleic acid, methylphosphonate, methylphosphorothioate, phosphorodithioate, p-ethoxy, and combinations thereof. Each of these combinations and their particular effects on immune cells is discussed in more detail with respect to CpG nucleic acids in PCT Published Patent Applications PCT/US95/01570 (WO 96/02555) and PCT/US97/19791 (WO 98/18810) claiming priority to U.S. Ser. No. 08/386,063, now U.S. Pat. No. 6,194,388, and Ser. No. 08/960,774, now U.S. Pat. No. 6,239,116, filed on Feb. 7, 1995 and Oct. 30, 1997 respectively, the entire contents of which are hereby incorporated by reference. It is believed that these modified nucleic acids may show more stimulatory activity due to enhanced nuclease resistance, increased cellular uptake, increased protein binding, and/or altered intracellular localization.

The compositions of the invention may optionally be chimeric oligonucleotides. The chimeric oligonucleotides are oligonucleotides having a formula: 5' $Y_1N_1ZN_2Y_2$ 3'. $Y_1$ and $Y_2$ are nucleic acid molecules having between 1 and 10 nucleotides. $Y_1$ and $Y_2$ each include at least one modified internucleotide linkage. Since at least 2 nucleotides of the chimeric oligonucleotides include backbone modifications these nucleic acids are an example of one type of "stabilized immunostimulatory nucleic acids."

With respect to the chimeric oligonucleotides, $Y_1$ and $Y_2$ are considered independent of one another. This means that each of $Y_1$ and $Y_2$ may or may not have different sequences and different backbone linkages from one anther in the same molecule. The sequences vary, but in some cases $Y_1$ and $Y_2$ have a poly-G sequence. A poly-G sequence refers to at least 3 Gs in a row. In other embodiments the poly-G sequence refers to at least 4, 5, 6, 7, or 8 Gs in a row. In other embodiments $Y_1$ and $Y_2$ may be TCGTCG, TCGTCGT, or TCGTCGTT (SEQ ID NO: 1145). $Y_1$ and $Y_2$ may also have a poly-C, poly-T, or poly-A sequence. In some embodiments $Y_1$ and/or $Y_2$ have between 3 and 8 nucleotides.

$N_1$ and $N_2$ are nucleic acid molecules having between 0 and 5 nucleotides as long as $N_1ZN_2$ has at least 6 nucleotides in total. The nucleotides of $N_1ZN_2$ have a phosphodiester backbone and do not include nucleic acids having a modified backbone.

Z is an immunostimulatory nucleic acid motif but does not include a CG. For instance, Z may be a nucleic acid a T-rich sequence, e.g. including a TTTT motif or a sequence wherein at least 50% of the bases of the sequence are Ts or Z may be a TG sequence.

The center nucleotides ($N_1ZN_2$) of the formula $Y_1N_1ZN_2Y_2$ have phosphodiester internucleotide linkages and $Y_1$ and $Y_2$ have at least one, but may have more than one or even may have all modified internucleotide linkages. In preferred embodiments $Y_1$ and/or $Y_2$ have at least two or between two and five modified internucleotide linkages or $Y_1$ has two modified internucleotide linkages and $Y_2$ has five modified internucleotide linkages or $Y_1$ has five modified internucleotide linkages and $Y_2$ has two modified internucleotide linkages. The modified internucleotide linkage, in some embodiments is a phosphorothioate modified linkage, a phosphorodithioate modified linkage or a p-ethoxy modified linkage.

Modified backbones such as phosphorothioates may be synthesized using automated techniques employing either phosphoramidate or H-phosphonate chemistries. Aryl-and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A., *Chem. Rev.* 90:544, 1990; Goodchild, J., *Bioconjugate Chem.* 1:165, 1990).

Other stabilized nucleic acids include: nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

In the case when the Py-rich or TG nucleic acid is administered in conjunction with an antigen which is encoded in a nucleic acid vector, it is preferred that the backbone of the Py-rich or TG nucleic acid be a chimeric combination of phosphodiester and phosphorothioate (or other phosphate modification). The cell may have a problem taking up a plasmid vector in the presence of completely phosphorothioate nucleic acid. Thus when both a vector and a nucleic acid are delivered to a subject, it is preferred that the nucleic acid have a chimeric backbone or have a phosphorothioate backbone but that the plasmid be associated with a vehicle that delivers it directly into the cell, thus avoiding the need for cellular uptake. Such vehicles are known in the art and include, for example, liposomes and gene guns.

The nucleic acids described herein as well as various control nucleic acids are presented below in Table A.

TABLE A

| SEQ ID NO: | ODN SEQUENCE | BACKBONE |
|---|---|---|
| 1 | tctcccagcgtgcgccat | s |
| 2 | ataatccagcttgaaccaag | s |
| 3 | ataatcgacgttcaagcaag | s |
| 4 | taccgcgtgcgaccctct | s |
| 5 | ggggagggt | s |
| 6 | ggggagggg | s |
| 7 | ggtgaggtg | s |
| 8 | tccatgtzgttcctgatgct | o |
| 9 | gctaccttagzgtga | o |
| 10 | tccatgazgttcctgatgct | o |
| 11 | tccatgacgttcztgatgct | o |
| 12 | gctagazgttagtgt | o |
| 13 | agctccatggtgctcactg | s |
| 14 | ccacgtcgaccctcaggcga | s |
| 15 | gcacatcgtcccgcagccga | s |
| 16 | gtcactcgtggtacctcga | s |
| 17 | gttggatacaggccagactttgttg | o |
| 18 | gattcaacttgcgctcatcttaggc | o |
| 19 | accatggacgaactgtttccctc | s |
| 20 | accatggacgagctgtttccctc | s |
| 21 | accatggacgacctgtttccctc | s |
| 22 | accatggacgtactgtttccctc | s |
| 23 | accatggacggtctgtttccctc | s |
| 24 | accatggacgttctgtttccctc | s |
| 25 | ccactcacatctgctgctccacaag | o |
| 26 | acttctcatagtcccttggtccag | o |
| 27 | tccatgagcttcctgagtct | o |
| 28 | gaggaaggigiggaigacgt | o |
| 29 | gtgaaticgttcicggglct | o |
| 30 | aaaaaa | s |
| 31 | cccccc | s |
| 32 | ctgtca | s |
| 33 | tcgtag | s |
| 34 | tcgtgg | s |

TABLE A-continued

| SEQ ID NO: | ODN SEQUENCE | BACKBONE |
|---|---|---|
| 35 | cgtcgt | s |
| 36 | tccatgtcggtcctgagtct | sos |
| 37 | tccatgccggtcctgagtct | sos |
| 38 | tccatgacggtcctgagtct | sos |
| 39 | tccatgacggtcctgagtct | sos |
| 40 | tccatgtcgatcctgagtct | sos |
| 41 | tccatgtcgctcctgagtct | sos |
| 42 | tccatgtcgttcctgagtct | sos |
| 43 | tccatgacgttcctgagtct | sos |
| 44 | tccataacgttcctgagtct | sos |
| 45 | tccatgacgtccctgagtct | sos |
| 46 | tccatcacgtgcctgagtct | sos |
| 47 | tccatgctggtcctgagtct | sos |
| 48 | tccatgtzggtcctgagtct | sos |
| 49 | ccgcttcctccagatgagctcatgggtttctccaccaag | o |
| 50 | cttggtggagaaacccatgagctcatctggaggaagcgg | o |
| 51 | ccccaaagggatgagaagtt | o |
| 52 | agatagcaaatcggctgacg | o |
| 53 | ggttcacgtgctcatggctg | o |
| 54 | tctcccagcgtgcgccat | s |
| 55 | tctcccagcgtgcgccat | s |
| 56 | taccgcgtgcgaccctct | s |
| 57 | ataatccagcttgaaccaag | s |
| 58 | ataatcgacgttcaagcaag | s |
| 59 | tccatgattttcctgattttt | o |
| 60 | ttgttttttttgtttttttgttttt | s |
| 61 | ttttttttgtttttttgttttt | o |
| 62 | tgctgcttttgtgcttttgtgctt | s |
| 63 | tgctgcttgtgcttttgtgctt | o |
| 64 | gcattcatcaggcgggcaagaat | o |
| 65 | taccgagcttcgacgagatttca | o |
| 66 | gcatgacgttgagct | s |
| 67 | cacgttgaggggcat | s |
| 68 | ctgctgagactggag | s |
| 69 | tccatgacgttcctgacgtt | s |
| 70 | gcatgagcttgagctga | o |
| 71 | tcagcgtgcgcc | s |
| 72 | atgacgttcctgacgtt | s |

TABLE A-continued

| SEQ ID NO: | ODN SEQUENCE | BACKBONE |
|---|---|---|
| 73 | ttttgggttttggggtttt | s |
| 74 | tctaggcttttaggcttcc | s |
| 75 | gcattttttaggccaccat | s |
| 76 | tctcccagcgtgcgtgcgccat | s |
| 77 | tctcccagcgggcgcat | s |
| 78 | tctcccagcgagcgccat | s |
| 79 | tctcccagcgcgcgccat | s |
| 80 | ggggtgacgttcagggggg | sos |
| 81 | ggggtccagcgtgcgccatggggg | sos |
| 82 | ggggtgtcgttcagggggg | sos |
| 83 | tccatgtcgttcctgtcgtt | s |
| 84 | tccatagcgttcctagcgtt | s |
| 85 | tcgtcgctgtctccgcttctt | s |
| 86 | gcatgacgttgagct | sos |
| 87 | tctcccagcgtgcgccatat | sos |
| 88 | tccatgazgttcctgazgtt | s |
| 89 | gcatgazgttgagct | o |
| 90 | tccagcgtgcgccata | sos |
| 91 | tctcccagcgtgcgccat | o |
| 92 | tccatgagcttcctgagtct | o |
| 93 | gcatgtcgttgagct | sos |
| 94 | tcctgacgttcctgacgtt | s |
| 95 | gcatgatgttgagct | o |
| 96 | gcatttcgaggagct | o |
| 97 | gcatgtagctgagct | o |
| 98 | tccaggacgttcctagttct | o |
| 99 | tccaggagcttcctagttct | o |
| 100 | tccaggatgttcctagttct | o |
| 101 | tccagtctaggcctagttct | o |
| 102 | tccagttcgagcctagttct | o |
| 103 | gcatggcgttgagct | sos |
| 104 | gcatagcgttgagct | sos |
| 105 | gcattgcgttgagct | sos |
| 106 | gcttgcgttgcgttt | sos |
| 107 | tctcccagcgttgcgccatat | sos |
| 108 | tctcccagcgtgcgttatat | sos |
| 109 | tctccctgcgtgcgccatat | sos |
| 110 | tctgcgtgcgtgcgccatat | sos |
| 111 | tctcctagcgtgcgccatat | sos |

TABLE A-continued

| SEQ ID NO: | ODN SEQUENCE | BACKBONE |
|---|---|---|
| 112 | tctcccagcgtgcgccttttt | sos |
| 113 | gctandcghhagc | o |
| 114 | tcctgacgttccc | o |
| 115 | ggaagacgttaga | o |
| 116 | tcctgacgttaga | o |
| 117 | tcagaccagctggtcgggtgttcctga | o |
| 118 | tcaggaacacccgaccagctggtctga | o |
| 119 | gctagtcgatagc | o |
| 120 | gctagtcgctagc | o |
| 121 | gcttgacgtctagc | o |
| 122 | gcttgacgtttagc | o |
| 123 | gcttgacgtcaagc | o |
| 124 | gctagacgtttagc | o |
| 125 | tccatgacattcctgatgct | o |
| 126 | gctagacgtctagc | o |
| 127 | ggctatgtcgttcctagcc | o |
| 128 | ggctatgtcgatcctagcc | o |
| 129 | ctcatgggttctccaccaag | o |
| 130 | cttggtggagaaacccatgag | o |
| 131 | tccatgacgttcctagttct | o |
| 132 | ccgcttcctccagatgagctcatg | o |
| 133 | catgagctcatctggaggaagcgg | o |
| 134 | ccagatgagctcatgggtttctcc | o |
| 135 | ggagaaacccatgagctcatctgg | o |
| 136 | agcatcaggaacgacatgga | o |
| 137 | tccatgacgttcctgacgtt | rna |
| 138 | gcgcgcgcgcgcgcgcgcg | o |
| 139 | ccggccggccggccggccgg | o |
| 140 | ttccaatcagccccacccgctctggccccaccctcaccctcca | o |
| 141 | tggagggtgagggtggggccagagcgggtggggctgattggaa | o |
| 142 | tcaaatgtgggattttcccatgagtct | o |
| 143 | agactcatgggaaaatcccacatttga | o |
| 144 | tgccaagtgctgagtcactaataaaga | o |
| 145 | tctttattagtgactcagcacttggca | o |
| 146 | tgcaggaagtccgggttttccccaaccccc | o |
| 147 | gggggttggggaaaacccggacttcctgca | o |
| 148 | ggggactttccgctggggacttccaggggacttttcc | sos |
| 149 | tccatgacgttcctctccatgacgttcctctccatgacgttcctc | o |

TABLE A-continued

| SEQ ID NO: | ODN SEQUENCE | BACKBONE |
|---|---|---|
| 150 | gaggaacgtcatggagaggaacgtcatggagaggaacgtcatgga | o |
| 151 | ataatagagcttcaagcaag | s |
| 152 | tccatgacgttcctgacgtt | s |
| 153 | tccatgacgttcctgacgtt | sos |
| 154 | tccaggactttcctcaggtt | s |
| 155 | tcttgcgatgctaaaggacgtcacattgcacaatcttaataaggt | o |
| 156 | accttattaagattgtgcaatgtgacgtcctttagcatcgcaaga | o |
| 157 | tcctgacgttcctggcggtcctgtcgct | o |
| 158 | tcctgtcgctcctgtcgct | o |
| 159 | tcctgacgttgaagt | o |
| 160 | tcctgtcgttgaagt | o |
| 161 | tcctggcgttgaagt | o |
| 162 | tcctgccgttgaagt | o |
| 163 | tccttacgttgaagt | o |
| 164 | tcctaacgttgaagt | o |
| 165 | tcctcacgttgaagt | o |
| 166 | tcctgacgatgaagt | o |
| 167 | tcctgacgctgaagt | o |
| 168 | tcctgacggtgaagt | o |
| 169 | tcctgacgtagaagt | o |
| 170 | tcctgacgtcgaagt | o |
| 171 | tcctgacgtggaagt | o |
| 172 | tcctgagcttgaagt | o |
| 173 | gggggacgttggggg | o |
| 174 | tcctgacgttccttc | o |
| 175 | tctcccagcgagcgagcgccat | s |
| 176 | tcctgacgttcccctggcggtccctgtcgct | o |
| 177 | tcctgtcgctcctgtcgctcctgtcgct | o |
| 178 | tcctggcggggaagt | o |
| 179 | tcctgazgttgaagt | o |
| 180 | tcztgacgttgaagt | o |
| 181 | tcctagcgttgaagt | o |
| 182 | tccagacgttgaagt | o |
| 183 | tcctgacggggaagt | o |
| 184 | tcctggcggtgaagt | o |
| 185 | ggctccggggagggaattttttgtctat | o |
| 186 | atagacaaaaattccctccccggagcc | o |
| 187 | tccatgagcttccttgagtct | rna |
| 188 | tcgtcgctgtctccgcttctt | so |

TABLE A-continued

| SEQ ID NO: | ODN SEQUENCE | BACKBONE |
|---|---|---|
| 189 | tcgtcgct[ ]tctccgcttctt | s20 |
| 190 | tcgagacattgcacaatcatctg | o |
| 191 | cagattgtgcaatgtctcga | o |
| 192 | tccatgtcgttcctgatgcg | o |
| 193 | gcgatgtcgttcctgatgct | o |
| 194 | gcgatgtcgttcctgatgcg | o |
| 195 | tccatgtcgttccgcgcgcg | o |
| 196 | tccatgtcgttcctgccgct | o |
| 197 | tccatgtcgttcctgtagct | o |
| 198 | gcggcgggcggcgcgcgccc | o |
| 199 | atcaggaacgtcatgggaagc | o |
| 200 | tccatgagcttcctgagtct | p-ethoxy |
| 201 | tcaacgtt | p-ethoxy |
| 202 | tcaagctt | p-ethoxy |
| 203 | tcctgtcgttcctgtcgtt | s |
| 204 | tccatgtcgtttttgtcgtt | s |
| 205 | tcctgtcgttccttgtcgtt | s |
| 206 | tccttgtcgttcctgtcgtt | s |
| 207 | btccattccatgacgttcctgatgcttcca | os |
| 208 | tcctgtcgttttttgtcgtt | s |
| 209 | tcgtcgctgtctccgcttctt | s |
| 210 | tcgtcgctgtctgcccttctt | s |
| 211 | tcgtcgctgttgtcgtttctt | s |
| 212 | tcctgtcgttcctgtcgttggaacgacagg | o |
| 213 | tcctgtcgttcctgtcgtttcaacgtcaggaacgacagga | o |
| 214 | ggggtctgtcgttttgggggg | sos |
| 215 | ggggtctgtgcttttgggggg | sos |
| 216 | tccggccgttgaagt | o |
| 217 | tccggacggtgaagt | o |
| 218 | tcccgccgttgaagt | o |
| 219 | tccagacggtgaagt | o |
| 220 | tcccgacggtgaagt | o |
| 221 | tccagagcttgaagt | o |
| 222 | tccatgtzgttcctgtzgtt | s |
| 223 | tccatgacgttcctgacgtt | sos |
| 224 | ggggttgacgttttgggggg | sos |
| 225 | tccaggacttctctcaggtt | s |
| 226 | tttttttttttttttttttt | s |

TABLE A-continued

| SEQ ID NO: | ODN SEQUENCE | BACKBONE |
|---|---|---|
| 227 | tccatgccgttcctgccgtt | s |
| 228 | tccatggcgggcctggcggg | s |
| 229 | tccatgacgttcctgccgtt | s |
| 230 | tccatgacgttcctggcggg | s |
| 231 | tccatgacgttcctgcgttt | s |
| 232 | tccatgacggtcctgacggt | s |
| 233 | tccatgcgtgcgtgcgtttt | s |
| 234 | tccatgcgttgcgttgcgtt | s |
| 235 | btccattccattctaggcctgagtcttccat | os |
| 236 | tccatagcgttcctagcgtt | o |
| 237 | tccatgtcgttcctgtcgtt | o |
| 238 | tccatagcgatcctagcgat | o |
| 239 | tccattgcgttccttgcgtt | o |
| 240 | tccatagcggtcctagcggt | o |
| 241 | tccatgattttcctgcagttcctgatttt | |
| 242 | tccatgacgttcctgcagttcctgacgtt | s |
| 243 | ggcggcggcggcggcggcgg | o |
| 244 | tccacgacgttttcgacgtt | s |
| 245 | tcgtcgttgtcgttgtcgtt | s |
| 246 | tcgtcgttttgtcgttttgtcgtt | s |
| 247 | tcgtcgttgtcgttttgtcgtt | s |
| 248 | gcgtgcgttgtcgttgtcgtt | s |
| 249 | czggczggcxgggcxccgg | o |
| 250 | gcggcgggcggcgcgcgccc | s |
| 251 | agicccgigaacgiattcac | o |
| 252 | tgtcgtttgtcgtttgtcgtt | s |
| 253 | tgtcgttgtcgttgtcgttgtcgtt | s |
| 254 | tgtcgttgtcgttgtcgttgtcgtt | s |
| 255 | tcgtcgtcgtcgtt | s |
| 256 | tgtcgttgtcgtt | s |
| 257 | cccccccccccccccccccc | s |
| 258 | tctagcgttttagcgttcc | sos |
| 259 | tgcatccccaggccaccat | s |
| 260 | tcgtcgtcgtcgtcgtcgtt | sos |
| 261 | tcgtcgttgtcgttgtcgtt | sos |
| 262 | tcgtcgttttgtcgttttgtcgtt | sos |
| 263 | tcgtcgttgtcgttttgtcgtt | sos |
| 264 | ggggagggaggaacttcttaaaattcccccagaatgttt | o |
| 265 | aaacattctgggggaattttaagaagttcctccctcccc | o |

TABLE A-continued

| SEQ ID NO: | ODN SEQUENCE | BACKBONE |
|---|---|---|
| 266 | atgtttacttcttaaaattcccccagaatgttt | o |
| 267 | aaacattctgggggaatttttaagaagtaaacat | o |
| 268 | atgtttactagacaaaattcccccagaatgttt | o |
| 269 | aaacattctgggggaattttgtctagtaaacat | o |
| 270 | aaaattgacgttttaaaaaa | sos |
| 271 | cccccttgacgttttcccccc | sos |
| 272 | ttttcgttgttttttgtcgtt | |
| 273 | tcgtcgttttgtcgttttgtcgtt | sos |
| 274 | ctgcagcctgggac | o |
| 275 | acccgtcgtaattatagtaaaaccc | o |
| 276 | ggtacctgtggggacattgtg | o |
| 277 | agcaccgaacgtgagagg | o |
| 278 | tccatgccgttcctgccgtt | o |
| 279 | tccatgacggtcctgacggt | o |
| 280 | tccatgccggtcctgccggt | o |
| 281 | tccatgcgcgtcctgcgcgt | o |
| 282 | ctggtctttctggttttttttctgg | s |
| 283 | tcagggtgggggaacctt | sos |
| 284 | tccatgazgttcctagttct | o |
| 285 | tccatgatgttcctagttct | o |
| 286 | cccgaagtcatttcctcttaacctgg | o |
| 287 | ccaggttaagaggaaatgacttcggg | o |
| 288 | tcctggzggggaagt | o |
| 289 | gzggzgggzggzgzgzgccc | x |
| 290 | tccatgtgcttcctgatgct | o |
| 291 | tccatgtccttcctgatgct | o |
| 292 | tccatgtcgttcctagttct | |
| 293 | tccaagtagttcctagttct | o |
| 294 | tccatgtagttcctagttct | o |
| 295 | tcccgcgcgttccgcgcgtt | s |
| 296 | tcctggcggtcctggcggtt | s |
| 297 | tcctggagggaagt | o |
| 298 | tcctgggggaagt | o |
| 299 | tcctggtggggaagt | o |
| 300 | tcgtcgttttgtcgttttgtcgtt | o |
| 301 | ctggtctttctggttttttttctgg | o |
| 302 | tccatgacgttcctgacgtt | o |
| 303 | tccaggacttctctcaggtt | sos |

TABLE A-continued

| SEQ ID NO: | ODN SEQUENCE | BACKBONE |
|---|---|---|
| 304 | tzgtzgttttgtzgttttgtzgtt | o |
| 305 | btcgtcgttttgtcgttttgtcgttttttt | os |
| 306 | gctatgacgttccaaggg | s |
| 307 | tcaacgtt | s |
| 308 | tccaggactttcctcaggtt | o |
| 309 | ctctctgtaggcccgcttgg | s |
| 310 | ctttccgttggaccccTggg | s |
| 311 | gtccgggccaggccaaagtc | s |
| 312 | gtgcgcgcgagcccgaaatc | s |
| 313 | tccatgaigttcctgaigtt | s |
| 314 | aatagtcgccataacaaaac | o |
| 315 | aatagtcgccatggcggggc | o |
| 316 | bttttTccatgtcgttcctgatgcttttt | os |
| 317 | tcctgtcgttgaagtttttt | o |
| 318 | gctagctttagagctttagagctt | o |
| 319 | tgctgcttcccccccccccc | o |
| 320 | tcgacgttcccccccccccc | o |
| 321 | tcgtcgttcccccccccccc | o |
| 322 | tcgtcgttcccccccccccc | o |
| 323 | tcgccgttcccccccccccc | o |
| 324 | tcgtcgatcccccccccccc | o |
| 325 | tcctgacgttgaagt | s |
| 326 | tcctgccgttgaagt | s |
| 327 | tcctgacggtgaagt | s |
| 328 | tcctgagcttgaagt | s |
| 329 | tcctggcggggaagt | s |
| 330 | aaaatctgtgcttttaaaaaa | sos |
| 331 | gatccagtcacagtgacctggcagaatctggat | o |
| 332 | gatccagattctgccaggtcactgtgactggat | o |
| 333 | gatccagtcacagtgactcagcagaatctggat | o |
| 334 | gatccagattctgctgagtcactgtgactggat | o |
| 335 | tcgtcgttccccccczcccc | o |
| 336 | tzgtggttcccccccccccc | o |
| 337 | tzgtcgttcccccccccccc | o |
| 338 | tcgtzgttcccccccccccc | o |
| 339 | tcgtcgctcccccccccccc | o |
| 340 | tcgtcggtcccccccccccc | o |
| 341 | tcggcgttcccccccccccc | o |
| 342 | ggccttttcccccccccccc | o |

TABLE A-continued

| SEQ ID NO: | ODN SEQUENCE | BACKBONE |
|---|---|---|
| 343 | tcgtcgttttgacgttttgtcgtt | s |
| 344 | tcgtcgttttgacgttttgacgtt | s |
| 345 | ccgtcgttccccccccccc | o |
| 346 | gcgtcgttccccccccccc | o |
| 347 | tcgtcattccccccccccc | o |
| 348 | acgtcgttccccccccccc | o |
| 349 | ctgtcgttccccccccccc | o |
| 350 | bttttcgtcgttccccccccccc | os |
| 351 | tcgtcgttccccccccccb | o |
| 352 | tcgtcgttttgtcgttttgtcgttb | o |
| 353 | tccagttccttcctcagtct | o |
| 354 | tzgtcgttttgtcgttttgtcgtt | o |
| 355 | tcctggaggggaagt | s |
| 356 | tcctgaaaaggaagt | s |
| 357 | tcgtcgttccccccccc | s |
| 358 | tzgtzgttttgtzgttttgtzgtt | s |
| 359 | ggggtcaagcttgaggggggg | sos |
| 360 | tgctgttccccccccccc | s |
| 361 | tcgtcgtcgtcgtt | s2 |
| 362 | tcgtcgtcgtcgtt | s20 |
| 363 | tcgtcgtcgtcgtt | os2 |
| 364 | tcaacgttga | s |
| 365 | tcaacgtt | s |
| 366 | atagttttccatttttttac | |
| 367 | aatagtcgccatcgcgcgac | o |
| 368 | aatagtcgccatcccgggac | o |
| 369 | aatagtcgccatcccccccc | o |
| 370 | tgctgcttttgtgcttttgtgctt | o |
| 371 | ctgtgctttctgtgttttctgtg | s |
| 372 | ctaatctttctaatttttttctaa | s |
| 373 | tcgtcgttggtgtcgttggtgtcgtt | s |
| 374 | tcgtcgttggttgtcgttttggtt | s |
| 375 | accatggacgagctgttccctc | |
| 376 | tcgtcgttttgcgtgcgttt | s |
| 377 | ctgtaagtgagcttggagag | |
| 378 | gagaacgctggaccttcc | |
| 379 | cgggcgactcagtctatcgg | |
| 380 | gttctcagataaagcggaaccagcaacagacacagaa | |

TABLE A-continued

| SEQ ID NO: | ODN SEQUENCE | BACKBONE |
|---|---|---|
| 381 | ttctgtgtctgttgctggttccgctttatctgagaac | |
| 382 | cagacacagaagcccgatagacg | |
| 383 | agacagacacgaaacgaccg | |
| 384 | gtctgtcccatgatctcgaa | |
| 385 | gctggccagcttacctcccg | |
| 386 | ggggcctctatacaacctggg | |
| 387 | ggggtccctgagactgcc | |
| 388 | gagaacgctggaccttccat | |
| 389 | tccatgtcggtcctgatgct | |
| 390 | ctcttgcgacctggaaggta | |
| 391 | aggtacagccaggactacga | |
| 392 | accatggacgacctgtttcccctc | |
| 393 | accatggattaccttttcccctt | |
| 394 | atggaaggtccagcgttctc | o |
| 395 | agcatcaggaccgacatgga | o |
| 396 | ctctccaagctcacttacag | |
| 397 | tccctgagactgccccaccttt | |
| 398 | gccaccaaaacttgtccatg | |
| 399 | gtccatggcgtgcgggatga | |
| 400 | cctctatacaacctgggac | |
| 401 | cgggcgactcagtctatcgg | |
| 402 | gcgctaccggtagcctgagt | |
| 403 | cgactgccgaacaggatatcggtgatcagcactgg | |
| 404 | ccagtgctgatcaccgatatcctgttcggcagtcg | |
| 405 | ccaggttgtatagaggc | |
| 406 | tctcccagcgtacgccat | s |
| 407 | tctcccagcgtgcgtttt | s |
| 408 | tctcccgacgtgcgccat | s |
| 409 | tctcccgtcgtgcgccat | s |
| 410 | ataatcgtcgttcaagcaag | s |
| 411 | tcgtcgttttgtcgttttgtcgt | s2 |
| 412 | tcgtcgttttgtcgttttgtcgtt | s2 |
| 413 | tcgtcgttttgtcgttttgtcgtt | s2 |
| 414 | tcntcgtnttntcgtnttntcgtn | s |
| 415 | tctcccagcgtcgccat | s |
| 416 | tctcccatcgtcgccat | s |
| 417 | ataatcgtgcgttcaagaaag | s |
| 418 | ataatcgacgttccccccccc | s |
| 419 | tctatcgacgttcaagcaag | s |

TABLE A-continued

| SEQ ID NO: | ODN SEQUENCE | BACKBONE |
|---|---|---|
| 420 | tcc tga cgg gg agt | s |
| 421 | tccatgacgttcctgatcc | |
| 422 | tccatgacgttcctgatcc | |
| 423 | tccatgacgttcctgatcc | |
| 424 | tcc tgg cgt gga agt | s |
| 425 | tccatgacgttcctgatcc | |
| 426 | tcgtcgctgttgtcgtttctt | s |
| 427 | agcagctttagagctttagagctt | s |
| 428 | cccccccccccccccccccccc | s |
| 429 | tcgtcgttttgtcgttttgtcgttttgtcgtt | s |
| 430 | tcgtcgtttttgtcgttttttgtcgtt | s |
| 431 | tcgtcgtttttttttttttt | s |
| 432 | tttttcaacgttgatttttt | sos |
| 433 | tttttttttttttttttttttttt | s |
| 434 | ggggtcgtcgttttgggggg | |
| 435 | tcgtcgttttgtcgttttgggggg | |
| 436 | tcgtcgctgtctccgcttcttcttgcc | s |
| 437 | tcgtcgctgtctccg | s |
| 438 | ctgtaagtgagcttggagag | |
| 439 | gagaacgctggaccttccat | |
| 440 | ccaggttgtatagaggc | |
| 441 | gctagacgttagcgtga | |
| 442 | ggagctcttcgaacgccata | |
| 443 | tctccatgatggttttatcg | |
| 444 | aaggtggggcagtctcaggga | |
| 445 | atcggaggactggcgcgccg | |
| 446 | ttaggacaaggtctagggtg | |
| 447 | accacaacgagaggaacgca | |
| 448 | ggcagtgcaggctcaccggg | |
| 449 | gaaccttccatgctgtt | |
| 450 | gctagacgttagcgtga | |
| 451 | gcttggagggcctgtaagtg | |
| 452 | gtagccttccta | |
| 453 | cggtagccttccta | |
| 454 | cacggtagccttccta | |
| 455 | agcacggtagccttccta | |
| 456 | gaacgctggaccttccat | |
| 457 | gaccttccat | |

TABLE A-continued

| SEQ ID NO: | ODN SEQUENCE | BACKBONE |
|---|---|---|
| 458 | tggaccttccat | |
| 459 | gctggaccttccat | |
| 460 | acgctggaccttccat | |
| 461 | taagctctgtcaacgccagg | |
| 462 | gagaacgctggaccttccatgt | |
| 463 | tccatgtcggtcctgatgct | |
| 464 | ttcatgccttgcaaaatggcg | |
| 465 | tgctagctgtgcctgtacct | |
| 466 | agcatcaggaccgacatgga | |
| 467 | gaccttccatgtcggtcctgat | |
| 468 | acaaccacgagaacgggaac | |
| 469 | gaaccttccatgctgttccg | |
| 470 | caatcaatctgaggagaccc | |
| 471 | tcagctctggtacttttca | |
| 472 | tggttacggtctgtcccatg | |
| 473 | gtctatcggaggactggcgc | |
| 474 | cattttacgggcgggcgggc | |
| 475 | gaggggaccattttacgggc | |
| 476 | tgtccagccgaggggaccat | |
| 477 | cgggcttacggcggatgctg | |
| 478 | tggaccttctatgtcggtcc | |
| 479 | tgtcccatgtttttagaagc | |
| 480 | gtggttacggtcgtgcccat | |
| 481 | cctccaaatgaaagaccccc | |
| 482 | ttgtactctccatgatggtt | |
| 483 | ttccatgctgttccggctgg | |
| 484 | gaccttctatgtcggtcctg | |
| 485 | gagaccgctcgaccttcgat | |
| 486 | ttgccccatattttagaaac | |
| 487 | ttgaaactgaggtgggac | |
| 488 | ctatcggaggactggcgcgcc | |
| 489 | cttggagggcctcccggcgg | |
| 490 | gctgaaccttccatgctgtt | |
| 491 | tagaaacagcattcttcttttagggcagcaca | |
| 492 | agatggttctcagataaagcggaa | |
| 493 | ttccgctttatctgagaaccatct | |
| 494 | gtcccaggttgtatagaggctgc | |
| 495 | gcgccagtcctccgatagac | |
| 496 | atcggaggactggcgcgccg | |

TABLE A-continued

| SEQ ID NO: | ODN SEQUENCE | BACKBONE |
|---|---|---|
| 497 | ggtctgtcccatattttag | |
| 498 | tttttcaacgttgagggggg | sos |
| 499 | tttttcaagcgttgatttttt | sos |
| 500 | ggggtcaacgttgattttttt | sos |
| 501 | ggggttttcaacgttttgagggggg | sos |
| 502 | ggttacggtctgtcccatat | |
| 503 | ctgtcccatattttagaca | |
| 504 | accatcctgaggccattcgg | |
| 505 | cgtctatcgggcttctgtgtctg | |
| 506 | ggccatcccacattgaaagtt | |
| 507 | ccaaatatcggtggtcaagcac | |
| 508 | gtgcttgaccaccgatatttgg | |
| 509 | gtgctgatcaccgatatcctgttcgg | |
| 510 | ggccaactttcaatgtgggatggcctc | |
| 511 | ttccgccgaatggcctcaggatggtac | |
| 512 | tatagtccctgagactgccccaccttctcaacaacc | |
| 513 | gcagcctctatacaacctgggacggga | |
| 514 | ctatcggaggactggcgcgccg | |
| 515 | tatcggaggactggcgcgccg | |
| 516 | gatcggaggactggcgcgccg | |
| 517 | ccgaacaggatatcggtgatcagcac | |
| 518 | ttttgggtcaacgttgagggggg | |
| 519 | ggggtcaacgttgagggggg | sos |
| 520 | cgcgcgcgcgcgcgcgcgcg | s |
| 521 | ggggcatgacgttcgggggg | ss |
| 522 | ggggcatgacgttcaaaaaa | s |
| 523 | ggggcatgagcttcgggggg | s |
| 524 | ggggcatgacgttcgggggg | sos |
| 525 | aaaacatgacgttcaaaaaa | sos |
| 526 | aaaacatgacgttcgggggg | sos |
| 527 | ggggcatgacgttcaaaaaa | sos |
| 528 | accatggacgatctgtttcccctc | s |
| 529 | gccatggacgaactgttccccctc | s |
| 530 | cccccccccccccccccccc | sos |
| 531 | gggggggggggggggggggg | sos |
| 532 | gctgtaaaatgaatcggccg | sos |
| 533 | ttcgggcggactcctccatt | sos |
| 534 | tatgccgcgcccggacttat | sos |

TABLE A-continued

| SEQ ID NO: | ODN SEQUENCE | BACKBONE |
|---|---|---|
| 535 | ggggtaatcgatcagggggg | SOS |
| 536 | tttgagaacgctggaccttc | SOS |
| 537 | gatcgctgatctaatgctcg | SOS |
| 538 | gtcggtcctgatgctgttcc | SOS |
| 539 | tcgtcgtcagttcgctgtcg | SOS |
| 540 | ctggaccttccatgtcgg | SOS |
| 541 | gctcgttcagcgcgtct | SOS |
| 542 | ctggaccttccatgtc | SOS |
| 543 | cactgtccttcgtcga | SOS |
| 544 | cgctggaccttccatgtcgg | SOS |
| 545 | gctgagctcatgccgtctgc | SOS |
| 546 | aacgctggaccttccatgtc | SOS |
| 547 | tgcatgccgtacacagctct | SOS |
| 548 | ccttccatgtcggtcctgat | SOS |
| 549 | tactcttcggatcccttgcg | 505 |
| 550 | ttccatgtcggtcctgat | SOS |
| 551 | ctgattgctctctcgtga | SOS |
| 552 | ggcgttattcctgactcgcc | o |
| 553 | cctacgttgtatgcgcccagct | o |
| 554 | ggggtaatcgatgagggggg | o |
| 555 | ttcgggcggactcctccatt | o |
| 556 | tttttttttttttttttttt | o |
| 557 | gggggtttttttttggggg | o |
| 558 | tttttgggggggggttttt | o |
| 559 | ggggggggggggggggggt | o |
| 560 | aaaaaaaaaaaaaaaaaaaa | o |
| 561 | cccccaaaaaaaaaaccccc | o |
| 562 | aaaaaccccccccccaaaaa | o |
| 563 | tttgaattcaggactggtgaggttgag | o |
| 564 | tttgaatcctcagcggtctccagtggc | o |
| 565 | aattctctatcggggcttctgtgtctgttgctggttccgctttat | o |
| 566 | ctagataaagcggaaccagcaacagacacagaagccccgatagag | o |
| 567 | ttttctagagaggtgcacaatgctctgg | o |
| 568 | tttgaattccgtgtacagaagcgagaagc | o |
| 569 | tttgcggccgctagacttaacctgagagata | o |
| 570 | tttgggcccacgagagacagagacacttc | o |
| 571 | tttgggcccgcttctcgcttctgtacacg | o |
| 572 | gagaacgctggaccttccat | s |
| 573 | tccatgtcggtcctgatgct | s |

TABLE A-continued

| SEQ ID NO: | ODN SEQUENCE | BACKBONE |
|---|---|---|
| 574 | ctgtcg | s |
| 575 | tcgtga | s |
| 576 | cgtcga | s |
| 577 | agtgct | s |
| 578 | ctgtcg | o |
| 579 | agtgct | o |
| 580 | cgtcga | o |
| 581 | tcgtga | o |
| 582 | gagaacgctccagcttcgat | o |
| 583 | gctagacgtaagcgtga | o |
| 584 | gagaacgctcgaccttccat | o |
| 585 | gagaacgctggacctatccat | o |
| 586 | gctagaggttagcgtga | o |
| 587 | gagaacgctggacttccat | o |
| 588 | tcacgctaacgtctagc | o |
| 589 | bgctagacgttagcgtga | o |
| 590 | atggaaggtcgagcgttctc | o |
| 591 | gagaacgctggaccttcgat | o |
| 592 | gagaacgatggaccttccat | o |
| 593 | gagaacgctggatccat | o |
| 594 | gagaacgctccagcactgat | o |
| 595 | tccatgtcggtcctgctgat | o |
| 596 | atgtcctcggtcctgatgct | o |
| 597 | gagaacgctccaccttccat | 0 |
| 598 | gagaacgctggaccttcgta | o |
| 599 | batggaaggtccagcgttctc | o |
| 600 | tcctga | o |
| 601 | tcaacgtt | o |
| 602 | aacgtt | o |
| 603 | aacgttga | o |
| 604 | tcacgctaacctctagc | o |
| 605 | gagaacgctggaccttgcat | o |
| 606 | gctggaccttccat | o |
| 607 | gagaacgctggacctcatccat | o |
| 608 | gagaacgctggacgctcatccat | o |
| 609 | aacgttgaggggcat | o |
| 610 | atgcccctcaacgtt | o |
| 611 | tcaacgttga | o |

TABLE A-continued

| SEQ ID NO: | ODN SEQUENCE | BACKBONE |
|---|---|---|
| 612 | gctggaccttccat | o |
| 613 | caacgtt | o |
| 614 | acaacgttga | o |
| 615 | tcacgt | o |
| 616 | tcaagctt | o |
| 617 | tcgtca | o |
| 618 | aggatatc | o |
| 619 | tagacgtc | o |
| 620 | gacgtcat | o |
| 621 | ccatcgat | o |
| 622 | atcgatgt | o |
| 623 | atgcatgt | o |
| 624 | ccatgcat | o |
| 625 | agcgctga | o |
| 626 | tcagcgct | o |
| 627 | ccttcgat | o |
| 628 | gtgccggggtctccgggc | s |
| 629 | gctgtgggcggctcctg | s |
| 630 | btcaacgtt | o |
| 631 | ftcaacgtt | o |
| 632 | faacgttga | o |
| 633 | tcaacgt | s |
| 634 | aacgttg | s |
| 635 | cgacga | o |
| 636 | tcaacgtt | o |
| 637 | togga | o |
| 638 | agaacgtt | o |
| 639 | tcatcgat | o |
| 640 | taaacgtt | s |
| 641 | ccaacgtt | s |
| 642 | gctcga | s |
| 643 | cgacgt | s |
| 644 | cgtcgt | s |
| 645 | acgtgt | s |
| 646 | cgttcg | s |
| 647 | gagcaagctggaccttccat | s |
| 648 | cgcgta | s |
| 649 | cgtacg | s |
| 650 | tcaccgt | s |

TABLE A-continued

| SEQ ID NO: | ODN SEQUENCE | BACKBONE |
|---|---|---|
| 651 | caagagatgctaacaatgca | s |
| 652 | acccatcaatagctctgtgc | s |
| 653 | ccatcgat | o |
| 654 | tcgacgtc | o |
| 655 | ctagcgct | o |
| 656 | taagcgct | o |
| 657 | tcgcgaattcgcg | o |
| 658 | atggaaggtccagcgttct | o |
| 659 | actggacgttagcgtga | o |
| 660 | cgcctggggctggtctgg | o |
| 661 | gtgtcgggtctccgggc | o |
| 662 | gtgccggggtctccgggc | o |
| 663 | cgccgtcgcggcggttgg | o |
| 664 | gaagttcacgttgaggggcat | o |
| 665 | atctggtgagggcaagctatg | s |
| 666 | gttgaaacccgagaacatcat | s |
| 667 | gcaacgtt | o |
| 668 | gtaacgtt | o |
| 669 | cgaacgtt | o |
| 670 | gaaacgtt | o |
| 671 | caaacgtt | o |
| 672 | ctaacgtt | o |
| 673 | ggaacgtt | o |
| 674 | tgaacgtt | o |
| 675 | acaacgtt | o |
| 676 | ttaacgtt | o |
| 677 | aaaacgtt | o |
| 678 | ataacgtt | o |
| 679 | aacgttct | o |
| 680 | tccgatcg | o |
| 681 | tccgtacg | o |
| 682 | gctagacgctagcgtga | o |
| 683 | gagaacgctggacctcatcatccat | o |
| 684 | gagaacgctagaccttctat | o |
| 685 | actagacgttagtgtga | o |
| 686 | cacaccttggtcaatgtcacgt | o |
| 687 | tctccatcctatggttttatcg | o |
| 688 | cgctggaccttccat | o |

TABLE A-continued

| SEQ ID NO: | ODN SEQUENCE | BACKBONE |
|---|---|---|
| 689 | caccaccttggtcaatgtcacgt | o |
| 690 | gctagacgttagctgga | o |
| 691 | agtgcgattgcagatcg | o |
| 692 | ttttcgttttgtggttttgtggtt | |
| 693 | ttttcgtttgtcgttttgtcgtt | |
| 694 | tttttgttttgtggttttgtggtt | |
| 695 | accgcatggattctaggcca | s |
| 696 | gctagacgttagcgt | o |
| 697 | aacgctggaccttccat | o |
| 698 | tcaazgtt | o |
| 699 | ccttcgat | o |
| 700 | actagacgttagtgtga | s |
| 701 | gctagaggttagcgtga | s |
| 702 | atggactctccagcgttctc | o |
| 703 | atcgactctcgagcgttctc | o |
| 704 | gctagacgttagc | o |
| 705 | gctagacgt | o |
| 706 | agtgcgattcgagatcg | o |
| 707 | tcagzgct | o |
| 708 | ctgattgctctctcgtga | o |
| 709 | tzaacgtt | o |
| 710 | gagaazgctggaccttccat | o |
| 711 | gctagacgttaggctga | o |
| 712 | gctacttagcgtga | o |
| 713 | gctaccttagcgtga | o |
| 714 | atcgacttcgagcgttctc | o |
| 715 | atgcactctgcagcgttctc | o |
| 716 | agtgactctccagcgttctc | o |
| 717 | gccagatgttagctgga | o |
| 718 | atcgactcgagcgttctc | o |
| 719 | atcgatcgagcgttctc | o |
| 720 | bgagaacgctcgaccttcgat | o |
| 721 | gctagacgttagctgga | sos |
| 722 | atcgactctcgagcgttctc | sos |
| 723 | tagacgttagcgtga | o |
| 724 | cgactctcgagcgttctc | o |
| 725 | ggggtcgaccttggaggggg | sos |
| 726 | gctaacgttagcgtga | o |
| 727 | cgtcgtcgt | o |

TABLE A-continued

| SEQ ID NO: | ODN SEQUENCE | BACKBONE |
|---|---|---|
| 728 | gagaacgctggaczttccat | o |
| 729 | atcgacctacgtgcgtttztc | o |
| 730 | atzgacctacgtgcgttctc | o |
| 731 | gctagazgttagcgt | o |
| 732 | atcgactctcgagzgttctc | o |
| 733 | ggggtaatgcatcagggggg | sos |
| 734 | ggctgtattcctgactgccc | s |
| 735 | ccatgctaacctctagc | o |
| 736 | gctagatgttagcgtga | o |
| 737 | cgtaccttacggtga | o |
| 738 | tccatgctggtcctgatgct | o |
| 739 | atcgactctctcgagcgttctc | o |
| 740 | gctagagcttagcgtga | o |
| 741 | atcgactctcgagtgttctc | o |
| 742 | aacgctcgaccttcgat | o |
| 743 | ctcaacgctggaccttccat | o |
| 744 | atcgacctacgtgcgttctc | o |
| 745 | gagaatgctggaccttccat | o |
| 746 | tcacgctaacctctgac | o |
| 747 | bgagaacgctccagcactgat | o |
| 748 | bgagcaagctggaccttccat | o |
| 749 | cgctagaggttagcgtga | o |
| 750 | gctagatgttaacgt | o |
| 751 | atggaaggtccacgttctc | o |
| 752 | gctagatgttagcgt | o |
| 753 | gctagacgttagtgt | o |
| 754 | tccatgacggtcctgatgct | o |
| 755 | tccatggcggtcctgatgct | o |
| 756 | gctagacgatagcgt | o |
| 757 | gctagtcgatagcgt | o |
| 758 | tccatgacgttcctgatgct | o |
| 759 | tccatgtcgttcctgatgct | o |
| 760 | gctagacgttagzgt | o |
| 761 | gctaggcgttagcgt | o |
| 762 | tccatgtzggtcctgatgct | o |
| 763 | tccatgtcggtzctgatgct | o |
| 764 | atzgactctzgagzgttctc | o |
| 765 | atggaaggtccagtgttctc | o |

TABLE A-continued

| SEQ ID NO: | ODN SEQUENCE | BACKBONE |
|---|---|---|
| 766 | gcatgacgttgagct | o |
| 767 | ggggtcaacgttgagggggg | s |
| 768 | ggggtcaagtctgagggggg | sos |
| 769 | cgcgcgcgcgcgcgcgcg | o |
| 770 | cccccccccccccccccccccccc | s |
| 771 | cccccccccccccccccccccccccccccccc | s |
| 772 | tccatgtcgctcctgatcct | o |
| 773 | gctaaacgttagcgt | o |
| 774 | tccatgtcgatcctgatgct | o |
| 775 | tccatgccggtcctgatgct | o |
| 776 | aaaatcaacgttgaaaaaaa | sos |
| 777 | tccataacgttcctgatgct | o |
| 778 | tggaggtcccaccgagatcggag | o |
| 779 | cgtcgtcgtcgtcgtcgt | s |
| 780 | ctgctgctgctgctgctg | s |
| 781 | gagaacgctccgaccttcgat | s |
| 782 | gctagatgttagcgt | s |
| 783 | gcatgacgttgagct | s |
| 784 | tcaatgctgaf | o |
| 785 | tcaacgttgaf | o |
| 786 | tcaacgttgab | o |
| 787 | gcaatattgcb | o |
| 788 | gcaatattgcf | o |
| 789 | agttgcaact | o |
| 790 | tcttcgaa | o |
| 791 | tcaacgtc | o |
| 792 | ccatgtcggtcctgatgct | o |
| 793 | gtttttatataatttggg | 0 |
| 794 | tttttgtttgtcgttttgtcgtt | o |
| 795 | ttggggggggtt | s |
| 796 | ggggttggggtt | s |
| 797 | ggtggtgtaggttttgg | o |
| 798 | bgagaazgctcgaccttcgat | o |
| 799 | tcaacgttaacgttaacgtt | o |
| 800 | bgagcaagztggaccttccat | o |
| 801 | bgagaazgctccagcactgat | o |
| 802 | tcaazgttgax | o |
| 803 | gzaatattgcx | o |
| 804 | tgctgcttttgtcgttttgtgctt | o |

TABLE A-continued

| SEQ ID NO: | ODN SEQUENCE | BACKBONE |
|---|---|---|
| 805 | ctgcgttagcaatttaactgtg | o |
| 806 | tccatgacgttcctgatgct | s |
| 807 | tgcatgccgtgcatccgtacacagctct | s |
| 808 | tgcatgccgtacacagctct | s |
| 809 | tgcatcagctct | s |
| 810 | tgcgctct | s |
| 811 | cccccccccccccccccccc | s |
| 812 | cccccccccccc | s |
| 813 | cccccccc | s |
| 814 | tgcatcagctct | sos |
| 815 | tgcatgccgtacacagctct | o |
| 816 | gagcaagctggaccttccat | s |
| 817 | tcaacgttaacgttaacgttaacgttaacgtt | s |
| 818 | gagaacgctcgaccttcgat | s |
| 819 | gtccccatttcccagaggaggaaat | o |
| 820 | ctagcggctgacgtcatcaagctag | o |
| 821 | ctagcttgatgacgtcagccgctag | o |
| 822 | cggctgacgtcatcaa | s |
| 823 | ctgacgtg | o |
| 824 | ctgacgtcat | o |
| 825 | attcgatcggggcggggcgag | o |
| 826 | ctcgccccgccccgatcgaat | o |
| 827 | gactgacgtcagcgt | o |
| 828 | ctagcggctgacgtcataaagctagc | s |
| 829 | ctagctttatgacgtcagccgctagc | s |
| 830 | ctagcggctgagctcataaagctagc | s |
| 831 | ctagtggctgacgtcatcaagctag | s |
| 832 | tccaccacgtggtctatgct | s |
| 833 | gggaatgaaagatttattataag | o |
| 834 | tctaaaaaccatctattcttaaccct | o |
| 835 | agctcaacgtcatgc | o |
| 836 | ttaacggtggtagcggtattggtc | o |
| 837 | ttaagaccaataccgctaccaccg | o |
| 838 | gatctagtgatgagtcagccggatc | o |
| 839 | gatccggctgactcatcactagatc | o |
| 840 | tccaagacgttcctgatgct | o |
| 841 | tccatgacgtccctgatgct | o |
| 842 | tccaccacgtggctgatgct | o |

TABLE A-continued

| SEQ ID NO: | ODN SEQUENCE | BACKBONE |
|---|---|---|
| 843 | ccacgtggacctctagc | o |
| 844 | tcagaccacgtggtcgggtgttcctga | o |
| 845 | tcaggaacacccgaccacgtggtctga | o |
| 846 | catttccacgatttccca | o |
| 847 | ttcctctctgcaagagact | o |
| 848 | tgtatctctctgaaggact | o |
| 849 | ataaagcgaaactagcagcagtttc | o |
| 850 | gaaactgctgctagtttcgctttat | o |
| 851 | tgcccaaagaggaaaatttgtttcatacag | o |
| 852 | ctgtatgaaacaaattttcctctttgggca | o |
| 853 | ttagggttagggttagggtt | ss |
| 854 | tccatgagcttcctgatgct | ss |
| 855 | aaaacatgacgttcaaaaaa | ss |
| 856 | aaaacatgacgttcgggggg | ss |
| 857 | ggggcatgagcttcgggggg | sos |
| 858 | ctaggctgacgtcatcaagctagt | o |
| 859 | tctgacgtcatctgacgttggctgacgtct | o |
| 860 | ggaattagtaatagatatagaagtt | o |
| 861 | tttaccttttataaacataactaaaacaaa | o |
| 862 | gcgttttttttttgcg | s |
| 863 | atatctaatcaaaacattaacaaa | o |
| 864 | tctatcccaggtggttcctgttag | o |
| 865 | btccatgacgttcctgatgct | o |
| 866 | btccatgagcttcctgatgct | o |
| 867 | tttttttttttttf | o |
| 868 | tttttttttttttf | so |
| 869 | ctagcttgatgagctcagccgctag | o |
| 870 | ttcagttgtcttgctgcttagctaa | o |
| 871 | tccatgagcttcctgagtct | s |
| 872 | ctagcggctgacgtcatcaatctag | o |
| 873 | tgctagctgtgcctgtacct | s |
| 874 | atgctaaaggacgtcacattgca | o |
| 875 | tgcaatgtgacgtcctttagcat | o |
| 876 | gtagggactttccgagctcgagatcctatg | o |
| 877 | cataggatctcgagctcggaaagtcccctac | o |
| 878 | ctgtcaggaactgcaggtaagg | o |
| 879 | cataacataggaatatttactcctcgc | o |
| 880 | ctccagctccaagaaaggacg | o |
| 881 | gaagtttctggtaagtcttcg | o |

TABLE A-continued

| SEQ ID NO: | ODN SEQUENCE | BACKBONE |
|---|---|---|
| 882 | tgctgcttttgtgcttttgtgctt | s |
| 883 | tcgtcgttttgtggttttgtggtt | s |
| 884 | tcgtcgtttgtcgttttgtcgtt | s |
| 885 | tcctgacgttcggcgcgcgccc | s |
| 886 | tgctgcttttgtgcttttgtgctt | |
| 887 | tccatgagcttcctgagctt | s |
| 888 | tcgtcgtttcgtcgttttgacgtt | s |
| 889 | tcgtcgtttgcgtgcgtttcgtcgtt | s |
| 890 | tcgcgtgcgttttgtcgttttgacgtt | s |
| 891 | ttcgtcgttttgtcgttttgtcgtt | s |
| 892 | tcctgacggggaagt | s |
| 893 | tcctggcgtggaagt | s |
| 894 | tcctggcggtgaagt | s |
| 895 | tcctggcgttgaagt | s |
| 896 | tcctgacgtggaagt | s |
| 897 | gcgacgttcggcgcgcgccc | s |
| 898 | gcgacgggcggcgcgcgccc | s |
| 899 | gcggcgtgcggcgcgcgccc | s |
| 900 | gcggcggtcggcgcgcgccc | s |
| 901 | gcgacggtcggcgcgcgccc | s |
| 902 | gcggcgttcggcgcgcgccc | s |
| 903 | gcgacgtgcggcgcgcgccc | s |
| 904 | tcgtcgctgtctccg | s |
| 905 | tgtgggggttttggttttgg | s |
| 906 | aggggaggcggaggggaggggg | s |
| 907 | tgtgtgtgtgtgtgtgtgt | s |
| 908 | ctctctctctctctctctct | chimeric |
| 909 | ggggtcgacgtcgagggggg | s |
| 910 | atatatatatatatatatat | s |
| 911 | tttttttttttttttttttttttttt | s |
| 912 | tttttttttttttttttttt | s |
| 913 | tttttttttttttttttt | s |
| 914 | gctagaggggagggt | |
| 915 | gctagatgttagggg | |
| 916 | gcatgagggggagct | |
| 917 | atggaaggtccagggggctc | |
| 918 | atggactctggaggggggctc | |
| 919 | atggaaggtccaaggggctc | |

TABLE A-continued

| SEQ ID NO: | ODN SEQUENCE | BACKBONE |
|---|---|---|
| 920 | gagaagggggaccttggat | |
| 921 | gagaagggggaccttccat | |
| 922 | gagaagggccagcactgat | |
| 923 | tccatgtgggcctgatgct | |
| 924 | tccatgagggcctgatgct | |
| 925 | tccatgtgggcctgctgat | |
| 926 | atggactctccggggttctc | |
| 927 | atggaaggtccggggttctc | |
| 928 | atggactctggaggggtctc | |
| 929 | atggaggctccatggggctc | |
| 930 | atggactctgggggttctc | |
| 931 | tccatgtgggtggggatgct | |
| 932 | tccatgcgggtggggatgct | |
| 933 | tccatgggggtcctgatgct | |
| 934 | tccatgggtccctgatgct | |
| 935 | tccatgggtgcctgatgct | |
| 936 | tccatggggttcctgatgct | |
| 937 | tccatcggggcctgatgct | |
| 938 | gctagagggagtgt | |
| 939 | tttttttttttttttttt | s |
| 940 | gmggtcaacgttgagggmggg | s |
| 941 | ggggagttcgttgagggggg | s |
| 942 | tcgtcgtttcccccccccc | s |
| 943 | ttgggggttttttttttttttttt | s |
| 944 | tttaaatttttaaaatttaaaata | s |
| 945 | ttggttttttttggttttttttttgg | s |
| 946 | tttccctttccccttttcccctc | s |
| 947 | ggggtcatcgatgagggggg s | sos |
| 948 | tccatgacgttcctgacgtt | |
| 949 | tccatgacgttcctgacgtt | |
| 950 | tccatgacgttcctgacgtt | |
| 951 | tccatgacgttcctgacgtt | |
| 952 | tccatgacgttcctgacgtt | |
| 953 | tccatgacgttcctgacgtt | |
| 954 | tccatgacgttcctgacgtt | |
| 955 | tccatgacgttcctgacgtt | |
| 956 | tccatgacgttcctgacgtt | |
| 957 | tccatgacgttcctgacgtt | |
| 958 | tccatgacgttcctgacgtt | |

TABLE A-continued

| SEQ ID NO: | ODN SEQUENCE | BACKBONE |
|---|---|---|
| 959 | gggggacgatcgtcgggggg | sos |
| 960 | gggggtcgtacgacggggggg | sos |
| 961 | tttttttttttttttttttttttt | po |
| 962 | aaaaaaaaaaaaaaaaaaaaaaaa | po |
| 963 | cccccccccccccccccccccccc | po |
| 964 | tcgtcgttttgtcgttttgtcgtt | |
| 965 | tcgtcgttttgtcgttttgtcgtt | |
| 966 | tcgtcgttttgtcgttttgtcgtt | |
| 967 | tcgtcgttttgtcgttttgtcgtt | |
| 968 | ggggtcaacgttgagggggg | |
| 969 | ggggtcaacgttgagggggg | |
| 970 | ggggtcaagcttgagggggg | |
| 971 | tgctgcttccccccccccccc | |
| 972 | ggggacgtcgacgtgggggg | sos |
| 973 | ggggtcgtcgacgaggggggg | sos |
| 974 | ggggtcgacgtacgtcgagggggg | sos |
| 975 | ggggaccggtaccggtgggggg | sos |
| 976 | gggtcgacgtcgaggggggg | sos |
| 977 | ggggtcgacgtcgagggggg | sos |
| 978 | ggggaacgttaacgttggggggg | sos |
| 979 | ggggtcaccggtgagggggg | sos |
| 980 | ggggtcgttcgaacgaggggggg | sos |
| 981 | ggggacgttcgaacgtggggggg | sos |
| 982 | tcaactttga | s |
| 983 | tcaagcttga | s |
| 984 | tcacgatcgtga | s |
| 985 | tcagcatgctga | s |
| 986 | gggggagcatgctggggggg | sos |
| 987 | gggggggggggggggggggggg | sos |
| 988 | gggggacgatatcgtcggggggg | sos |
| 989 | gggggacgacgtcgtcggggggg | sos |
| 990 | gggggacgagctcgtcggggggg | sos |
| 991 | gggggacgtacgtcggggggg | sos |
| 992 | tcaacgtt | |
| 993 | tccataccggtcctgatgct | |
| 994 | tccataccggtcctaccggt | s |
| 995 | gggggacgatcgttggggggg | sos |
| 996 | gggggaacgatcgtcgggggg | sos |

TABLE A-continued

| SEQ ID NO: | ODN SEQUENCE | BACKBONE |
|---|---|---|
| 997 | ggg ggg acg atc gtc ggg ggg | sos |
| 998 | ggg gga ega tcg tcg ggg ggg | sos |
| 999 | aaa gac gtt aaa | po |
| 1000 | aaagagcttaaa | po |
| 1001 | aaagazgttaaa | po |
| 1002 | aaattcggaaaa | po |
| 1003 | gggggtcatcgatgaggggggg | sos |
| 1004 | gggggtcaacgttgaggggggg | sos |
| 1005 | atgtagcttaataacaaagc | po |
| 1006 | ggatcccttgagttacttct | po |
| 1007 | ccattccacttctgattacc | po |
| 1008 | tatgtattatcatgtagata | po |
| 1009 | agcctacgtattcaccctcc | po |
| 1010 | ttcctgcaactactatttgta | po |
| 1011 | atagaaggccctacaccagt | po |
| 1012 | ttacaccggtctatggaggt | po |
| 1013 | ctaaccagatcaagtctagg | po |
| 1014 | cctagacttgatctggttag | po |
| 1015 | tataagcctcgtccgacatg | po |
| 1016 | catgtcggacgaggcttata | po |
| 1017 | tggtggtggggagtaagctc | po |
| 1018 | gagctactcccccaccacca | po |
| 1019 | gccttcgatcttcgttggga | po |
| 1020 | tggacttctcttttgccgtct | po |
| 1021 | atgctgtagcccagcgataa | po |
| 1022 | accgaatcagcggaaagtga | po |
| 1023 | tccatgacgttcctgacgtt | |
| 1024 | ggagaaacccatgagctcatctgg | |
| 1025 | accacagaccagcaggcaga | |
| 1026 | gagcgtgaactgcgcgaaga | |
| 1027 | tcggtacccttgcagcggtt | |
| 1028 | ctggagccctagccaaggat | |
| 1029 | gcgactccatcaccagcgat | |
| 1030 | cctgaagtaagaaccagatgt | |
| 1031 | ctgtgttatctgacatacacc | |
| 1032 | aattagccttaggtgattggg | |
| 1033 | acatctggttcttacttcagg | |
| 1034 | ataagtcatattttgggaactac | |
| 1035 | cccaatcacctaaggctaatt | |

TABLE A-continued

| SEQ ID NO: | ODN SEQUENCE | BACKBONE |
|---|---|---|
| 1036 | ggggtcgtcgacgagggggg | sos |
| 1037 | ggggtcgttcgaacgagggggg | sos |
| 1038 | gggggacgttcgaacgtggggggg | sos |
| 1039 | tcctggcggggaagt | s |
| 1040 | ggggaacgacgtcgttgggggg | sos |
| 1041 | ggggaacgtacgtcgggggg | sos |
| 1042 | ggggaacgtacgtacgttgggggg | sos |
| 1043 | ggggtcaccggtgagggggg | sos |
| 1044 | ggggtcgacgtacgtcgagggggg | sos |
| 1045 | ggggaccggtaccggtgggggg | sos |
| 1046 | gggtcgacgtcgagggggg | sos |
| 1047 | ggggtcgacgtcgagggg | sos |
| 1048 | ggggaacgttaacgttgggggg | sos |
| 1049 | ggggacgtcgacgtgggggg | sos |
| 1050 | gcactcttcgaagctacagccggcagcctctgat | |
| 1051 | cggctcttccatgaggtctttgctaatcttgg | |
| 1052 | cggctcttccatgaaagtctttggacgatgtgagc | |
| 1053 | tcctgcaggttaagt | s |
| 1054 | gggggtcgttcgttgggggg | sos |
| 1055 | gggggatgattgttgggggg | sos |
| 1056 | gggggazgatzgttgggggg | sos |
| 1057 | gggggagctagcttgggggg | sos |
| 1058 | ggttcttttggtccttgtct | s |
| 1059 | ggttcttttggtcctcgtct | s |
| 1060 | ggttcttttggtccttatct | s |
| 1061 | ggttcttggtttccttgtct | s |
| 1062 | tggtcttttggtccttgtct | s |
| 1063 | ggttcaaatggtccttgtct | s |
| 1064 | gggtcttttgggccttgtct | s |
| 1065 | tccaggacttctctcaggtttttt | s |
| 1066 | tccaaaacttctctcaaatt | s |
| 1067 | tactacttttatacttttatactt | s |
| 1068 | tgtgtgtgtgtgtgtgtgtg | s |
| 1069 | ttgttgttgttgtttgttgttgttg | s |
| 1070 | ggctccggggagggaattttttgtctat | s |
| 1071 | gggacgatcgtcgggggg | sos |
| 1072 | gggtcgtcgacgagggggg | sos |
| 1073 | ggtcgtcgacgagggggggg | sos |

TABLE A-continued

| SEQ ID NO: | ODN SEQUENCE | BACKBONE |
|---|---|---|
| 1074 | gggtcgtcgtcgtgggggggg | sos |
| 1075 | ggggacgatcgtcggggggg | sos |
| 1076 | ggggacgtcgtcgtggggggg | sos |
| 1077 | ggggtcgacgtcgacgtcgaggggggg | sos |
| 1078 | ggggaaccgcggttggggggg | sos |
| 1079 | ggggacgacgtcgtggggggg | sos |
| 1080 | tcgtcgtcgtcgtcgtggggggg | sos |
| 1081 | tcctgccggggaagt | s |
| 1082 | tcctgcaggggaagt | s |
| 1083 | tcctgaaggggaagt | s |
| 1084 | tcctggcgggcaagt | s |
| 1085 | tcctggcgggtaagt | s |
| 1086 | tcctggcgggaaagt | s |
| 1087 | tccgggcggggaagt | s |
| 1088 | tcggggcggggaagt | s |
| 1089 | tcccggcggggaagt | s |
| 1090 | gggggacgttggggg | s |
| 1091 | ggggttttttttttgggggg | sos |
| 1092 | ggggccccccccccgggggg | sos |
| 1093 | ggggttgttgttgttgggggg | sos |
| 1095 | aaaaaaaaaaaaaaaaaaaaaaaaaaaaa | |
| 1096 | cccccccccccccccccccccccccccc | |
| 1097 | cgcgcgcgcgcgcgcgcgcgcgcgcgcg | |

While CpG effects in mice are well characterized, information regarding the human system is limited. CpG phosphorothioate oligonucleotides with strong stimulatory activity in the mouse system show lower activity on human and other non-rodent immune cells. In the examples the development of a potent human CpG motif and the characterization of its effects and mechanisms of action on human primary B-cells is described. DNA containing this CpG motif strongly stimulated primary human B-cells to proliferate, to produce IL-6 and to express increased levels of CD86, CD40, CD54 and MHC II. It increased DNA binding activity of the transcription factors NFκB and AP-1, as well as phosphorylation of the stress activated protein kinases JNK and p38, and the transcription factor ATF-2. B-cell signaling pathways activated by CpG DNA were different from those activated by the B-cell receptor which activated ERK and a different isoform of JNK, but did not activate p38 and ATF-2. In general the data on CpG DNA-initiated signal transduction are consistent with those obtained in mice (Hacker H., Mischak H., Miethke T., Liptay S., Schmid R., Sparwasser T., Heeg K., Lipford G. B., and Wagner H. 1998. CpG-DNA-specific activation of antigen-presenting cells requires stress kinase activity and is preceded by non-specific endocytosis and endosomal maturation. *Embo J* 17:6230, Yi A. K., and Krieg A. M. 1998. Rapid induction of mitogen-activated protein kinases by immune stimulatory CpG DNA. *J Immunol* 161:4493).

The preferred non-rodent motif is 5' TCGTCGTT 3'. Base exchanges within the most potent 8mer CpG motif (5' TCGTCGTT 3') diminished the activity of the oligonucleotide. The thymidines at the 5' and the 3' position of this motif were more important than the thymidine at the middle position. An adenine or guanosine at the middle position produced a decrease in the activity.

Of note, our studies demonstrate that one human CpG motif within a phosphodiester oligonucleotide (2080) is sufficient to produce the maximal effect, and that additional CpG motifs (2059) did not further enhance the activity. The oligonucleotide with the 8mer motif 5' TCG TCG TT 3' (2080) containing two CpG dinucleotides showed the highest activity in the studies. Replacement of the bases flanking the two CpG dinucleotides (5' position, middle position, 3' position) reduced the activity of this sequence. Both CpG dinucleotides within the 8mer CpG motif were required for the optimal activity (2108, 2106). Cytidine methylation of the CpG dinucleotides (2095) abolished the activity of 2080, while methylation of an unrelated cytidine (2094) did not. The addition of two CpG motifs into the sequence of 2080 resulting in 2059 did not further increase the activity of the phosphodiester oligonucleotide. The sequence of 2080 with a phosphorothioate backbone (2116) demonstrated less activity, suggesting that additional CpG motifs are preferred for a potent phosphorothioate oligonucleotide.

It has been discovered according to the invention that the immunostimulatory nucleic acids have dramatic immune stimulatory effects on human cells such as NK cells, B cells, and DCs in vitro. It has been demonstrated that that the in vitro assays used herein predict in vivo effectiveness as a vaccine adjuvant in non-rodent vertebrates (Example 12), suggesting that immunostimulatory nucleic acids are effective therapeutic agents for human vaccination, cancer immunotherapy, asthma immunotherapy, general enhancement of immune function, enhancement of hematopoietic recovery following radiation or chemotherapy, and other immune modulatory applications.

Thus the immunostimulatory nucleic acids are useful in some aspects of the invention as a prophylactic vaccine for the treatment of a subject at risk of developing an infection with an infectious organism or a cancer in which a specific cancer antigen has been identified or an allergy or asthma where the allergen or predisposition to asthma is known. The immunostimulatory nucleic acids can also be given without the antigen or allergen for shorter term protection against infection, allergy or cancer, and in this case repeated doses will allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing an allergy to asthma includes those subjects that have been identified as having an allergy or asthma but that don't have the active disease during the immunostimulatory nucleic acid treatment as well as subjects that are considered to be at risk of developing these diseases because of genetic or environmental factors.

A subject at risk of developing a cancer is one who is who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with an antigen specific for the type of cancer to which the subject is at risk of developing and a immunostimulatory nucleic acid, the subject may be able to kill the cancer cells as they develop. If a tumor begins to form in the subject, the subject will develop a specific immune response against the tumor antigen.

In addition to the use of the immunostimulatory nucleic acids for prophylactic treatment, the invention also encompasses the use of the immunostimulatory nucleic acids for the treatment of a subject having an infection, an allergy, asthma, or a cancer.

A subject having an infection is a subject that has been exposed to an infectious pathogen and has acute or chronic detectable levels of the pathogen in the body. The immunostimulatory nucleic acids can be used with an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

Currently, allergic diseases are generally treated by the injection of small doses of antigen followed by subsequent increasing dosage of antigen. It is believed that this procedure induces tolerization to the allergen to prevent further allergic reactions. These methods, however, can take several years to be effective and are associated with the risk of side effects such as anaphylactic shock. The methods of the invention avoid these problems.

Allergies are generally caused by IgE antibody generation against harmless allergens. The cytokines that are induced by systemic or mucosal administration of immunostimulatory nucleic acids are predominantly of a class called Th1 (examples are IL-12 and IFN-γ) and these induce both humoral and cellular immune responses. The types of antibodies associated with a Th1 response are generally more protective because they have high neutralization and opsonization capabilities. The other major type of immune response, which is associated with the production of IL-4, IL-5 and IL-10 cytokines, is termed a Th2 immune response. Th2 responses involve predominately antibodies and these have less protective effect against infection and some Th2 isotypes (e.g., IgE) are associated with allergy. In general, it appears that allergic diseases are mediated by Th2 type immune responses while Th1 responses provide the best protection against infection, although excessive Th1 responses are associated with autoimmune disease. Based on the ability of the immunostimulatory nucleic acids to shift the immune response in a subject from a Th2 (which is associated with production of IgE antibodies and allergy) to a Th1 response (which is protective against allergic reactions), an effective dose for inducing an immune response of a immunostimulatory nucleic acid can be administered to a subject to treat or prevent an allergy.

Thus, the immunostimulatory nucleic acids have significant therapeutic utility in the treatment of allergic and non-allergic conditions such as asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject according to the invention is a non-rodent subject. A non-rodent subject shall mean a human or vertebrate animal including but not limited to a dog, cat, horse, cow, pig, sheep, goat, chicken, primate, e.g., monkey, and fish (aquaculture species), e.g. salmon, but specifically excluding rodents such as rats and mice.

Thus, the invention can also be used to treat cancer and tumors in non human subjects. Cancer is one of the leading causes of death in companion animals (i.e., cats and dogs). Cancer usually strikes older animals which, in the case of house pets, have become integrated into the family. Forty-five % of dogs older than 10 years of age, are likely to succumb to the disease. The most common treatment options include surgery, chemotherapy and radiation therapy. Others treatment modalities which have been used with some success are laser therapy, cryotherapy, hyperthermia and immunotherapy. The choice of treatment depends on type of cancer and degree of dissemination. Unless the malignant growth is confined to a discrete area in the body, it is difficult to remove only malignant tissue without also affecting normal cells.

Malignant disorders commonly diagnosed in dogs and cats include but are not limited to lymphosarcoma, osteosarcoma, mammary tumors, mastocytoma, brain tumor, melanoma, adenosquamous carcinoma, carcinoid lung tumor, bronchial gland tumor, bronchiolar adenocarcinoma, fibroma, myxochondroma, pulmonary sarcoma, neurosarcoma, osteoma, papilloma, retinoblastoma, Ewing's sarcoma, Wilm's tumor, Burkitt's lymphoma, microglioma, neuroblastoma, osteoclastoma, oral neoplasia, fibrosarcoma, osteosarcoma and rhabdomyosarcoma. Other neoplasias in dogs include genital squamous cell carcinoma, transmissable veneral tumor, testicular tumor, seminoma, Sertoli cell tumor, hemangiopericytoma, histiocytoma, chloroma (granulocytic sarcoma), corneal papilloma, corneal squamous cell carcinoma, hemangiosarcoma, pleural mesothelioma, basal cell tumor, thymoma, stomach tumor, adrenal gland carcinoma, oral papillomatosis, hemangioendothelioma and cystadenoma. Additional malignancies diagnosed in cats include follicular lymphoma, intestinal lymphosarcoma, fibrosarcoma and pulmonary squamous cell carcinoma. The ferret, an ever-more popular house pet is known to develop insulinoma, lymphoma, sarcoma, neuroma, pancreatic islet cell tumor, gastric MALT lymphoma and gastric adenocarcinoma.

Neoplasias affecting agricultural livestock include leukemia, hemangiopericytoma and bovine ocular neoplasia (in cattle); preputial fibrosarcoma, ulcerative squamous cell carcinoma, preputial carcinoma, connective tissue neoplasia and mastocytoma (in horses); hepatocellular carcinoma (in swine); lymphoma and pulmonary adenomatosis (in sheep); pulmonary sarcoma, lymphoma, Rous sarcoma, reticulendotheliosis, fibrosarcoma, nephroblastoma, B-cell lymphoma and lymphoid leukosis (in avian species); retinoblastoma, hepatic neoplasia, lymphosarcoma (lymphoblastic lymphoma), plasmacytoid leukemia and swimbladder sarcoma (in fish), caseous lumphadenitis (CLA): chronic, infectious, contagious disease of sheep and goats caused by the bacterium Corynebacterium pseudotuberculosis, and contagious lung tumor of sheep caused by jaagsiekte.

The subject is exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the immunostimulatory nucleic acid are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the immunostimulatory nucleic acid. For instance, in a subject at risk of developing a cancer or an infectious disease or an allergic or asthmatic response, the subject may be administered the immunostimulatory nucleic acid on a regular basis when that risk is greatest, i.e., during allergy season or after exposure to a cancer causing agent. Additionally the immunostimulatory nucleic acid may be administered to travelers before they travel to foreign lands where they are at risk of exposure to infectious agents. Likewise the immunostimulatory nucleic acid may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Both gram negative and gram positive bacteria serve as antigens in vertebrate animals. Such gram positive bacteria include, but are not limited to, Pasteurella species, Staphylococci species, and Streptococcus species. Gram negative bacteria include, but are not limited to, *Escherichia coli*, Pseudomonas species, and Salmonella species. Specific examples of infectious bacteria include but are not limited to, *Helicobacter pyloris, Borelia burgdorferi, Legionella pneumophilia*, Mycobacteria sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), Streptococcus (viridans group), *Streptococcus faecalis, Streptococcus bovis*, Streptococcus (anaerobic sps.), *Streptococcus pneumoniae*, pathogenic Campylobacter sp., Enterococcus sp., *Haemophilus influenzae, Bacillus antracis*, corynebacterium diphtheriae, corynebacterium sp., *Erysipelothrix rhusiopathiae, Clostridium perfringers, Clostridium tetani, Enterobacter aerogenes, Klebsiella pneumoniae, Pasturella multocida*, Bacteroides sp., *Fusobacterium nucleatum, Streptobacillus moniliformis, Treponema pallidium, Treponema pertenue*, Leptospira, Rickettsia, and *Actinomyces israelli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include Plasmodium spp. such as *Plasmodium falciparum, Plasmodium malariae*, Plasmodium ova/e, and *Plasmodium vivax* and *Toxoplasma gondii*. Blood-borne and/or tissues parasites include Plasmodium spp., *Babesia microti, Babesia divergens, Leishmania tropica*, Leishmania spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

Although many of the microbial antigens described above relate to human disorders, the invention is also useful for treating other nonhuman vertebrates. Nonhuman vertebrates are also capable of developing infections which can be prevented or treated with the Immunostimulatory nucleic acids disclosed herein. For instance, in addition to the treatment of infectious human diseases, the methods of the invention are useful for treating infections of animals.

As used herein, the term treat, treated, or treating when used with respect to an infectious disease refers to a prophylactic treatment which increases the resistance of a subject (a subject at risk of infection) to infection with a pathogen or, in other words, decreases the likelihood that the subject will become infected with the pathogen as well as a treatment after the subject (a subject who has been infected) has become infected in order to fight the infection, e.g., reduce or eliminate the infection or prevent it from becoming worse.

Many vaccines for the treatment of non-human vertebrates are disclosed in Bennett, K. *Compendium of Veterinary Products*, 3rd ed. North American Compendiums, Inc., 1995. As discussed above, antigens include infectious microbes such as virus, parasite, bacteria and fungi and fragments thereof, derived from natural sources or synthetically. Infectious viruses of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Hepatitis virus, Human enteric corona virus, and Feline infectious peritonitis (Feline coronavirus).

Illustrative DNA viruses that are antigens in vertebrate animals include, but are not limited to, the family Poxyiridae, including the genus Orthopoxyirus (Variola major, Variolaminor, Monkey pox Vaccinia, Cowpox, Buffalopox, Rabbitpox, Ectromelia), the genus Leporipoxyirus (Myxoma, Fibroma), the genus Avipoxyirus (Fowlpox, other avian poxyirus), the genus Capripoxyirus (sheeppox, goatpox), the genus Suipoxyirus (Swinepox), the genus Parapoxyirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A,B,C,D,E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents (CHINA virus).

Each of the foregoing lists is illustrative, and is not intended to be limiting.

In addition to the use of the immunostimulatory nucleic acids to induce an antigen specific immune response in humans, the methods of the preferred embodiments are particularly well suited for treatment of birds such as hens, chickens, turkeys, ducks, geese, quail, and pheasant. Birds are prime targets for many types of infections.

Hatching birds are exposed to pathogenic microorganisms shortly after birth. Although these birds are initially protected against pathogens by maternal derived antibodies, this protection is only temporary, and the bird's own immature immune system must begin to protect the bird against the pathogens. It is often desirable to prevent infection in young birds when they are most susceptible. It is also desirable to prevent against infection in older birds, especially when the birds are housed in closed quarters, leading to the rapid spread of disease. Thus, it is desirable to administer the Immunostimulatory nucleic acid and the non-nucleic acid adjuvant of the invention to birds to enhance an antigen-specific immune response when antigen is present.

An example of a common infection in chickens is chicken infectious anemia virus (CIAV). CIAV was first isolated in Japan in 1979 during an investigation of a Marek's disease vaccination break (Yuasa et al., 1979, Avian Dis. 23:366-385). Since that time, CIAV has been detected in commercial poultry in all major poultry producing countries (van Bulow et al., 1991, pp.690-699) in Diseases of Poultry, 9th edition, Iowa State University Press).

CIAV infection results in a clinical disease, characterized by anemia, hemorrhage and immunosuppression, in young susceptible chickens. Atrophy of the thymus and of the bone marrow and consistent lesions of CIAV-infected chickens are also characteristic of CIAV infection. Lymphocyte depletion in the thymus, and occasionally in the bursa of Fabricius, results in immunosuppression and increased susceptibility to secondary viral, bacterial, or fungal infections which then complicate the course of the disease. The immunosuppression may cause aggravated disease after infection with one or more of Marek's disease virus (MDV), infectious bursal disease virus, reticuloendotheliosis virus, adenovirus, or reovirus. It has been reported that pathogenesis of MDV is enhanced by CIAV (DeBoer et al., 1989, p. 28 In Proceedings of the 38th Western Poultry Diseases Conference, Tempe, Ariz.). Further, it has been reported that CIAV aggravates the signs of infectious bursal disease (Rosenberger et al., 1989, Avian Dis. 33:707-713). Chickens develop an age resistance to experimentally induced disease due to CAA. This is essentially complete by the age of 2 weeks, but older birds are still susceptible to infection (Yuasa, N. et al., 1979 supra; Yuasa, N. et al., Arian Diseases 24, 202-209, 1980). However, if chickens are dually infected with CAA and an immunosuppressive agent (IBDV, MDV etc.), age resistance against the disease is delayed (Yuasa, N. et al., 1979 and 1980 supra; Bulow von V. et al., J. Veterinary Medicine 33, 93-116, 1986). Characteristics of CIAV that may potentiate disease transmission include high resistance to environmental inactivation and some common disinfectants. The economic impact of CIAV infection on the poultry industry is clear from the fact that 10% to 30% of infected birds in disease outbreaks die.

Vaccination of birds, like other vertebrate animals can be performed at any age. Normally, vaccinations are performed at up to 12 weeks of age for a live microorganism and between 14-18 weeks for an inactivated microorganism or other type of vaccine. For in ovo vaccination, vaccination can be performed in the last quarter of embryo development. The vaccine may be administered subcutaneously, by spray, orally, intraocularly, intratracheally, nasally, or by other mucosal delivery methods described herein. Thus, the immunostimulatory nucleic acids of the invention can be administered to birds and other non-human vertebrates using routine vaccination schedules and the antigen can be administered after an appropriate time period as described herein.

Cattle and livestock are also susceptible to infection. Diseases which affect these animals can produce severe economic losses, especially amongst cattle. The methods of the invention can be used to protect against infection in livestock, such as cows, horses, pigs, sheep, and goats.

Cows can be infected by bovine viruses. Bovine viral diarrhea virus (BVDV) is a small enveloped positive-stranded RNA virus and is classified, along with hog cholera virus (HOCV) and sheep border disease virus (BDV), in the pestivirus genus. Although, Pestiviruses were previously classified in the Togaviridae family, some studies have suggested their reclassification within the Flaviviridae family along with the flavivirus and hepatitis C virus (HCV) groups (Francki, et al., 1991).

BVDV, which is an important pathogen of cattle can be distinguished, based on cell culture analysis, into cytopathogenic (CP) and noncytopathogenic (NCP) biotypes. The NCP biotype is more widespread although both biotypes can be found in cattle. If a pregnant cow becomes infected with an NCP strain, the cow can give birth to a persistently infected and specifically immunotolerant calf that will spread virus during its lifetime. The persistently infected cattle can succumb to mucosal disease and both biotypes can then be isolated from the animal. Clinical manifestations can include abortion, teratogenesis, and respiratory problems, mucosal disease and mild diarrhea. In addition, severe thrombocytopenia, associated with herd epidemics, that may result in the death of the animal has been described and strains associated with this disease seem more virulent than the classical BVDVs.

Equine herpes viruses (EHV) comprise a group of antigenically distinct biological agents which cause a variety of infections in horses ranging from subclinical to fatal disease. These include Equine herpesvirus-1 (EHV-1), a ubiquitous pathogen in horses. EHV-1 is associated with epidemics of abortion, respiratory tract disease, and central nervous system disorders. Primary infection of upper respiratory tract of young horses results in a febrile illness which lasts for 8 to 10 days. Immunologically experienced mares may be re-infected via the respiratory tract without disease becoming apparent, so that abortion usually occurs without warning. The neurological syndrome is associated with respiratory disease or abortion and can affect animals of either sex at any age, leading to lack of co-ordination, weakness and posterior paralysis (Telford, E. A. R. et al., Virology 189, 304-316, 1992). Other EHV's include EHV-2, or equine cytomegalovirus, EHV-3, equine coital exanthema virus, and EHV-4, previously classified as EHV-1 subtype 2.

Sheep and goats can be infected by a variety of dangerous microorganisms including visna-maedi.

Primates such as monkeys, apes and macaques can be infected by simian immunodeficiency virus. Inactivated cell-virus and cell-free whole simian immunodeficiency vaccines have been reported to afford protection in macaques (Stott et al. (1990) Lancet 36:1538-1541; Desrosiers et al. PNAS USA (1989) 86:6353-6357; Murphey-Corb et al. (1989) Science 246:1293-1297; and Carlson et al. (1990) AIDS Res. Human Retroviruses 6:1239-1246). A recombinant HIV gp120 vaccine has been reported to afford protection in chimpanzees (Berman et al. (1990) Nature 345:622-625).

Cats, both domestic and wild, are susceptible to infection with a variety of microorganisms. For instance, feline infectious peritonitis is a disease which occurs in both domestic and wild cats, such as lions, leopards, cheetahs, and jaguars. When it is desirable to prevent infection with this and other types of pathogenic organisms in cats, the methods of the invention can be used to vaccinate cats to protect them against infection.

Domestic cats may become infected with several retroviruses, including but not limited to feline leukemia virus (FeLV), feline sarcoma virus (FeSV), endogenous type Concornavirus (RD-114), and feline syncytia-forming virus (FeSFV). Of these, FeLV is the most significant pathogen, causing diverse symptoms, including lymphoreticular and myeloid neoplasms, anemias, immune mediated disorders, and an immunodeficiency syndrome which is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (also referred to as feline immunodeficiency) was first reported in Pedersen et al. (1987) Science 235:790-793. Characteristics of FIV have been reported in Yamamoto et al. (1988) Leukemia, December Supplement 2:204S-215S; Yamamoto et al. (1988) Am. J. Vet. Res. 49:1246-1258; and Ackley et al. (1990) J. Virol. 64:5652-5655. Cloning and sequence analysis of FIV have been reported in Olmsted et al. (1989) Proc. Natl. Acad. Sci. USA 86:2448-2452 and 86:4355-4360.

Feline infectious peritonitis (FIP) is a sporadic disease occurring unpredictably in domestic and wild Felidae. While FIP is primarily a disease of domestic cats, it has been diagnosed in lions, mountain lions, leopards, cheetahs, and the jaguar. Smaller wild cats that have been afflicted with FIP include the lynx and caracal, sand cat, and pallas cat. In domestic cats, the disease occurs predominantly in young animals, although cats of all ages are susceptible. A peak incidence occurs between 6 and 12 months of age. A decline in incidence is noted from 5 to 13 years of age, followed by an increased incidence in cats 14 to 15 years old.

Viral, bacterial, and parasitic diseases in fin-fish, shellfish or other aquatic life forms pose a serious problem for the aquaculture industry. Owing to the high density of animals in the hatchery tanks or enclosed marine farming areas, infectious diseases may eradicate a large proportion of the stock in, for example, a fin-fish, shellfish, or other aquatic life forms facility. Prevention of disease is a more desired remedy to these threats to fish than intervention once the disease is in progress. Vaccination of fish is the only preventative method which may offer long-term protection through immunity. Nucleic acid based vaccinations are described in U.S. Pat. No. 5,780,448 issued to Davis.

The fish immune system has many features similar to the mammalian immune system, such as the presence of B cells, T cells, lymphokines, complement, and immunoglobulins. Fish have lymphocyte subclasses with roles that appear similar in many respects to those of the B and T cells of mammals. Vaccines can be administered by immersion or orally.

Aquaculture species include but are not limited to fin-fish, shellfish, and other aquatic animals. Fin-fish include all vertebrate fish, which may be bony or cartilaginous fish, such as, for example, salmonids, carp, catfish, yellowtail, seabream, and seabass. Salmonids are a family of fin-fish which include trout (including rainbow trout), salmon, and Arctic char. Examples of shellfish include, but are not limited to, clams, lobster, shrimp, crab, and oysters. Other cultured aquatic animals include, but are not limited to eels, squid, and octopi.

Polypeptides of viral aquaculture pathogens include but are not limited to glycoprotein (G) or nucleoprotein (N) of viral hemorrhagic septicemia virus (VHSV); G or N proteins of infectious hematopoietic necrosis virus (1HNV); VP1, VP2, VP3 or N structural proteins of infectious pancreatic necrosis virus (IPNV); G protein of spring viremia of carp (SVC); and a membrane-associated protein, tegumin or capsid protein or glycoprotein of channel catfish virus (CCV).

Typical parasites infecting horses are Gasterophilus spp.; *Eimeria leuckarti*, Giardia spp.; *Tritrichomonas equi*; Babesia spp. (RBC's), *Theileria equi*; Trypanosoma spp.; *Klossiella equi*; Sarcocystis spp.

Typical parasites infecting swine include *Eimeria bebliecki, Eimeria scabra, Isospora suis*, Giardia spp.; *Balantidium coli, Entamoeba histolytica; Toxoplasma gondii* and Sarcocystis spp., and *Trichinella spiralis*.

The major parasites of dairy and beef cattle include Eimeria spp., Cryptosporidium sp., Giardia spp.; *Toxoplasma gondii; Babesia bovis* (RBC), *Babesia bigemina* (RBC), Trypanosoma spp. (plasma), Theileria spp. (RBC); *Theileria parva* (lymphocytes); *Tritrichomonas foetus*; and Sarcocystis spp.

The major parasites of raptors include *Trichomonas gallinae*; Coccidia (Eimeria spp.); *Plasmodium relictum, Leucocytozoon danilewskyi* (owls), Haemoproteus spp., Trypanosoma spp.; Histomonas; *Cryptosporidium meleagridis, Cryptosporidium baileyi*, Giardia, Eimeria; Toxoplasma.

Typical parasites infecting sheep and goats include Eimeria spp., Cryptosporidium sp., Giardia sp.; *Toxoplasma gondii*; Babesia spp. (RBC), Trypanosoma spp. (plasma), Theileria spp. (RBC); and Sarcocystis spp.

Typical parasitic infections in poultry include coccidiosis caused by *Eimeria acervulina, E. necatrix, E. tenella*, Isospora spp. and *Eimeria truncata*; histomoniasis, caused by *Histomonas meleagridis* and *Histomonas gallinarum*; trichomoniasis caused by *Trichomonas gallinae*; and hexamitiasis caused by *Hexamita meleagridis*. Poultry can also be infected *Emeria maxima, Emeria meleagridis, Eimeria adenoeides, Eimeria meleagrimitis*, Cryptosporidium, *Eimeria brunetti, Emeria adenoeides*, Leucocytozoon spp., Plasmodium spp., *Hemoproteus meleagridis, Toxoplasma gondii* and Sarcocystis.

The methods of the invention can also be applied to the treatment and/or prevention of parasitic infection in dogs, cats, birds, fish and ferrets. Typical parasites of birds include *Trichomonas gallinae*; Eimeria spp., Isospora spp., Giardia; Cryptosporidium; Sarcocystis spp., *Toxoplasma gondii*, Haemoproteus/Parahaemoproteus, Plasmodium spp., Leucocytozoon/Akiba, Atoxoplasma, Trypanosoma spp. Typical parasites infecting dogs include *Trichinella spiralis*; Isospora spp., Sarcocystis spp., Cryptosporidium spp., Hammondia spp., *Giardia duodenalis (canis)*; *Balantidium coli, Entamoeba histolytica; Hepatozoon canis; Toxoplasma gondii, Trypanosoma cruzi; Babesia canis; Leishmania amastigotes; Neospora caninum*.

Typical parasites infecting feline species include Isospora spp., *Toxoplasma gondii*, Sarcocystis spp., *Hammondia hammondi*, Besnoitia spp., Giardia spp.; *Entamoeba histolytica; Hepatozoon canis*, Cytauxzoon sp., Cytauxzoon sp., Cytauxzoon sp. (red cells, RE cells).

Typical parasites infecting fish include Hexamita spp., Eimeria spp.; Cryptobia spp., Nosema spp., Myxosoma spp., Chilodonella spp., Trichodina spp.; Plistophora spp., *Myxosoma Henneguya*; Costia spp., Ichthyophithirius spp., and Oodinium spp.

Typical parasites of wild mammals include Giardia spp. (carnivores, herbivores), Isospora spp. (carnivores), Eimeria spp. (carnivores, herbivores); Theileria spp. (herbivores), Babesia spp. (carnivores, herbivores), Trypanosoma spp. (carnivores, herbivores); Schistosoma spp. (herbivores); *Fasciola hepatica* (herbivores), *Fascioloides magna* (herbivores), *Fasciola gigantica* (herbivores), *Trichinella spiralis* (carnivores, herbivores).

Parasitic infections in zoos can also pose serious problems. Typical parasites of the bovidae family (blesbok, antelope, banteng, eland, gaur, impala, klipspringer, kudu, gazelle) include Eimeria spp. Typical parasites in the pinnipedae family (seal, sea lion) include *Eimeria phocae*. Typical parasites in the camelidae family (camels, llamas) include Eimeria spp. Typical parasites of the giraffidae family (giraffes) include Eimeria spp. Typical parasites in the elephantidae family (African and Asian) include Fasciola spp. Typical parasites of lower primates (chimpanzees, orangutans, apes, baboons, macaques, monkeys) include Giardia sp.; Balantidium coli, *Entamoeba histolytica*, Sarcocystis spp., *Toxoplasma gondii*; Plasmodim spp. (RBC), Babesia spp. (RBC), Trypanosoma spp. (plasma), Leishmania spp. (macrophages).

Polypeptides of bacterial pathogens include but are not limited to an iron-regulated outer membrane protein, (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an iron-regulated outer membrane protein (IROMP), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of Rickettsia.

Polypeptides of a parasitic pathogen include but are not limited to the surface antigens of Ichthyophthirius.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemiisfolia*; Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); Agropyron (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*).

The antigen may be an antigen that is encoded by a nucleic acid vector or it may be not encoded in a nucleic acid vector. In the former case the nucleic acid vector is administered to the subject and the antigen is expressed in vivo. In the latter case the antigen may be administered directly to the subject. An antigen not encoded in a nucleic acid vector as used herein refers to any type of antigen that is not a nucleic acid. For instance, in some aspects of the invention the antigen not encoded in a nucleic acid vector is a polypeptide. Minor modifications of the primary amino acid sequences of polypeptide antigens may also result in a polypeptide which has substantially equivalent antigenic activity as compared to the unmodified counterpart polypeptide. Such modifications may be deliberate, as by site-directed mutagenesis, or may be spontaneous. All of the polypeptides produced by these modifications are included herein as long as antigenicity still exists. The polypeptide may be, for example, a viral polypeptide.

The term substantially purified as used herein refers to a polypeptide which is substantially free of other proteins, lipids, carbohydrates or other materials with which it is naturally associated. One skilled in the art can purify viral or bacterial polypeptides using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the viral or bacterial polypeptide can also be determined by amino-terminal amino acid sequence analysis. Other types of antigens not encoded by a nucleic acid vector such as polysaccharides, small molecule, mimics etc are described above, and included within the invention.

The invention also utilizes polynucleotides encoding the antigenic polypeptides. It is envisioned that the antigen may be delivered to the subject in a nucleic acid molecule which encodes for the antigen such that the antigen must be expressed in vivo. Such antigens delivered to the subject in a nucleic acid vector are referred to as antigens encoded by a nucleic acid vector. The nucleic acid encoding the antigen is operatively linked to a gene expression sequence which directs the expression of the antigen nucleic acid within a eukaryotic cell. The gene expression sequence is any regulatory nucleotide sequence, such as a promoter sequence or promoter-enhancer combination, which facilitates the efficient transcription and translation of the antigen nucleic acid to which it is operatively linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, b-actin promoter and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined antigen nucleic acid. The gene expression sequences optionally include enhancer sequences or upstream activator sequences as desired.

The antigen nucleic acid is operatively linked to the gene expression sequence. As used herein, the antigen nucleic acid sequence and the gene expression sequence are said to be operably linked when they are covalently linked in such a way as to place the expression or transcription and/or translation of the antigen coding sequence under the influence or control of the gene expression sequence. Two DNA sequences are said to be operably linked if induction of a promoter in the 5' gene expression sequence results in the transcription of the antigen sequence and if the nature of the linkage between the two DNA sequences does not (1) result in the introduction of a frame-shift mutation, (2) interfere with the ability of the promoter region to direct the transcription of the antigen sequence, or (3) interfere with the ability of the corresponding RNA transcript to be translated into a protein. Thus, a gene expression sequence would be operably linked to an antigen nucleic acid sequence if the gene expression sequence were capable of effecting transcription of that antigen nucleic acid sequence such that the resulting transcript is translated into the desired protein or polypeptide.

The antigen nucleic acid of the invention may be delivered to the immune system alone or in association with a vector. In its broadest sense, a vector is any vehicle capable of facilitating the transfer of the antigen nucleic acid to the cells of the immune system so that the antigen can be expressed and presented on the surface of the immune cell. The vector generally transports the nucleic acid to the immune cells with reduced degradation relative to the extent of degradation that would result in the absence of the vector. The vector optionally includes the above-described gene expression sequence to enhance expression of the antigen nucleic acid in immune cells. In general, the vectors useful in the invention include, but are not limited to, plasmids, phagemids, viruses, other vehicles derived from viral or bacterial sources that have been manipulated by the insertion or incorporation of the antigen nucleic acid sequences. Viral vectors are a preferred type of vector and include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., Gene Transfer and Expression, A Laboratory Manual W. H. Freeman C.O., New York (1990) and Murry, E. J. Methods in Molecular Biology, vol. 7, Humana Press, Inc., Cliffton, New Jersey (1991).

A preferred virus for certain applications is the adeno-associated virus, a double-stranded DNA virus. The adeno-associated virus can be engineered to be replication-deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom designed using restriction enzymes and ligation reactions to remove and add specific fragments of DNA.

It has recently been discovered that gene carrying plasmids can be delivered to the immune system using bacteria. Modified forms of bacteria such as Salmonella can be transfected with the plasmid and used as delivery vehicles. The bacterial delivery vehicles can be administered to a host subject orally or by other administration means. The bacteria deliver the plasmid to immune cells, e.g. B cells, dendritic cells, likely by passing through the gut barrier. High levels of immune protection have been established using this methodology. Such methods of delivery are useful for the aspects of the invention utilizing systemic delivery of antigen, Immunostimulatory nucleic acid and/or other therapeutic agent.

Thus, the immunostimulatory nucleic acids are useful as vaccine adjuvants. It was previously established that CpG oligonucleotides are excellent vaccine adjuvants. It was also demonstrated, however, that CpG ODN which are superb vaccine adjuvants in mice are not the preferred adjuvants in non-rodent animals. In order to identify the best immunostimulatory nucleic acids for use as a vaccine adjuvant in humans and other non-rodent animals, in vivo screening of different nucleic acids for this purpose was conducted. Several in vitro assays were evaluated in mice for their predictive value of adjuvant activity in vivo in mice. During the course of this study, an in vitro test that is predictive of in vivo efficacy was identified. It was discovered, rather surprisingly, that both B cell and NK cell activation correlated particularly well with the ability of an immunostimulatory nucleic acid to enhance an in vivo immune response against an antigen.

The good predictive value of B cell activation for in vivo vaccine adjuvant activity is most likely linked to the central role of B cells in the establishment of a specific immune response. Polyclonal proliferation of B cells (induced by immunostimulatory nucleic acids) increases the likelihood of an antigen specific B cell/T helper cell match. Furthermore, enhanced expression of the co-stimulatory molecule CD86 on polyclonally expanded B cells activates antigen specific T helper cells. B cells also increase their CD40 expression in response to immunostimulatory nucleic acids improving the capability of CD40L expressing activated T helper cells to stimulate B cells. Increased ICAM-1 synthesis on B cells facilitates the cell to cell contact. Thus, the activation status of polyclonal B cells plays a critical role during the initiation of a specific antibody response.

The contribution of NK cell activity for the establishment of specific antibodies was, however, surprising. NK cells are part of the innate immune system and as such are involved in the first line of defense against pathogens. Most likely the cytokine pattern produced by NK cells upon activation is closely related to the initiation of a specific immune response. Thus, in one aspect the invention relates to a method of identifying an adjuvant, by detecting NK cell activation. The NK cell activation assay may be carried out as described in the Examples below or using other known NK cell activity assays. It is preferred, however that a mixed cell population such as PBMC be used because of the likelihood that NK cell activation is an indirect effect. The assay is preferably useful for identifying immunostimulatory nucleic acids which are useful as adjuvants in human and other non-rodent animals.

Cytokine induction was also identified as an important predictor of in vivo adjuvant activity. As there is a 2 log higher endotoxin sensitivity of human than mouse primary monocytes, some caution, however, is required to avoid endotoxin contamination of immunostimulatory nucleic acids used for testing in the human system (Hartmann G., and Krieg A. M. 1999. *Gene Therapy* 6:893). Since TNF-α, IL-6 and IL-12 are produced by human monocytes in response to even low amounts of endotoxin, their value for high throughput in vitro screening assays is limited. On the other hand, human B cells and NK cells show only minor activation by endotoxin and thus are far more useful in testing for immunostimulatory activity.

Stimulation of cellular function in either NK or B cells (i.e., lytic activity, proliferation) requires a stronger immunostimulatory nucleic acid than the induction of activation markers at their surface (CD69, CD86). For both cell types, the use of cell surface activation markers showed a higher nonspecific background attributable to the phosphorothioate backbone compared to the functional assays. This high sensitivity of surface markers requires the use of low immunostimulatory nucleic acid concentrations for optimal discrimination between immunostimulatory nucleic acid of similar activity. Thus, the use of surface markers allows the comparison of immunostimulatory nucleic acids with weak activity, while functional assays are preferred for comparing immunostimulatory nucleic acids with high activity. It is of note that the optimal immunostimulatory nucleic acid concentrations for stimulating B cells and NK cells differ. While 0.6 μg/ml ODN is already maximal to stimulate B cells, optimal NK cell activation may require 6 μg/ml ODN. Both B cell activation and NK cell functional activity were measured within freshly isolated PBMC. It was previously found that highly purified human primary B cells are activated by CpG DNA. The existence of a direct effect of CpG DNA on NK cells is less clear, and a secondary mechanism mediated by another cell type within PBMC might contribute to CpG-induced functional activity of NK cells.

The nucleic acids of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxamide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, timidazole, trimethroprim-sulfamethoxazole, and tryparsamide some of which are used alone or in combination with others.

Parasiticides used in non-human subjects include piperazine, diethylcarbamazine, thiabendazole, fenbendazole, albendazole, oxfendazole, oxibendazole, febantel, levamisole, pyrantel tartrate, pyrantel pamoate, dichlorvos, ivermectin, doramectic, milbemycin oxime, iprinomectin, moxidectin, N-butyl chloride, toluene, hygromycin B thiacetarsemide sodium, melarsomine, praziquantel, epsiprantel, benzimidazoles such as fenbendazole, albendazole, oxfendazole, clorsulon, albendazole, amprolium; decoquinate, lasalocid, monensin sulfadimethoxine; sulfamethazine, sulfaquinoxaline, metronidazole.

Parasiticides used in horses include mebendazole, oxfendazole, febantel, pyrantel, dichlorvos, trichlorfon, ivermectin, piperazine; for *S. westeri*: ivermectin, benzimiddazoles such as thiabendazole, cambendazole, oxibendazole and fenbendazole. Useful parasiticides in dogs include milbemycin oxine, ivermectin, pyrantel pamoate and the combination of ivermectin and pyrantel. The treatment of parasites in swine can include the use of levamisole, piperazine, pyrantel, thiabendazole, dichlorvos and fenbendazole. In sheep and goats anthelmintic agents include levamisole or ivermectin. Caparsolate has shown some efficacy in the treatment of *D. immitis* (heartworm) in cats.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Anti-bacterial agents useful in the invention include but are not limited to natural penicillins, semi-synthetic penicillins, clavulanic acid, cephalolsporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefcefuroxine, cefoxitin, cefotaxime, cefsulodin, cefetamet, cefixime, ceftriaxone, cefoperazone, ceftazidine, moxalactam, carbapenems, imipenems, monobactems, euztreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforamide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate;

Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. $\alpha$ and $\beta$-interferons are available as recombinant forms and have been used for the treatment of chronic hepatitis B and C infection. At the dosages which are effective for anti-viral therapy, interferons have severe side effects such as fever, malaise and weight loss.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immuno-compromised children and neonates), human rabies immunoglobulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Another type of immunoglobulin therapy is active immunization. This involves the administration of antibodies or antibody fragments to viral surface proteins. Two types of vaccines which are available for active immunization of hepatitis B include serum-derived hepatitis B antibodies and recombinant hepatitis B antibodies. Both are prepared from HBsAg. The antibodies are administered in three doses to subjects at high risk of infection with hepatitis B virus, such as health care workers, sexual partners of chronic carriers, and infants.

Thus, anti-viral agents useful in the invention include but are not limited to immunoglobulins, amantadine, interferon, nucleoside analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream). Some examples of commercially-available agents are shown in Table B and other therapeutic agent may be administered simultaneously or sequentially. When the other therapeutic agents are administered simultaneously they can be administered in the same or separate formulations, but are administered at the same time. The other therapeutic agents are administered sequentially with one another and with immunostimulatory nucleic acid, when the administration of the other therapeutic agents and the immunostimulatory nucleic acid is temporally separated. The separation in time between the

TABLE B

| Company | Brand Name | Generic Name | Indication | Mechanism of Action |
| --- | --- | --- | --- | --- |
| PHARMACIA & Lilly | PNU 196443 LY 303366 | PNU 196443 Basiungin/ECB | Anti Fungal Fungal Infections | n/k Anti-fungal/cell wall inhibitor, glucose synthase inhibitor |
| Bayer | Canesten ® | Clotrimazole | Fungal Infections | Membrane integrity destabilizer |
| Fujisawa | FK 463 | FK 463 | Fungal Infections | Membrane integrity destabilizer |
| Mylan | Sertaconzaole | Sertaconzole | Fungal Infections | Membrane integrity destabilizer |
| Genzyme | Chitinase | Chitinase | Fungal Infections, Systemic | Chitin Breakdown |
| Liposome | Abelcet ™ | Amphotericin B, Liposomal | Fungal Infections, Systemic | Membrane integrity destabilizer |
| Sequus | Amphotec ™ | Amphotericin B, Liposomal | Fungal Infections, Systemic | Membrane integrity destabilizer |
| Bayer | BAY 38-9502 | BAY 38-9502 | Fungal Infections, Systemic | Membrane integrity destabilizer |
| Pfizer | Diflucan ® | Fluconazole | Fungal Infections, Systemic | Membrane integrity destabilizer |
| Johnson & Johnson | Sporanox ™ | Itraconazole | Fungal Infections, Systemic | Membrane integrity destabilizer |
| Sepracor | Itraconzole (2R, 4S) | Itraconzole (2R, 4S) | Fungal Infections, Systemic | Membrane integrity destabilizer |
| Johnson & Johnson | Nizoral ™ | Ketoconazole | Fungal Infections, Systemic | Membrane integrity destabilizer |
| Johnson & Johnson | Monistat ® | Miconazole | Fungal Infections, Systemic | Membrane integrity destabilizer |
| Merck | MK 991 | MK 991 | Fungal Infections, Systemic | Membrane integrity destabilizer |
| Bristol Myers Sq'b | Pradimicin | Pradimicin | Fungal Infections, Systemic | Membrane integrity destabilizer |
| Pfizer | UK-292, 663 | UK-292, 663 | Fungal Infections, Systemic | Membrane integrity destabilizer |
| Pfizer | Voriconazole | Voriconazole | Fungal Infections, Systemic | Membrane integrity destabilizer |
| Mylan | 501 Cream | 501 Cream | Inflammatory Fungal Conditions | Immunosuppression |
| Mylan | Mentax ® | Bulenafine | Nail Fungus | Membrane integrity destabilizer |
| Schering Plough | Anti Fungal | Anti Fungal | Opportunistic Infections | Membrane integrity destabilizer |
| Aiza | Mycelex ® Troche | Clotrimazole | Oral Thrush | Membrane integrity stablizer |
| Novartis | Lamisil ® | terbinafine | Systemic Fungal Infections, Onychomycosis | Membrane integrity destabilizer |

Thus, the anti-fungal agents useful in the invention include but are not limited to imidazoles, FK 463, amphotericin B, BAY 38-9502, MK 991, pradimicin, UK 292, butenafine, chitinase, 501 cream, Acrisorcin; Ambruticin; Amorolfine, Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofuingin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole to Itraconazole; Kalafungin; Ketoconazole; Lomofungin; Lydimycin; Mepartricin Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide Proclonol; Pyrithione Zinc; Pyrrolnitrin; Rutamycin; Sanguinarium Chloride Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

Immunostimulatory nucleic acids can be combined with other therapeutic agents such as adjuvants to enhance immune responses. The immunostimulatory nucleic acid and other therapeutic agent may be administered simultaneously or sequentially. administration of these compounds may be a matter of minutes or it may be longer. Other therapeutic agents include but are not limited to adjuvants, cytokines, antibodies, antigens, etc.

The immunostimulatory nucleic acids are useful as adjuvants for inducing a systemic immune response. Thus either can be delivered to a subject exposed to an antigen to produce an enhanced immune response to the antigen.

In addition to the immunostimulatory nucleic acids, the compositions of the invention may also be administered with non-nucleic acid adjuvants. A non-nucleic acid adjuvant is any molecule or compound except for the immunostimulatory nucleic acids described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

An adjuvant that creates a depo effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montamide adjuvants (e.g., Montamide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

An immune stimulating adjuvant is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the $21^{st}$ peak with HPLC fractionation; Aquila Biopharmaceuticals, Inc., Worcester, MA); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants that create a depo effect and stimulate the immune system are those compounds which have both of the above-identified functions. This class of adjuvants includes but is not limited to ISCOMS (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxpropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The immunostimulatory nucleic acids are also useful as mucosal adjuvants. It has previously been discovered that both systemic and mucosal immunity are induced by mucosal delivery of CpG nucleic acids. The systemic immunity induced in response to CpG nucleic acids included both humoral and cell-mediated responses to specific antigens that were not capable of inducing systemic immunity when administered alone to the mucosa. Furthermore, both CpG nucleic acids and cholera toxin (CT, a mucosal adjuvant that induces a Th2-like response) induced CTL. This was surprising since with systemic immunization, the presence of Th2-like antibodies is normally associated with a lack of CTL (Schirmbeck et al., 1995). Based on the results presented herein it is expected that the immunostimulatory nucleic acids will function in a similar manner.

Additionally, the immunostimulatory nucleic acids induce a mucosal response at both local (e.g., lung) and remote (e.g., lower digestive tract) mucosal sites. Significant levels of IgA antibodies are induced at distant mucosal sites by the immunostimulatory nucleic acids. CT is generally considered to be a highly effective mucosal adjuvant. As has been previously reported (Snider 1995), CT induces predominantly IgG1 isotype of antibodies, which are indicative of Th2-type response. In contrast, the immunostimulatory nucleic acids are more Th1 with predominantly IgG2a antibodies, especially after boost or when the two adjuvants are combined. Th1-type antibodies in general have better neutralizing capabilities, and furthermore, a Th2 response in the lung is highly undesirable because it is associated with asthma (Kay, 1996, Hogg, 1997). Thus the use of immunostimulatory nucleic acids as a mucosal adjuvant has benefits that other mucosal adjuvants cannot achieve. The immunostimulatory nucleic acids of the invention also are useful as mucosal adjuvants for induction of both a systemic and a mucosal immune response.

Mucosal adjuvants referred to as non-nucleic acid mucosal adjuvants may also be administered with the Immunostimulatory nucleic acids. A non-nucleic acid mucosal adjuvant as used herein is an adjuvant other than a immunostimulatory nucleic acid that is capable of inducing a mucosal immune response in a subject when administered to a mucosal surface in conjunction with an antigen. Mucosal adjuvants include but are not limited to Bacterial toxins e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); $CTN_{107}$ (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS106 (Pro to Lys) (Douce et al., 1997, Fontana et al., 1995); and CTK63 (Ser to Lys) (Douce et al., 1997, Fontana et al., 1995), Zonula occludens toxin, zot, *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), Pertussis toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); Bacterial outer membrane proteins (e.g., outer surface protein A (OspA) lipoprotein of *Borrelia burgdorferi*, outer membrane protine of *Neisseria meningitidis*) (Marinaro et al., 1999, Van de Verg et al., 1996); Oil-in-water emulsions (e.g., MF59) (Barchfield et al., 1999, Verschoor et al., 1999, O'Hagan, 1998); Aluminum salts (Isaka et al., 1998, 1999); and Saponins (e.g., QS21) Aquila Biopharmaceuticals, Inc., Worster, Mass.) (Sasaki et al., 1998, MacNeal et al., 1998), ISCOMS, MF-59 (a squalene-in-water emulsion stabilized with Span 85 and Tween 80; Chiron Corporation, Emeryville, Calif.); the Seppic ISA series of Montamide adjuvants (e.g., Montamide ISA 720; AirLiquide, Paris, France); PROVAX (an oil-in-water emulsion containing a stabilizing detergent and a micelle-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)phosphazene (PCPP polymer; Virus Research Institute, USA) and Leishmania elongation factor (Corixa Corporation, Seattle, Wash.).

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or B-7 costimulatory molecules (Iwasaki et al., 1997; Tsuji et al., 1997) with the Immunostimulatory nucleic acids. The cytokines can be administered directly with Immunostimulatory nucleic acids or may be administered in the form of a nucleic acid vector that encodes the cytokine, such that the cytokine can be expressed in vivo. In one embodiment, the cytokine is administered in the form of a plasmid expression vector. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-$\gamma$ ($\gamma$-IFN), IFN-$\alpha$, tumor necrosis factor (TNF), TGF-$\beta$, FLT-3 ligand, and CD40 ligand.

Cytokines play a role in directing the T cell response. Helper (CD4+) T cells orchestrate the immune response of mammals through production of soluble factors that act on other immune system cells, including other T cells. Most mature CD4+ T helper cells express one of two cytokine profiles: Th1 or Th2. The Th1 subset promotes delayed-type hypersensitivity, cell-mediated immunity, and immunoglobulin class switching to IgG$_{2a}$. The Th2 subset induces humoral immunity by activating B cells, promoting antibody production, and inducing class switching to IgG$_1$ and IgE. In some embodiments, it is preferred that the cytokine be a Th1 cytokine.

The nucleic acids are also useful for redirecting an immune response from a Th2 immune response to a Th1 immune response. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-$\gamma$ and GM-CSF). The redirection or rebalance of the immune response from a Th2 to a Th1 response is particularly useful for the treatment or prevention of asthma. For instance, an effective amount for treating asthma can be that amount; useful for redirecting a Th2 type of immune response that is associated with asthma to a Th1 type of response. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-$\gamma$ and IL-12, can suppress the formation of Th2 clones and production of Th2 cytokines. The immunostimulatory nucleic acids of the invention cause an increase in Th1 cytokines which helps to rebalance the immune system, preventing or reducing the adverse effects associated with a predominately Th2 immune response.

The nucleic acids are also useful for improving survival, differentiation, activation and maturation of dendritic cells. The immunostimulatory nucleic acids have the unique capability to promote cell survival, differentiation, activation and maturation of dendritic cells. Dendritic precursor cells isolated from blood by immunomagnetic cell sorting develop morphologic and functional characteristics of dendritic cells during a two day incubation with GM-CSF. Without GM-CSF these cells undergo apoptosis. The immunostimulatory nucleic acids are superior to GM-CSF in promoting survival and differentiation of dendritic cells (MHC II expression, cell size, granularity). The immunostimulatory nucleic acids also induce maturation of dendritic cells. Since dendritic cells form the link between the innate and the acquired immune system, by presenting antigens as well as through their expression of pattern recognition receptors which detect microbial molecules like LPS in their local environment, the ability to activate dendritic cells with immunostimulatory nucleic acids supports the use of these immunostimulatory nucleic acid based strategies for in vivo and ex-vivo immunotherapy against disorders such as cancer and allergic or infectious diseases. The immunostimulatory nucleic acids are also useful for activating and inducing maturation of dendritic cells.

Immunostimulatory nucleic acids also increase natural killer cell lytic activity and antibody dependent cellular cytotoxicity (ADCC). ADCC can be performed using a immunostimulatory nucleic acid in combination with an antibody specific for a cellular target, such as a cancer cell. When the immunostimulatory nucleic acid is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available. Examples of these antibodies are listed below among the list of cancer immunotherapies.

The immunostimulatory nucleic acids may also be administered in conjunction with an anti-cancer therapy. Anti-cancer therapies include cancer medicaments, radiation and surgical procedures. As used herein, a "cancer medicament" refers to a agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers. Additionally, the methods of the invention are intended to embrace the use of more than one cancer medicament along with the immunostimulatory nucleic acids. As an example, where appropriate, the immunostimulatory nucleic acids may be administered with a both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to herein as immunotherapy.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Since the most malignant cancers are able to metastasize (i.e., exist the primary tumor site and seed a distal tissue, thereby forming a secondary tumor), medicaments that impede this metastasis are also useful in the treatment of cancer. Angiogenic mediators include basic FGF, VEGF, angiopoietins, angiostatin, endostatin, TNF$\alpha$, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

Some cancer cells are antigenic and thus can be targeted by the immune system. In one aspect, the combined administration of immunostimulatory nucleic acids and cancer medicaments, particularly those which are classified as cancer immunotherapies, is useful for stimulating a specific immune response against a cancer antigen. A "cancer antigen" as used herein is a compound, such as a peptide, associated with a tumor or cancer cell surface and which is capable of provoking an immune response when expressed on the surface of an antigen presenting cell in the context of an MHC molecule. Cancer antigens, such as those present in cancer vaccines or those used to prepare cancer immunotherapies, can be prepared from crude cancer cell extracts, as described in Cohen, et al., 1994, *Cancer Research,* 54:1055, or by partially purifying the antigens, using recombinant technology, or de novo synthesis of known antigens. Cancer antigens can be used in the form of immunogenic portions of a particular antigen or in some instances a whole cell or a tumor mass can be used as the antigen. Such antigens can be isolated or prepared recombinantly or by any other means known in the art.

The theory of immune surveillance is that a prime function of the immune system is to detect and eliminate neoplastic cells before a tumor forms. A basic principle of this theory is that cancer cells are antigenically different from normal cells and thus elicit immune reactions that are similar to those that cause rejection of immunologically incompatible allografts. Studies have confirmed that tumor cells differ, either qualitatively or quantitatively, in their expression of antigens. For example, "tumor-specific antigens" are antigens that are specifically associated with tumor cells but not normal cells. Examples of tumor specific antigens are viral antigens in tumors induced by DNA or RNA viruses. "Tumor-associated" antigens are present in both tumor cells and normal cells but are present in a different quantity or a different form in tumor cells. Examples of such antigens are oncofetal antigens (e.g., carcinoembryonic antigen), differentiation antigens (e.g., T and Tn antigens), and oncogene products (e.g., HER/neu).

Different types of cells that can kill tumor targets in vitro and in vivo have been identified: natural killer cells (NK cells), cytolytic T lymphocytes (CTLs), lymphokine-activated killer cells (LAKs), and activated macrophages. NK cells can kill tumor cells without having been previously sensitized to specific antigens, and the activity does not require the presence of class I antigens encoded by the major histocompatibility complex (MHC) on target cells. NK cells are thought to participate in the control of nascent tumors and in the control of metastatic growth. In contrast to NK cells, CTLs can kill tumor cells only after they have been sensitized to tumor antigens and when the target antigen is expressed on the tumor cells that also express MHC class I. CTLs are thought to be effector cells in the rejection of transplanted tumors and of tumors caused by DNA viruses. LAK cells are a subset of null lymphocytes distinct from the NK and CTL populations. Activated macrophages can kill tumor cells in a manner that is not antigen dependent nor MHC restricted once activated. Activated macrophages are through to decrease the growth rate of the tumors they infiltrate. In vitro assays have identified other immune mechanisms such as antibody-dependent, cell-mediated cytotoxic reactions and lysis by antibody plus complement. However, these immune effector mechanisms are thought to be less important in vivo than the function of NK, CTLs, LAK, and macrophages in vivo (for review see Piessens, W. F., and David, J., "Tumor Immunology", In: *Scientific American Medicine,* Vol. 2, Scientific American Books, N.Y., pp. 1-13, 1996.

The goal of immunotherapy is to augment a patient's immune response to an established tumor. One method of immunotherapy includes the use of adjuvants. Adjuvant substances derived from microorganisms, such as bacillus Calmette-Guerin, heighten the immune response and enhance resistance to tumors in animals.

Immunotherapeutic agents are medicaments which derive from antibodies or antibody fragments which specifically bind or recognize a cancer antigen. As used herein a cancer antigen is broadly defined as an antigen expressed by a cancer cell. Preferably, the antigen is expressed at the cell surface of the cancer cell. Even more preferably, the antigen is one which is not expressed by normal cells, or at least not expressed to the same level as in cancer cells. Antibody-based immunotherapies may function by binding to the cell surface of a cancer cell and thereby stimulate the endogenous immune system to attack the cancer cell. Another way in which antibody-based therapy functions is as a delivery system for the specific targeting of toxic substances to cancer cells. Antibodies are usually conjugated to toxins such as ricin (e.g., from castor beans), calicheamicin and maytansinoids, to radioactive isotopes such as Iodine-131 and Yttrium-90, to chemotherapeutic agents (as described herein), or to biological response modifiers. In this way, the toxic substances can be concentrated in the region of the cancer and non-specific toxicity to normal cells can be minimized. In addition to the use of antibodies which are specific for cancer antigens, antibodies which bind to vasculature, such as those which bind to endothelial cells, are also useful in the invention. This is because generally solid tumors are dependent upon newly formed blood vessels to survive, and thus most tumors are capable of recruiting and stimulating the growth of new blood vessels. As a result, one strategy of many cancer medicaments is to attack the blood vessels feeding a tumor and/or the connective tissues (or stroma) supporting such blood vessels.

The use of immunostimulatory nucleic acids in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

Examples of cancer immunotherapies which are currently being used or which are in development are listed in Table C.

Table C

Cancer Immunotherapies in Development or on the Market

| MARKETER | BRAND NAME (GENERIC NAME) | INDICATION |
|---|---|---|
| IDEC/Genentech, Inc./Hoffmann-LaRoche (first monoclonal antibody licensed for the treatment of cancer in the U.S.) | Rituxan ™ (rituximab, Mabthera) (IDEC-C2B8, chimeric murine/human anti-CD20 MAb) | non-Hodgkin's lymphoma |
| Genentech/Hoffmann-La Roche | Herceptin, anti-Her2 hMAb | Breast/ovarian |
| Cytogen Corp. | Quadramet ™ (CYT-424) radiotherapeutic agent | Bone metastases |
| Centocor/Glaxo/Ajinomoto | Panorex ® (17-IA) (murine monoclonal antibody) | Adjuvant therapy for colorectal (Dukes-C) |
| Centocor/Ajinomoto | Panorex ® (17-1A) (chimeric murine monoclonal antibody) | Pancreatic, lung, breast, ovary |
| IDEC | IDEC-Y2B8 (murine, anti-CD2O MAb labeled with Yttrium-90) | non-Hodgkin's lymhoma |
| ImClone Systems | BEC2 (anti-idiotypic MAb, mimics the $GD_3$ epitope) (with BCG) | Small cell lung |
| ImClone Systems | C225 (chimeric monoclonal antibody to epidermal growth factor receptor (EGFr)) | Renal cell |
| Techniclone International/Alpha Therapeutics | Oncolym ™ (Lym-1 monoclonal antibody linked to 131 iodine) | non-Hodgkin's lymphoma |
| Protein Design Labs | SMART ™ M195 Ab, humanized | Acute myeloid leukemia |
| Techniclone Corporation/Cambridge Antibody Technology | $^{131}$ I LYM-1 (Oncolym ™) | non-Hodgkin's lymphoma |
| Aronex Pharmaceuticals, Inc. | ATRAGEN ® | Acute promyelocytic leukemia |
| ImClone Systems | C225 (chimeric anti-EGFr monoclonal antibody) + cisplatin or radiation | Head & neck, non-small cell lung cancer |
| Altarex, Canada | Ovarex (B43.13, anti-idiotypic CA 125, mouse MAb) | Ovarian |
| Coulter Pharma (Clinical results have been positive, but the drug has been associated with significant bone marrow toxicity) | Bexxar (anti-CD20 Mab labeled with $^{131}$ I) | non-Hodgkin's lymphoma |
| Aronex Pharmaceuticals, Inc. | ATRAGEN ® | Kaposi's sarcoma |
| IDEC Pharmaceuticals Corp./Genentech | Rituxan ® (MAb against CD20) pan-B Ab in combo. with chemotherapy | B cell lymphoma |
| LeukoSite/Ilex Oncology | LDP-03, huMAb to the leukocyte antigen CAMPATH | Chronic lymphocytic leukemia (CLL) |
| Center of Molecular Immunology | ior t6 (anti CD6, murine MAb) CTCL | Cancer |
| Medarex/Novartis | MDX-210 (humanized anti-HER-2 bispecific antibody) | Breast, ovarian |
| Medarex/Novartis | MDX-210 (humanized anti-HER-2 bispecific antibody) | Prostate, non-small cell lung, pancreatic, breast |
| Medarex | MDX- 11 (complement activating receptor (CAR) monoclonal antibody) | Acute myelogenous leukemia (AML) |
| Medarex/Novartis | MDX-210 (humanized anti-HER-2 bispecific antibody) | Renal and colon |
| Medarex | MDX-11 (complement activating receptor (CAR) monoclonal antibody) | Lx vivo bone marrow purging in acute myelogenous leukemia (AML) |
| Medarex | MDX-22 (humanized bispecific antibody, MAb-conjugates) (complement cascade activators) | Acute myleoid leukemia |
| Cytogen | OV103 (Yttrium-90 labelled antibody) | Ovarian |
| Cytogen | OV103 (Yttrium-90 labelled antibody) | Prostate |
| Aronex Pharmaceuticals, Inc. | ATRAGEN ® | non-Hodgkin's lymphoma |
| Glaxo Wellcome plc | 3622W94 MAb that binds to EGP40 (17-IA) pancarcinoma antigen on adenocarcinomas | non-small cell lung, prostate (adjuvant) |
| Genentech | Anti-VEGF, RhuMAb (inhibits angiogenesis) | Lung, breast, prostate, colorectal |
| Protein Design Labs | Zenapax (SMART ™ Anti-Tac (IL-2 receptor) Ab, humanized) | Leukemia, lymphoma |

Table C-continued

Cancer Immunotherapies in Development or on the Market

| MARKETER | BRAND NAME (GENERIC NAME) | INDICATION |
| --- | --- | --- |
| Protein Design Labs | SMART ™ M195 Ab, humanized | Acute promyelocytic leukemia |
| ImClone Systems | C225 (chimeric anti-EGFr monoclonal antibody) + taxol | Breast |
| ImClone Systems (licensed from RPR) | C225 (chimeric anti-EGFr monoclonal antibody ) + doxorubicin | prostate |
| ImClone Systems | C225 (chimeric anti-EGFr monoclonal antibody) + adriamycin | prostate |
| ImClone Systems | BEC2 (anti-idiotypic MAb, mimics the GD3 epitope) | Melanoma |
| Medarex | MDX-210 (humanized anti-HER-2 bispecific antibody) | Cancer |
| Medarex | MDX-220 (bispecific for tumors that express TAG-72) | Lung, colon, prostate, ovarian, endometrial, pancreatic and gastric |
| Medarex/Novartis | MDX-210 (humanized anti-HER-2 bispecific antibody) | Prostate |
| Medarex/Merck KgaA | MDX-447 (humanized anti-EGF receptor bispecific antibody) | EGF receptor cancers (head & neck, prostate, lung, bladder, cervical, ovarian) |
| Medarex/Novartis | MDX-210 (humanized anti-HER-2 bispecific antibody) | Comb. Therapy with G-CSF for various cancers, esp. breast |
| IDEC | MELIMMUNE ™-2 (murine monoclonal antibody therapeutic vaccine) | Melanoma |
| IDEC | MELIMMUNE ™-1 (murine monoclonal antibody therapeutic vaccine) | Melanoma |
| Immunomedics, Inc. | CEACIDE ™ (I-131) | Colorectal and other |
| NeoRx | Pretarget ™ radioactive antibodies | non-Hodgkin's B cell lymphoma |
| Novopharm Biotech, Inc. | NovoMAb-G2 (pancarcinoma specific Ab) | Cancer |
| Techniclone Corporation/ Cambridge Antibody Technology | TNT (chimeric MAb to histone antigens) | Brain |
| Techniclone International/ Cambridge Antibody Technology | TNT (chimeric MAb to histone antigens) | Brain |
| Novopharm | Gliomab-H (Monoclonals - Humanized Abs) | Brain, melanomas, neuroblastomas |
| Genetics Institute/AHP | GNI-250 Mab | Colorectal |
| Merck KgaA | EMD-72000 (chimeric-EGF antagonist) | Cancer |
| Immunomedics | LymphoCide ™ (humanized LL2 | non-Hodgkin's B-cell antibody) lymphoma |
| Immunex/AHP | CMA 676 (monoclonal antibody conjugate) | Acute myelogenous leukemia |
| Novopharm Biotech, Inc. | Monopharm-C | Colon, lung, pancreatic |
| Novopharm Biotech, Inc. | 4B5 anti-idiotype Ab | Melanoma, small-cell lung |
| Center of Molecular Immunology | ior egf/r3 (anti EGF-R humanized Ab) | Radioimmunotherapy |
| Center of Molecular Immunology | ior c5 (murine MAb colorectal) for radioimmunotherapy | Colorectal |
| Creative BioMolecules/ Chiron | BABS (biosynthetic antibody binding site) Proteins | Breast cancer |
| ImClone Systems/Chugai | FLK-2 (monoclonal antibody to fetal liver kinase-2 (FLK-2)) | Tumor-associated angiogenesis |
| ImmunoGen, Inc. | Humanized MAb/small-drug conjugate | Small-cell lung |
| Medarex, Inc. | MDX-260 bispecific, targets GD-2 | Melanoma, glioma, neuroblastoma |
| Procyon Biopharma, Inc. | ANA Ab | Cancer |
| Protein Design Labs | SMART ™ 1D10 Ab | B-cell lymphoma |
| Protein Design Labs/Novartis | SMART ™ ABL 364 Ab | Breast, lung, colon |
| Immunomedics, Inc. | ImmuRAIT-CEA | Colorectal |

Yet other types of chemotherapeutic agents which can be used according to the invention include Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

Cancer vaccines are medicaments which are intended to stimulate an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells.

Although cancer vaccines may take one of several forms, as discussed infra, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. Lysates of tumor cells can also be used as cancer vaccines to elicit an immune response. Another form cancer vaccine is a peptide vaccine which uses cancer-specific or cancer-associated small proteins to activate T cells. Cancer-associated proteins are proteins which are not exclusively expressed by cancer cells (i.e., other normal cells may still express these antigens). However, the expression of cancer-associated antigens is generally consistently upregulated with cancers of a particular type. Yet another form of cancer vaccine is a dendritic cell vaccine which includes whole dendritic cells which have been exposed to a cancer antigen or a cancer-associated antigen in vitro. Lysates or membrane fractions of dendritic cells may also be used as cancer vaccines. Dendritic cell vaccines are able to activate antigen-presenting cells directly. Other cancer vaccines include ganglioside vaccines, heat-shock protein vaccines, viral and bacterial vaccines, and nucleic acid vaccines.

The use of immunostimulatory nucleic acids in conjunction with cancer vaccines provides an improved antigen-specific humoral and cell mediated immune response, in addition to activating NK cells and endogenous dendritic cells, and increasing IFNα levels. This enhancement allows a vaccine with a reduced antigen dose to be used to achieve the same beneficial effect. In some instances, cancer vaccines may be used along with adjuvants, such as those described above.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Other vaccines take the form of dendritic cells which have been exposed to cancer antigens in vitro, have processed the antigens and are able to express the cancer antigens at their cell surface in the context of MHC molecules for effective antigen presentation to other immune system cells.

The immunostimulatory nucleic acids are used in one aspect of the invention in conjunction with cancer vaccines which are dendritic cell based. A dendritic cell is a professional antigen presenting cell. Dendritic cells form the link between the innate and the acquired immune system by presenting antigens and through their expression of pattern recognition receptors which detect microbial molecules like LPS in their local environment. Dendritic cells efficiently internalize, process, and present soluble specific antigen to which it is exposed. The process of internalizing and presenting antigen causes rapid upregulation of the expression of major histocompatibility complex (MHC) and costimulatory molecules, the production of cytokines, and migration toward lymphatic organs where they are believed to be involved in the activation of T cells.

Table D lists a variety of cancer vaccines which are either currently being used or are in development.

TABLE D

Cancer Vaccines in Development or on the Market

| MARKETER | BRAND NAME (GENERIC NAME) | INDICATION |
|---|---|---|
| Center of Molecular Immunology | EGF | Cancer |
| Center of Molecular Immunology | | Ganglioside cancer vaccine |
| Center of Molecular Immunology | Anti-idiotypic | Cancer vaccine |
| ImClone Systems/Memorial Sloan-Kettering Cancer Center | Gp75 antigen | Melanoma |
| ImClone Systems/Memorial Sloan-Kettering Cancer Center | Anti-idiotypic Abs | Cancer vaccines |
| Progenics Pharmaceuticals, Inc. | GMK melanoma vaccine | Melanoma |
| Progenics Pharmaceuticals, Inc, | MGV ganglioside conjugate vaccine | Lymphoma, colorectal, lung |
| Corixa | Her2/neu | Breast, ovarian |
| AltaRex | Ovarex | Ovarian |
| AVAX Technologies Inc. | M-Vax, autologous whole cell | Melanoma |
| AVAX Technologies Inc. | O-Vax, autologous whole cell | Ovarian |
| AVAX Technologies Inc. | L-Vax, autologous whole cell | Leukemia-AML |
| Biomira Iric./Chiron | Theratope, STn-KLH | Breast, Colorectal |

TABLE D-continued

Cancer Vaccines in Development or on the Market

| MARKETER | BRAND NAME (GENERIC NAME) | INDICATION |
|---|---|---|
| Biomira Inc. | BLP25, MUC-1 peptide vaccine encapsulated in liposomal delivery system | Lung |
| Biomira Inc. | BLP25, MUC-1 peptide vaccine encapsulated in liposomal delivery system + Liposomal IL-2 | Lung |
| Biomira Inc. | Liposomal idiotypic vaccine | Lymphoma B-cell malignancies |
| Ribi Immunochem | Melacine, cell lysate | Melanoma |
| Corixa | Peptide antigens, microsphere delivery sysem and LeIF adjuvant | Breast |
| Corixa | Peptide antigens, microsphere delivery sysem and LeIF adjuvant | Prostate |
| Corixa | Peptide antigens, microsphere delivery sysem and LeIF adjuvant | Ovarian |
| Corixa | Peptide antigens, microsphere delivery sysem and LeIF adjuvant | Lymphoma |
| Corixa | Peptide antigens, microsphere delivery sysem and LeIF adjuvant | Lung |
| Virus Research Institute | Toxin/antigen recombinant delivery system | All cancers |
| Apollon Inc. | Genevax-TCR | T-cell lymphoma |
| Bavarian Nordic Research Institute A/S | MVA-based (vaccinia virus) vaccine | Melanoma |
| BioChem Pharma/BioChem Vaccine | PAGIS, BCG vaccine | Bladder |
| Cantab Pharmaceuticals | TA-HPV | Cervical |
| Cantab Pharmaceuticals | TA-CIN | Cervical |
| Cantab Pharmaceuticals | DISC-Virus, immunotherapy | Cancer |
| Pasteur Merieux Connaught | ImmuCyst ®/TheraCys ®- BCG Immunotherapeutic (Bacillus Calmette-Guerin/Connaught), for intravesical treatment of superficial bladder cancer | Bladder |

As used herein, chemotherapeutic agents embrace all other forms of cancer medicaments which do not fall into the categories of immunotherapeutic agents or cancer vaccines. Chemotherapeutic agents as used herein encompass both chemical and biological agents. These agents function to inhibit a cellular activity which the cancer cell is dependent upon for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. Combination chemotherapy and immunostimulatory nucleic acid administration increases the maximum tolerable dose of chemotherapy.

Chemotherapeutic agents which are currently in development or in use in a clinical setting are shown in Table E.

TABLE E

Cancer Drugs in Development or on the Market

| Marketer | Brand Name | Generic Name | Indication |
|---|---|---|---|
| Abbott | TNP 470/AGM 1470 | Fragyline | Anti-Angiogenesis in Cancer |
| Takeda | TNP 470/AGM 1470 | Fragyline | Anti-Angiogenesis in Cancer |
| Scotia | Meglamine GLA | Meglamine GLA | Bladder Cancer |
| Medeva | Vaistar | Valrubicin | Bladder Cancer - Refractory in situ carcinoma |
| Medeva | Valstar | Valrubicin | Bladder Cancer - Papillary Cancer |
| Rhone Poulenc | Gliadel Wafer | Carmustaine + Polifepr Osan | Brain Tumor |
| Warner Lambert | Undisclosed Cancer (b) | Undisclosed Cancer (b) | Cancer |
| Bristol Myers Squib | RAS Farnesyl Transferase Inhibitor | RAS FarnesylTransferase Inhibitor | Cancer |
| Novartis | MMI 270 | MMI 270 | Cancer |
| Bayer | BAY 12-9566 | BAY 12-9566 | Cancer |
| Merck | Farnesyl Transferase Inhibitor | Farnesyl Transferase Inhibitor | Cancer (Solid tumors - pancrease, colon, lung, breast) |
| Pfizer | PFE | MMP | Cancer, angiogenesis |
| Pfizer | PFE | Tyrosine Kinase | Cancer, angiogenesis |
| Lilly | MTA/LY 231514 | MTA/LY 231514 | Cancer Solid Tumors |
| Lilly | LY 264618/Lometexol | Lometexol | Cancer Solid Tumors |
| Scotia | Glamolec | LiGLA (lithium-gamma linolenate) | Cancer, pancreatic, breast, colon |

TABLE E-continued

Cancer Drugs in Development or on the Market

| Marketer | Brand Name | Generic Name | Indication |
|---|---|---|---|
| Warner Lambert | CI-994 | CI-994 | Cancer, Solid Tumors / Leukemia |
| Schering AG | Angiogenesis inhibitor | Angiogenesis Inhibitor | Cancer / Cardio |
| Takeda | TNP-470 | n/k | Malignant Tumor |
| Smithkline Beecham | Hycamtin | Topotecan | Metastatic Ovarian Cancer |
| Novartis | PKC 412 | PKC 412 | Multi-Drug Resistant Cancer |
| Novartis | Valspodar | PSC 833 | Myeloid Leukemia/Ovarian Cancer |
| Immunex | Novantrone | Mitoxantrone | Pain related to hormone refractory prostate cancer. |
| Warner Lambert | Metaret | Suramin | Prostate |
| Genentech | Anti-VEGF | Anti-VEGF | Prostate / Breast / Colorectal / NSCL Cancer |
| British Biotech | Batimastat | Batimastat (BB94) | Pterygium |
| Eisai | E 7070 | E 7070 | Solid Tumors |
| Biochem Pharma | BCH-4556 | BCH-4556 | Solid Tumors |
| Sankyo | CS-682 | CS-682 | Solid Tumors |
| Agouron | AG2037 | AG2037 | Solid Tumors |
| IDEC Pharma | 9-AC | 9-AC | Solid Tumors |
| Agouron | VEGF/b-FGF Inhibitors | VEGF/b-FGF Inhibitors | Solid Tumors |
| Agouron | AG3340 | AG3340 | Solid Tumors / Macular Degen |
| Vertex | Incel | VX-710 | Solid Tumors - IV |
| Vertex | VX-853 | VX-853 | Solid Tumors - Oral |
| Zeneca | ZD 0101 (inj) | ZD 0101 | Solid Tumors |
| Novartis | ISI 641 | ISI 641 | Solid Tumors |
| Novartis | ODN 698 | ODN 698 | Solid Tumors |
| Tanube Seiyaku | TA 2516 | Marimistat | Solid Tumors |
| British Biotech | Marimastat | Marimastat (BB 2516) | Solid Tumors |
| Celltech | CDP 845 | Aggrecanase Inhibitor | Solid Tumors / Breast Cancer |
| Chiroscience | D2163 | D2163 | Solid Tumors / Metastases |
| Warner Lambert | PD 183805 | PD 183805 | |
| Daiichi | DX8951f | DX8951f | Anti-Cancer |
| Daiichi | Lemonal DP 2202 | Lemonal DP 2202 | Anti-Cancer |
| Fujisawa | FK 317 | FK 317 | Anticancer Antibiotic |
| Chugai | Picibanil | OK-432 | Antimalignant Tumor |
| Nycomed Amersham | AD 32/valrubicin | Valrubicin | Bladder Cancer-Refractory Insitu Carcinoma |
| Nycomed Amersham | Metastron | Strontium Derivative | Bone Cancer (adjunt therapy, Pain) |
| Schering Plough | Temodal | Temozolomide | Brain Tumours |
| Schering Plough | Temodal | Temozolonide | Brain Tumours |
| Liposome | Evacet | Doxorubicin, Liposomal | Breast Cancer |
| Nycomed Amersham | Yewtaxan | Paclitaxel | Breast Cancer Advanced, Ovarian Cancer Advanced |
| Bristol Myers Squib | Taxol | Paclitaxel | Breast Cancer Advanced, Ovarian Cancer Advanced, NSCLC |
| Roche | Xeloda | Capecitabine | Breast Cancer, Colorectal Cancer |
| Roche | Furtulon | Doxifluridine | Breast Cancer, Colorectal Cancer, Gastric Cancer |
| Pharmacia & Upjohn | Adriamycin | Doxorubicin | Breast Cancer, Leukemia |
| Ivax | Cyclopax | Paclitaxel, Oral | Breast/Ovarian Cancer |
| Rhone Poulenc | Oral Taxoid | Oral Taxoid | Broad Cancer |
| AHP | Novantrone | Mitoxantrone | Cancer |
| Sequus | SPI-077 | Cisplatin, Stealth | Cancer |
| Hoechst | HMR 1275 | Flavopiridol | Cancer |
| Pfizer | CP-358, 774 | EGFR | Cancer |
| Pfizer | CP-609, 754 | RAS Oncogene Inhibitor | Cancer |
| Bristol Myers Squib | BMS-182751 | Oral Platinum | Cancer (Lung, Ovarian) |
| Bristol Myers Squib | UFT (Tegafur/Uracil) | UFT (Tegafur/Uracil) | Cancer Oral |
| Johnson & Johnson | Ergamisol | Levamisole | Cancer Therapy |
| Glaxo Wellcome | Eniluracil/776C85 | 5FU Enhancer | Cancer, Refractory Solid & Colorectal Cancer |
| Johnson & Johnson | Ergamisol | Levamisole | Colon Cancer |

TABLE E-continued

Cancer Drugs in Development or on the Market

| Marketer | Brand Name | Generic Name | Indication |
|---|---|---|---|
| Rhone Poulene | Campto | Irinotecan | Colorectal Cancer, Cervical Cancer |
| Pharmacia & Upjohn | Camptosar | Irinotecan | Colorectal Cancer, Cervical Cancer |
| Zeneca | Tomudex | Ralitrexed | Colorectal Cancer, Lung Cancer, Breast Cancer |
| Johnson & Johnson | Leustain | Cladribine | Hairy Cell Leukaemia |
| Ivax | Paxene | Paclitaxel | Kaposi Sarcoma |
| Sequus | Doxil | Doxorubicin, Liposomal | KS/Cancer |
| Sequus | Caelyx | Doxorubicin, Liposomal | KS/Cancer |
| Schering AG | Fludara | Fludarabine | Leukaemia |
| Pharmacia & Upjohn | Pharmorubicin | Epirubicin | Lung/Breast Cancer |
| Chiron | DepoCyt | DepoCyt | Neoplastic Meningitis |
| Zeneca | ZD1839 | ZD 1839 | Non Small Cell Lung Cancer, Pancreatic Cancer |
| BASF | LU 79553 | Bis-Naphtalimide | Oncology |
| BASF | LU 103793 | Dolastain | Oncology |
| Shering Plough | Caetyx | Doxorubicin-Liposorne | Ovarian/Breast Cancer |
| Lilly | Gemzar | Gemcitabine | Pancreatic Cancer, Non Small Cell Lung Cancer, Breast, Bladder and Ovarian |
| Zeneca | ZD 0473/Anormed | ZD O473/Anormed | Platinum based NSCL, ovarian etc. |
| Yamanouchi | YM 116 | YM 116 | Prostate Cancer |
| Nycomed Amersham | Seeds/I-125 Rapid St | Lodine Seeds | Prostate Cancer |
| Agouron | Cdk4/cdk2 inhibitors | cdk4/cdk2 inhibitors | Solid Tumors |
| Agouron | PARP inhibitors | PARP Inhibitors | Solid Tumors |
| Chiroscience | D4809 | Dexifosamide | Solid Tumors |
| Bristol Myers Squib | UFT (Tegafur/Uracil) | UFT (Tegafur/Uracil) | Solid Tumors |
| Sankyo | Krestin | Krestin | Solid Tumors |
| Asta Medica | Ifex/Mesnex | Ifosamide | Solid Tumors |
| Bristol Meyers Squib | Ifex/Mesnex | Ifosamide | Solid Tumors |
| Bristol Myers Squib | Vumon | Teniposide | Solid Tumors |
| Bristol Myers Squib | Paraplatin | Carboplatin | Solid Tumors |
| Bristol Myers Squib | Plantinol | Cisplatin, Stealth | Solid Tumors |
| Bristol Myers Squib | Plantinol | Cisplatin | Solid Tumors |
| Bristol Myers Squib | Vepeside | Etoposide | Solid Tumors Melanoma |
| Zeneca | ZD 9331 | ZD 9331 | Solid Tumors, Advanced Colorectal |
| Chugai | Taxotere | Docetaxel | Solid Tumors, Breast Cancer |
| Rhone Poulenc | Taxotere | Docetaxel | Solid Tumors, Breast Cancer |
| Glaxo Welicome | Prodrug of guanine arabinside | Prodrug of arabinside | T Cell Leukemia/Lymphoma & B Cell Neoplasm |
| Bristol Myers Squib | Taxane Analog | Taxane Analog | Taxol follow up |

In one embodiment, the methods of the invention use immunostimulatory nucleic acids as a replacement to the use of IFNα therapy in the treatment of cancer. Currently, some treatment protocols call for the use of IFNα. Since IFNα is produced following the administration of some immunostimulatory nucleic acids, these nucleic acids can be used to generate IFNα endogenously.

The invention also includes a method for inducing antigen non-specific innate immune activation and broad spectrum resistance to infectious challenge using the immunostimulatory nucleic acids. The term antigen non-specific innate immune activation as used herein refers to the activation of immune cells other than B cells and for instance can include the activation of NK cells, T cells or other immune cells that can respond in an antigen independent fashion or some combination of these cells. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The stimulation index of a particular immunostimulatory nucleic acid can be tested in various immune cell assays. Preferably, the stimulation index of the immunostimulatory nucleic acid with regard to B cell proliferation is at least about 5, preferably at least about 10, more preferably at least about 15 and most preferably at least about 20 as determined by incorporation of $^3$H uridine in a murine B cell culture, which has been contacted with 20 µM of nucleic acid for 20 h at 37° C. and has been pulsed with 1 µCi of $^3$H uridine; and harvested and counted 4 h later as described in detail in PCT Published Patent Applications PCT/US95/01570 (WO 96/02555) and PCT/US97/19791 (WO 98/18810) claiming priority to U.S. Ser. No. 08/386,063, now U.S. Pat. No. 6,194,388, and Ser. No. 08/960,774, now U.S. Pat. No. 6,239,116, filed on Feb. 7, 1995 and Oct. 30, 1997 respectively. For use in vivo, for example, it is important that the immunostimulatory nucleic acids be capable of effectively inducing an immune response, such as, for example, antibody production.

Immunostimulatory nucleic acids are effective in non-rodent vertebrate. Different immunostimulatory nucleic acid can cause optimal immune stimulation depending on the type of subject and the sequence of the immunostimulatory nucleic acid. Many vertebrates have been found according to the invention to be responsive to the same class of immunostimulatory nucleic acids, sometimes referred to as human specific immunostimulatory nucleic acids. Rodents, however, respond to different nucleic acids. As shown herein an immunostimulatory nucleic acid causing optimal stimulation in humans may not generally cause optimal stimulation in a mouse and vice versa. An immunostimulatory nucleic acid causing optimal stimulation in humans often does, however, cause optimal stimulation in other animals such as cow, horses, sheep, etc. One of skill in the art can identify the optimal nucleic acid sequences useful for a particular species of interest using routine assays described herein and/or known in the art, using the guidance supplied herein.

The immunostimulatory nucleic acids may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell (e.g., B cell surfaces and/or increased cellular uptake by target cells). Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the nucleic acid is released in a functional form.

Delivery vehicles or delivery devices for delivering antigen and nucleic acids to surfaces have been described. The Immunostimulatory nucleic acid and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., Salmonella, *Escherichia coli, Bacillus calmatte-guerin*, Shigella, Lactobacillus) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art and some additional examples are provided below in the discussion of vectors.

The term effective amount of a immunostimulatory nucleic acid refers to the amount necessary or sufficient to realize a desired biologic effect. For example, an effective amount of a immunostimulatory nucleic acid for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular immunostimulatory nucleic acid being administered, the antigen, the size of the subject, or the severity of the disease or condition. One of ordinary skill in the art can empirically determine the effective amount of a particular immunostimulatory nucleic acid and/or antigen and/or other therapeutic agent without necessitating undue experimentation.

Subject doses of the compounds described herein for mucosal or local delivery typically range from about 0.1 µg to 10 mg per administration, which depending on the application could be given daily, weekly, or monthly and any other amount of time therebetween. More typically mucosal or local doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the immunostimulatory nucleic acids are administered in combination with other therapeutic agents or in specialized delivery vehicles typically range from about 0.1 µg to 10 mg per administration, which depending on the application could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (human clinical trials have been initiated) and for compounds which are known to exhibit similar pharmacological activities, such as other mucosal adjuvants, e.g., LT and other antigens for vaccination purposes, for the mucosal or local administration. Higher doses are required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the immunostimulatory nucleic acid can be administered to a subject by any mode that delivers the nucleic acid to the desired surface, e.g., mucosal, systemic. Administering the pharmaceutical composition of the present invention may be accomplished by any means known to the skilled artisan. Preferred routes of administration include but are not limited to oral, parenteral, intramuscular, intranasal, intratracheal, inhalation, ocular, vaginal, and rectal.

For oral administration, the compounds (i.e., immunostimulatory nucleic acids, antigens and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The immunostimulatory nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a Immunostimulatory nucleic acid and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The immunostimulatory nucleic acids useful in the invention may be delivered in mixtures with additional adjuvant (s), other therapeutics, or antigen(s). A mixture may consist of several adjuvants in addition to the Immunostimulatory nucleic acid or several antigens or other therapeutics.

A variety of administration routes are available. The particular mode selected will depend, of course, upon the particular adjuvants or antigen selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the immunization (i.e., prophylactic or therapeutic), nature and severity of the disorder, age and body weight of the patient, different doses may be necessary. The administration of a given dose can be carried out both by single administration in the form of an individual dose unit or else several smaller dose units. Multiple administration of doses at specific intervals of weeks or months apart is usual for boosting the antigen-specific responses.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and triglycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods:

Oligodeoxynucleotides: Native phosphodiester and phosphorothioate-modified ODN were purchased from Operon Technologies (Alameda, Calif.) and Hybridon Specialty Products (Milford, Mass.). ODN were tested for endotoxin using the LAL-assay (LAL-assay BioWhittaker, Walkersville, Md.; lower detection limit 0.1 EU/ml). For in vitro assays, ODN were diluted in TE-buffer (10 mM Tris, pH 7.0, 1 mM EDTA), and stored at −20° C. For in vivo use, ODN were diluted in phosphate buffered saline (0.1 M PBS, pH 7.3) and stored at 4° C. All dilutions were carried out using pyrogen-free reagents.

Isolation of human PBMC and cell culture: Peripheral blood mononuclear cells (PBMC) were isolated from peripheral blood of healthy volunteers by Ficoll-Paque density gradient centrifugation (Histopaque-1077, Sigma Chemical Co., St. Louis, Mo.) as described (Hartmann et al., 1999 Proc. Natl. Acad. Sci USA 96:9305-10). Cells were suspended in RPMI 1640 culture medium supplemented with 10% (v/v) heat-inactivated (56° C., 1 h) FCS (HyClone, Logan, Utah), 1.5 mM L-glutamine, 100 U/ml penicillin and 100 µg/ml streptomycin (all from Gibco BRL, Grand Island, N.Y.) (complete medium). Cells (final concentration $1 \times 10^6$ cells/ml) were cultured in complete medium in a 5% $CO_2$ humidified incubator at 37° C. ODN and LPS (from *Salmonella typhimurium*, Sigma Chemical Co., St. Louis, Mo.) or anti-IgM were used as stimuli. For measurement of human NK lytic activity, PBMC were incubated at $5 \times 10^6$/well in 24-well plates. Cultures were harvested after 24 hours, and cells were used as effectors in a standard 4 hours $^{51}$Cr-release assay against K562 target cells as previously described (Ballas et al., 1996 J. Immunol. 157:1840-1845). For B cell proliferation, 1 µCi of $^3$H thymidine was added 18 hours before harvest, and the amount of $^3$H thymidine incorporation was determined by scintillation counting at day 5. Standard deviations of the triplicate wells were <5%.

Flow cytometry on human PBMC: Surface antigens on primate PBMC were stained as previously described (Hartmann et al., 1998 J. Pharmacol. Exp. Ther. 285:920-928). Monoclonal antibodies to CD3 (UCHT1), CD14 (M5E2), CD19 (B43), CD56 (B159), CD69 (FN50) and CD86 (2331 [FUN-1]) were purchased from Pharmingen, San Diego, Calif. $IgG_1,\kappa$ (MOPC-21) and $IgG_{2b},\kappa$ (Hartmann et al., 1999 Proc. Natl. Acad. Sci USA 96:9305-10) were used to control for non-specific staining. NK cells were identified by CD56 expression on CD3, CD14 and CD19 negative cells, whereas B cells were identified by expression of CD19. Flow cytometric data of 10000 cells per sample were acquired on a FACScan (Beckton Dickinson Immunocytometry Systems, San Jose, Calif.). The viability of cells within the FSC/SSC gate used for analysis was examined by propidium iodide staining (2 µg/ml) and found to be higher than 98%. Data were analyzed using the computer program FlowJo (version 2.5.1, Tree Star, Inc., Stanford, Calif.).

Results:

Example 1

CpG-dependent Stimulation of Human B Cells Depends on Methylation and ODN Length Human PBMC were obtained from normal donors and cultured for five days at $2 \times 10^5$ cells/well with the indicated concentrations of the indicated ODN sequences. As shown in Table F, human PBMCs proliferate above the background when cultured with a variety of different CpG ODN, but also show some proliferation even with ODN that do not contain any CpG motifs. The importance of unmethylated CpG motifs in providing optimal immune stimulation with these ODN is demonstrated by the fact that ODN 1840 (SEQ ID NO. 83) induces 56,603 counts of $^3$H-thymidine incorporation whereas the same T-rich ODN with the CpG motifs methylated (non-CpG), 1979 (SEQ ID NO. 222), induces lower, but still increased over background, activity (only 18,618 counts) at the same concentration of 0.6 µg/ml. The reduced proliferation at higher ODN concentrations may be an artifact of the cells becoming exhausted under these experimental conditions or could reflect some toxicity of the higher ODN concentrations. Interestingly, shorter ODN containing CpG motifs, such as the 13-14 mers 2015 and 2016, are less stimulatory despite the fact that their molar concentration would actually be higher since the ODNs were added on the basis of mass rather than molarity. This demonstrates that ODN length may also be an important determinant in the immune effects of the ODN. A non-CpG ODN but slight T-rich ODN (about 30% T), 1982 (SEQ ID NO. 225), caused only a small amount of background cell proliferation.

TABLE F

| ODN# | Oligo Concentration | | |
|---|---|---|---|
| | 0.15 µg/ml | 0.6 µg/ml | 2 µg/ml |
| Cues only | 648 | 837 | 799 |
| 1840 (SEQ ID NO. 83) | 5744 | 56,603 | 31,787 |
| 2016 (SEQ ID NO. 256) | 768 | 4607 | 20,497 |
| 1979 (SEQ ID NO. 222) | 971 | 18,618 | 29,246 |
| 1892 (SEQ ID NO. 135) | 787 | 10,078 | 22,850 |
| 2010 (SEQ ID NO. 250) | 849 | 20,741 | 8,054 |
| 2012 (SEQ ID NO. 252) | 2586 | 62,955 | 52,462 |
| 2013 (SEQ ID NO. 253) | 1043 | 47,960 | 47,231 |
| 2014 (SEQ ID NO. 254) | 2700 | 50,708 | 46,625 |
| 2015 (SEQ ID NO. 255) | 1059 | 23,239 | 36,119 |

Numbers represent cpm of $^3$H-thymidine incorporation for cultures of human PBMCs set up as described above.

Example 2

Concentration-dependent Activation of Human NK Cell Activity with Thymidine-Rich ODN Human PBMCs were cultured for 24 hours with a panel of different CpG or non-CpG ODN at two different concentrations, and then tested for their ability to kill NK target cells as described previously (Ballas et al., 1996 J. Immunol. 157:1840-1845). Killing is measured as lytic units, or L.U. The human donor used in this experiment had a background level of 3.69 L.U. which increased to 180.36 L.U. using the positive control, IL-2. A CpG oligo, 2006 (SEQ ID NO. 246), induced high levels of NK lytic function at a low concentration of 0.6, and a lower level at a concentration of 6.0. Surprisingly, a T-rich ODN in which the CpG motifs of 2006 were methylated (ODN at 2117 (SEQ ID NO. 358)) or inverted to GpCs (ODN 2137 (SEQ ID NO. 886)) retained strong immune stimulatory function at the higher ODN concentrations, as shown in Table G. These concentration-dependent immune stimulatory effects are not a general property of the phosphorothioate backbone since the experiments described below demonstrate that a poly-A ODN, is nonstimulatory above background levels. Some stimulation is seen with a 24-base long ODN in which all of the base positions are randomized so that A, C, G, and T will occur at a frequency of 25% in each of the base positions (ODN 2182 (SEQ ID NO. 432)). However, the stimulatory effect of such a 24-base ODN is greatly enhanced if it is pure poly-T, in which case stimulation is also seen at the lowest concentration of 0.6 µg/ml (ODN 2183 (SEQ ID NO. 433)). In fact, the stimulatory activity of ODN SEQ ID NO. 433 at this low concentration is higher than that of any other ODN tested at this low concentration, aside from the optimal human immune stimulatory ODN of SEQ ID NO. 246. In fact, the higher concentration of ODN SEQ ID NO. 433 stimulated more NK activity than any other phosphorothioate ODN except for the strong CpG ODN 2142 (SEQ ID NO. 890), which was marginally higher. If the G content of ODN SEQ ID NO. 246 is increased relative to the T content by addition of more Gs, thus resulting in a decrease in the proportion of T nucleotides the immune stimulatory effect of the ODN is reduced (see ODN 2132 (SEQ ID NO. 373)). Thus, the T content of an ODN is an important determinant of its immune stimulatory effect. Although a poly-T ODN is the most stimulatory of the non-CpG ODN, other bases are also important in determining the immune stimulatory effect of a non-CpG ODN. ODN 2131 (SEQ ID NO. 372), in which slightly more than half of the bases are T and in which there are no Gs, is immune stimulatory at a concentration of 6 µg/ml but has less activity than other T-rich ODN. If the 6 A's in ODN 2131 (SEQ ID NO. 372) are replaced by 6 Gs, the immune stimulatory effect of the ODN can be increased (see ODN 2130 (SEQ ID NO. 371)).

TABLE G

HUMAN PBL CULTURED OVERNIGHT WITH OLIGOS

| | | | | | | | |
|---|---|---|---|---|---|---|---|
| MR | 3605 | | | | | | |
| SR | 256 | | | | | | |
| % SR | 7.11 | | | | | | |
| EFFECTOR | 0.63 | 1.25 | 2.50 | 5.00 | 10.00 | 20.00 | |
| CONTROL [RM] | | | | | | | L.U. |
| ALONE | 2.65 | 5.45 | 10.15 | 17.65 | 29.92 | 39.98 | 3.69 |
| + IL2 (100 U/ml) | 35.95 | 57.66 | 86.26 | 100.39 | 99.71 | 93.64 | 180.36 |
| + 1585 (0.6 ug/ml) | 3.75 | 6.10 | 12.14 | 23.70 | 36.06 | 43.98 | 5.48 |
| + 1585 (6.0 ug/ml) | 15.42 | 31.09 | 47.07 | 73.34 | 94.29 | 97.73 | 35.85 |
| + 2006 (0.6 ug/ml) | 6.71 | 15.99 | 26.92 | 44.75 | 64.12 | 68.83 | 16.96 |
| + 2006 (6.0 ug/ml) | 6.19 | 8.18 | 16.13 | 24.35 | 39.35 | 56.07 | 8.04 |
| + 2117 (0.6 ug/ml) | 4.54 | 4.73 | 9.56 | 18.04 | 28.57 | 39.85 | 3.49 |
| + 2117 (6.0 ug/ml) | 7.03 | 10.76 | 16.90 | 30.59 | 52.14 | 59.46 | 10.96 |
| + 2137 (0.6 ug/ml) | 4.61 | 5.35 | 10.04 | 15.16 | 23.79 | 37.86 | 2.57 |
| + 2137 (6.0 ug/ml) | 7.99 | 10.37 | 16.55 | 32.32 | 49.78 | 60.30 | 11.01 |
| + 2178 (0.6 ug/ml) | 2.88 | 4.52 | 11.47 | 16.05 | 24.85 | 34.27 | 2.37 |
| + 2178 (6.0 ug/ml) | 4.21 | 5.03 | 11.16 | 16.39 | 28.22 | 36.45 | 2.94 |
| + 2182 (0.6 ug/ml) | 2.42 | 6.57 | 10.49 | 19.73 | 26.55 | 35.30 | 2.89 |
| + 2182 (6.0 ug/ml) | 4.11 | 7.98 | 14.60 | 26.56 | 40.40 | 51.98 | 7.59 |
| + 2183 (0.6 ug/ml) | 3.73 | 8.46 | 15.52 | 24.48 | 37.78 | 56.77 | 7.80 |
| + 2183 (0.6 ug/ml) | 8.86 | 12.89 | 23.08 | 41.49 | 66.26 | 75.85 | 16.57 |
| + 2140 (0.6 ug/ml) | 3.78 | 5.27 | 12.30 | 20.79 | 35.75 | 45.62 | 5.40 |
| + 2140 (6.0 ug/ml) | 6.56 | 13.24 | 21.26 | 37.96 | 60.80 | 73.05 | 14.82 |
| + 2141 (0.6 ug/ml) | 2.63 | 6.34 | 10.21 | 17.73 | 30.93 | 43.57 | 4.29 |
| + 2141 (6.0 ug/ml) | 4.98 | 15.30 | 25.22 | 37.88 | 58.47 | 69.12 | 14.83 |
| + 2142 (0.6 ug/ml) | 3.18 | 3.66 | 6.99 | 14.62 | 19.68 | 32.52 | 1.56 |
| + 2142 (6.0 ug/ml) | 7.08 | 15.80 | 25.65 | 41.72 | 68.09 | 73.14 | 17.11 |
| + 2143 (0.6 ug/ml) | 4.12 | 6.90 | 10.77 | 22.96 | 35.78 | 42.94 | 5.19 |
| + 2143 (6.0 ug/ml) | 3.16 | 8.40 | 12.38 | 21.69 | 34.80 | 54.21 | 6.64 |
| + 2159 (6.0 ug/ml) | 5.05 | 11.76 | 21.67 | 41.12 | 51.68 | 65.47 | 13.19 |
| + 2132 (6.0 ug/ml) | 4.23 | 6.06 | 10.50 | 18.74 | 32.68 | 44.06 | 4.61 |
| + 2179 (6.0 ug/ml) | 6.14 | 9.49 | 21.06 | 42.48 | 60.12 | 71.87 | 14.54 |
| + 2180 (6.0 ug/ml) | 2.37 | 8.57 | 15.44 | 29.66 | 44.35 | 61.31 | 9.47 |
| + 2133 (6.0 ug/ml) | 6.53 | 12.58 | 23.10 | 38.03 | 61.16 | 68.36 | 14.62 |
| + 2134 (6.0 ug/ml) | 7.51 | 12.14 | 21.14 | 32.46 | 54.47 | 67.12 | 12.98 |
| + 2184 (6.0 ug/ml) | 5.22 | 9.19 | 17.54 | 30.76 | 45.35 | 63.55 | 10.42 |
| + 2185 (6.0 ug/ml) | 8.11 | 14.77 | 26.27 | 40.31 | 55.61 | 70.65 | 15.60 |
| + 2116 (6.0 ug/ml) | 5.58 | 10.54 | 16.77 | 37.82 | 59.80 | 66.33 | 13.07 |
| + 2181 (6.0 ug/ml) | 4.43 | 9.85 | 17.55 | 27.05 | 53.16 | 69.16 | 11.43 |
| + 2130 (6.0 ug/ml) | 3.81 | 8.07 | 17.11 | 27.17 | 42.04 | 53.73 | 8.27 |
| + 2131 (6.0 ug/ml) | 2.29 | 6.73 | 7.30 | 18.02 | 32.73 | 49.06 | 5.08 |
| + 2156 (0.3 ug/ml) | 2.50 | 5.26 | 8.20 | 15.95 | 26.64 | 33.07 | 2.31 |
| + 2156 (1.0 ug/ml) | 5.91 | 10.99 | 17.31 | 26.97 | 50.64 | 63.78 | 10.84 |
| + 2157 (0.3 ug/ml) | 2.36 | 4.00 | 6.65 | 12.94 | 24.13 | 38.86 | 2.58 |
| + 2157 (1.0 ug/ml) | 3.72 | 9.55 | 17.15 | 34.55 | 52.27 | 65.33 | 11.58 |
| + 2158 (0.3 ug/ml) | 1.25 | 2.36 | 6.90 | 16.39 | 15.63 | 29.82 | 1.17 |
| + 2158 (1.0 ug/ml) | 4.73 | 7.26 | 11.07 | 15.55 | 30.80 | 43.71 | 4.16 |
| + 2118 (0.6 ug/ml) | 1.55 | 3.38 | 6.85 | 13.36 | 20.15 | 27.71 | 1.13 |
| + 2118 (6.0 ug/ml) | 2.65 | 3.88 | 9.29 | 12.19 | 22.47 | 28.99 | 1.34 |

Example 3

Induction of B Cell Proliferation by T-rich Non-CpG ODN

Figure 1C:
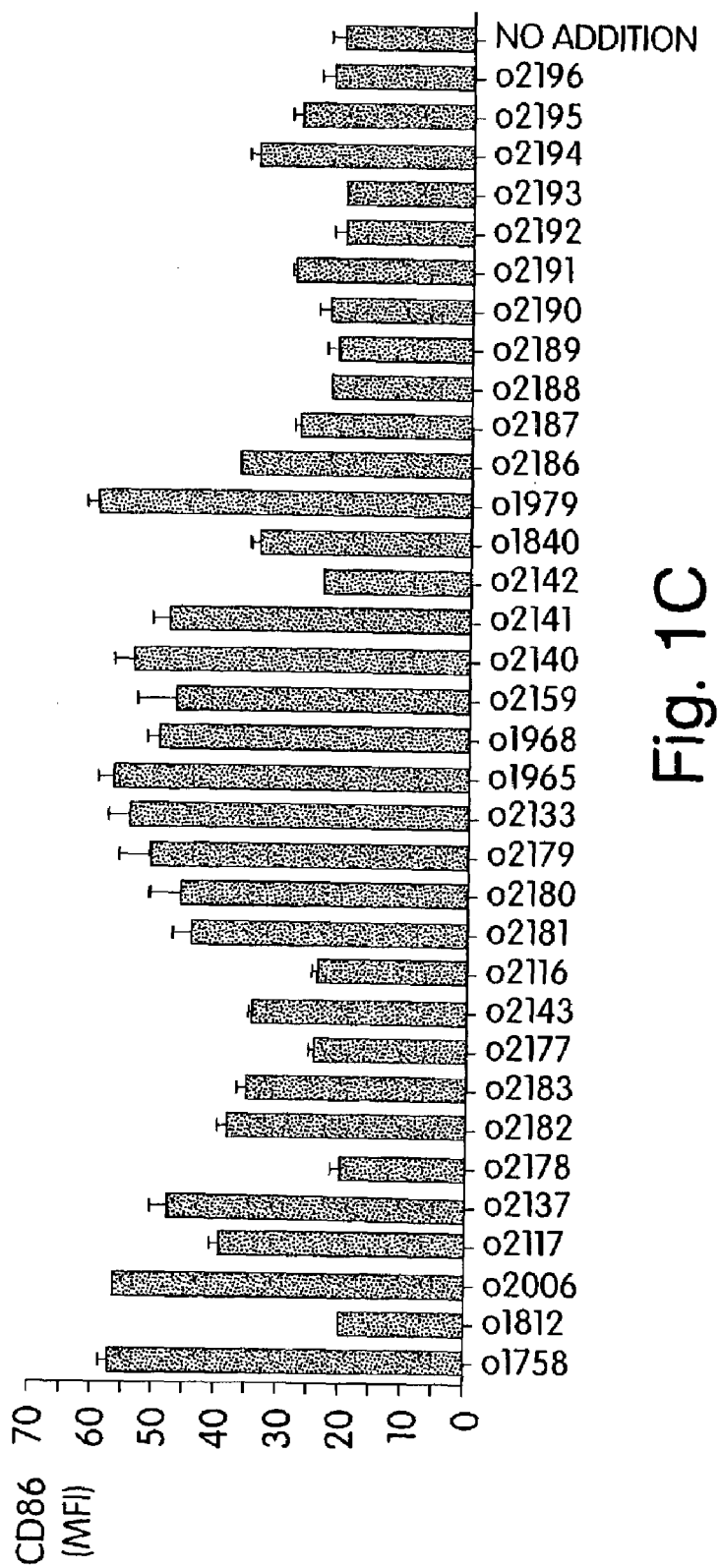
FIG. 1C is a histogram of the expression of CD86 (Y-axis) by CD19+ cells following exposure of these cells to the oligonucleotides shown on the X-axis at a concentration of 0.30 µg/ml.

To assess the ability of T-rich ODN to activate B cell proliferation, human PBMCs were stained with the cytoplasmic dye CSFE, incubated with five days with the indicated ODN at either 0.15 or 0.3 ug/ml, and then analyzed by flow cytometry. B cells were identified by gating on cells positive for the lineage marker CD19). CpG ODN 2006 was a strong inducer of B cell proliferation, and this effect was reduced if the CpG motifs were methylated or inverted to GpC as shown in FIG. 1 at an ODN concentration of 0.3 ug/ml. The base composition of the ODN appears to be important in determining the immune stimulatory effect. Reducing the T content of an ODN substantially reduces immune stimulatory effect, as exemplified by ODN 2177 (SEQ ID NO. 427) in which 6 of the Ts present in ODN 2137

(SEQ ID NO. 886) have been switched to A's, resulting in a greatly reduced immune stimulatory effect. The importance of T's in the immune stimulatory effect of an ODN is also shown by comparison of ODN 2116 (SEQ ID NO. 357) and 2181 (SEQ ID NO. 431), which differ in the 3' end of the ODN. ODN 2181, in which the 3' end is poly-T is more stimulatory than ODN 2116, in which the 3' end is poly-C, despite the fact that both ODN have a TCGTCG at the 5' end.

Example 4

B Cell Proliferation Induced by TG Oligonucleotides

Figure 2:
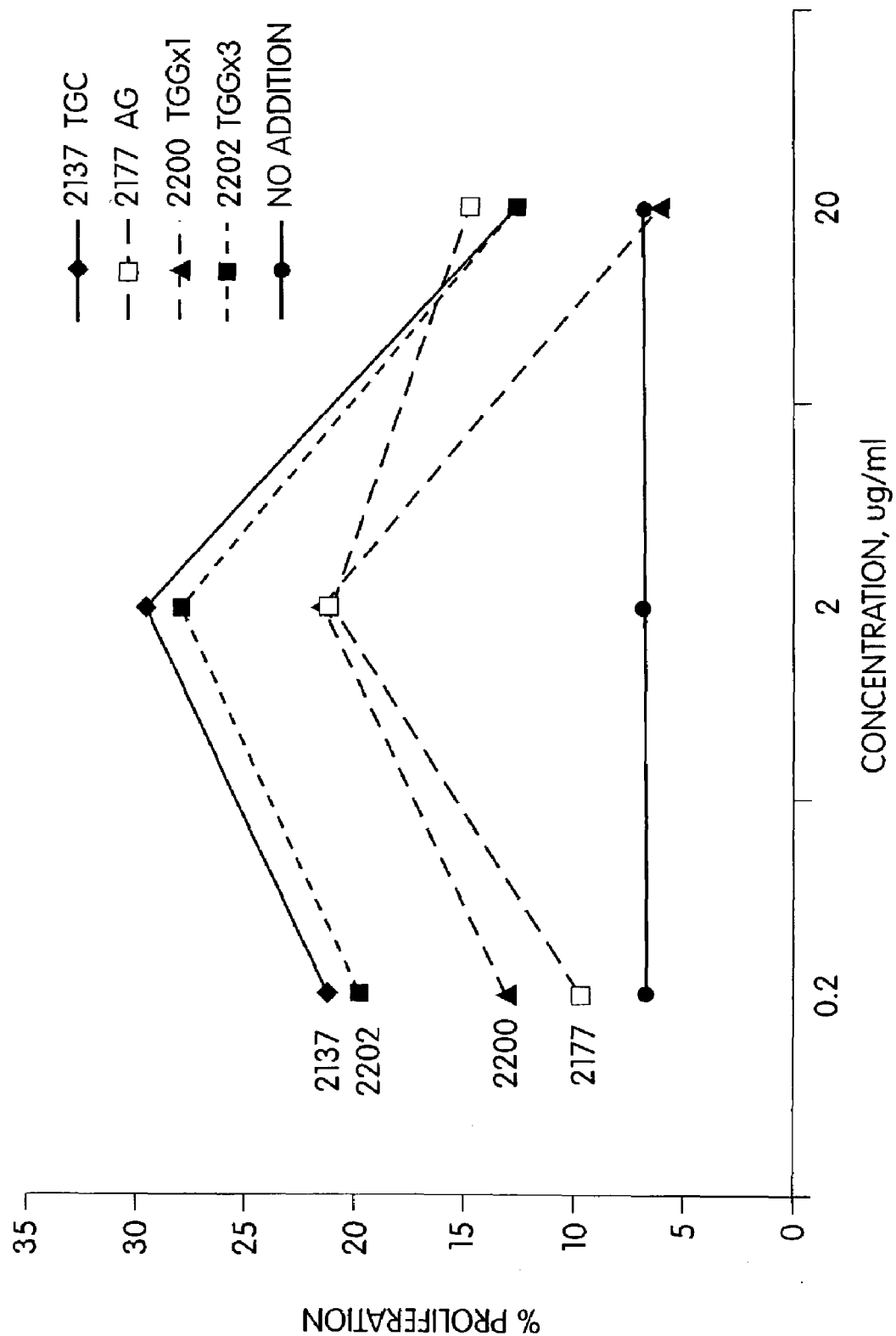
FIG. 2 is a graph comparing the abilities of ODN 2137, ODN 2177, ODN 2200 and ODN 2202 to stimulate B cell proliferation at concentrations ranging from 0.2 µg/ml to 20 µg/ml.

The stimulatory effects of TG motifs are shown in FIG. 2. ODN 2137 has the identical base composition as ODN 2006, but the CG motifs have all been inverted to GC's resulting in a CG-free nucleic acid. ODN does however contain 6 TG dinucleotides. In ODN 2177, all the TG dinucleotides of ODN 2137 have been changed to AG. Although ODN 2177 contains only 6 adenines, it is virtually nonstimulatory at a concentration of 0.2 µg/ml. For comparison, an ODN 24 bases in length in which each position is randomized to be any of the four bases (ODN 2182) induces >12% of B cells to proliferate at a concentration of 0.2 µg/ml. These results indicate that the stimulatory effects of ODN 2137 are not simply those of a phosphorothioate backbone, but relate to the presence of TG dinucleotides.

In order to determine the effect of varying the number of TG dinucleotide motifs, ODN 2200 and ODN 2202 were compared, as shown in FIG. 2. Both ODN contain 18 Ts and 6 Gs, but in ODN 2200 all of the Gs are consecutive, so that there is only one TG dinucleotide, whereas in ODN 2202, the Gs are split up as GG dinucleotides throughout the ODN so that there are three TGs. ODN 2202 is significantly more stimulatory than ODN 2200, consistent with the model that at least three TG motifs in an ODN are required for optimal stimulatory activity. It is likely that even higher levels of stimulation could be achieved if the TG motifs had been optimized as taught herein.

Example 5

Effects of TTG Versus TTG Motifs

Figure 3:
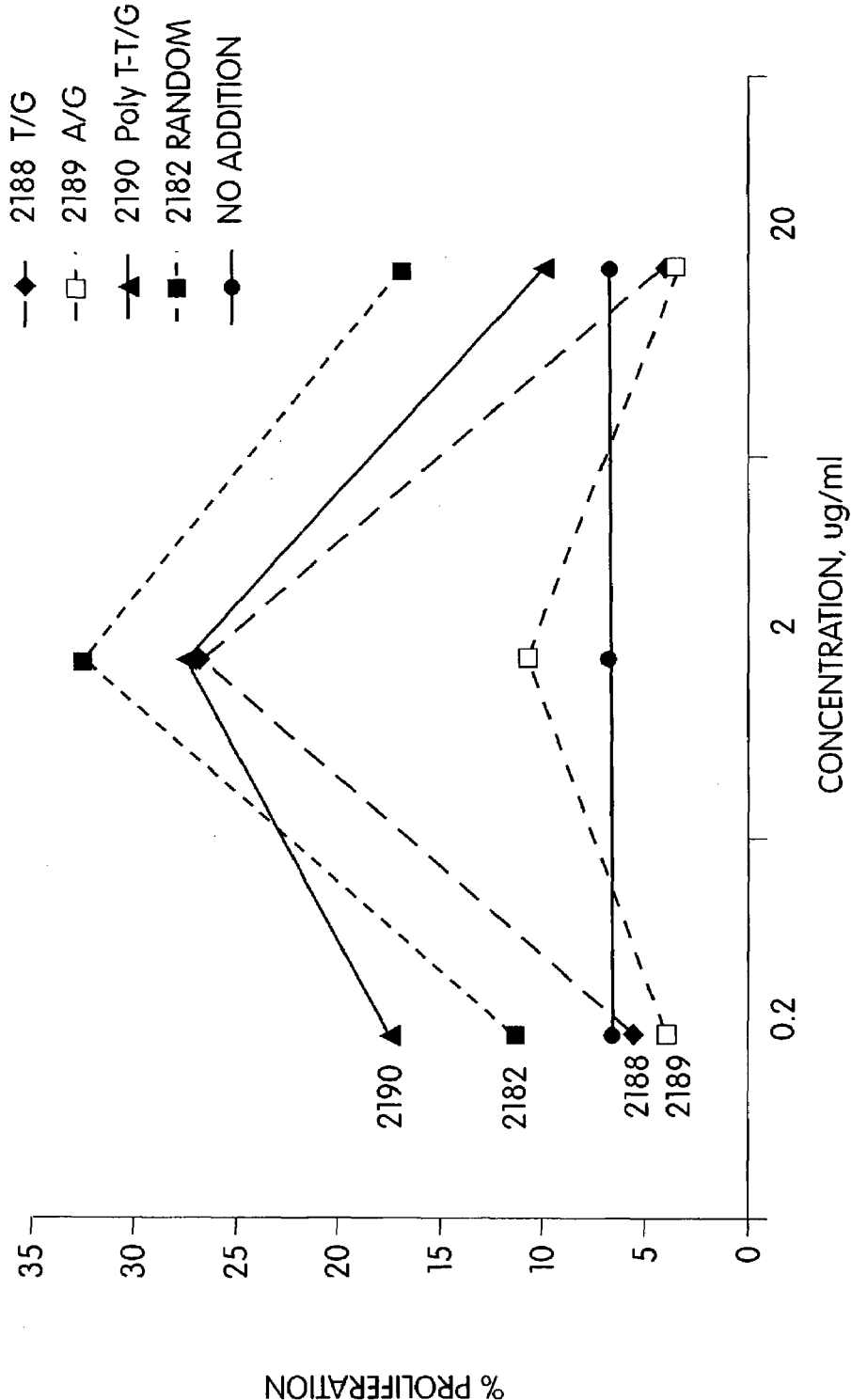
FIG. 3 is a graph comparing the abilities of ODN 2188, ODN 2189, ODN 2190 and ODN 2182 to stimulate B cell proliferation at concentrations ranging from 0.2 µg/ml to 20 µg/ml.

FIG. 3 shows the results of experiments conducted to study TG content in terms of the relative levels of Ts versus Gs as it relates to the stimulatory effect of an ODN. The Figure shows that an ODN in which all of the bases are randomized to be either T or G (ODN 2188 (SEQ ID NO. 905)) is nonstimulatory at a concentration of 0.2 µg/ml, similar to an ODN in which all of the bases are randomized to be either A or G (ODN 2189 (SEQ ID NO. 906)). However, at the higher concentration of 2 µg/ml, the randomized T/G ODN 2188 is significantly more stimulatory. This latter level of stimulation is still lower than that which occurs with a totally randomized ODN (ODN 2182 (SEQ ID NO. 432)). The highest stimulation at low concentrations is seen with an ODN in which half of the bases are fixed at T and the other half of the bases are randomized to be either T or G (ODN 2190 (SEQ ID NO. 907)). Since every other base is fixed to be a T, there cannot be any TG motifs. The data in FIG. 3 show that increasing the TG content of an ODN improves its stimulatory activity.

In yet other experiments, the results of which are not diagrammed herein, ODN 2190 (SEQ ID NO. 907) exhibited a stimulation of NK activity compared to ODN 2188 (SEQ ID NO. 905) or ODN 2189 (SEQ ID NO. 906).

Examples 6-8

Introduction:

Above, we demonstrated that Poly T sequences are able to enhance stimulation of B and NK cells. Here and below we investigate the effect of a variety of non-CpG T-rich ODN as well as Poly C ODN for their ability to stimulate human B cells, NK cells and monocytes.

Materials and Methods:

Oligonucleotides: Phosphorothioate-modified ODN were purchased from ARK Scientific GmbH (Darmstadt, Germany). The sequences used were: 1982: 5'-tccaggacttctct-caggtt-3' (SEQ ID NO.: 225), 2006: 5'-tcgtcgttttgtcgttttgtcgtt-3' (SEQ ID NO.: 246), 2041: 5'-ctggtctttctggttttttctgg-3' (SEQ ID NO.: 282), 2117: 5'-tzgtzgttttgtgtzgttttgtzgtt-3' (SEQ ID NO.: 358), 2137: 5'-tgctgcttttgtgcttttgtgctt-3' (SEQ ID NO.: 886), 2183: 5'-ttttttttttttttttttt-3' (SEQ ID NO.: 433), 2194: 5'-ttttttttttttttttttttttt-3' (SEQ ID NO.: 911), 2196: 5'-tttttttttttttttttt-3' (SEQ ID NO.: 913), 5126: 5'-ggttctttg-gtccttgtct-3' (SEQ ID NO.: 1058), 5162: 5'-ttttttttttttttttttttttttttttttt-3' (SEQ ID NO.: 1094), 5163: 5'-aaaaaaaaaaaaaaaaaaaaaaaaaaaaa-3' (SEQ ID NO.: 1095), 5168: 5'-ccccccccccccccccccccccccccccc-3' (SEQ ID NO.: 1096) and 5169: 5'-cgcgcgcgcgcgcgcgcgcgcgcgcgcgcg-3' (SEQ ID NO.: 1097). Most ODN were tested for LPS content using the LAL assay (BioWhittaker, Belgium) (lower detection limit 0.1 EU/ml) also described herein. For all assays ODN were diluted in TE buffer and stored at −20° C. All dilutions were conducted using pyrogen-free reagents.

Cell preparation and cell culture: Human PBMC were isolated from peripheral blood of healthy volunteers, obtained by the German Red Cross (Ratingen, Germany), as described above in Example 1, but all material were purchased from Life Technologies, Germany and were endotoxin-tested. For the B cell, NK cell and monocyte activation assays PBMC were cultured in complete medium at a concentration of $2 \times 10^6$ cells/ml in 200 µl in 96 round bottom plates in a humidified incubator at 37° C. Different ODNs, LPS (Sigma) or IL-2 (R&D Systems, USA) were used as stimuli. At the indicated time points, cells were harvested for flow cytometry.

Flow cytometry: MAbs used for staining of surface antigens were: CD3, CD14, CD19, CD56, CD69, CD80 and CD86 (all obtained from Pharmingen/Becton Dickinson, Germany). For monocytes Fc receptors were blocked using human IgG (Myltenyi, Germany) as previously described (Bauer, M., K. Heeg, H. Wagner, and G. B. Lipford. 1999. DNA activates human immune cells through a CpG sequence dependent manner. *Immunology* 97:699). Flow cytometric data of at least 1000 cells of a specified subpopulation (B cells, monocytes, NK cells, NKT cells or T cells) were acquired on a FACSCalibur (Becton Dickinson). Data were analyzed using the program CellQuest (Becton Dickinson).

NK-mediated cytotoxicity: PBMC were cultured overnight with or without 6 µg/ml ODN or 100U/ml IL-2 at 37° C., 5% $CO_2$. The next morning, K-562 target cells were labeled with a fluorescent dye, CFSE, as described previously for human B cells (Hartmann, G., and A. M. Krieg. 2000. Mechanism and function of a newly identified CpG DNA motif in human primary B cells. *J. Immunol.* 164:944). PBMC were added in different ratios (50:1, 25:1 and 12.5:1) to $2 \times 10^5$ target cells and incubated for 4 h at 37° C. Cells were harvested and incubated with the DNA-specific dye 7-AAD (Pharmingen) for detection of apoptotic cells. Results were measured by flow cytometry.

ELISA: PBMC ($3\times10^6$ cells/ml) were cultured with the specified concentrations of ODN or LPS for 24 h (IL-6, IFNγ and TNFα) or 8 h (IL-1β) in 48 well plates in a humidified atmosphere at 37° C. Supernatants were collected and cytokines were measured using OPTeia ELISA Kits (Pharmingen) for IL-6, IFNγ and TNFα or an Eli-pair ELISA assay (Hoelzel, Germany) for IL-1β according to the manufacturer protocols.

Example 6

B Cell Activation Induced by ODNs Lacking CpG Motifs

In the Experiments described above in Example 3, we demonstrate that T-rich ODN were capable of activating B cells. We expand those studies here using additional ODN and different cell and reagent sources. In a first set of experiments, we compared the activation potential of different non-CpG T-rich ODNs with the very potent known CpG ODN 2006 (SEQ ID NO.: 246). PBMC ($2\times10^6$ cells/ml) of a blood donor (n=2) were incubated with the indicated concentrations of ODNs 2006 (SEQ ID NO.: 246), 2117 (SEQ ID NO.: 358), 2137 (SEQ ID NO.: 886), 5126 (SEQ ID NO.: 1058), and 5162 (SEQ ID NO.: 1094). Cells were incubated for 48 h at 37° C. as described above and stained with mAb for CD19 (B cell marker) and CD86 (B cell activation marker, B7-2). Expression was measured by flow cytometry.

Figure 4:
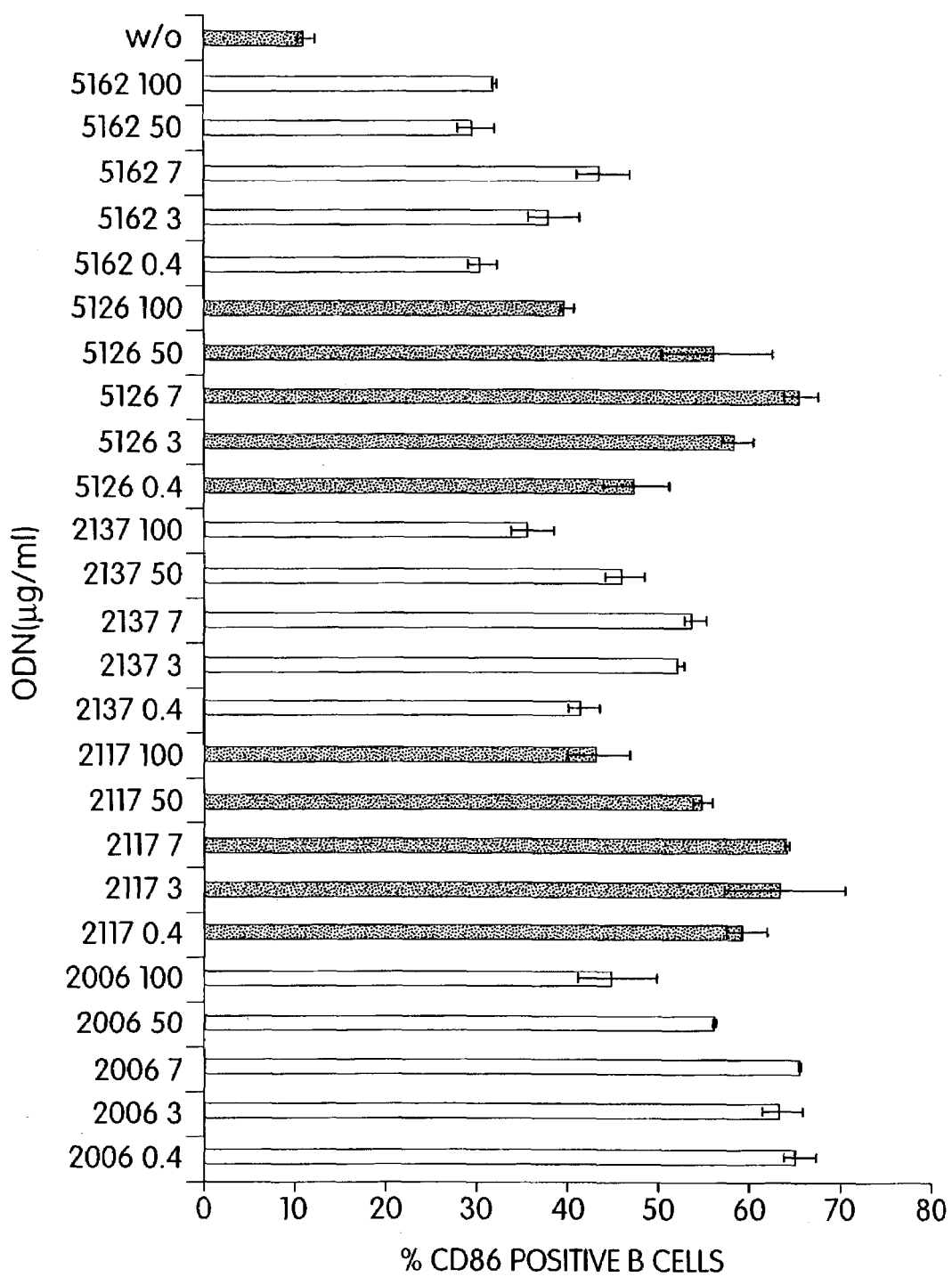
FIG. 4 is a bar graph depicting dose-dependent B cell activation induced by non-CpG ODN. PBMC of a blood donor were incubated with the indicated concentrations of ODNs 2006 (SEQ ID NO.: 246), 2117 (SEQ ID NO.: 358), 2137 (SEQ ID NO.: 886), 5126 (SEQ ID NO.: 1058) and 5162 (SEQ ID NO.: 1094) and stained with mAb for CD 19 (B cell marker) and CD86 (B cell activation marker, B7-2). Expression was measured by flow cytometry.

Using different concentrations of ODNs, we showed (FIG. 4) that T-rich ODNs without a CpG motif, can induce stimulation of human B cells. ODN 5126 (SEQ ID NO.: 1058) which contains only a single poly-T sequence but is greater than 50% T, caused high levels of human B cell activation. Although there are some similarities to SEQ ID NO.: 246 (e.g. more than 80% T/G content), this ODN clearly lacks any known immunostimulatory CpG motif. Surprisingly, for all tested T-rich ODNs, the highest stimulatory index was obtained at concentrations between 3 and 10 μg/ml. The highest stimulatory index of the tested ODNs was achieved by CpG/T-rich ODN SEQ ID NO.: 246 at 0.4 μg/ml. Interestingly, the activity decreased at high concentrations.

Poly A, Poly C and Poly T sequences were synthesized and tested for biological activity. PBMC ($2\times10^6$ cells/ml) of one representative donor (n=3) were stimulated as described above by 0.4 μg/ml, 1.0 g/ml or 10.0 g/ml of the following ODNs: 2006 (SEQ ID NO.: 246), 2196 (SEQ ID NO.: 913) (Poly T, 18 bases), 2194 (SEQ ID NO.: 911) (Poly T, 27 bases), 5162 (SEQ ID NO.: 1094) (Poly T, 30 bases), 5163 (SEQ ID NO.: 1095) (Poly A, 30 bases), 5168 (SEQ ID NO.: 1096) (Poly C, 30 bases) and 5169 (SEQ ID NO.: 1097) (Poly CG, 30 bases). Expression of the activation marker CD86 (B7-2) on CD19-positive B cells was measured by flow cytometry.

Figure 5:
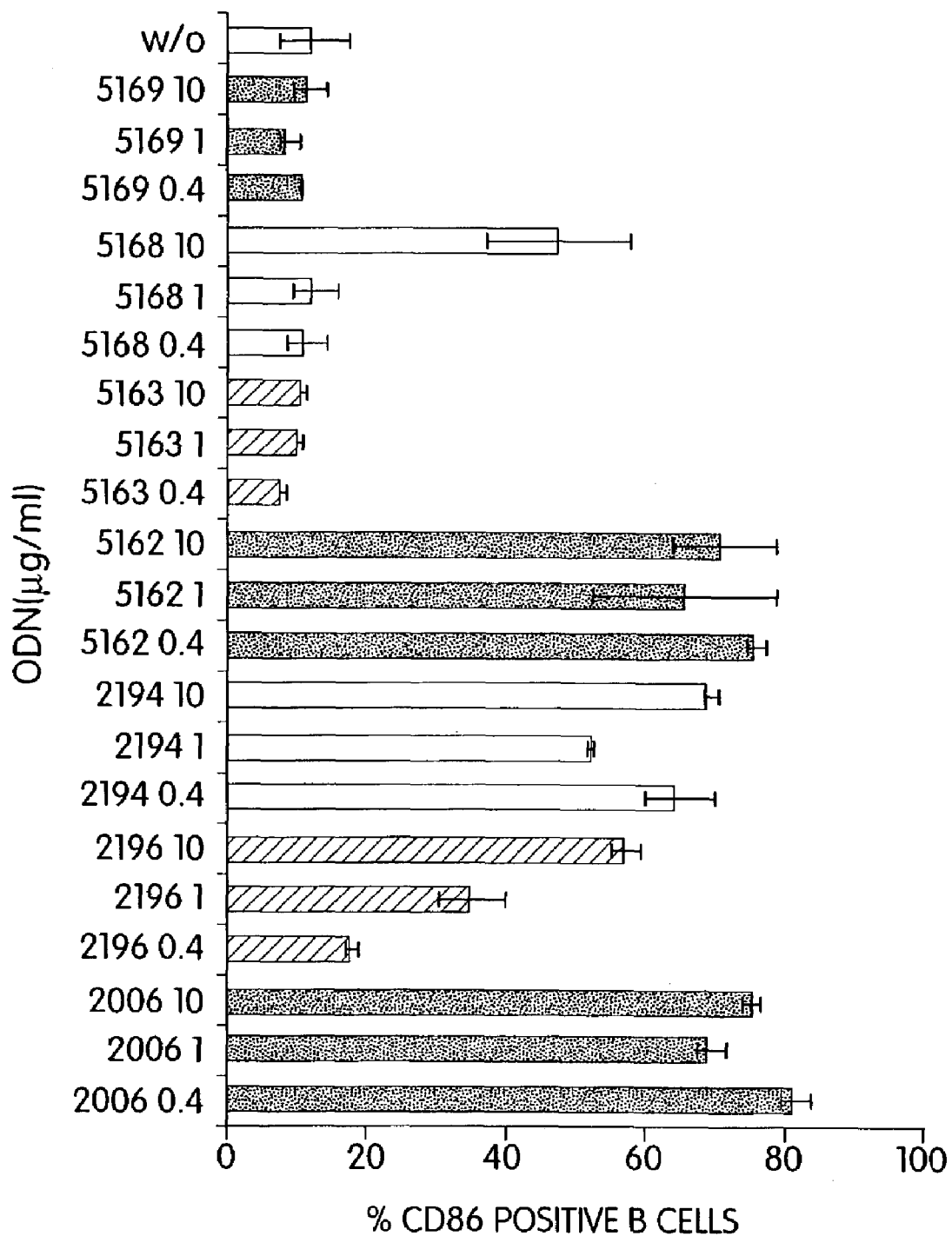
FIG. 5 is a bar graph depicting stimulation of B cells by a diverse set of non-CpG ODNs. PBMC of one representative donor were stimulated by 0.4 µg/ml, 1.0 µg/ml or 10.0 µg/ml of the following ODNs: 2006 (SEQ ID NO.: 246), 2196 (SEQ ID NO.: 913), 2194 (SEQ ID NO.: 911), 5162 (SEQ ID NO.: 1094), 5163 (SEQ ID NO.: 1095), 5168 (SEQ ID NO.: 1096) and 5169 (SEQ ID NO.: 1097) and expression of the activation marker CD86 (B7-2) on CD19-positive B cells was measured by flow cytometry.

FIG. 5 demonstrates that the length of the sequence, at least for Poly T ODNs, has an important impact on its activity. A Poly T sequence containing only 18 bases (SEQ ID NO.: 913) was shown to be less stimulatory than one with 27 bases (SEQ ID NO.: 911) or one with 30 bases (SEQ ID NO.: 1094) with a clear rank of stimulation: SEQ ID NO.: 1094>SEQ ID NO.: 911>SEQ ID NO.: 913. Poly A (SEQ ID NO.: 1095) or Poly CG (SEQ ID NO.: 1097) sequences, in contrast, do not induce activation of human B cells. Surprisingly it was also discovered that Poly C sequences (SEQ ID NO.: 1096) can activate human B cells at least at high concentrations (10 μg/ml) (FIG. 5).

Two other T-rich ODNs, namely 1982 (SEQ ID NO.: 225) and 2041 (SEQ ID NO.: 282) lacking CpG motifs were tested for their effect on human B cells. PBMC (n=2) were incubated with the indicated concentrations of ODN 2006 (SEQ ID NO.: 246), 1982 (SEQ ID NO.: 225) and 2041 (SEQ ID NO.: 282) as described above. B cell activation (expression of the activation marker CD86) was measured by flow cytometry.

FIG. 6 demonstrates that T-rich non-CpG ODN are immunostimulatory at concentrations higher than 1 μg/ml. Incorporation of a CpG motif into 1982 enhanced the immunostimulatory activity. Elongation with a Poly T sequence did not enhance the immunostimulatory activity of this already T-rich ODN but rather, decreased the activation potential slightly.

Example 7

Immunostimulation of Non-CpG ODNs is Reflected in the Enhancement of NK Activation, NK Cytotoxicity and Monocyte Activation NK cells as well as monocytes were tested for their response to non-CpG ODNs. PBMC ($2\times10^6$ cells/ml) were incubated with 6 μg/ml of the following ODNs (n=4): 2006 (SEQ ID NO.: 246), 2117 (SEQ ID NO.: 358), 2137 (SEQ ID NO.: 886), 2183 (SEQ ID NO.: 433), 2194 (SEQ ID NO.: 911) and 5126 (SEQ ID NO.: 1058). After 24 h of cultivation at 37° C. cells were harvested and stained with mAb for CD3 (T cell marker), CD56 (NK cell marker) and CD69 (early activation marker) as described above. Expression of CD69 on CD56-positive NK cells was measured by flow cytometry.

Figure 7:
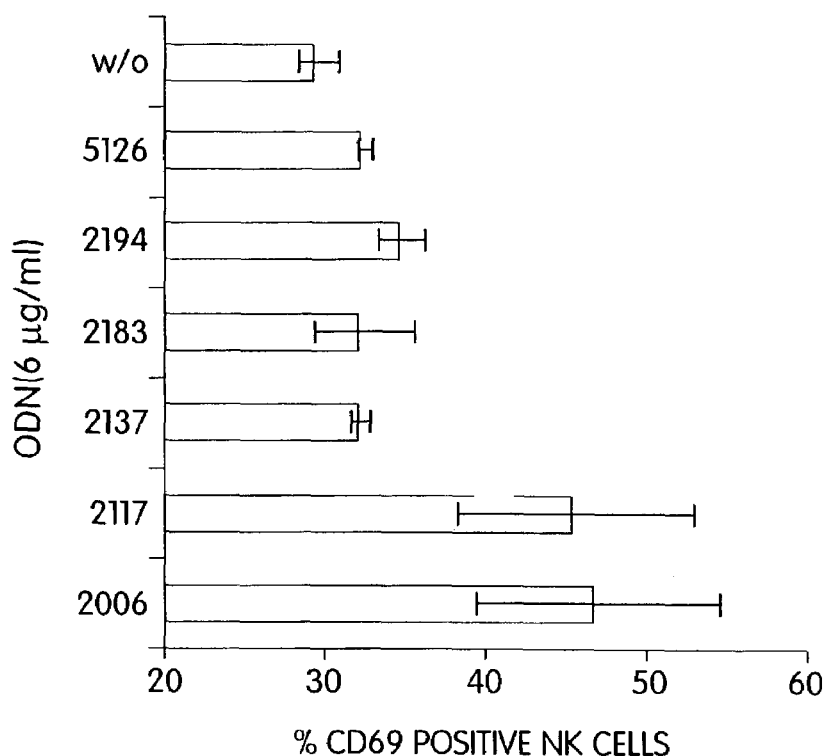
FIG. 7 is a bar graph depicting NK cells are activated by non-CpG ODNs. PBMC were incubated with 6 µg/ml of the following ODNs: 2006 (SEQ ID NO.: 246), 2117 (SEQ ID NO.: 358), 2137 (SEQ ID NO.: 886), 2183 (SEQ ID NO.: 433), 2194 (SEQ ID NO.: 911) and 5126 (SEQ ID NO.: 1058) and stained with mAb for CD3 (T cell marker), CD56 (NK cell marker) and CD69 (early activation marker). Expression of CD69 on CD56-positive NK cells was measured by flow cytometry.

FIG. 7 shows that for Poly T ODNs similar effects can be observed as described in FIG. 5. The stimulation of NK cells, like B cells, may be influenced by the length of the ODN. ODN 2183 (SEQ ID NO.: 433) (21 bases) induced activation of NK cells but to a lesser extent than the longer ODN 2194 (SEQ ID NO.: 911) (27 bases), as measured by enhanced expression of the early activation marker CD69. ODN 5126 (SEQ ID NO.: 1058) was also demonstrated to activate human NK cells (FIG. 7).

Figure 8:
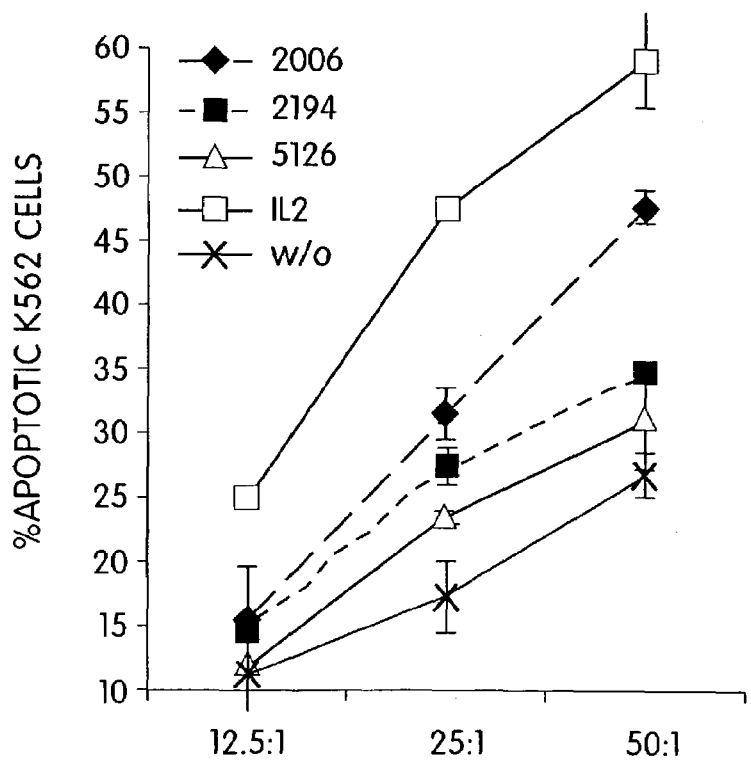
FIG. 8 is a bar graph depicting NK-mediated cytotoxicity is enhanced by non-CpG ODN. NK-mediated lysis of K-562 target cells was measured after over night incubation of PBMC with 6 µg/ml of the ODN 2006 (SEQ ID NO.: 246), 2194 (SEQ ID NO.: 911) and 5126 (SEQ ID NO.: 1058).

It is believed that the anti-tumor activity of CpG ODNs can be assessed by the ability of the ODN to enhance NK-mediated cytotoxicity in vitro. ODNs containing at the 5' and 3' ends stretches of Poly G were shown to result in the highest induction of cytotoxicity (Ballas, Z. K., W. L. Rasmussen, and A. M. Krieg. 1996. Induction of natural killer cell activity in murine and human cells by CpG motifs in oligodeoxynucleotides and bacterial DNA. *J. Immunol.* 157:1840). To investigate the influence of non-CpG T-rich ODN on NK cytotoxicity, we analyzed the effect of the ODNs 2194 (SEQ ID NO.: 911) and 5126 (SEQ ID NO.: 1058) on NK-mediated lysis (FIG. 8). NK-mediated lysis of K-562 target cells was measured after over night incubation of PBMC with 6 μg/ml of the ODN 2006 (SEQ ID NO.: 246), SEQ ID NO.: 911 (SEQ ID NO.: 911) (Poly T, 27 bases) and 5126 (SEQ ID NO.: 1058) as described above. SEQ ID NO.: 1058 demonstrated small increases in lysis by human NK cells as compared to no ODN. SEQ ID NO.: 911 and SEQ ID NO.: 246 enhanced human NK cell cytotoxicity to an even higher extent.

Previous reports demonstrated that not only NK cells but also NKT cells are mediators of cytotoxic responses to tumor cells (14). We, therefore, looked at the potential activation of human NKT cells by T-rich non-CpG ODN. PBMC of one representative donor (n=2) were incubated with 6 μg/ml ODN 2006 (SEQ ID NO.: 246), 2117 (SEQ ID NO.: 358), 2137 (SEQ ID NO.: 886), 2183 (SEQ ID NO.: 433), 2194 (SEQ ID NO.: 913) and 5126 (SEQ ID NO.: 1058) for 24 h as described above. Activation of NKT cells was measured by flow cytometry after staining of cells with mAb for CD3 (T cell marker), CD56 (NK cell marker) and CD69 (early activation marker). Shown is the expression of CD69 on CD3 and CD56 double-positive cells (NKT cells).

Figure 9:
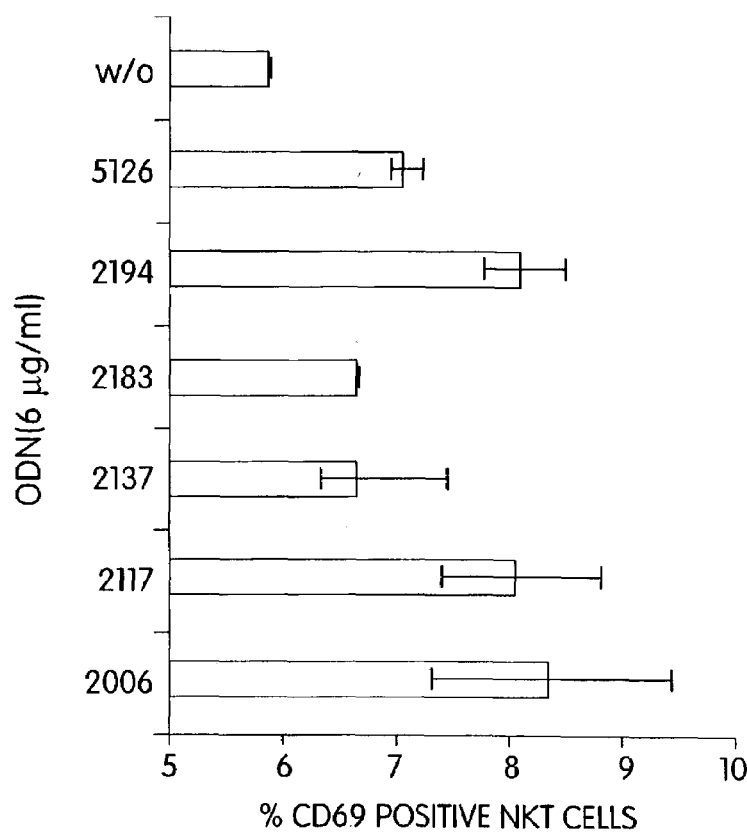
FIG. 9 is a bar graph depicting NKT cells can be activated by non-CpG ODN. PBMC of one representative donor were incubated with 6 µg/ml ODN 2006 (SEQ ID NO.: 246), 2117 (SEQ ID NO.: 358), 2137 (SEQ ID NO.: 886), 2183 (SEQ ID NO.: 433), 2194 (SEQ ID NO.: 911) and 5126 (SEQ ID NO.: 1058) for 24 h and activation of NKT cells was measured by flow cytometry after staining of cells with mAb for CD3 (T cell marker), CD56 (NK cell marker) and CD69 (early activation marker).

In FIG. 9, SEQ ID NO.: 911 as well as SEQ ID NO.: 1058 were found to stimulate NKT cells. Similar to NK cells SEQ ID NO.: 911 (Poly T) was more active than SEQ ID NO. 1058. In addition, as described above for B cells and NK cells, the length of the ODN has some influence on the immunostimulatory potential, with the longer ODN having stronger effects on NKT cells. Similar results were observed for human T cells.

Figure 10:
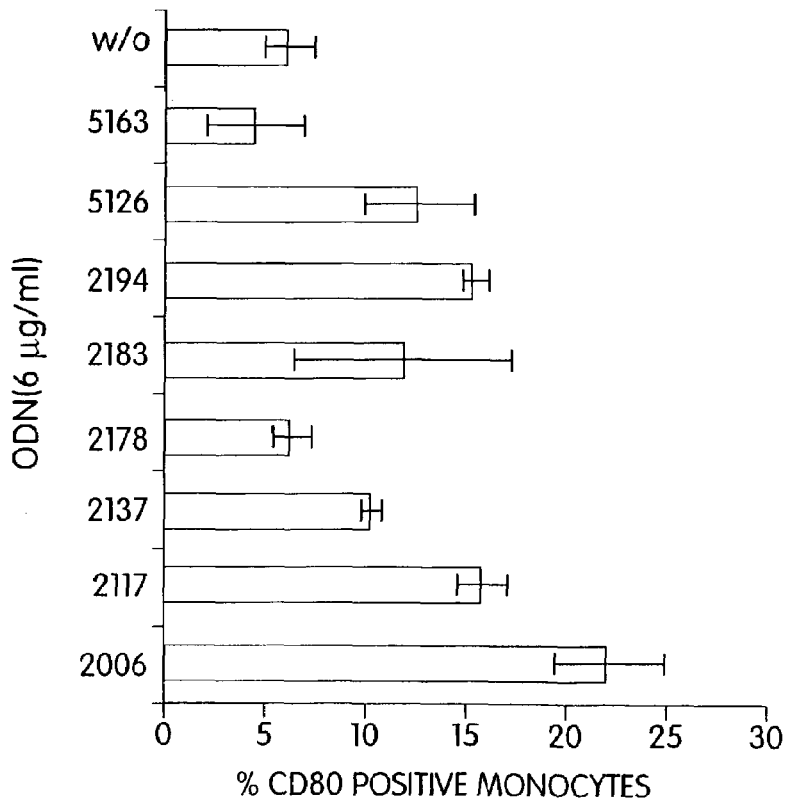
FIG. 10 is a bar graph depicting stimulation of monocytes by different CpG and non-CpG ODN. PBMC were incubated with 6 µg/ml 2006 (SEQ ID NO.: 246), 2117 (SEQ ID NO.: 358), 2137 (SEQ ID NO.: 886), 2178 (SEQ ID NO.: 428), 2183 (SEQ ID NO.: 433), 2194 (SEQ ID NO.: 911), 5126 (SEQ ID NO.: 1058) and 5163 (SEQ ID NO.: 1095) and stained for CD14 (monocyte marker) and CD80 (B7-1, activation marker). Expression was measured by flow cytometry.

Another type of cell of the immune system involved in fighting infections is the monocytes. These cells release upon activation a variety of cytokines and can mature into dendritic cells (DC), professional antigen-presenting cells (Roitt, I., J. Brostoff, and D. Male. 1998. *Immunology*. Mosby, London). FIG. 10 shows activation of human monocytes after culturing of PBMC with different ODNs. PBMC ($2\times10^6$ cells/ml) were incubated with 6 μg/ml 2006 (SEQ ID NO.: 246), 2117 (SEQ ID NO.: 358), 2137 (SEQ ID NO.: 886), 2178 (SEQ ID NO.:1096), 2183 (SEQ ID NO.: 433), 2194 (SEQ ID NO.: 911), 5126 (SEQ ID NO.: 1058) and 5163 (SEQ ID NO.: 1095) overnight at 37° C. as described above (n=3). Cells were harvested and stained for CD14 (monocyte marker) and CD80 (B7-1, activation marker). Expression was measured by flow cytometry.

As demonstrated above for NK and B cells, T-rich sequences (e.g., SEQ ID NO.: 433, SEQ ID NO.: 911) of different length induce monocyte stimulation but have different levels of activity e.g., SEQ ID NO.: 433>SEQ ID NO.: 911. Poly A (SEQ ID NO.: 1095) as well as Poly C (SEQ ID NO.: 1096 (2178) sequences, in contrast, did not lead to activation of monocytes (measured by the upregulation of CD80 at a concentration of 6 μg/ml ODN).

Example 8

Induction of Cytokine Release by Non-CpG ODNs

Next the ability of different T-rich ODNs to influence the cytokine milieu was examined. PBMC ($3\times10^6$ cells/ml) were cultured for 24 h with or without 6 μg/ml of the indicated ODNs or 1 μg/ml LPS as positive control (n=2). After incubation supernatants were collected and TNFα measured by ELISA as described above and the results are shown in FIG. 11. PBMC were cultured with the indicated ODNs (1.0 μg/ml) as described in FIG. 11 and IL-6 was measured in the supernatants by ELISA and the results are shown in FIG. 12.

Figure 11:
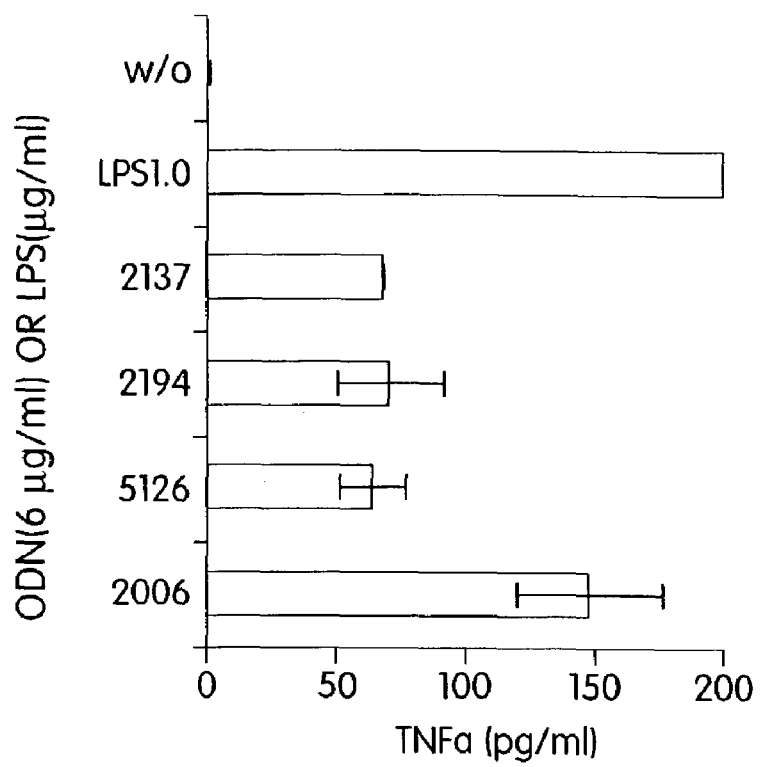
FIG. 11 is a bar graph depicting release of TNFα upon culture of human cells with non-CpG ODN. PBMC were cultured for 24 h with or without 6 µg/ml of the indicated ODNs or 1 µg/ml LPS as positive control and TNFα measured by ELISA.
Figure 12:
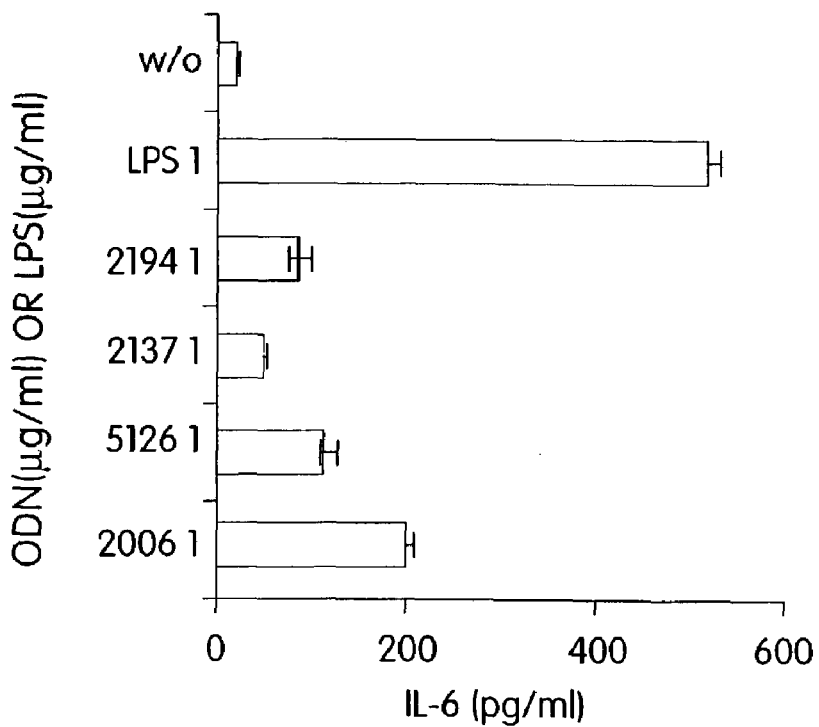
FIG. 12 is a bar graph depicting release of IL-6 after culture with non-CpG ODNs shows the same pattern as for TNFα. PBMC were cultured with the indicated ODNs (1.0 µg/ml) and IL-6 was measured in the supernatants by ELISA.

FIGS. 11 and 12 demonstrate that T-rich non-CpG and T-rich/CpG ODNs can induce the secretion of the pro-inflammatory cytokines TNFα and IL-6. For both cytokines, ODN 5126 (SEQ ID NO.: 1058) was found in most assays to be as potent as ODN 2194 (SEQ ID NO.: 911). It is known that CpG ODNs influence the Th1/Th2 balance by preferentially inducing Th1 cytokines (Krieg, A. M. 1999. Mechanism and applications of immune stimulatory CpG oligodeoxynucleotides. Biochemica et Biophysica Acta 93321:1). To test whether T-rich ODN caused a similar shift to Th1 cytokines, IFNγ production in PBMC was measured. In a first set of experiments, it was demonstrated that, as described for IL-6 and TNFα, ODNs SEQ ID NO.: 1058 and SEQ ID NO.: 911 induced the release of comparable amounts of this Th1 cytokine IFNγ. In addition, it was demonstrated that another pro-inflammatory cytokine, IL-1β, was released upon culture of PBMC with these two ODNs. Although the amount of these cytokines induced by the T-rich ODN lacking CpG motifs was less than when CpG ODN SEQ ID NO.: 246 was used the amounts induced by T-rich ODN were significantly higher than the control.

Examples 9-11

Introduction:

An optimal CpG motif for immune system activation in non-rodent vertebrates is described herein. A phosphodiester oligonucleotide containing this motif was found to strongly stimulate CD86, CD40, CD54 and MHC II expression, IL-6 synthesis and proliferation of primary human B-cells. These effects required internalisation of the oligonucleotide and endosomal maturation. This CpG motif was associated with the sustained induction of the NFκB p50/p65 heterodimer and of the transcription factor complex activating protein-1 (AP-1). Transcription factor activation by CpG DNA was preceded by increased phosphorylation of the stress kinases c-jun $NH_2$ terminal kinase (JNK) and p38, and of activating transcription factor-2 (ATF-2). In contrast to CpG, signaling through the B-cell receptor led to activation of extracellular receptor kinase (ERK) and to phosphorylation of a different isoform of JNK.

Materials and Methods:

Oligodeoxynucleotides: Unmodified (phosphodiester, PE) and modified nuclease-resistant (phosphorothioate, PS) ODN were purchased from Operon Technologies (Alameda, Calif.) and Hybridon Specialty Products (Milford, Mass.). The sequences used are provided in Table H. *E. coli* DNA and calf thymus DNA were purchased from Sigma Chemical Co., St. Louis, Mo. Genomic DNA samples were purified by extraction with phenol-chloroform-isoamyl alcohol (25/24/1) and ethanol precipitation. DNA was purified from endotoxin by repeated extraction with triton x-114 (Sigma Chemical Co., St. Louis, Mo.) and tested for endotoxin using the LAL-assay (LAL-assay BioWhittaker, Walkersville, Md.; lower detection limit 0.1 EU/ml) and the high sensitivity assay for endotoxin described earlier (lower detection limit 0.0014 EU/ml) (Hartmann G., and Krieg A. M. 1999. CpG DNA and LPS induce distinct patterns of activation in human monocytes. *Gene Therapy* 6:893). Endotoxin content of DNA samples was below 0.0014 U/ml. *E. coli* and calf thymus DNA were made single stranded before use by boiling for 10 minutes, followed by cooling on ice for 5 minutes. DNA samples were diluted in TE-buffer using pyrogen-free reagents.

TABLE H

Oligonucleotide panel used[1]

| | Name (SEQ ID NO) | Sequence 5' to 3' |
|---|---|---|
| Starting sequence | PE 2079 (320) | T<u>CG</u> A<u>CG</u> TTC CCC CCC CCC CC |
| Middle base | PE 2100 (341) | TCG GCG TTC CCC CCC CCC CC |
| | PE 2082 (323) | TCG CCG TTC CCC CCC CCC CC |
| Human CpG motif | PE 2080 (321) | TCG TCG TTC CCC CCC CCC CC |
| 5' flanking base | PE 2105 (346) | GCG TCG TTC CCC CCC CCC CC |
| | PE 2107 (348) | ACG TCG TTC CCC CCC CCC CC |
| | PE 2104 (345) | CCG TCG TTC CCC CCC CCC CC |
| 3' flanking base | PE 2098 (339) | TCG TCG CTC CCC CCC CCC CC |
| | PE 2099 (340) | TCG TCG GTC CCC CCC CCC CC |
| | PE 2083 (324) | TCG TCG ATC CCC CCC CCC CC |
| First CpG deleted | PE 2108 (349) | CTG T<u>CG</u> TTC CCC CCC CCC CC |
| Second CpG deleted | PE 2106 (347) | T<u>CG</u> TCA TTC CCC CCC CCC CC |
| Methylation | PE 2095 (336) | TZG TZG TTC CCC CCC CCC CC |
| | PE 2094 (335) | TCG TCG TTC CCC CCC ZCC CC |
| Non-CpG control of 2080 | PE 2078 (319) | TGC TGC TTC CCC CCC CCC CC |
| | PE 2101 (342) | GGC CTT TTC CCC CCC CCC CC |
| PS form of 2080 | PS 2116 (357) | T<u>CG</u> T<u>CG</u> TTC CCC CCC CCC CC |
| Additional CpG motifs | PE 2059 (300) | T<u>CG</u> T<u>CG</u> TTT TGT <u>CG</u>T TTT GT<u>C G</u>TT |
| Best Ps | PS 2006 (246) | T<u>CG</u> T<u>CG</u> TTT TGT <u>CG</u>T TTT GT<u>C G</u>TT |
| Methylated 2006 | PS 2117 (358) | TZG TZG TTT TGT ZGT TTT GTZ GTT |

[1]PE, phosphodiester; PS, phosphorothioate; bold, base exchange; bold Z, methylated cytidine; underlined, CpG dinucleotides.

Cell preparation and cell culture: Human peripheral blood mononuclear cells (PBMC) were isolated from peripheral blood of healthy volunteers by Ficoll-Paque density gradient centrifugation (Histopaque-1077, Sigma Chemical Co., St. Louis, Mo.) as described (Hartmann G., Krug A., Eigler A., Moeller J., Murphy J., Albrecht R., and Endres S. 1996. Specific suppression of human tumor necrosis factor-alpha synthesis by antisense oligodeoxynucleotides. *Antisense Nucleic Acid Drug Dev* 6:291)). Cells were suspended in RPMI 1640 culture medium supplemented with 10% (v/v) heat-inactivated (56° C., 1 h) FCS (HyClone, Logan, Utah), 1.5 mM L-glutamine, 100 U/ml penicillin and 100 µg/ml streptomycin (all from Gibco BRL, Grand Island, N.Y.) (complete medium). All compounds were purchased endotoxin-tested. Viability was determined before and after incubation with ODN by trypan blue exclusion (conventional microscopy) or by propidium iodide exclusion (flow cytometric analysis). In all experiments, 96% to 99% of PBMC were viable. Cells (final concentration 1×10⁶ cells/ml) were cultured in complete medium in a 5% $CO_2$ humidified incubator at 37° C. Different oligonucleotides (see table I, concentration as indicated in the figure legends), LPS (from salmonella typhimurium, Sigma Chemical Co., St. Louis, Mo.) or anti-IgM were used as stimuli. Chloroquine (5 µg/ml; Sigma Chemical Co., St. Louis, Mo.) was used to block endosomal maturation/acidification. At the indicated time points, cells were harvested for flow cytometry as described below.

For signal transduction studies, human primary B-cells were isolated by immunomagnetic cell sorting using the VARIOMACS technique (Miltenyi Biotec Inc., Auburn, Calif.) as described by the manufacturer. In brief, PBMC obtained from buffy coats of healthy blood donors (Elmer L. DeGowin Blood Center, University of Iowa) were incubated with a microbeads-conjugated antibody to CD19 and passed over a positive selection column. Purity of B-cells was higher than 95%. After stimulation, whole cellular extracts (Western blot) and nuclear extracts (EMSA) for signal transduction studies were prepared.

For CpG binding protein studies, Ramos cells (human Burkitt lymphoma B cell line, ATCC CRL-1923 or CRL-1596; Intervirology 5: 319-334, 1975) were grown in complete medium. Untreated cells were harvested and cytosolic protein extracts were prepared and analyzed for the presence of CpG oligonucleotide binding proteins by EMSA and UV-crosslink as described below.

Flow cytometry: Staining of surface antigens was performed as previously described (Hartmann G., Krug A., Bidlingmaier M., Hacker U., Eigler A., Albrecht R., Strasburger C. J., and Endres S. 1998. Spontaneous and cationic lipid-mediated uptake of antisense oligonucleotides in human monocytes and lymphocytes. *J Pharmacol Exp Ther* 285:920). Monoclonal antibodies to HLA-DR were purchased from Immunotech, Marseille, France. All other antibodies were purchased from Pharmingen, San Diego, Calif.: mABs to CD19 (B43), CD40 (5C3), CD54 (HA58), CD86 (2331 (FUN-1)). IgG$_1$,κ (MOPC-21) and IgG$_{2b}$,κ were used to control for specific staining. Intracellular cytokine staining for IL-6 was performed as described (Hartmann G., and Krieg A. M. 1999. CpG DNA and LPS induce distinct patterns of activation in human monocytes. *Gene Therapy* 6:893). In brief, PBMC (final concentration 1×10$^6$ cells/ml) were incubated in the presence of brefeldin A (final concentration 1 µg/ml, Sigma Chemical Co., St. Louis, Mo.). After incubation, cells were harvested and stained using a FITC-labeled mAB to CD19 (B43), a PE-labeled rat anti-human IL-6 mAb (MQ2-6A3, Pharmingen) and the Fix and Perm Kit (Caltag Laboratories, Burlingame, Calif.). Flow cytometric data of 5000 cells per sample were acquired on a FACScan (Beckton Dickinson Immunocytometry Systems, San Jose, Calif.). Non-viable cells were excluded from analysis by propidium iodide staining (2 µg/ml). Data were analyzed using the computer program FlowJo (version 2.5.1, Tree Star, Inc., Stanford, Calif.).

Proliferation assay: CFSE (5-(and-6-) carboxyfluorescein diacetate succinimidyl ester, Molecular Probes, USA) is a fluorescein-derived intracellular fluorescent label which is divided equally between daughter cells upon cell division. Staining of cells with CFSE allows both quantification and immunophenotyping (phycoerythrin-labeled antibodies) of proliferating cells in a mixed cell suspension. Briefly, PBMC were washed twice in PBS, resuspended in PBS containing CFSE at a final concentration of 5 µM, and incubated at 37° C. for 10 minutes. Cells were washed three times with PBS and incubated for five days as indicated in the figure legends. Proliferating CD19-positive B-cells were identified by decreased CFSE content using flow cytometry.

Preparation of whole cell, nuclear and cytosolic protein extracts: For Western blot analysis, whole cell extracts were prepared. Primary B-cells were treated with medium, the phosphodiester oligonucleotides 2080 (SEQ ID NO.: 321) or 2078 (SEQ ID NO.: 319) at 30 µg/ml, or anti-IgM (10 µg/ml). Cells were harvested, washed twice with ice-cold PBS containing 1 mM Na$_3$VO$_4$, resuspended in lysis buffer (150 mM NaCl, 10 mM TRIS pH 7.4, 1% NP40, 1 mM Na$_3$VO$_4$, 50 mM NaF, 30 mg/ml leupeptin, 50 mg/ml aprotinin, 5 mg/ml antipain, 5 mg/ml pepstatin, 50 µg/ml phenylmethylsulfonylfluoride (PMSF)), incubated for 15 min on ice and spun at 14000 rpm for 10 min. The supernatant was frozen at −80 C. For the preparation of nuclear extracts, primary B-cells were resuspended in hypotonic buffer (10 mM HEPES/KOH (pH 7.9), 10 mM KCl, 0.05% NP40, 1.5 mM MgCl$_2$, 0.5 mM dithiothreitol (DTT), 0.5 mM PMSF, 30 mg/ml leupeptin, 50 mg/ml aprotinin, 5 mg/ml antipain, 5 mg/ml pepstatin). After 15 minutes incubation on ice, the suspension was centrifuged at 1000×g for 5 minutes. The pelleted nuclei were resuspended in extraction buffer (20 mM HEPES (pH 7.9), 450 mM NaCl, 50 mM NaF, 20% glycerol, 1 mM EDTA, 1 mM EGTA, 1 mM DTT, 1 mM PMSF, 30 mg/ml leupeptin, 50 mg/ml aprotinin, 5 mg/ml antipain, 5 mg/ml pepstatin) and incubated on ice for one hour. The nuclear suspension was centrifuged for 10 minutes at 16,000 g at 4° C. Supernatant was collected and stored at −80° C. Cytosolic extracts for the CpG binding protein studies were prepared from unstimulated Ramos cells, which were lysed with hypotonic buffer as described for the preparation of the nuclear extract. After centrifugation, the supernatant was removed as cytoplasmic fraction and stored at −80° C. Protein concentrations were measured using a Bradford protein assay (Bio-Rad, Hercules, Calif.) according to the manufacturer.

Western blot analysis: Equal concentrations of whole cell protein extracts (25 µg/lane) were boiled in SDS sample buffer (50 mM Tris-Cl, pH 6.8; 1% β-mercaptoethanol; 2% SDS; 0.1% bromphenolblue; 10% glycerol) for 4 min before being subjected to electrophoresis on a 10% polyacrylamide gel containing 0.1% SDS (SDS-PAGE). After electrophoresis, proteins were transferred to Immobilon-P transfer membranes (Millipore Corp. Bedford, Mass.). Blots were blocked with 5% nonfat dry milk. Specific antibodies against the phosphorylated form of extracellular receptor kinase (ERK), c-jun NH2-terminal kinase (JNK), p38 and activating transcription factor-2 (ATF-2) were used (New England BioLabs, Beverly, Mass.). Blots were developed in enhanced chemiluminescence reagent (ECL; Amersham International, Aylesbury, U.K.) according to the manufacturer's recommended procedure.

Electrophoretic mobility shift assay (EMSA): To detect the DNA-binding activity of the transcription factor activator protein-1 (AP-1) and NFκB, nuclear extracts (1 µg/lane) were analyzed by EMSA using the dsODNs 5' GAT CTA GTG ATG AGT CAG CCG GAT C$_3$' (SEQ ID NO.: 838) containing the AP-1 binding sequence, and the NFκB URE from the c-myc promotor region 5' TGC AGG AAG TCC GGG TTT TCC CCA ACC CCC C$_3$' (SEQ ID NO.: 1142), as probes. ODNs were end labeled with T4-polynucleotide kinase (New England Biolabs) and (γ-$^{32}$P) ATP (Amersham, Arlington Heights, Ill.). Binding reactions were performed with 1 µg nuclear protein extract in DNA-binding buffer (10 mM Tris-HCl (pH 7.5), 40 mM MgCl$_2$, 20 mM EDTA, 1 mM dithiothreitol, 8% glycerol and 100-400 ng of poly (dI-dC) with 20.000-40.000 cpm labeled ODN in 10 µl total volume. Specificity of the NFκB bands was confirmed by competition studies with cold oligonucleotides from unrelated transcription factor binding sites (10-100 ng). For the supershift assay, 2 µg of specific antibodies for c-Rel, p50 and p65 (Santa Cruz Biotechnology, Inc., Santa Cruz, Calif.) were added into the reaction mixture for 30 min before the radiolabeled probe was added. Following incubation for 30 minutes at room temperature loading buffer was added and the probes were electrophoresed on a 6% polyacrylamide gel in Tris-borate-EDTA running buffer (90 mM Tris, 90 mM boric acid, 2 mM EDTA, pH 8.0). Gels were dried and then autoradiographed.

UV-crosslinking and denaturing protein electrophoresis: Nuclear extracts were incubated with labeled phosphodiester oligonucleotide as described for the EMSA. DNA-protein complexes were crosslinked with UV-light in a Stratalinker (Stratagene) for 10 minutes. Probes were mixed with SDS-sample buffer, boiled for 10 minutes and loaded on a 7.5% SDS-PAGE. The gel was dried on Whatman paper and autoradiographed. Plotting the distance against the molecular weight of the marker proteins yielded a standard curve which was used to calculate the approximate molecular weight of the crosslinked protein-ODN complexes. The molecular weight of the oligonucleotide was subtracted from this value to give the size.

Example 9

Identification of an Optimal CpG Motif for Use Alone or in Combination with a T-Rich ODN Phosphorothioate oligonucleotides containing the murine CpG motif GACGTT (SEQ ID NO.: 1143) (for example 1826 (SEQ ID NO.: 69)) and used at concentrations which are active in murine B-cells (Yi A. K., Chang M., Peckham D. W., Krieg A. M., and Ashman R. F. 1998. CpG oligodeoxyribonucleotides rescue mature spleen B cells from spontaneous apoptosis and promote cell cycle entry. *J Immunol* 160:5898), have showed little or no immunostimulatory activity on human immune cells. At higher concentrations this ODN was found to demonstrate some stimulatory effect on human B cells.

In earlier studies on B-cell activation in mice, it was found that a CpG-dinucleotide flanked by two 5' purines and two 3' pyrimidines and preferably the 6mer motif 5' GACGTT 3' (SEQ ID NO: 1143) was optimal for a phosphodiester oligonucleotide to be active (Krieg A. M., et al. 1995 *Nature* 374:546, Yi A. K., Chang M., et al. 1998 *J Immunol* 160:5898).

In order to identify an optimal motif for stimulation of an immune response in humans and non-rodent vertebrates we designed a series of ODN and tested their activity. First we designed a 20 mer phosphodiester oligonucleotide with a TC dinucleotide at the 5' end preceding the optimal murine CpG motif 5' GACGTT 3' (SEQ ID NO: 1143) and followed by a poly C tail (2079: 5' TCG ACG TTC CCC CCC CCC CC 3' (SEQ ID NO.: 320)). This oligonucleotide if added to human primary B-cells under the same conditions as found to be optimal for *E. coli* DNA (repeated addition at 0 hours, 4 hours and 18 hours; 30 μg/ml for each time point) stimulated high levels of CD86 expression on human primary B-cells after two days. To determine the structure-function relationship of the CpG motifs, we replaced the bases adjacent to the CpG dinucleotides while maintaining the two CpG dinucleotides within the sequence. Exchange of the adenine located between both CpG dinucleotides by thymidine (2080 (SEQ ID NO.: 321)) resulted in slightly higher activity. Replacement by guanosine (2100 (SEQ ID NO.: 341)) or cytidine (2082 (SEQ ID NO.: 323)) at this position showed no major changes compared to 2079 (SEQ ID NO.: 320). In contrast, replacement of the thymidine 3' to the second CpG dinucleotide by the purines guanosine (2099 (SEQ ID NO.: 340)) or adenine (2083 (SEQ ID NO.: 324)) resulted in a major drop in activity of the oligonucleotide, while the pyrimidine cytidine caused only a minor decrease. The thymidine immediately 5' to the first CpG dinucleotide was also important. Replacement of the thymidine by any other base (2105 (SEQ ID NO.: 346), guanosine; 2107 (SEQ ID NO.: 348), adenine; 2104 (SEQ ID NO.: 345), cytidine) led to a marked decrease in activity of the oligonucleotide. Elimination of the first (2108 (SEQ ID NO.: 349)) or the second (2106 (SEQ ID NO.: 347)) CpG dinucleotide also partially reduced the activity.

The addition of more 5' GTCGTT 3' (SEQ ID NO.: 1144) CpG motifs to the phosphodiester oligonucleotide containing the 8mer duplex CpG motif (5' TCGTCGTT 3' (SEQ ID NO:1145), 2080 (SEQ ID NO.: 321)) did not further enhance CD86 expression on B-cells (2059 (SEQ ID NO.: 300)). An oligonucleotide with the same sequence as 2080 (SEQ ID NO.: 321) but with a phosphorothioate backbone showed no activity above background (2116 (SEQ ID NO.: 357)). This was surprising since the phosphorothioate backbone has been reported to greatly stabilize oligonucleotides and enhance CpG-induced stimulation (Krieg A. M., Yi A. K., Matson S., Waldschmidt T. J., Bishop G. A., Teasdale R., Koretzky G. A., and Klinman D. M. 1995. CpG motifs in bacterial DNA trigger direct B-cell activation. *Nature* 374: 546). We therefore performed further structure-function analysis of phosphorothioate oligonucleotides containing the 5' GTCGTT 3' (SEQ ID NO: 1144) and 5' TCGTCGTT 3' (SEQ ID NO:1145) motifs, which showed that additional CpG motifs (2006 (SEQ ID NO.: 246)) tended to increase the activity of phosphorothioate oligonucleotides.

Purified B-cells isolated from peripheral blood by immunomagnetic cell sorting were activated by CpG DNA to the same extent as unpurified B-cells within PBMC. Thus, activation of B-cells is a primary response and not a secondary effect caused by cytokines secreted by other cells.

In addition to the co-stimulatory molecule CD86, the functional stage of B-cells is characterized by other surface markers. For example, activated T helper cells stimulate B-cells by CD40 ligation, the intercellular adhesion molecule-1 (ICAM-1, CD54) mediates binding to other immune cells, and major histocompatibility complex II (MHC II) is responsible for antigen presentation. We found that B cell expression of CD40, CD54 and MHC II was upregulated by the CpG oligonucleotide 2080 (SEQ ID NO.: 321). The non-CpG control oligonucleotide 2078 (SEQ ID NO.: 319) showed no activity compared to medium alone.

When PBMC were incubated for 5 days in the presence of 2080 (SEQ ID NO.: 321) (added at 0 hours, 4 hours, 18 hours and every subsequent morning), it was intriguing that a subpopulation of lymphocytes increased in cell size (FSC) and became more granular (SSC). To examine if this subpopulation represented proliferating B-cells, we stained freshly isolated PBMC with CFSE (5-(and-6-) carboxyfluorescein diacetate succinimidyl ester) at day 0 and incubated them for 5 days with 2080 (SEQ ID NO.: 321) as above. CFSE is a fluorescent molecule that binds irreversibly to cell proteins. Each cell division decreases CFSE stain by 50%. Cells staining low with CFSE (proliferating cells) were found to be mainly CD19-positive B-cells. The oligonucleotide 2080 (SEQ ID NO.: 321) induced 60 to 70% of CD19 positive B-cells to proliferate within 5 days. The control oligonucleotide 2078 (SEQ ID NO.: 319) induced less than 5% of B-cells to proliferate. Proliferating B-cells (CFSE low) showed a larger cell size (FSC) and higher granularity.

Proliferating B-cells expressed higher levels of CD86 than non-proliferating cells (not shown). In agreement with this finding, the oligonucleotide panel tested above for induction of CD86 expression resulted in an almost identical pattern of B-cell proliferation. Replacement of the 3' thymidine reduced activity more than changing the thymidine in the middle position.

Example 10

B-Cell Activation Requires Endosomal Maturation/Acidification

It has previously been shown that chloroquine, an inhibitor of endosomal acidification, blocks CpG-mediated stimulation of murine antigen presenting cells and B-cells, while not influencing LPS-mediated effects (Hacker H., et al 1998 *Embo J* 17:6230, Yi A. K. et al 1998 *J Immunol* 160:4755, Macfarlane D. E., and Manzel L. 1998 *J Immunol* 160: 1122). We found that the addition of 5 μg/ml chloroquine completely blocked CpG DNA-mediated induction of CD86 expression on primary B-cells (MFI CD86: 2006 (SEQ ID NO.: 246), 4.7 vs 1.4; *E. coli* DNA, 3.4 vs. 1.4; medium only, 0.9; n=4). Furthermore, chloroquine completely inhibited the induction of B-cell proliferation by the phosphorothioate oligonucleotide 2006 (SEQ ID NO.: 246) measured with the CFSE proliferation assay as well as with the standard. These results suggest that as with murine cells, activation of human B-cells by CpG DNA requires the uptake of DNA in endosomes and subsequent endosomal acidification.

Example 11

Analysis of Sub-Cellular Events Resulting Upon Human B Cell Stimulation with Optimal Human ODN Since the CpG motif requirement for maximal B-cell activation is substantially different between mouse (GACGTT) (SEQ ID NO: 1143) and humans (TCGTCGTT) (SEQ ID NO:1145), we were interested if the basic intracellular signaling events are comparable. Rapid induction of NFκB binding activity has been found earlier in murine B-cells and macrophages (Stacey K. J., et al 1996 *J Immunol* 157:2116, Yi A. K et al 1998 *J Immunol* 160:4755). To investigate the NFκB response to CpG DNA in humans, human primary B-cells were isolated from peripheral blood by immunomagnetic cell sorting and incubated with the CpG oligonucleotide 2080 (SEQ ID NO.: 321), the non-CpG control oligonucleotide 2078 (SEQ ID NO.: 319), or medium. At the indicated time points, cells were harvested and nuclear extracts were prepared. In the presence of CpG oligonucleotide, NFκB binding activity was increased within one hour and maintained up to 18 hours (latest time point examined). The non-CpG control oligonucleotide 2078 (SEQ ID NO.: 319) did not show enhanced NFκB activity compared to cells incubated with medium only. The NFκB band was identified by cold competition, and shown to consist of p50 and p65 subunits by supershift assay.

The activating protein-1 (AP-1) transcription factor is involved in the regulation of immediate early genes and cytokine expression (Karin M. 1995. The regulation of AP-1 activity by mitogen-activated protein kinases. *J Biol Chem* 270:16483). In murine B-cells, AP-1 binding activity is induced in response to CpG DNA (Yi A. K., and Krieg A. M. 1998. Rapid induction of mitogen-activated protein kinases by immune stimulatory CpG DNA. *J Immunol* 161:4493). To determine whether this transcription factor would also be induced by CpG DNA in humans, we examined AP-1 DNA binding activity in human primary B-cells. Cells were incubated with the CpG oligonucleotide 2080 (SEQ ID NO.: 321) or the control oligonucleotide 2078 (SEQ ID NO.: 319). Nuclear extracts were prepared and the AP-1 binding activity was analyzed by EMSA. AP-1 binding activity was enhanced within one hour, and increased up to 18 hours (latest time point examined), showing a sustained response.

Since AP-1 activity is induced by many stimuli (Angel P., and Karin M. 1991. The role of Jun, Fos and the AP-1 complex in cell-proliferation and transformation. *Biochim Biophys Acta* 1072:129), we were interested in signal transduction pathways upstream of AP-1. The AP-1 transcription factor complex integrates different mitogen activated protein kinase (MAPK) pathways (Karin M. 1995. The regulation of AP-1 activity by mitogen-activated protein kinases. *J Biol Chem* 270:16483). Western blots were performed using whole cell extracts from primary B-cells incubated with the CpG oligonucleotide 2080 (SEQ ID NO.: 321), the control 2078 (SEQ ID NO.: 319), or medium only. Specific antibodies to the phosphorylated form of JNK, p38, ATF-2 and ERK were used. Strong induction of JNK phosphorylation was found 30 min and 60 min after exposure to CpG-DNA, while the non-CpG oligonucleotide showed no activity above background. The protein kinase p38, another stress activated protein kinase (SAPK), was also phosphorylated in response to CpG DNA within 60 min. ATF-2, a substrate of both p38 and JNK (Gupta S., Campbell D., Derijard B., and Davis R. J. 1995. Transcription factor ATF2 regulation by the JNK signal transduction pathway. *Science* 267:389) a component of the AP-1 complex, showed weak phosphorylation after 30 min which increased after 60 min. CpG DNA failed to induce substantial phosphorylation of ERK. In contrast, anti-IgM, stimulating the B-cell receptor, did trigger phosphorylation of ERK. Anti-IgM activated different isoforms of JNK than CpG DNA.

Example 12

Assay for In Vivo Adjuvant Activity

An in vitro screening assay to identify ODN useful as an adjuvant in vivo in humans and other non-rodent animals was developed. Since we saw not only quantitative but also qualitative differences in activities of different CpG ODN in mice, we first screened a panel of CpG and non-CpG control ODN on mouse cells to find in vitro assays with reliable and strong correlation to in vivo adjuvant activity with hepatitis B surface antigen (HBsAg). We then systematically tested a panel of more than 250 ODN in corresponding human assays to identify sequences with in vitro immunostimulatory activity. We next examined if the ODN with the highest activity in these human assays also activate B cell proliferation in chimpanzees and monkeys, and finally, if they are active as adjuvants with HBsAg in chimpanzees and cynomolgus monkeys in vivo. These studies revealed that the sequence, number and spacing of individual CpG motifs contribute to the immunostimulatory activity of a CpG phosphorothioate ODN. An ODN with a TC dinucleotide at the 5' end followed by three 6mer CpG motifs (5' GTCGTT 3') separated by TT dinucleotides consistently showed the highest activity for human, chimpanzee, and rhesus monkey leukocytes. Chimpanzees or monkeys vaccinated once against hepatitis B with this CpG ODN adjuvant developed 15 times higher anti-HBs antibody titers than those receiving vaccine alone.

Materials and Methods

Oligodeoxynucleotides: Phosphorothioate-modified ODN were purchased from Operon Technologies (Alameda, Calif.) and Hybridon Specialty Products (Milford, Mass.). ODN were tested for endotoxin using the LAL-assay (LAL-assay BioWhittaker, Walkersville, Md.; lower detection limit 0.1 EU/ml). For in vitro assays, ODN were diluted in TE-buffer (10 mM Tris, pH 7.0, 1 mM EDTA), and stored at −20° C. For in vivo use, ODN were diluted in phosphate buffered saline (0.1 M PBS, pH 7.3) and stored at 4° C. All dilutions were carried out using pyrogen-free reagents.

Mouse spleen cell cultures: Spleens were removed from 6-12 week old female BALB/c (The Jackson Laboratory), $2 \times 10^6$ splenocytes were cultured with 0.2 μM ODN for 4 hours (TNF-α) or 24 hours (IL-6, IFN-γ, IL-12), and cytokines were detected by ELISA as previously described (Yi A. K., Klinman D. M., Martin T. L., Matson S., and Krieg A. M. 1996. Rapid immune activation by CpG motifs in bacterial DNA. Systemic induction of IL-6 transcription through an antioxidant-sensitive pathway. *J Immunol* 157: 5394). To evaluate CpG-induced B cell proliferation, spleen cells were depleted of T cells with anti-Thy-1.2 and complement and centrifugation over lympholyte M® (Cedarlane Laboratories, Hornby, ON, Canada), cultured for 44 hours with the indicated ODN, and then pulsed for 4 hours with 1 μCi of $^3$H thymidine as described previously (Krieg A. M., Yi A. K., Matson S., Waldschmidt T. J., Bishop G. A., Teasdale R., Koretzky G. A., and Klinman D. M. 1995. CpG motifs in bacterial DNA trigger direct B-cell activation. *Nature* 374:546). To examine NK cell lytic activity murine spleen cells were depleted of B cells using magnetic beads coated with goat anti-mouse Ig as previously detailed (Ballas Z. K., and Rasmussen W. 1993. Lymphokine-activated killer cells. VII. IL-4 induces an NK1.1$^+$CD8 $\alpha^+\beta^-$ TCR-$\alpha\beta$ B220$^+$ lymphokine-activated killer subset. *J Immunol* 150: 17). Cells were cultured at 5×10$^6$/well in 24-well plates and harvested at 18 hours for use as effector cells in a standard 4 hour $^{51}$Cr-release assay against YAC-1 target cells. One unit (LU) was defined as the number of cells needed to effect 30% specific lysis.

Immunization of mice against HBsAg and evaluation of the humoral response: Groups of 6-8 week old female BALB/c mice (n=5 or 10, Charles River, Montreal, QC) were immunized against HBsAg as previously described (Davis H. L., et al 1998 *J Immunol* 160:870). In brief, each mouse received a single IM injection of 50 µl PBS containing 1 µg recombinant HBsAg (Medix Biotech, Foster City, Calif.) and 10 µg of CpG ODN or non-CpG ODN as a sole adjuvant or combined with alum (Alhydrogel "85", Superfos Biosector, Vedbaek, Denmark; 25 mg Al$^{3+}$/mg HBsAg). Control mice were immunized with HBsAg without adjuvant or with alum. Plasma was recovered from mice at various times after immunization and Abs specific to HBsAg (anti-HBs) were quantified by end-point dilution ELISA assay (in triplicate) as described previously (Davis H. L et al 1998 *J Immunol* 160:870). End-point titers were defined as the highest plasma dilution that resulted in an absorbance value (OD450) two times higher than that of non-immune plasma with a cut-off value of 0.05.

Isolation of primate PBMC and cell culture: Peripheral blood mononuclear cells (PBMC) were isolated from peripheral blood of healthy volunteers, chimpanzees or rhesus or cynomolgus monkeys by Ficoll-hypaque density gradient centrifugation (Histopaque-1077, Sigma Chemical Co., St. Louis, Mo.) as described (Hartmann G., et al 1996 *Antisense Nucleic Acid Drug Dev* 6:291). Cells were suspended in RPMI 1640 culture medium supplemented with 10% (v/v) heat-inactivated (56° C., 1 h) FCS (HyClone, Logan, Utah), 1.5 mM L-glutamine, 100 U/ml penicillin and 100 µg/ml streptomycin (all from Gibco BRL, Grand Island, N.Y.) (complete medium). Cells (final concentration 1×10$^6$ cells/ml) were cultured in complete medium in a 5% CO$_2$ humidified incubator at 37° C. ODN and LPS (from *Salmonella typhimurium*, Sigma Chemical Co., St. Louis, Mo.) or anti-IgM were used as stimuli. For measurement of human NK lytic activity, PBMC were incubated at 5×10$^6$/well in 24-well plates. Cultures were harvested after 24 hours, and cells were used as effectors in a standard 4 hours $^{51}$Cr-release assay against K562 target cells as previously described (Ballas Z. K., Rasmussen W. L., and Krieg A. M. 1996. Induction of NK activity in murine and human cells by CpG motifs in oligodeoxynucleotides and bacterial DNA. *J Immunol* 157:1840; Ballas Z. K., and Rasmussen W. 1993. Lymphokine-activated killer cells. VII. IL-4 induces an NK1.1$^+$CD8 $\alpha^+\beta^-$ TCR-$\alpha\beta$ B220$^+$ lymphokine-activated killer subset. *J Immunol* 150:17). For B cell proliferation, 1 µCi of $^3$H thymidine was added 18 hours before harvest, and the amount of $^3$H thymidine incorporation was determined by scintillation counting at day 5. Standard deviations of the triplicate wells were <5%.

Flow cytometry on primate PBMC: Surface antigens on primate PBMC were stained as previously described (Hartmann G et al 1998 *J Pharmacol Exp Ther* 285:920). Monoclonal antibodies to CD3 (UCHT1), CD14 (M5E2), CD19 (B43), CD56 (B159), CD69 (FN50) and CD86 (2331 (FUN-1)) were purchased from Pharmingen, San Diego, Calif. IgG$_1$,κ (MOPC-21) and IgG$_{2b}$,κ (Hartmann G et al 1999 *PNAS* 96:9305) were used to control for non-specific staining. NK cells were identified by CD56 expression on CD3, CD14 and CD19 negative cells, whereas B cells were identified by expression of CD19. Flow cytometric data from 10000 cells per sample were acquired on a FACScan (Beckton Dickinson Immunocytometry Systems, San Jose, Calif.). The viability of cells within the FSC/SSC gate used for analysis was examined by propidium iodide staining (2 µg/ml) and found to be higher than 98%. Data were analyzed using the computer program FlowJo (version 2.5.1, Tree Star, Inc., Stanford, Calif.).

Immunization of chimpanzees and cynomolgus monkeys against HBsAg and evaluation of the humoral response: Fourteen cynomolgus monkeys (2.0-3.5 kg) were immunized with a pediatric dose of Engerix-B (SmithKline Beecham Biologicals, Rixensart, BE) containing 10 µg HBsAg adsorbed to alum (25 mg Al$^{3+}$/mg HBsAg). This was administered alone (n=5), or combined with CpG ODN 1968 (n=5, 500 µg) or CpG ODN 2006 (SEQ ID NO.: 246) (n=4, 150 µg). Four chimpanzees (10-20 kg) were immunized in the same fashion with two receiving control vaccine (Engerix-B only) and two receiving experimental vaccine (Engerix-B plus 1 mg CpG ODN 2006). All vaccines were administered IM in the-right anterior thigh in a total volume of 1 ml. Monkeys were maintained in the animal facility of the Primate Research Center (Bogor, Indonesia) and chimpanzees were housed at Bioqual (Rockville, Md.). Animals were monitored daily by animal care specialists. No symptoms of general ill health or local adverse reactions at the injection site were noted. Plasma was recovered by IV puncture prior to and at various times after immunization and was stored frozen (−20° C.) until assayed for antibodies. Anti-HBs antibodies were detected using a commercial ELISA kit (Monolisa Anti-HBs; Sanofi-Pasteur, Montreal, QC) and titers were expressed in mIU/ml based on comparison with WHO defined standards (Monolisa Anti-HBs Standards; Sanofi-Pasteur).

Results

Identification of CpG ODN with different profiles of in vitro immune activities: Our studies showed that the precise bases on the 5' and 3' sides of a CpG dinucleotide within a CpG motif may have an impact on the level of immune activation of a synthetic ODN, but it has been unclear whether different CpG motifs might display different immune effects. To evaluate this possibility, we tested a panel of CpG ODN for their ability to induce NK lytic activity, B cell proliferation, and to stimulate synthesis of TNF-α, IL-6, IFN-γ and IL-12 in murine spleen cells. Immunostimulatory activity of ODN without CpG motifs (ODN 1982 (SEQ ID NO.: 225), ODN 1983 (SEQ ID NO.: 226)) was negative or weak compared to CpG ODN. ODN with non optimal CpG motifs (ODN 1628 (SEQ ID NO.: 767), ODN 1758 (SEQ ID NO.: 1)) were less active than ODN containing CpG motifs flanked by two 5' purines and two 3' pyrimidines (ODN 1760 (SEQ ID NO.: 3), ODN 1826 (SEQ ID NO.: 69), ODN 1841 (SEQ ID NO.: 84)). ODN 1826 containing two optimal murine CpG motifs (5' GACGTT 3') (SEQ ID NO:1143) had the highest activity for 5 of 6 measured endpoints. Except for ODN 1628, all ODN showed a generally similar pattern of activity (NK cell-mediated lysis, B cell proliferation, IL-12, IL-6, TNF a, IFN-γ). Of note, ODN 1628, which was unique in this panel for containing two G-rich regions, showed preferential induction of IFN-γ synthesis but relatively low stimulation of the other activities.

Identification of in vitro assays which correlate with in vivo adjuvant activity: Since adjuvant activity is an in vivo endpoint, we were interested in identifying in vitro assays that would predict the adjuvant activity of a CpG ODN in vivo. The same ODN used for in vitro endpoints therefore were tested for their adjuvant activity to immunize mice against HBsAg. This was carried out both with ODN alone and with ODN combined with alum, since earlier studies had shown strong synergy for CpG ODN and alum adjuvants (PCT Published Patent Application WO98/40100).

BALB/c mice immunized with HBsAg without adjuvant attained only low titers of anti-HBs by 4 weeks, and this was not affected by addition of control ODN. In contrast, addition of CpG ODN raised anti-HBs titers by 5 to 40 fold, depending on the sequence used. When alum was added, titers of anti HBs were approximately 6 times higher than with HBsAg alone. Specifically, control ODN had no effect and the various CpG ODN augmented these titers 2 to 36 fold. Results obtained with the different ODN alone correlated very strongly (r=0.96) with those obtained using the same ODN plus alum. When linear regression was performed, a very high degree of correlation was found between certain in vitro assays and in vivo augmentation of anti-HBs titers. Of all the in vitro endpoints examined, the induction of NK lytic activity showed the best correlation to in vivo adjuvant activity (without alum, r=0.98; with alum, r=0.95; p<0.0001). A good correlation regarding adjuvant activity was also obtained for B-cell stimulation (r=0.84 and 0.7), as well as secretion of TNF-α (r=0.9 and 0.88), IL-12 (r=0.88 and 0.86) and IL-6 (r=0.85 and 0.91). The one in vitro assay that did not correlate well with the in vivo results was IFN-γ secretion (r=0.57 and 0.68). These data demonstrate that in vitro assays for NK lytic activity, B cell activation and production of TNF-α, IL-6 and IL-12 provide valuable information in vitro to predict the adjuvant activity of a given ODN in vivo.

Screening of a phosphorothioate ODN panel to activate human NK cells: In previous studies we found that synthesis of inflammatory cytokines by human PBMC is induced by extremely low amounts of endotoxin (induced TNF-α secretion is detectable with just 6 pg/ml endotoxin, 2 logs more sensitive than murine immune cells). In contrast, activation of human B cells and induction of human NK cell lytic activity with endotoxin is low even at high endotoxin concentrations. Based on these results we selected activation of NK cells (lytic activity and CD69 expression) and B cells (proliferation and CD86 expression) as the most highly specific and reproducible assays with low inter-subject variability and used these assays for in vitro screening of a pool of ODN.

First we studied the effect of phosphorothioate ODN containing various combinations and permutations of CpG motifs on NK cell-mediated lysis of target cells. For clarity and ease of presentation, only data with selected representative CpG and control ODN are shown. Human PBMC were incubated with different phosphorothioate ODN (6 μg/ml) for 24 hours and tested for their ability to lyse $^{51}$Cr-labeled K562 cells. ODN with two 6-mer CpG motifs (either 5' GACGTT 3' (SEQ ID NO.: 1143) or 5' GTCGTT 3' (SEQ ID NO.: 1144)) in combination with a TpC at the 5'end of the ODN (ODN 1840 5' TCCATGTCGTTCCT-GTCGTT 3' (SEQ ID NO.: 83), ODN 1851 5' TCCT-GACGTTCCTGACGTT 3' (SEQ ID NO.: 94) or with at least three 6-mer motifs without a TpC at the 5' end (ODN 2013 (SEQ ID NO.: 253)) show intermediate activity. High activity was found when the 5' TpC directly preceded a 6-mer human CpG motif (5' TCGTCGTT 3' (SEQ ID NO:1145) (in SEQ ID NO.: 246)) and was followed by two 6-mer motifs (ODN 2005 (SEQ ID NO.: 245), ODN 2006 (SEQ ID NO.: 246) and ODN 2007 (SEQ ID NO.: 247)). The best results were obtained when the 6-mer CpG motifs were separated from each other and from the 5' 8-mer CpG motif by TpT (ODN 2006 (SEQ ID NO.: 246)).

Expression of the activation marker CD69 is rapidly upregulated on the surface of NK cells subsequent to stimulation. To confirm the results from the NK cell lysis assay, PBMC were incubated for 18 hours with ODN (2 μg/ml). CD69 expression was examined on CD56 positive NK cells (CD3, CD14 and CD19 negative). Although induction of CD69 expression was less sequence restricted than stimulation of NK cell functional activity, control ODN (ODN 1982, ODN 2116, ODN 2117, ODN 2010) showed only low activity similar to background levels. ODN with two human CpG motifs separated by 5' TTTT 3' (ODN 1965 (SEQ ID NO.: 208)) or four human CpG motifs without spacing (ODN 2013 (SEQ ID NO.: 253)) were relatively more active at inducing CD69 expression than at stimulating NK cell lytic activity. Optimal NK cell functional activity, as well as CD69 expression, was obtained with ODNs containing a TpC dinucleotide preceding the human CpG motif, and additional human motifs within the sequence (ODN 2006 (SEQ ID NO.: 246), ODN 2007 (SEQ ID NO.: 247)).

Activity of phosphorothioate ODN for stimulating human B cells: In preliminary experiments we found that the percentage of proliferating B cells (CFSE assay, see methods section) correlated with the surface expression of the co-stimulatory CD86 on B cells, as measured by flow cytometry. Thus we used CD86 expression on B cells to screen a panel of ODN for their immunostimulatory activity. PBMC were incubated with 0.6 μg/ml ODN. Expression of CD86 (mean fluorescence intensity, MFI) was examined on CD19 positive B cells. A poly C ODN (ODN 2017 (SEQ ID NO.: 257)) or ODN without CpG dinucleotides (ODN 1982 (SEQ ID NO.: 225)) failed to stimulate human B cells under these experimental conditions. A phosphorothioate ODN (ODN 2116 (SEQ ID NO.: 256)) with one optimal human CpG motif preceded by a TpC (5' TCGTCGTT 3' (SEQ ID NO: 1145) (in SEQ ID NO.: 246)) was inactive. The presence of one human 6-mer CpG motif (5' GTCGTT 3' (SEQ ID NO.: 1144)) had no activating effect. Two of these CpG motifs within the sequence showed no (ODN 1960 (SEQ ID NO.: 203), ODN 2016 (SEQ ID NO.: 256)) or intermediate (ODN 1965 (SEQ ID NO.: 208)) activity dependent on the sequence context. If the ODN was composed of three or four copies of this motif (ODN 2012 (SEQ ID NO.: 252), ODN 2013 (SEQ ID NO.: 253), ODN 2014 (SEQ ID NO.: 254)), intermediate activity on B cells could be detected. The combination of the human 8-mer CpG motif on the 5' end of the ODN with two 6-mer CpG motifs (ODN 2005 (SEQ ID NO.: 245), ODN 2006 (SEQ ID NO.: 246), ODN 2007 (SEQ ID NO.: 247), ODN 2102 (SEQ ID NO.: 343), ODN 2103 (SEQ ID NO.: 344)) led to a considerable increase in the ability of the ODN to stimulate B cells. The spacing between the single motifs was critical. The separation of CpG motifs by TpT was preferable (ODN 2006 (SEQ ID NO.: 246)) compared to unseparated CpG motifs (ODN 2005 (SEQ ID NO.:); also compare ODN 1965 (SEQ ID NO.: 208) to ODN 1960 (SEQ ID NO.: 203)). The human 6-mer CpG motif (5' GTCGTT 3') was better than the optimal mouse 6-mer CpG motif (5' GACGTT 3' (SEQ ID NO.: 246)) when combined with the human 8-mer CpG motif on the 5' end (ODN 2006 vs. ODN 2102 (SEQ ID NO.: 343) and ODN 2103 (SEQ ID NO.: 344)). A (TCG)$_{poly}$ ODN was inactive or only weakly active, as were ODN containing CpG dinucleotides flanked by guanines or other CpG dinucleotides (ODN 2010 (SEQ ID NO.: 250)). Taken together, the findings for NK cells and B cells showed consistently that of the ODN tested, ODN 2006 (SEQ ID NO.: 246) has the highest immunostimulatory activity on human immune cells.

Comparative analysis of potency of CpG phosphorothioate ODNs in different primates: Different CpG motifs are optimal to activate murine and human immune cells. Furthermore, the number and location of CpG motifs within an active phosphorothioate ODN is different in mice and humans. We were interested to know if CpG phosphorothioate ODN show a similar activity among different species of primates. We compared a panel of CpG ODN for their ability to induce B cell proliferation in humans, chimpanzees and rhesus or cynomolgus monkeys. The capability of ODN to stimulate human B cell proliferation (Table J) correlated well with their ability to induce CD86 expression on B cells. ODN 2006 (SEQ ID NO.: 246), which showed the highest activity in human B cells and NK cells, was also the most active in stimulating chimpanzee and rhesus monkey B cell proliferation (Table J). ODN 1968 (SEQ ID NO.: 211) and ODN 2006 (SEQ ID NO.: 246) gave the highest activation of cynomolgus monkey B-cells in vitro (SI of 25 and 29 respectively at 6 µg ODN/ml). Surprisingly, CpG ODN 2007 (SEQ ID NO.: 247), which displayed similarly high activity as the optimal ODN 2006 (SEQ ID NO.: 246) in human cells, did not stimulate Rhesus monkey or chimpanzee B cell proliferation, and the ODN 1968 (SEQ ID NO.: 211) showed low activity. CpG ODN originally identified with high activity in mice (ODN 1760 (SEQ ID NO.: 3), ODN 1826 (SEQ ID NO.: 69)) showed little activity in monkeys (Table J).

TABLE J

Proliferative response of PBMC to phosphorothioate CpG ODN in primates

|  | Humans | Chimpanzee | Rhesus monkey |
|---|---|---|---|
| No addition | 0.5 +− 0.1 | 0.5 +− 0.1 | 0.5 +− 0.0 |
| ODN 1760 (SEQ ID NO.: 3) | 23 +− 7 | 0.3 +− 0.1 | 0.5 +− 0.3 |
| ODN 1826 (SEQ ID NO.: 69) | 0.8 +− 0.1 | 0.4 +− 0.1 | 0.6 +− 0.1 |
| ODN 1968 (SEQ ID NO.: 211) | 35 +− 9 | 20.0 +− 3.8 | 1.9 +− 0.7 |
| ODN 1982 (SEQ ID NO.: 225) | 9.7 +− 1.1 | 2.5 +− 1.1 | 0.7 +− 0.1 |
| ODN 2006 (SEQ ID NO.: 246) | 58 +− 8 | 27.4 +− 8.9 | 6.3 +− 3.3 |
| ODN 2007 (SEQ ID NO.: 247) | 47 +− 11 | 0.5 +− 0.1 | 0.4 +− 0.2 |

PBMC were prepared from peripheral blood and incubated with ODN (0.6 µg/ml) as indicated for five days. Proliferation was measured by uptake of $^3$H/thymidine (cpm/1000) during the last 18 hours. More than 95% of proliferating cells were B-cells as determined using the CFSE assay. Four human probands, six chimpanzees and two rhesus monkeys were tested.

In vivo adjuvant activity of CpG ODN in chimpanzees and cynomolgus monkeys: In order to evaluate whether CpG ODN with strong in vitro stimulatory effects on primate cells had detectable adjuvant activity in vivo, Cynomolgus monkeys and chimpanzees were immunized with Engerix B, which comprises HBsAg adsorbed to alum, alone or with added ODN 1968 (500 µg) or ODN 2006 (SEQ ID NO.: 246) (1 mg) respectively. Compared to controls not receiving CpG ODN, anti-HBs titers at 4 weeks post-prime and 2 weeks post-boost were 66- and 16-fold higher respectively in the monkeys, and 15- and 3-fold higher in the chimpanzees (Table K). Thus a clear adjuvant effect of CpG ODN was seen, and this was particularly striking after a single immunization.

TABLE K

Anti-HBs responses in primates immunized against HBsAg with CpG ODN[3]

| | | | Anti-HBs (mIU/ml) | |
|---|---|---|---|---|
| Primate species | n | CpG ODN | 4 wks post-prime | 2 wks post-boost |
| Cynomolgus monkey | 5 | None | 15 ± 44 | 4880 ± 13113 |
| | 5 | ODN 1968 (500 µg) (SEQ ID NO. 211) | 995 ± 1309 | 76449 ± 42094 |
| Chimpanzee | 2 | None | 6,11 | 3712, 4706 |
| | 2 | ODN 2006 (1 mg) (SEQ ID NO. 246) | 125, 135 | 9640, 16800 |

[3]Animals were immunized by IM injection of Engerix B containing 10 µg HBsAg adsorbed to alum, alone or with added CpG ODN. Cynomolgus monkeys were boosted at 10 wks and chimpanzees were boosted at 4 wks post-prime. Anti-HBs was determinedby ELISA assay; values for monkeys are GMT ± SEM (n = 5) whereas individual values for the two chimpanzees in each group are provided.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. A composition comprising an immunostimulatory nucleic acid comprising

5' TCGTCGTTTTGACGTTTTGTCGTT 3' (SEQ ID NO:343).

2. The composition of claim 1, wherein the immunostimulatory nucleic acid consists of SEQ ID NO:343.

3. The composition of claim 1, wherein the immunostimulatory nucleic acid is equal to or less than 100 nucleotides in length.

4. The composition of claim 1, further comprising a pharmaceutically acceptable carrier.

5. The composition of claim 1, wherein the immunostimulatory nucleic acid is a T-rich immunostimulatory nucleic acid.

6. The composition of claim 1, wherein the immunostimulatory nucleic acid comprises at least three poly T motifs.

7. The composition of claim 6, wherein at least one poly T nucleic acid motif comprises

5' $X_1X_2TTTTX_3 X_4$ 3' wherein $X_1$, $X_2$, $X_3$ and $X_4$ are nucleotides, and $X_1X_2$ is selected from the group consisting of TT, TA, TG, TC, AT, AA, AG, AC, CT, CC, CA, GT, GG, GA, and GC, and $X_3X_4$ is selected from the group consisting of TT, TA, TG, TC, AT, AA, AG, AC, CT, CC, CA, GT, GG, GA, and GC.

8. The composition of claim 6, wherein the immunostimulatory nucleic acid comprises at least 4, at least 5, at least 6, at least 7, or at least 8 poly T motifs.

9. The composition of claim 6, wherein at least two of the at least three poly T motifs each comprises a motif selected from the group consisting of at least five contiguous T nucleotide residues and at least six contiguous T nucleotide residues.

10. The composition of claim 6, wherein at least three poly T motifs each comprises at least five contiguous T nucleotide residues.

11. The composition of claim 6, wherein the at least three poly T motifs is at least four motifs.

12. The composition of claim 1, wherein the immunostimulatory nucleic acid comprises a nucleotide composition selected from the group consisting of greater than 25% T, greater than 35% T, greater than 40% T, greater than 50% T, greater than 60% T, greater than 80% T, greater than 25% C, and greater than 25% A.

13. The composition of claim 1, wherein the immunostimulatory nucleic acid comprises a length selected from the group consisting of at least 27 nucleotides and at least 30 nucleotides.

14. The composition of claim 1, wherein the immunostimulatory nucleic acid has a niicleotide backbone that includes at least one backbone modification.

15. The composition of claim 14, wherein the backbone modification is a phosphorothioate modification.

16. The composition of claim 14, wherein the nucleotide backbone is chimeric.

17. The composition of claim 14, wherein the nucleotide backbone is entirely modified.

18. The composition of claim 1, wherein the immunostimulatory nucleic acid is formulated for delivery by a route selected from the group consisting of oral, nasal, rectal, vaginal, and ocular.

19. The composition of claim 1, wherein the immunostimulatory nucleic acid is provided in a sustained release device.

20. The composition of claim 19, wherein the sustained release device is a microparticle.

21. The composition of claim 1, wherein the immunostimulatory nucleic acid is formulated in a delivery device selected from the group consisting of a capsule, a pill, and a sublingual tablet.

22. The composition of claim 1, wherein the immunostimulatory nucleic acid is formulated for delivery locally or systemically.

23. The composition of claim 1, wherein the immunostimulatory nucleic acid is formulated for delivery mucosally.

24. The composition of claim 1, wherein the immunostimulatory nucleic acid is provided in an amount effective to induce an immune response in a non-rodent subject.

25. The composition of claim 24, wherein the non-rodent subject is selected from the group consisting of a human, a dog, a cat, a horse, a cow, a pig, a sheep, a goat, a chicken, a monkey, and a fish.

26. The composition of claim 24, wherein the immune response is selected from the group consisting of a local immune response, a systemic immune response, a mucosal immune response, an antigen specific immune response, and an innate immune response.

27. The composition of claim 1, wherein the immunostimulatory nucleic acid is provided in an amount effective to treat asthma in a subject in need thereof.

28. The composition of claim 27, further comprising an asthma medicament.

29. The composition of claim 1, wherein the immunostimulatory nucleic acid is provided in an amount effective to treat allergy in a subject in need thereof.

30. The composition of claim 29, further comprising an allergy medicament.

31. The composition of claim 1, wherein the immunostimulatory nucleic acid comprises $$5'\ N_1X_1X_2TGX_3X_4N_2\ 3'$$

wherein $X_1X_2$ are nucleotides selected from the group consisting of GT, GG, GA, AA, AT, AG, CT, CA, CG, TA and TT, and $X_3X_4$ are nucleotides selected from the group consisting of TT, TC, TG, TA, CT, CG, CC, CA, AC, AT, AG and AA, and $N_1$ and $N_2$ are nucleic acid sequences composed of any number of nucleotides provided that the sum total of $N_1$ and $N_2$ is in the range of 9 to 19.

32. A method of stimulating an immune response, comprising administering the composition of claim 1, to a non-rodent subject in an amount effective to induce an immune response in the non-rodent subject, wherein the non-rodent subject has asthma or allergy.

33. The composition of claim 22, wherein the nucleotide backbone is entirely phosphorothioate.

* * * * *

UNITED STATES PATENT AND TRADEMARK OFFICE
CERTIFICATE OF CORRECTION

PATENT NO.        : 7,271,156 B2                                    Page 1 of 1
APPLICATION NO.   : 10/314578
DATED             : September 18, 2007
INVENTOR(S)       : Arthur M. Krieg et al.

It is certified that error appears in the above-identified patent and that said Letters Patent is hereby corrected as shown below:

Title page of the patent, line 6 of the Abstract, please delete "and/ore greater than 50% c" and replace with -- and/or greater than 50% C --.

Title page 1, under Related U.S. Application Data, section 63, please delete "Continuation" and insert -- Divisional --.

In Claim 14, column 517, line 20, please delete "niicleotide" and insert -- nucleotide --.

Signed and Sealed this

Twentieth Day of May, 2008

JON W. DUDAS
*Director of the United States Patent and Trademark Office*